(12) United States Patent
Ashkenazi et al.

(10) Patent No.: US 7,741,056 B2
(45) Date of Patent: *Jun. 22, 2010

(54) USE OF A33 ANTIGENS AND JAM-IT

(75) Inventors: Avi Ashkenazi, San Mateo, CA (US); Sherman Fong, Alameda, CA (US); Audrey Goddard, San Francisco, CA (US); Austin L. Gurney, Belmont, CA (US); Mary A. Napier, Hillsborough, CA (US); Daniel Tumas, Orinda, CA (US); Menno Van Lookeren, San Francisco, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 581 days.

This patent is subject to a terminal disclaimer.

(21) Appl. No.: 11/725,063

(22) Filed: Mar. 15, 2007
(Under 37 CFR 1.47)

(65) Prior Publication Data

US 2009/0275738 A1 Nov. 5, 2009

Related U.S. Application Data

(60) Division of application No. 10/633,008, filed on Jul. 31, 2003, now Pat. No. 7,192,589, which is a continuation-in-part of application No. 10/265,542, filed on Oct. 3, 2002, now abandoned, which is a continuation-in-part of application No. PCT/US00/04414, filed on Feb. 22, 2000, and a continuation-in-part of application No. PCT/US00/14042, filed on May 22, 2000, and a continuation-in-part of application No. PCT/US00/32678, filed on Dec. 1, 2000, and a continuation-in-part of application No. 09/254,465, filed on Mar. 5, 1999, now Pat. No. 6,410,708, and a continuation-in-part of application No. PCT/US99/05028, filed on Mar. 8, 1999, and a continuation-in-part of application No. 09/380,138, filed on Aug. 25, 1999, now abandoned, and a continuation-in-part of application No. 09/380,139, filed on Aug. 25, 1999, now abandoned, and a continuation-in-part of application No. PCT/US98/19330, filed on Sep. 16, 1998, and a continuation-in-part of application No. 09/953,499, filed on Sep. 14, 2001, now Pat. No. 6,838,554, which is a continuation of application No. PCT/US98/24855, filed on Nov. 20, 1998.

(51) Int. Cl.
*C07K 14/00* (2006.01)
*C12Q 1/68* (2006.01)
(52) U.S. Cl. ......................... 435/7.1; 530/350
(58) Field of Classification Search ............. None
See application file for complete search history.

(56) References Cited

U.S. PATENT DOCUMENTS

| 4,579,827 | A | 4/1986 | Sakamoto et al. ........... 436/536 |
| 6,410,708 | B1 | 6/2002 | Askenazi et al. ........... 536/23.5 |
| 7,282,565 | B2 * | 10/2007 | Goddard et al. ............. 530/350 |

FOREIGN PATENT DOCUMENTS

| EP | 0 199 141 | | 10/1986 |
| EP | 0 616 812 | A1 | 9/1994 |
| EP | 0 616 812 | B1 | 9/1994 |
| WO | WO 99/27098 | | 6/1999 |
| WO | WO 99/40100 | A1 | 8/1999 |
| WO | WO 99/46281 | | 9/1999 |
| WO | WO 00/12703 | A2 | 3/2000 |
| WO | WO 00/29583 | A2 | 5/2000 |
| WO | WO 00/36102 | | 6/2000 |
| WO | WO 00/37638 | A2 | 6/2000 |
| WO | WO 00/53758 | | 9/2000 |
| WO | WO 01/04311 | | 1/2001 |
| WO | WO 01/36432 | A2 | 5/2001 |
| WO | WO 01/40466 | | 6/2001 |
| WO | WO 02/00690 | | 1/2002 |
| WO | WO 02/08284 | | 1/2002 |

OTHER PUBLICATIONS

Database Genebank (Apr. 24, 2001), Ashkenazi et al., "Human Pro 1868 Protein" Database Accession No. AAB80272, XP002448361.
Boyum, A. "A One Stage Procedure for Isolation of Granulocytes and Lymphocytes from Human Blood," Norweigan Defense Establishment, Div. Of Toxicology, pp. 51-76.
Martin-Padura, I. et al, "Junctional Adhesion Molecule, a Novel Member of the Immunoglobulin Superfamily That Distributes at Intercellular Junctions and Modulates Monocyte Transmigration," J. Cell Biol. 142 (1): 117-27 (1998).
Monks, A. et al., "Feasibility of High-Flux Anticancer Drug Screen Using a Diverse Panel of Cultured Human Tumor Cell Lines," Natl. Cancer Inst. 83: 757-766 (1991).
Skehan, P. et al., "New Colorimetric Cytoxicity Assay for Anticancer-Drug Screening," J. Natl. Cancer Inst. 82: 1107-1112 (1990).
Spencer, S. et al., "The Orphan Receptor CRF2-4 Is an Essential Subunit of the Interleukin 10 Recepto," J. Exp. Med. 187: 571-578 (1998).
Taylor, S. et al., "The Human Homologue of Bub3 Is Required for Kinetochore Localization of Bub1 and a Mad3/Bub1-Related Protein Kinase," J. Cell. Biol. 142 (1):1-11 (1998).

(Continued)

*Primary Examiner*—Maher M Haddad
(74) *Attorney, Agent, or Firm*—Bonny Yeung; Ginger P. Dreger; Arnold & Porter LLP

(57) ABSTRACT

The present invention relates to compositions and methods of treating and diagnosing disorders characterized the by the presence of antigens associated with inflammatory diseases and/or cancer.

4 Claims, 75 Drawing Sheets

OTHER PUBLICATIONS

Welt, S. et al., "Quantative Analysis of Antibody Localization in Human Metastatic Colon Cancer: A Phase I Study of Monoclonal Antibody A33," J. Clin. Oncol. 8: 1894-1906 (1990).

Welt, S. et al., "Phase I/II Study of Iodine 131-Labeled Monoclonal Antibody A33 in Patients with Advanced Colon Cancer," J. Clin. Oncol. 12: 1561-1571 (1994).

Martin-Padura et al., "Junctional Adhesion Molecule, A Novel Member of the Immunoglobin Superfamily that Distributes at Intercellular Junctions and Modulates Monocyte Transmigration", J. Cell Biology, vol. 142, No. 1, pp. 117-127, Jul. 13, 1998.

Ozaki et al, "Cutting Edge: Combined Treatment of the TNF-alpha and IFN-gamma causes Redistribution of Junctional Adhesion Molecule in Human Endothelial Cells", J. Immunol., vol. 163, No. 2, Jul. 15, 1999.

Walker MG. Z39Ig is co-expressed with activated macrophage genes. Biochim Biophys Acta. Apr. 12, 2002;1574(3):387-90.

Kahan BD. Immunosuppressive therapy. Curr Opin Immunol. Oct. 1992;4(5):553-60.

Kim et al. Characterization of monoclonal antibody specific to the Z39Ig protein, a member of immunoglobulin superfamily. Immunol Lett. Jul. 15, 2005;99(2):153-61.

* cited by examiner

| | | |
|---|---|---|
| SEQ ID NO:6 | A33 | 1 MVGKMWPVLWTLCAVRVTVDAISVETPQDVLRASQGKSVTLPCTYHTSTS |
| SEQ ID NO:1 | 40628 | 1 MGTKAQVERKLLCLFILAILLCSLALGSVTVHSSE--------PEVRIPE |
| SEQ ID NO:2 | 45416 | 1 ----MGILLGLLLLGHLTVDTYGRPILEVPESVTGPWKGDVNLPCTYDPL |
| SEQ ID NO:9 | 35638 | 1 MARRSRMRLLLLLLRYLVVALGYHKAYGFSAPKDQ--------QVVTAVE |
| SEQ ID NO:10 | JAM | 1 -MGTEGKAGRKLLFLFTSMILGSLVQGKGSVYTAQ--------SDVQVPE |

| | | |
|---|---|---|
| | A33 | 51 SREGLIQWDKLLLTHTERVVIWPFSNKNYIHGELYKNRVSISNNAEQSDA |
| | 40628 | 43 NNPYKLSCAYSGFSSPRVEWKFDQGDTTRLVCYNNKITASYEDRVTFLPT |
| | 45416 | 47 QGYTQVLVKWLVQRGSDPVTIFLRDSSGDHIQQAKYQGRLHVSHKVPGDV |
| | 35638 | 43 YQEAILACKTPKKTYSSRLEWKKLGRSVSFVYYQQTLQGDFKNRAEMIDF |
| | JAM | 42 NESIKLTCTYSGFSSPRVEWKFVQGSTTALVCYNSQITAPYADRVTFSSS |

| | | |
|---|---|---|
| | A33 | 101 SITIDQLTMADNGTYECSVSL-M------SDLEGNTKSRVRLLVLVPPSK |
| | 40628 | 93 GITFKSVTREDTGTYTCMVSE--------EGGNSYGEVKVKLIVLVPPSK |
| | 45416 | 97 SLQLSTLEMDDRSHYTCEVTWQTPDGNQYVRDKITELRVQKLSVSKPTVT |
| | 35638 | 93 NIRIKNVTRSDAGKYRCEVSAPS------EQGNLEEDTVTLEVLVAPAV |
| | JAM | 92 GITFSSVTRKDNGEYTCMVSE--------EGGONYGEVSIHLTVLVPPSK |

| | | |
|---|---|---|
| | A33 | 144 PECGIEGETIIGNNIQLTCQSKEGSPTPQYSWKRYNILNQEQ-------- |
| | 40628 | 135 PTVNIPSSATIGNRAVLTCSEQDGSPPSEYTWFKDGIVMPTN-PKSTRAF |
| | 45416 | 147 TGSGYGFTVPQGMRISLQCQAR-GSPPISYIWYKQQTNNQEP-------- |
| | 35638 | 137 PSCEVPSSALSGTVVELRCQDKEGNPAPEYTWFKDGIRLLEN-PRLGSQS |
| | JAM | 134 PTISVPSSVTIGNRAVLTCSEHDGSPPSEYSWFKDGISMLTADAKKTRAF |

| | | |
|---|---|---|
| | A33 | 186 ---PLAQPASGQPVSLKNISTDTSGYYICTSSNEEG------TQFCNITV |
| | 40628 | 184 SNSSYVLNPTTGELVFDPLSASDTGEYSCEARNGYG------TPMTSNAV |
| | 45416 | 188 -----IKVATLSTLLFKPAVIADSGSYFCTAKGQVGSEQHSDIVKFVVKD |
| | 35638 | 186 TNSSYTMNTKTGTLQFNTVSKLDTGEYSCEARNSVG------YRRCPGKR |
| | JAM | 184 MNSSFTIDPKSGDLIFDPVTAFDSGEYYCQAQNGYG------TAMRSEAA |

| | | |
|---|---|---|
| | A33 | 227 AVRSPSMNVALYVGIAVGVYAALIIIGIIIYCCCCRGKDDNTEDKEDA-- |
| | 40628 | 228 RMEAVERNVGVIVAAVLVTLILLGILVFGIWFAYSRGHFORTKKGTS--- |
| | 45416 | 233 SSKLLKTKTEAPTTMTYPLKATSTVKQSWDMTTDMDGYLGETSAGPGKSL |
| | 35638 | 230 -MQVDDLMISGIIAAVVYVALVISVCGLGVCYAQRKGYFSKETSFQKS-- |
| | JAM | 228 HMDAVELNVGGIVAAVLYTLILLGLLIFGVWFAYSRGYFETTKKGTAP-- |

| | | |
|---|---|---|
| | A33 | 275 -RPNREAYEEPPEQLRELSREREEEDDYRQEEQRSTGRESPDHLDQ |
| | 40628 | 275 -----------SKKVIYSQPSARSEGEFKQTSSFLV---------- |
| | 45416 | 283 PVFAIILIISLCCMVVFTMAYIMLCRKTSQQEHVYEAAR------- |
| | 35638 | 277 -NSSSKATTM-SENVQWLTPVIPALWKAAAGGSRGQEF-------- |
| | JAM | 276 -----------GKKVIYSQPSTRSEGEFKQTSSFLV---------- |

Figure 1

```
SEQ ID NO:1
Met Gly Thr Lys Ala Gln Val Glu Arg Lys Leu Leu Cys Leu Phe Ile Leu Ala Ile Leu Leu Cys Ser Leu Ala Leu Gly Ser Val Thr
1                   5                  10                  15                  20                  25                  30

Val His Ser Ser Glu Pro Glu Val Arg Ile Pro Glu Asn Asn Pro Val Lys Leu Ser Cys Ala Tyr Ser Gly Phe Ser Ser Pro Arg Val
                 35                  40                  45                  50                  55                  60

Glu Trp Lys Phe Asp Gln Gly Asp Thr Thr Arg Leu Val Cys Tyr Asn Asn Lys Ile Thr Ala Ser Tyr Glu Asp Arg Val Thr Phe Leu
                 65                  70                  75                  80                  85                  90

Pro Thr Gly Ile Thr Phe Lys Ser Val Thr Arg Gln Asp Thr Gly Thr Tyr Thr Cys Met Val Ser Glu Glu Gly Gly Asn Ser Tyr Gly
                 95                 100                 105                 110                 115                 120

Glu Val Lys Val Lys Leu Ile Val Leu Val Pro Pro Ser Lys Pro Thr Val Asn Ile Pro Ser Ser Ala Thr Ile Gly Asn Arg Ala Val
                125                 130                 135                 140                 145                 150

Leu Thr Cys Ser Glu Gln Asp Gly Ser Pro Pro Ser Glu Tyr Thr Trp Phe Lys Asp Gly Ile Val Met Pro Thr Asn Pro Lys Ser Thr
                155                 160                 165                 170                 175                 180

Arg Ala Phe Ser Asn Ser Ser Tyr Val Leu Asn Pro Thr Thr Gly Glu Leu Val Phe Asp Pro Leu Ser Ala Ser Asp Thr Gly Glu Tyr
                185                 190                 195                 200                 205                 210

Ser Cys Glu Ala Arg Asn Gly Tyr Gly Thr Pro Met Thr Ser Asn Ala Val Arg Met Glu Ala Val Glu Arg Asn Val Gly Val Ile Val
                215                 220                 225                 230                 235                 240

Ala Ala Val Leu Val Thr Leu Ile Leu Leu Gly Ile Leu Val Phe Gly Ile Trp Phe Ala Tyr Ser Arg Gly His Phe Asp Arg Thr Lys
                245                 250                 255                 260                 265                 270

Lys Gly Thr Ser Ser Lys Lys Val Ile Tyr Ser Gln Pro Ser Ala Arg Ser Glu Gly Glu Phe Lys Gln Thr Ser Ser Phe Leu Val
                275                 280                 285                 290                 295             299
```

Figure 2

SEQ ID NO:2

1   MGILLGLLLL GHLTVDTYGR PILEVPESVT GPWKGDVNLP CTYDPLQGYT QVLVKWLVQR GSDPVTIFLR DSSGDHIQQA KYQGRLHVSH KVPGDVSLQL
101 STLEMDDRSH YTCEVTWQTP DGNQVVRDKI TELRVQKLSV SKPTVTTG<u>SG YGFTVPQGMR</u> ISLQCQARGS PPISYIWYKQ QTNNQEPIKV ATLSTLLFKP
                                                      ^Glycosaminoglycan attachment site
201 AVIADSGSYF CTAKGQVGSE QHSDIVKFVV KDSSKLLKTK TEAPTTMTYP LKATSTVKQS WDWTTDMDGY LGETS<u>AGPGK SLPVFAIILI ISLCCMVVFT</u>
                                                                                      ^Transmembrane domain
301 <u>MAYIMLCRKT</u> SQQEHVYEAA R

Figure 3

DNA35936        (SEQ ID NO: 3)

```
CTTCTTGCCA ACTGGTATCA CCTTCAAGTC CGTGACACGG GAAGACACTG  50
GGACATACAC TTGTATGGTC TCTGAGGAAG GCGGCAACAG CTATGGGGAG 100
GTCAAGGTCA AGCTCATCGT GCTTGTGCCT CCATCCAAGC CTACAGTTAA 150
CATCCCCTCC TCTGCCACCA TTGGGAACCG GGCAGTGCTG ACATGCTCAG 200
AACAAGATGG TTCCCCACCT TCTGAATACA CCTGGTTCAA AGATGGGATA 250
GTGATGCCTA CGAATCCCAA AAGCACCCGT GCCTTCAGCA ACTCTTCCTA 300
TGTCCTGAAT CCCACAACAG GAGAGCTGGT CTTTGATCCC CTGTCAGCCT 350
CTGATACTGG AGAATACAGC TGTGAGGCAC GGAATGGGTA             390
```

Figure 4A consen01        (SEQ ID NO: 4)

```
TCTCAGTCCC CTCGCTGTAG TCGCGGAGCT GTGTTCTGTT TCCCAGGAGT  50
CCTTCGGCGG CTGTTGTGCT CAGGTGCGCC TGATCGCGAT GGGGACAAAG 100
GCGCAAGCTC GAGAGGAAAC TGTTGTGCCT CTTCATATTG GCGATCCTGT 150
TGTGCTCCCT GGCATTGGGC AGTGTTACAG TTGCACTCTT CTGAACCTGA 200
AGTCAGAATT CCTGAGAATA ATCCTGTGAA GTTGTCCTGT GCCTACTCGG 250
GCTTTTCTTC TCCCCGTGTG GAGTGGAAGT TTGACCAAGG AGACACCACC 300
AGACTCGTTT GCTATAATAA CAAGATCACA GCTTCCTATG AGGACCGGGT 350
GACCTTCTTG CCAACTGGTA TCACCTTCAA GTCCGTGACA CGGGAAGACA 400
CTGGGACATA CACTTGTATG GTCTCTGAGG AAGGCGGCAA CAGCTATGGG 450
GAGGTCAAGG TCAAGCTCAT CGTGCTTGTG CCTCCATCCA AGCCTACAGT 500
TAACATCCCC TCCTCTGCCA CCATTGGGAA CCGGGCAGTG CTGACATGCT 550
CAGAACAAGA TGGTTCCCCA CCTTCTGAAT ACACCTGGTT CAAAGATGGG 600
ATAGTGATGC CTACGAATCC CAAAAGCACC CGTGCCTTCA GCAACTCTTC 650
CTATGTCCTG AATCCCACAA CAGGAGAGCT GGTCTTTGAT CCCCTGTCAG 700
CCTCTGATAC TGGAGAATAC AGCTGT                           726
```

Figure 4B consen02 (SEQ ID NO:5)

```
GCAGGCAAAG TACCAGGGCC GCCTGCATGT GAGCCACAAG GTTCCAGGAG   50
ATGTATCCCT CCAATTGAGC ACCCTGGAGA TGGATGACCG GAGCCACTAC  100
ACGTGTGAAG TCACCTGGCA GACTCCTGAT GGCAACCAAG TCGTGAGAGA  150
TAAGATTACT GAGCTCCGTG TCCAGAAACT CTCTGTCTCC AAGCCCACAG  200
TGACAACTGG CAGCGGTTAT GGCTTCACGG TGCCCCAGGG AATGAGGATT  250
AGCCTTCAAT GCCAGGGTTC GGGGTTCTCC TCCCATCAGT TATATTTGGT  300
ATAAGCAACA GACTAATAAC CAGGGAACCC ATCAAAGTAG CAACCCTAAG  350
TACCTTACTC TTCAAGCCTG CGGTGATAGC CGACTCAGGC TCCTATTTCT  400
GCACTGCCAA GGGCCAGGTT GGCTCTGAGC AGCACAGCGA CATTGTGAAG  450
TTTGTGGTCA AAGACTCCTC AAAGCTACTC AAGACCAAGA CTGAGGCACC  500
TACAACCATG ACATACCCCT TGAAAGCAAC ATCTACAGTG AAGCAGTCCT  550
GGGACTGGAC CACTGACATG GATGGCTACC TTGGAGAGAC CAGTGCTGGG  600
CCAGGAAAGA GCCTGCCTGT CTTTGCCATC ATCCTCATCA TCTCCTTGTG  650
CTGTATGGTG GTTTTTACCA TGGCCTATAT CATGCTCTGT CGGAAGACAT  700
CCCAACAAGA GCATGTCTAC GAAGCAGCCA GGGCACATGC CAGAGAGGCC  750
AACGACTCTG AGAAACCAT GAGGGTGGCC ATCTTCGCAA GTGGCTGCTC  800
CAGTGATGAG CCAACTTCCC AGAATCTGGG GCAACAACTA CTCTGATGAG  850
CCCTGCATAG GACAGGAGTA CCAGATCATC GCCCAGATCA ATGGCAACTA  900
CGCCCGCCTG CTGGACACAG TTCCTCTGGA TTATGAGTTT CTGGCCACTG  950
AGGGCAAAAG TGTCTGTTAA AAATGCCCCA TTAGGCCAGG ATCTGCTGAC 1000
ATAATTGCCT AGTCAGTCCT TGCCTTCTGC ATGGCCTTCT TCCCTGCTAC 1050
CTCTCTTCCT GGATAGCCCA AAGTGTCCGC CTACCAACAC TGGAGCCGCT 1100
GGGAGTCACT GGCTTTGCCC TGGAATTTGC CAGATGCATC TCAAGTAAGC 1150
CAGCTGCTGG ATTTGGCTCT GGGCCTTCT AGTATCTCTG CCGGGGGCTT 1200
CTGGTACTCC TCTCTAAATA CCAGAGGGAA GATGCCCATA GCACTAGGAC 1250
TTGGTCATCA TGCCTACAGA CACTATTCAA CTTTGGCATC TTGCCACCAG 1300
AAGACCCGAG GGGAGGCTCA GCTCTGCCAG CTCAGAGGAC CAGCTATATC 1350
CAGGATCATT TCTCTTTCTT CAGGGCCAGA CAGCTTTTAA TTGAAATTGT 1400
TATTTCACAG GCCAGGGTTC AGTTCTGCTC CTCCACTATA AGTCTAATGT 1450
TCTGACTCTC TCCTGGTGCT CAATAAATAT CTAATCATAA CAGCAAAAAA 1500
AAA                                                   1503
```

Figure 4C

```
SEQ ID NO:11
GTCTGTTCCC AGGAGTCCTT CGGCGGCTGT TGTGTCAGTG GCCTGATCGC GATGGGGACA AAGGCGCAAG TCGAGAGGAA ACTGTTGTGC CTCTTCATAT 100
TGGCGATCCT GTTGTGCTCC CTGGCATTGG GCAGTGTTAC AGTGCACTCT TCTGAACCTG AAGTCAGAAT TCCTGAGAAT AATCCTGTGA AGTTGTCCTG 200
TGCCTACTCG GGCTTTTCTT CTCCCCGTGT GGAGTGGAAG TTTGACCAAG GAGACACCAC CAGACTCGTT TGCTATAATA ACAAGATCAC AGCTTCCTAT 300
GAGGACCGGG TGACCTTCTT GCCAACTGGT ATCACCTTCA AGTCCGTGAC ACGGGAAGAC ACTGGGACAT ACACTTGTAT GGTCTCTGAG GAAGGCGGCA 400
ACAGCTATGG GGAGGTCAAG GTCAAGCTCA TCGTGCTTGT GCCTCCATCC AAGCCTACAG TTAACATCCC CTCCCTCTGCC ACCATTGGGA ACCGGGCAGT 500
GCTGACATGC TCAGAACAAG ATGGTTCCCC ACCTTCTGAA TACACCTGGT TCAAAGATGG GATAGTGATG CCTACGAATC CCAAAAGCAC CCGTGCCTTC 600
AGCAACTCTT CCTATGTCCT GAATCCCACA ACAGGAGAGC TGGTCTTTGA TCCCCTGTCA GCCCTGTCAA CTGGAGAATA CAGCTGTGAG GCACGGAATG 700
GGTATGGGAC ACCCATGACT TCAAATGCTG TGCCGCATGGA AGCTGTGGAG CGGAATGTGG GGCATCATCG GCAGCCCGTC CTTGTAACCC TGATTCTCCT 800
GGGAATCTTG GTTTTTGGCA TCTGGTTTGC CTATAGCCGA ACCTCGTCAT TCCTGGTGTG GGCCACTTTG ACAGAACAAA GAAAGGGGACT TCGAGTAAGA AGGTGATTTA CAGCCAGCCT 900
AGTGCCCGAA GTGAAGGAGA ATTCAAACAG ACCTCGTAGTT TCCTGGTGTG GCTCACCGCC TATCATCTGC CCCTACTTCT TCGGATGTGT TTTTAATAAT 1000
ACCGGACTCT GGCCCCTGAT GTCTGTAGTT TCACAGGATG CCTTATTTGT CTTCTACACC CCACAGGGCC ACTCTCTTCT GTTTAAAGT GTTTATTCCC CATTTCTTTG 1200
GTCAGCTATG TGCCCCATCC TCCTTCATGC CCTTCCCTCC TTTCCTACCA CTGCTGAGTG GCCTGAACT CTGTTAAAGT ACAGCAAAAA TGGCGGGGGT TGCACTCAAC TGCCCACCTG 1300
AGGGATCAGG AAGGAATCCT GGGTATGCCA TTGACTTCCC TTCTAAGTAG TTCTAAGTAG GCCAGGAATC TGACGACCAG GGCCAGCTGT TCTAGAGCGG GAATTAGAGG 1400
GCTGGCAGGG ATCTTTGAAT AGGTATCTTG AGCTTGGTTC CCTTGTGTAC CCTTGTCTTT TGGGCTCTTT GACACCAGGG TCCTTCCATC TCTGGGGCCC ACTCTCTTCT GTCTTCCCAT GGGAAGTGCC ACTGGGATCC 1500
CTAGAGCGGC TGAAATGGTT GTTTGGTGAT GACACCAGGG TCCTTCCATC TCTGGGGCCC ACTCTCTTCT GTCTTCCCAT GGGAAGTGCC ACTGGGATCC 1500
CTCTGCCCTG TCCTCCTGAA TACAAGCTGA CTGTGTCTGT GGAAAATGGG AGCTCTTGT GTGGAGAGCA TAGTAAATTT TCAGAGAACT 1600
TGAAGCCAAA AGGATTTAAA ACCGCTGCTC TAAAGAAAAG GCTGGGCGCA CCTGTAATCC CAGAGGCTGA GGCAGGCGGA 1700
TCACCTGAGG TCGGGAGTTC GGGATCAGCC TGACCAACAT GGAGAAACCC TACTGAAAT ACAAAGTTAG CCAGGCATGG TGGTGCATGC CTGTAGTCCC 1800
AGCTGCTCAG GAGCCTGGCA ACAAGAGCAA AACTCCAGCT CA 1842
```

Figure 5

SEQ ID NO:7

```
  1 CCCACGCGTC CGCCACGCGG TCCGCCACAG GGTCCGCACG CCACCAGAAG TTTGAGCCTC TTTGGTAGCA GGAGGCTGGA AGAAAGGACA
    GGGTGCCGAG GCGGTGCGCG AGGCGGTGCC CCAGGCGGGT CGGTGTCTTC AAACTCGGAG AAACCATCGT CCTCCGACCT TCTTTCCTGT
101 GAAGTAGCTC TGGCTGTGAT CCGACACTA CTGGGCCTGC CTGGGATCTTA CTACTCCTGG GCACCTAACA GTGGACACTT ATGGCCCTCC CATCCTGAA GTGCCAGAGA
    CTTCATCGAG AGCCGACACT CCCCTAGAAT GACCCGGACG ATGAGGACCC CGTGGATTGT CACCTGTGAA TACCGGCAGG GTAGGACCTT CACGGTCTCT
  1                     M  G  I  L     L  G  L  L  L  G     I  L  F  P  W  K     M  A  L       I  L  E     V  P  E  S
                        *MET
                             SEQ ID NO:2
201 GTGTAACAGG ACCTTGGAAA GGGGATGTGA ATCTTCCCTG CACCTATGAC CCCCTGCAAG GCTACACCCA AGTCTTGGTG TACAACGTGG
    CACATTGTCC TGGAACCTTT CCCCTACACT TAGAAGGGAC GTGGATACTG GGGGACGTTC CGATGTGGGT TCAGAACCAC ATGTTGCACC
 29  V  T  G  P  W  K    G  D  V  N    L  P  C    T  Y  D    P  L  Q  G    Y  T  Q    V  L  V    Y  N  V
301 CTCAGACCCT GTCACCATCT TTCTACGTGA CTCTTCTGGA GACCATATCC AGCAGGCAAA GTACCAGGGC CGCCTGCATG TGAGCCACAA GGTTCCAGGA
    GAGTCTGGGA CAGTGGTAGA AAGATGCACT GAGAAGACCT CTGGTATAGG TCGTCCGTTT CATGGTCCCG GCGGACGTAC ACTCGGTGTT CCAAGGTCCT
 62  S  D  P  V  T  I    F  L  R  D    S  S  G    D  H  I  Q    Q  A  K    Y  Q  G    R  L  H  V    S  H  K    V  P  G
401 GATGTATCCC TCCAATTGAG CACCCTGGAG ATGGATGACC GGAGCCACTA GGAGCCACTG CACGTGTGAA GTCACCTGGC AGACTCCTGA GTCCTGAGAG
    CTACATAGGG AGGTTAACTC GTGGGACCTC TACCTACTGG CCTCGGTGAT GTGCACACTT CAGTGGACCG TCTGAGGACT CAGGACTCTC
 95  D  V  S  L    Q  L  S    T  L  E    M  D  D  R    S  H  Y    T  C  E    V  T  W  Q    T  P  D    G  N  Q    V  V  R  D
501 ATAAGATTAC TGAGCTCCGT GTCCAGAAAC TCTCTGTCTC CAAGCCCACA GTCCACCACT CAAGGTCGCTG GCAGCGGTTA TGGCTTCACG ACCGAAGTGC CACGGGGTCC GAATGAGGAT
    TATTCTAATG ACTCGAGGCA CAGGTCTTTG AGAGACAGAG GTTCGGGTGT CACTGTTGAC TCTGACCGAC CTGAGCGATG GACCAAGTGC GGCCCAGTCG CGCCCAGTCG CTTACTCCTA
129  K  I  T    E  L  R    V  Q  K  L    S  V  S    P  I  S    K  P  T    V  T  T  G    S  G  Y    G  F  T    V  P  Q  G    M  R  I
601 TAGCCCTTCAA TGCCAGGCTC GGGGTTCTCC TCCCATCAGT AGGTAGTCA ATATAAAACA TATTCGTTGT CTGATTATTG CAGGAACCA TCAAAGTAGC AACCCTAAGT
    ATCGGAAGTT ACGGTCCGAG CCCCAAGAGG AGGGTAGTCA ATATAAAACA TATTCGTTGT CTGATTATTG GTCCTTGGGT AGTTCATCG TTGGGATTCA
162  S  L  Q    C  Q  A  R    G  S  P    P  I  S    Y  I  W  Y    K  Q  Q    T  N  N    Q  E  P  I    K  V  A    T  L  S
701 ACCTTACTCT TCAAGCCTGC GGTGATAGCC GACTCAGGCT CCTATTCTG GGATAAAGAC CACTGCCAAG GGCCAGGTTG GCTCTGAGCA GCACAGGAC ATTGTGAAGT
    TGGAATGAGA AGTTCGGACG CCACTAGTCGG CTGAGTCCGA GGATAAAGAC CTATTTCTG CACTGCCAAG GTGACGGTTC CGAGACTCGT CGTGTCCGTG TAACACTTCA
195  T  L  F    K  P  A    V  I  A    D  S  G  S    Y  F  C    T  A  K    G  Q  V  G    S  E  Q    H  S  D    I  V  K  F
801 TTGTGGTCAA AGACTCCTCA AGCTACTCA AGCTTCAGT TTCGATGAGT TCTGGTTCTG ACTCCGTGA CATACCCCTT GAAAGCAACA TCTACACTGA AGCAGTCCTG
    AACACCAGTT TCTGAGGAGT TCGAATGAGT TCGAACTCA AGCTACACGGG AGACTTGCCT CTATGGGGAA CTTGTTGT AGATGTCACT TCGTCAGGAC
229  V  V  K    D  S  S    K  L  L  K    T  K  T    E  A  P    T  T  M  T    Y  P  L    K  A  T    S  T  V  K    Q  S  W
```

Figure 6A

```
SEQ ID NO:7   901 GGACTGGACC ACTGACATGG ATGGTACCT TGGAGAGACC TTTGCCATCA TCCTCATCAT CTCCTCTGTC
                  CCTGACCTG TGACTGTACC TACCGATGGA ACCTCTCTGG TCACGACCCG GTCCTTCTC GGACGACAG CCTGCCTGTC  AAACGTAGT AGGAGTAGTA GAGGAACACG
SEQ ID NO:2   262  D  W  T   T  D  M  D   G  Y  L    G  E  T    S  A  G  P    G  K  S    L  P  V    F  A  I  I    L  I  I    S  L  C

1001 TGTATGGTGG TTTTTACCAT GGCCTATATC ATGCTCTGTC GAAGACATC CCAACAAGAG CATGTCTACG AAGCAGCCAG GTAAGAAGT CTCTCCTCTT
                  ACATACCACC AAAAATGGTA CCGGATATAG TACGAGACAG CCTTCTGTAG GGTTGTTCTC GTACAGATGC TTCGTCGGTC CATTCTTTCA GAGAGGAGAA
              295  C  M  V  V   F  T  M   A  Y  I    M  L  C  R    K  T  S    Q  Q  E    H  V  Y  E    A  A  R    *

1101 CCATTTTGA CCCCGTCCCT TGGGCTCTCT GCAGGAAATG TGAGGAAGG ACCTCCTTCC ACAGACCCA GGGGTGTGGC TCCTAAGGCC GGAGGCCTTC
                  GGTAAAACT GGGGCAGGA ACCGAGTTAA CGTCCTTTAC ACTCCTTCC TGGAGGAAGG TGTCTGGGTT CCCCACACCG AGGATTCCGG CCTCCGAAG

1201 AGGGTCAGGA CATAGCTGCC TTCCCTCTCT CTGAGGTTGT TTTGGCCCTC TGAACACAAA GGATAATTTA GATCCATCTG CCTTCTGCTT
                  TCCCAGTCCT GTATCGACGG AAGGGAGAGA GACTCCAACA AAACGGGAG ACTTGTCTTT CCTATTAAAT CTAGGTAGAC GGAAGACGAA

1301 CCAGAATCCC TGGGTGGTAG GATCCTGATA ATTAATTGGC AAGAATTGAG GCAGAAGGGT GGGAAACCAG GACCACAGCC CCAAGTCCCT TCTTATGGT
                  GGTCTTAGGG ACCCACCATC CTAGGACTAT TAATTAACCG TTCTTAACTC CGTCTTCCCA CCCTTTGGTC CTGGTGTCGG GGTTCAGGGA AGAATACCCA

1401 GCTGGGCTCT TGGGCCATAG GGCACATGCC AGAGAACTGG ACGACTCTGG TCTTCGCAAG AGGTGGCCA TCTTCGCAAG AGGACGTTC AGTGATGAGC
                  CCACCCGAGA ACCCGGTATC CCGTGTACGG TCTCTCCGAC TGCTGAGACC CCTGTGCCGGT TCCACCGGT AGAAGCGTTC ACCGACGAGG TCACTACTCG

1501 CAACTTCCCA GAATCTGGGC AACAACTACT CTGATGAGCC CTGATAGGA ATCATCGG AGATCATCGC CCAGATCAAT GGCAACTACG CCCGCCTGCT
                  GTTGAAGGGT CTTAGACCCG TTGTTGATGA GACTACTCGG GACTATCCGG GTCTAGTTA TCTAGTAGCG GGTCTAGTTA CCGTTGATGC GGGGGACGA

1601 GGACACAGTT CCTCTGGATT ATGAGTTTCT GGCCACTGAG GGCAAAAGTG TCTGTTAAAA ATGCCCCATT AGGCCAGGAT CTGCTGACAT AATTGCCTAG
                  CCTGTGTCAA GGAGACCTAA TACTCAAAGA CCGGTGACTC CCGTTTTCAC AGACAATTTT TACGGGGTAA TCCGGTCCTA GACGACTGTA TTAACGGATC

1701 TCAGTCCTTG CCTTCTGCAT GGCCTTCCTC CCTGCTACCT ATACCCAAA GTGTCCCCCT ACCAACACTG GAGCCGCTGG GGGGCGTTCT GGTACTCCTC
                  AGTCAGGAAC GGAAGACGTA CCGGAAGAAC GGACGATGGA TATGGGTTT CACAGGCGGA TGGTTGTGAC CTCGGCGACC CCCCGAAGA CCATGAGGAG

1801 CTTTGCCCTG GAATTTGCCA GATGCATCTC AAGTAAGGCA GCTGCTGGAT AAGTAAGGCA TTGGCTCTGG GCCCTTCTAG TATCTCTGCC GGTACTCTT
                  GAAACGGGAC CTTAAACGGT CTACCGTAGG TTCATTCCGT CGACGACTTA TTCATTCCGT AACCGAGACC ATAGACGGG CCCCGAAGA CCATGAGGAG

1901 TCTAAATACC AGAGGGAAGA CTGCCAGCTC AGAGGACGAA TGCCCATAGA GATCATTCT CTTTCTTCAG GCCCAGACAG CTATTCAACT TGGCATCTT
                  AGATTTATGG TCTCCCTTCT GACGGTCGAG TCTCCTGCTT ACGGGTATCT CTAGTAAGA GAAAGAAGTC CGGTCTGTC GATAAGTTGA AACCGTAGAA

2001 AGGCTCAGTC CTGCCAGCTC AGAGGACGAA TGCCCATAGA GATCATTCAG GCCCAGACAG CCGGTCTGTC GAAAATTAAC TTTAACAATA AAGTGTCCGG
                  TCCGAGTCGA GACGGTCGAG TCTCCTGCTT ACGGGTAT CT CTAGTAAGA GAAAGAAGTC CGGTCTGTC GATAAGTTGA AACCGTAGAA

2101 AGGGTTCAGT TCTGCTCCTC TCTGCTCCTC GACTCTCTCC TGGTGCTCAA GGCCAGACAG CCGGTCTGTC TAAATATCTA ATCATAACAG C
                  TCCCAAGTCA AGACGAGGAG GACGAGGAG CTGAGAGAGG ACCACGAGTT GGCCAGACAG CCGGTCTGTC ATTTATAGAT TAGTATTGTC G
```

Figure 6B

SEQ ID NO:8

```
CCCAGAAGTTCAAGGGCCCCCGGCCTCCTGCGCTCCTGCCGCCGGGACCCTCGACCTCCT
CAGAGCAGCCGGCTGCCGCCCCGGGAAGATGGCGAGCAGGAGCCGCCACCGCCTCCTCCT
GCTGCTGCTGCGCTACCTGGTGGTCGCCCTGGGCTATCATAAGGCCTATGGGTTTTCTGC
CCCAAAAGACCAACAAGTAGTCACAGCAGTAGAGTACCAAGAGGCTATTTTAGCCTGCAA
AACCCCAAAGAAGACTGTTTCCTCCAGATTAGAGTGGAAGAAACTGGGTCGGAGTGTCTC
CTTTGTCTACTATCAACAGACTCTTCAAGGTGATTTTAAAAATCGAGCTGAGATGATAGA
TTTCAATATCCGGATCAAAAATGTGACAAGAAGTGATGCGGGGAAATATCGTTGTGAAGT
TAGTGCCCCATCTGAGCAAGGCCAAAACCTGGAAGAGGATACAGTCACTCTGGAAGTATT
AGTGGCTCCAGCAGTTCCATCATGTGAAGTACCCTCTTCTGCTCTGAGTGGAACTGTGGT
AGAGCTACGATGTCAAGACAAAGAAGGGAATCCAGCTCCTGAATACACATGGTTTAAGGA
TGGCATCCGTTTGCTAGAAAATCCCAGACTTGGCTCCCAAAGCACCAACAGCTCATACAC
AATGAATACAAAAACTGGAACTCTGCAATTTAATACTGTTTCCAAACTGGACACTGGAGA
ATATTCCTGTGAAGCCCGCAATTCTGTTGGATATCGCAGGTGTCCTGGGAAACGAATGCA
AGTAGATGATCTCAACATAAGTGGCATCATAGCAGCCGTAGTAGTTGTGGCCTTAGTGAT
TTCCGTTTGTGGCCTTGGTGTATGCTATGCTCAGAGGAAAGGCTACTTTTCAAAAGAAAC
CTCCTTCCAGAAGAGTAATTCTTCATCTAAAGCCACGACAATGAGTGAAAATGTGCAGTG
GCTCACGCCTGTAATCCCAGCACTTTGGAAGGCCGCGGCGGGCGGATCACGAGGTCAGGA
GTTCTAGACCAGTCTGGCCAATATGGTGAAACCCCATCTCTACTAAAATACAAAAATTAG
CTGGGCATGGTGGCATGTGCCTGCAGTTCCAGCTGCTTGGGAGACAGGAGAATCACTTGA
ACCCGGGAGGCGGAGGTTGCAGTGAGCTGAGATCACGCCACTGCAGTCCAGCCTGGGTAA
CAGAGCAAGATTCCATCTCAAAAAATAAAATAAATAAATAAATACTGGTTTTTACC
TGTAGAATTCTTACAATAAATATAGCTTGATATTC
```

Figure 7

OLI2162 (35936.f1)
SEQ ID NO:12

TCGCGGAGCTGTGTTCTGTTTCCC

OLI2163 (35936.p1)
SEQ ID NO:13

TGATCGCGATGGGGACAAAGGCGCAAGCTCGAGAGGAAACTGTTGTGCCT

OLI2164 (35936.f2)
SEQ ID NO:14

ACACCTGGTTCAAAGATGGG

OLI2165 (35936.r1)
SEQ ID NO:15

TAGGAAGAGTTGCTGAAGGCACGG

OLI2166 (35936.f3)
SEQ ID NO:16

TTGCCTTACTCAGGTGCTAC

OLI2167 (35936.r2)
SEQ ID NO:17

ACTCAGCAGTGGTAGGAAAG

Figure 8

```
SEQ ID NO:5
   1 GCAGGCAAAG TACCAGGGCC GCCTGCATGT GAGCCACAAG GTTCCAGGAG ATGTATCCCT CCAATTGAGC ACCCTGGAGA TGGATGACCG GAGCCACTAC
     CGTCCGTTTC ATGGTCCCGG CGGACGTACA CTCGGTGTTC CAAGGTCCTC TACATAGGGA GGTTAACTCG TGGGACCTCT ACCTACTGGC CTCGGTGATG
                                                                                         ^42257.p1 SEQ ID NO:22
 101 ACGTGTGAAG TCACCTGGCA GACTCCTGAT GGCAACCAAG TCGTGAGAGA TAAGATTACT GAGCTCCGTG TCCAGAAACT CTCTGTCTCC AAGCCCACAG
     TGCACACTTC AGTGGACCGT CTGAGGACTA CCGTTGGTTC AGCACTCTCT ATTCTAATGA CTCGAGGCAC AGTTCTTGA GAGACAGAGG TTCGGGTGTC
 201 TGACAACTGG CACGGGTTAT GGCTTCACGG TGCCCCAGGG ACGGGGTCCC AATGAGGATT AGCCTTCAAT GCCAGGGTTC GGGGTTCTCT TCCCATCAGT TATATTTGGT
     ACTGTTGACC GTGCCCAATA CCGAAGTGCC ACGGGGTCCC TTACTCCTAA TCGGAAGTTA CGGTCCCAAG CCCCAAGTAG AGGTAGTCA ATATAAACCA
 301 ATAAGCAACA GACTAATAAC CAGGGAACCC CAACCCTAAG TACCTTACTC TTCAAGCCTG CGGTGATAGC CGACTCAGGC TCCTATTTCT
     TATTCGTTGT CTGATTATTG GTCCCTTGGG GTTGGGATTC ATGGAATGAG AAGTTCGGAC GCCACTATCG GCTGAGTCCG AGGATAAGA
 401 GCACTGCCAA GGGCCAGGTT GGCTCTGAGC AGCACAGCGA TTTGTGAAG AAGACTCCTC AAAGCTACTC AAGACCAAGA CTGAGGCACC
     CGTGACGGTT CCCGGTCCAA CCGAGACTCG TCGTGTCGCT AAACACCAGT TCTGAGGAG TTTCGATGAG TTCTGGTTCT GACTCCGTGG
                                                 ^42257.r1 SEQ ID NO:20
 501 TACAACCATG ACATACCCCT TGAAAGCAAC ATCTACAGTG GGGACTGGAC CACTGACATG GATGGCTACC TTGGAGAGAC CAGTGCTGGG
     ATGTTGGTAC TGTATGGGGA ACTTTCGTTG TAGATGTCAC TCCTCAGGA CCCTGACCTG GTGACTGTAC CTACCGATGG AACCTCTCTG GTCACGACCC
 601 CCAGGAAAGA GCCTGCTGT CTTTGCCATC ATCCTCCATCA TCTCCTTGTG CTGTATGGTG GTTTTTACCA TGGCCTATAT CATGCTCTCT CGGAAGACAT
     GGTCCTTTCT CGGACGGACA GAAACGGTAG TAGGAGTAGT AGAGGAACAC GACATACCAC CAAAAATGGT ACCGGATATA GTACGAGACA GCCTTCTGTA
                                                                                         ^42257.f2 SEQ ID NO:19
 701 CCCAACAAGA GCATGTCTAC GAAGCAGGCA GGGCACATGC CAGAGAGGCC AACGACTCTG GAGAAACCAT GACGGTGCCC ATCTTCGCAA GTGGCTGCTC
     GGGTTGTTCT CGTACAGATG CTTCGTCCGT CCCGTGTACG GGTCTCTCCGG TTGCTGAGAC CTCTTTGGTA CTCCCACCGG TAGAAGCGTT CACCGACGAG
 801 CAGTGATGAG CCAACTTCCC AGAATCTGGG GCAACAACTA CCCTGATGAG GACAGGAGTA CCAGATCATC GCCCAGATCA ATGCCAACTA
     GTCACTACTC GGTTGAAGGG TCTTAGACCT CGTTGTTGAT GGGACTACTC CTGTCCTCAT GGTCTAGTAG CGGGTCTAGT TACCGTTGAT
 901 CGCCCGCCTG CTGGACACAG TTCCTCTGGA TGTCTGTTAA AATGCCCCA TGTCTGTTAA AGGCAAAG TGTCTGTTAA TTAGGCCAGG ATCTGCTGAC
     GCGGGCGGAC GACCTGTGTC AAGGAGACCT AACACAATT TTACGGGGT TCCCGTTTTC ACACAAAAT AATCCGGTCC TAGACGACTG
1001 ATAATTGCCT AGTCAGTCCT TGCCTTCTGC ATGGCCTTCT TCCCTGCTAC CTCTCTTCCT GGATAGCCCA AAGTGTCCGC CTACCAACAC TGGAGCCGCT
     TATTAACGGA TCAGTCAGGA ACGGAAGACG TACCGGAAGA AGGGACGATG GAGAAGAAGGA CCTATCGGGT TTCACAGGCG GATGGTTGTG ACCTCGGCGA
```

Figure 9A

SEQ ID NO:5

1101 GGGAGTCACT GGCTTTGCCC TGGAATTTGC CAGATGCATC TCAAGTAAGC CAGCTGCTGG ATTTGGCTCT GGGCCCTTCT AGTATCTCTG CCGGGGCTT
     CCCTCAGTGA CCGAAACGGG ACCTTAAACG GTCTACGTAG AGTTCATTCG GTCGACGACC TAAACCGAGA CCCGGAAGA TCATAGAGAC GGCCCCCGAA
                                                                     ^42257.r2  SEQ ID NO:21

1201 CTGGTACTCC TCTCTAAATA CCAGAGGGAA GATGCCCATA GCACTAGGAC TTGGTCATCA TGCCTACAGA CACTATTCAA CTTTGGCATC TTGCCACCAG
     GACCATGAGG AGAGATTTAT GGTCTCCCTT CTACGGGTAT CGTGATCCTG AACCAGTAGT ACGGATGTCT GTGATAAGTT GAAACCGTAG AACGGTGGTC

1301 AAGACCCGAG GGGAGGCTCA GCTCTGCCAG CTCAGAGGAC CAGCTATATC CAGGATCATT TCTCTTTCTT CAGGGCCAGA CAGCTTTTAA TTGAAATTGT
     TTCTGGGCTC CCCTCCGAGT CGAGACGGTC GAGTCTCCTG GTCGATATAG GTCCTAGTAA AGAGAAAGAA GTCCCGGTCT GTCGAAAATT AACTTTAACA

1401 TATTTCACAG GCCAGGGTTC AGTTCTGCTC CTCCACTATA AGTCTAATGT TCCTGGTGCT CAATAAATAT CTAATCATAA CAGCAAAAAA
     ATAAAGTGTC CGGTCCCAAG TCAAGACGAG GAGGTGATAT TCAGATTACA AGACTGAGAG AGGACCACGA GTTATTTATA GATTAGTATT GTCGTTTTTT

1501 AAA
     TTT

Figure 9B

|                |                                    | Frame | Score | Match Pct |
|----------------|------------------------------------|-------|-------|-----------|
| A33_human      | A33 antigen precursor - Homo sapiens | +1    | 246   | 81   30   |

A33_human - A33 antigen precursor - Homo sapiens (319 aa)
Score = 246 (86.6 bits), Expect = 2.8e-19, P = 2.8e-19
Identities = 81/268 (30%), Positives = 131/268 (48%), at 121,17, Frame = +1

```
DNA40628    121  LALGSVTVHSSEPEVRIPENNPVKLSCAYSGFSSPR---VEW-KFDQGDTTRLVC--YNN
SEQ ID NO:23          . ...*. . .   .*  .  * * * *   .* *   ..* *      * *.*    ..*
A33_human    17  VTVDAISVETPQDVLRASQGKSVTLPCTYHTSTSSREGLIQWDKLLLTHTERVVIWPFSN
SEQ ID NO:24

DNA40628    283  K--ITAS-YEDRVTFL------PTGITFKSVTREDTGTYTCMVS---EEGGNSYGEVKVK
                 *  *   *..**.          **   .* * *** * **     .  **.   .*.
A33_human    77  KNYIHGELYKNRVSISNNAEQSDASITIDQLTMADNGTYECSVSLMSDLEGNT--KSRVR DNA40628    427  LIVLVPPSKPTVNIPSSATIGNRAVLTCSEQDGSPPSEYTWFKDGIVMPTNPKSTRAFSN
                 *.********    *       *    *  ..***  .*.*..   *.      *
A33_human   135  LLVLVPPSKPECGIEGETIIGNNIQLTCQSKEGSPTPQYSWKRYNILNQEQP--------

DNA40628    607  SSYVLNPTTGELV-FDPLSASDTGEYSCEARNGYGTPMTSNAVRMEAVERNVGV---IVA
                  .  *.*. *    .*  .* * * * .  **    . *   **  .      *
A33_human   187  ----LAQPASGQPVSLKNISTDTSGYYICTSSNEEGTQFCNITVAVRSPSMNVALYVGIAV DNA40628    775  AVLVTLILLGILVFGIWFAYSRGHFDRT--KKGTSSKKVIYSQP
                 *. .....    **   * * *.       . * .*
A33_human   244  GVVAALIIIGIIIY---CCCCRGKDDNTEDKEDARPNREAYEEP
```

Figure 10A

Score = 245 (86.2 bits), Expect = 3.6e-19, P = 3.6e-19
Identities = 83/273 (30%), Positives = 131/273 (47%), at 112,12, Frame = +1

```
DNA40628    112 LCSL--ALGSVTVHSSEPEVRIPENNPVKLSCAYSGFSSPR---VEW-KFDQGDTTRLVC
SEQ ID NO:25    **..    ....*...  .*  .  ****   .* *   ..* *     * *.*
A33 human    12 LCAVRVTVDAISVETPQDVLRASQGKSVTLPCTYHTSTSSREGLIQWDKLLLTHTERVVI
SEQ ID NO:26

DNA40628    274 --YNNK--ITAS-YEDRVTFL------PTGITFKSVTREDTGTYTCMVSEEGGNSYGEVK
                ..**   *     *..**..         **  .* * *** * **     .  *   *
A33_human    72 WPFSNKNYIHGELYKNRVSISNNAEQSDASITIDQLTMADNGTYECSVSLMS-DLEGNTK DNA40628    421 --VKLIVLVPPSKPTVNIPSSATIGNRAVLTCSEQDGSPPSEYTWFKDGIVMPTNPKSTR
                 *.*.********  *   *   *  ..***  .*.*  .*.          *
A33_human   131 SRVRLLVLVPPSKPECGIEGETIIGNNIQLTCQSKEGSPTPQYSWKRYNILNQEQP----

DNA40628    595 AFSNSSYVLNPTTGELV-FDPLSASDTGEYSCEARNGYGTPMTSNAVRMEAVERNVGV--
                          . *.*.* .  .*  .* .****.*  **   .   *..    **  .
A33_human   187 -------LAQPASGQPVSLKNISTDTSGYYICTSSNEEGTQFCNITVAVRSPSMNVALYV DNA40628    766 -IVAAVLVTLILLGILVFGIWFAYSRGHFDRT--KKGTSSKKVIYSQP
                 *  *.  .....      **  * *.       . * .*
A33_human   240 GIAVGVVAALIIIGIIIY---CCCCRGKDDNTEDKEDARPNREAYEEP
```

Figure 10B

SEQ ID NO:9

MARRSRHRLLLLLLLRYLVVALGYHKAYGFSAPKDQQVVTAVEYQEAILACKTPKKTVSSR
LEWKKLGRSVSFVYYQQTLQGDFKNRAEMIDFNIRIKNVTRSDAGKYRCEVSAPSEQGQN
LEEDTVTLEVLVAPAVPSCEVPSSALSGTVVELRCQDKEGNPAPEYTWFKDGIRLLENPR
LGSQSTNSSYTMNTKTGTLQFNTVSKLDTGEYSCEARNSVGYRRCPGKRMQVDDLNISGI
IAAVVVVALVISVCGLGVCYAQRKGYFSKETSFQKSNSSSKATTMSENVQWLTPVIPALW
KAAAGGSRGQEF

SEQ ID NO:6 A33_hum    1 MVGKMWPYLWTLCAVRVTVDAISVETPQDVLRASQGKSVTLPCTYHTSTS
SEQ ID NO:2 45416      1 -MGILLGLLLLGHLTVDTYGRPILEVPESVTGPWKG-DVNLPCTYDPLQG A33_hum    51 SREGLIQWDKLLTHTERVIW-PFSNKNYIHGELYKNRVSISNNAEDSD
45416      49 YTQVLVKW--LVQRGSDPYTIFLRDSSGDHIQQAKYQGRLHVSHKV-PGD A33_hum   100 ASITIDQLTMADNGTYECSVS-LMSDLEGNTKSRV------RLLVLVPPS
45416      96 VSLQLSTLEMDDRSHYTCEVTWQTPDGNQVVRDKITELRVQKLSVSKPTV A33_hum   143 KPECGIEGETIIGNNIQLTCQSKEGSPTPQYSWKRYNILNQEQPLAQPAS
45416     146 TTGSGYGFTVPQGMRISLQCDAR-GSPPISYIW--YKQQTNNQEPIKVAT A33_hum   193 GQPVSLKNISTDTSGYYICTSSNEEGT-QFCNI-TVAVRSPSMNVALYVG
45416     193 LSTLLFKPAVIADSGSYFCTAKGQVGSEQHSDIVKFVVKDSSKLLKTKTE A33_hum   241 IAVGVVAALIIIGIIIYCCCCRGKDDNTEDKEDARPNREAYEEPPEQLRE
45416     243 APTTMTYPLKATSTVKQSWDWTTDMDGYLGETSAGPGKSLPVFAIILIIS A33_hum   291 LSREREEEDDVRQEEQRSTGRESPDHLDQ
45416     293 LCCMVVFTMAVIMLCRKTSQDEHVYEAAR

| | | |
|---|---|---|
| SEQ ID NO:10 | jam | 1 MGT EGKAG RKLL F L F T - S M I L G S L V Q G KGS V YTAQSD V QV PEN ES I KL T C |
| SEQ ID NO:1 | 40628 | 1 MGT KAQVE RKLL C L F I L A I L L C S L A L G S V T V HSSEPE V R I PEN N P V KL S C |

| | | |
|---|---|---|
| | jam | 50 T YSGFSSPRVEWK F V Q G S T T A LVCYN S Q I TA P Y A DRVTF SSS G ITF S S V T |
| | 40628 | 51 A YSGFSSPRVEWK F D Q G D T T R LVCYN N K I TA S Y E DRVTF L PT G ITF K S V T |

| | | |
|---|---|---|
| | jam | 100 R K D N G E YTCMVSEEGG Q N YGEV S I H L T VLVPPSKPT I S Y P S S V T IGNRAV |
| | 40628 | 101 R E D T G T YTCMVSEEGG N S YGEV K V K L I VLVPPSKPT V N I P S S A T IGNRAV |

| | | |
|---|---|---|
| | jam | 150 LTCSE H DGSPPSEY S WFKDGI S M L T A D A K K TRAF M NSS FTID P KS G D L I F |
| | 40628 | 151 LTCSE Q DGSPPSEY T WFKDGI - V M P T N P K S TRAF S NSS YVLN P TT G E L V F |

| | | |
|---|---|---|
| | jam | 200 D P V T A F D SGE V Y C Q A Q NGYGT A MR S E A A H M D AVE L NVG G IVAAVLVTLIL |
| | 40628 | 200 D P L S A S D T GE Y S C E A R NGYGT P M T S N A V R M E AVE R NVG V IVAAVLVTLIL |

| | | |
|---|---|---|
| | jam | 250 LG L L I FG V WFAYSRG Y F E T TKKGT A PG KKVIYSQPS T RSEGEFKQTSSFL |
| | 40628 | 250 LG I L V FG I WFAYSRG H F D R TKKGT - SS KKVIYSQPS A RSEGEFKQTSSFL |

| | | |
|---|---|---|
| | jam | 300 V |
| | 40628 | 299 V |

Figure 15

```
SEQ ID NO:10 jam    1 MGTEGKAGRKLLFLFTSMILGSL-VQGKG-SVYTAQSDVQVPENESIKLT
SEQ ID NO:2 45416   1 ----------MGILLGLLLLGHLTVDTYGRPILEVPESVTGPWKGDVNLP jam    49 CTYS---GFSSPRVEWKFVQGSTTALV----CYNSQI-TAPYADRVTFS-
45416  41 CTYDPLQGYTQVLVKWLVQRGSDPVTIFLRDSSGDHIQQAKYQGRLHVSH jam    90 ----SSGITFSSVTRKDNGEYTCMV---SEEGGQNYGEVSIHLTVL-VPP
45416  91 KVPGDYSLQLSTLEMDDRSHYTCEVTWQTPDGNQVVRDKITELRVQKLSV jam   132 SKPTISYPS----SVTIGNRAVLTCSEHDGSPPSEYSWFKDGISMLTADA
45416 141 SKPTVTTGSGYGFTVPQGMRISLQCQAR-GSPPISYIWYKQQTN--NQEP jam   178 KKTRAFMNSSFTIDPKSGDLIFDPVTAFDSGEYYCQAQNGYGTAMRSEAA
45416 188 IKVATL----------STLLFKPAVIADSGSYFCTAKGQVGSEQHSDIV jam   228 M---MDAVELNVGGIVAAVLVTLILLGLLIFG---VWFAYSRGYFETTKK
45416 227 KFVVKDSSKLLKTKTEAPTTMTYPLKATSTVKQSWDWTTDMDGYLGETSA jam   272 GTAPGKKVIYSQPSTRSEGEFKQTSSFLV
45416 277 GPGKSLPVFAIILIISLCCMVVFTMAYIMLCRKTSQQEHVYEAAR
```

Figure 16

```
SEQ ID NO:10  jam     1 MGTEGKAGRKLLFLFTSMILGSLVQGKGSVYTAQSDVQV---PENESIKL
SEQ ID NO:29  35638   1 --MARRSRHRLLLLLLRYLVVALGYHKAYGFSAPKDQQVVTAVEYQEAIL jam    48 TC-TYSGFSSPRVEWKFVQGSTTALVCYNSQITAPYADRVTFSSSGITFS
              35638  49 ACKTPKKTVSSRLEWKL-GRSVSFVYYQQTLQGDFKNRAEMIDFNIRIK jam    97 SVTRKDNGEYTCMVS--EEGGQNYGEVSIHLTVLVPPSKPTISVPSSVTI
              35638  98 NVTRSDAGKYRCEVSAPSEQGONLEEDTVTLEVLVAPAVPSCEVPSSALS jam   145 GNRAVLTCSEHDGSPPSEYSWFKDGISMLTADAKKTRAFMNSSFTIDPKS
              35638 148 GTVVELRCQDKEGNPAPEYTWFKDGIRLL-ENPRLGSQSTNSSYTMNTKT jam   195 GDLIFDPVTAFDSGEYCQAQNGYGTAMRSEAAHMDAVELNVGGIVAAVL
              35638 197 GTLQFNTVSKLDTGEYSCEARNSVG-YRRCPGKRMQVDDLNISGIIAAVV jam   245 VTLILLGLLIFGVWFAYSRGYFETTKKGTAPGKKVIYSQPSTRSEGEFKQ
              35638 246 VVALVISVCGLGVCYAQRKGYF---SKETSFQKSNSSSKATTMSENVQWL jam   295 TSSFLV
              35638 293 IPVIPALWKAAAGGSRGQEF
```

Figure 17

```
SEQ ID NO:6  A33_hum   1  ..... M V G K M W P V L W T . L C A V R V T V D A I S V E T P Q D V L R A S Q G K S V T L P C T
SEQ ID NO:10 jam       1  M G T E G K A G R K L L F L F T S M I L G S L V Q G K G S V Y T A Q S D V Q V P E N E S I K L T C T A33_hum  45  Y H T S T S S R E G L I Q W D K L L L T H T E R V V I W P F S N K N Y I H G E L Y K N R V S I S H N
             jam      51  Y S G F S S P R . . . V E W . K F V O G S T A L V C . . Y N S Q . . I T A P . Y A D R V T F S .

A33_hum  95  A E Q S D A S I T I D Q L T M A D N G T Y E C S V S L M S D L E G N T K S R V R L L V L V P P S K P
             jam      91  . . . . . S G I T F S S V T R K D N G E Y T C M V S E E G G . Q N Y G E V S I H L T V L V P P S K P A33_hum 145  E C G I E G E T I I G N N I Q L T C Q S K E G S P T P D Y S W K R Y N I L N Q E Q P L A Q P A S G Q
             jam     135  T I S V P S S V T I G N R A V L T C S E H D G S P P S E Y S W F K D G I S M L T A D A K K T R A F M A33_hum 195  P V S L K N I S T D T S G Y Y I C T S S N E E G T Q F C N . . . . I T V A V R S P S M N . . . V A L
             jam     185  N S S F T I D P K S G D L I F D P V T A F D S G E Y Y C Q A Q N G Y G T A M R S E A A H M D A V E L A33_hum 238  Y V . G I A V G V Y A A L I I G I I I Y C . . . C C C R G K D D N T E D K E D A R P N R E A Y E E
             jam     235  N V G G I V A A V L V T L I L L G L L I F G V W F A Y S R G Y F E . T T K K G T A P G K K V I Y S Q A33_hum 284  P P E Q L R E L S R E R E E E D D Y R Q E E Q R S T G R E S P D H L D Q
             jam     284  P S T R S E G E F K Q T S S F L V
```

Figure 18 cDNA hybridization of A33 homolog 40628 to human tissues

| Tissue | Expression |
|---|---|
| whole brain | + |
| amygdala | + |
| caudate nucleus | + |
| cerebellum | - |
| cerebral cortex | + |
| frontal lobe | + |
| hippocampus | + |
| medulla oblongata | + |
| occipital lobe | + |
| putamen | + |
| sustantia nigra | + |
| temporal lobe | + |
| thalamus | + |
| nucleus accumbeus | + |
| spinal cord | - |
| heart | ++ |
| aorta | + |
| skeletal muscle | + |
| colon | +++ |
| bladder | ++ |
| uterus | + |
| prostate | +++ |
| stomach | +++ |
| testis | ++ |
| ovary | +++ |
| pancreas | ++ |
| pituitary gland | ++ |
| adrenal gland | ++ |
| thyroid gland | ++ |
| salivary gland | +++ |
| mammary gland | ++ |
| kidney | +++ |
| liver | ++ |
| small intestine | ++ |
| spleen | ++ |
| thymus | ++ |
| peripheral leukocyte | + |
| lymph node | + |
| bone marrow | + |
| appendix | + |
| lung | ++++ |
| trachea | ++++ |
| placenta | ++++ |
| fetal brain | + |
| fetal heart | + |
| fetal kidney | ++ |
| fetal liver | +++ |
| fetal spleen | + |
| fetal lung | ++++ |

Figure 19

Elevated mRNA for Murine JAM in CRF2-4 -/- Colitic Mice as Compared to Wildtype Mice

Figure 22

1   MALRRPPRLRLCARLPDFFLLLFRGCLIGAVNLKSSNRTPVVQEFESVELSCIITDSQT
61  SDPRIEWKKIQDEQTTYVFEDNKIQGDLAGRAEIILGKTSLKIVVNVTRRDSALYRCEWAR
121 NDRKEIDEIVIELTVQVKPVTPVCRVPKAVPVGKMATLHCQESEGHPRPHYSWYRNDVPL
181 PTDSRANPRFRNSSFHLNSETGTLVFTAVHKDDSGQYYCIASNDAGSARCEEQEMEVYDL
241 NIGGIIGGVLVVLAVLALITLGICCAYRRGYFINNKQDGESYKNPGKPDGVNYIRTDEEG
301 DFRHKSSFVI

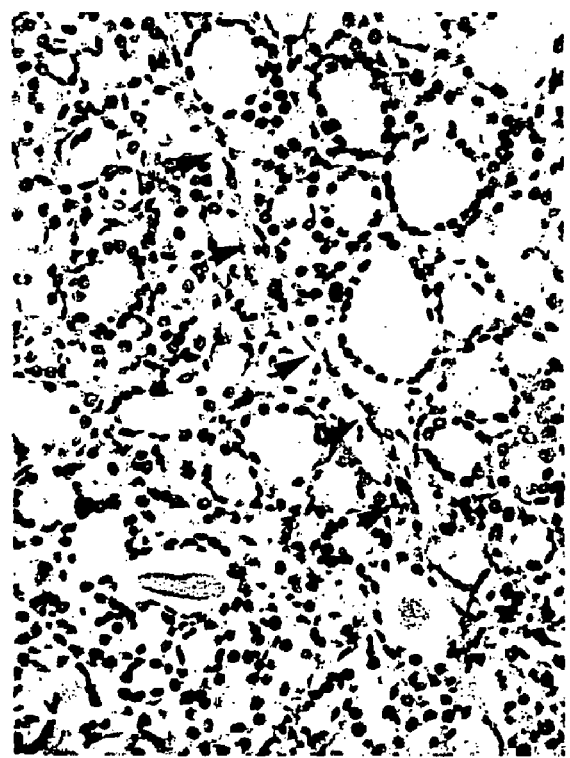
Figure 34

Figure 35
DUAL STIgMA-CD68 IHC
Adrenal gland macrophages
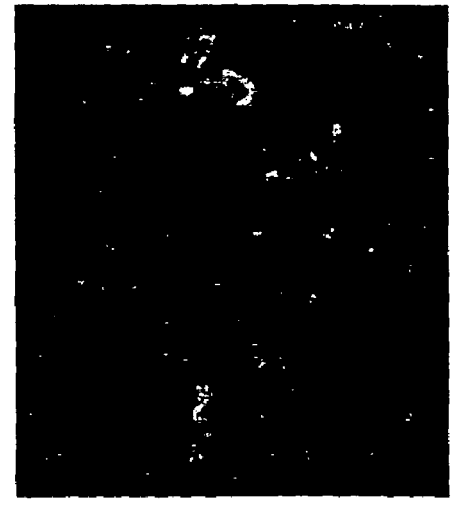
Adrenal-STIgMA
Adrenal-CD68
Adrenal-STIgMA/CD68

Figure 36
Liver Kupffer cells
Liver-CD68
Liver-STIgMA

Figure 38
Placental Hofbauer cells
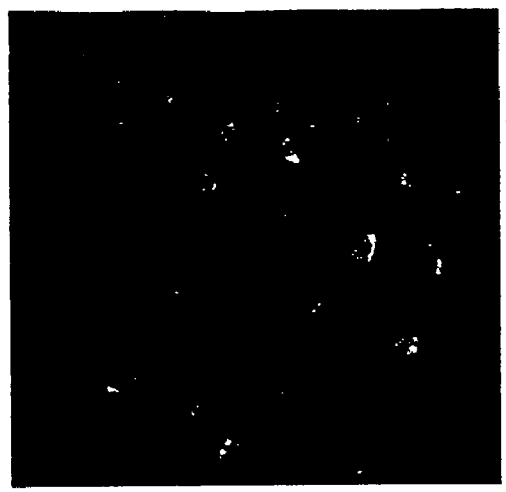
Placenta-STIgMA/CD68
Placenta-CD68
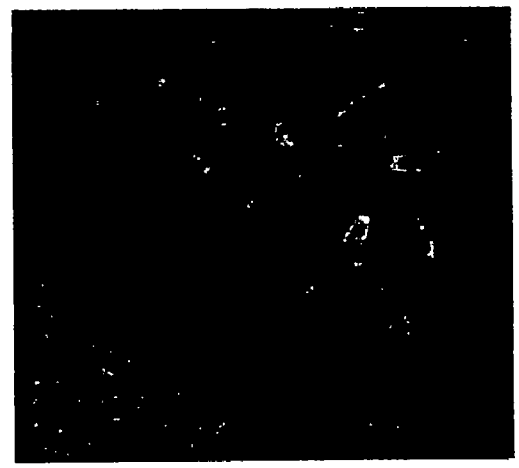
Placenta-STIgMA

Fig. 56

Murine STIgMA on X-chromosome
Human STIgMA on X-chromosome

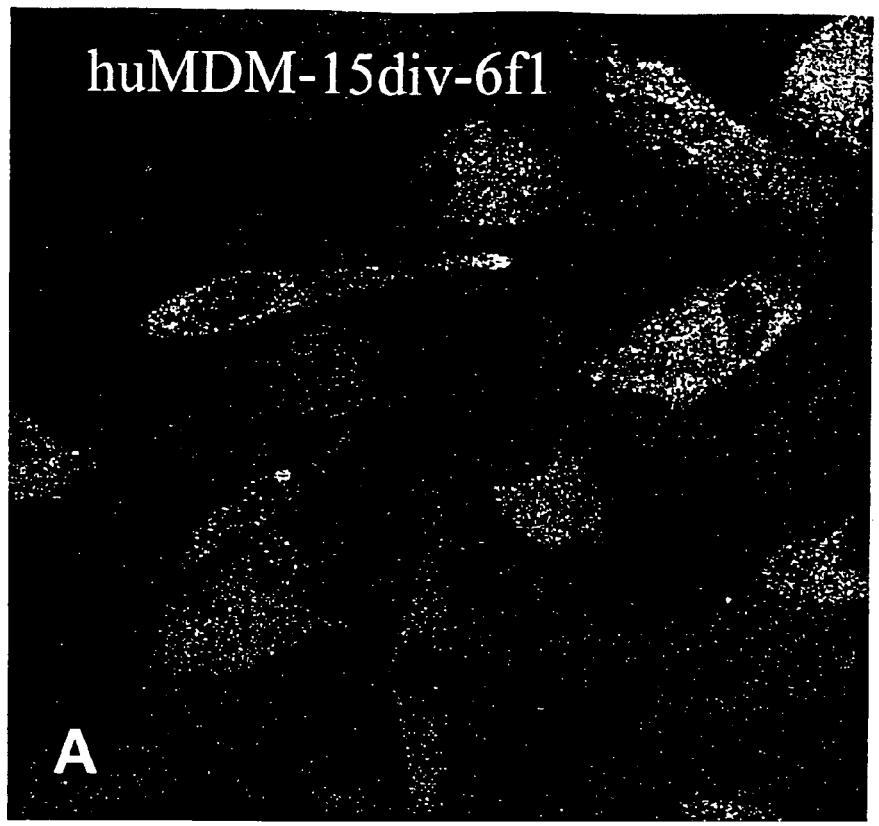
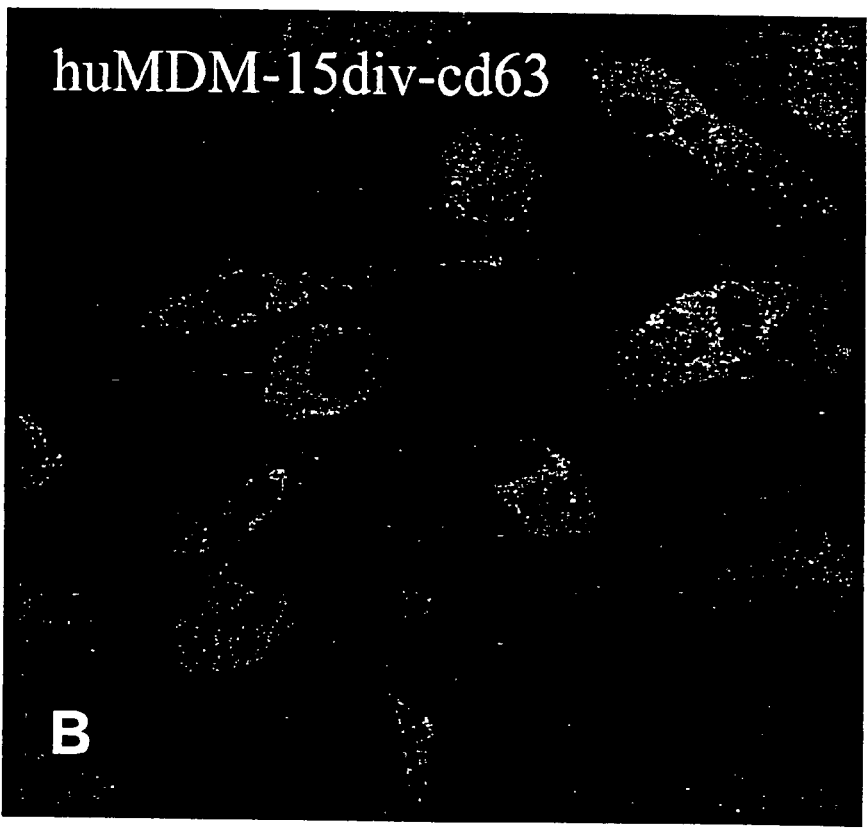
Fig.62

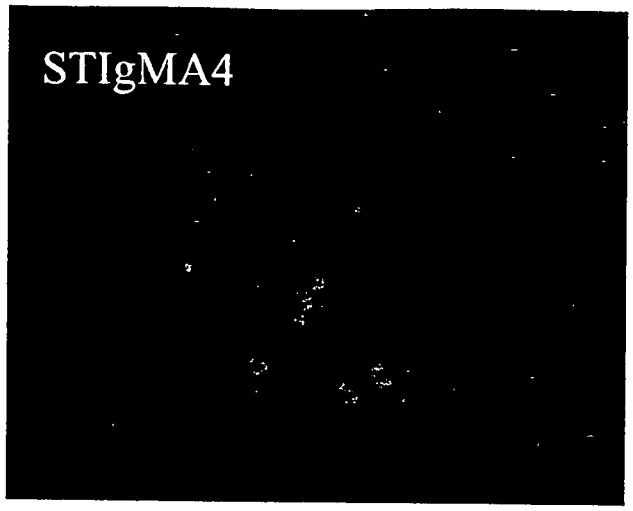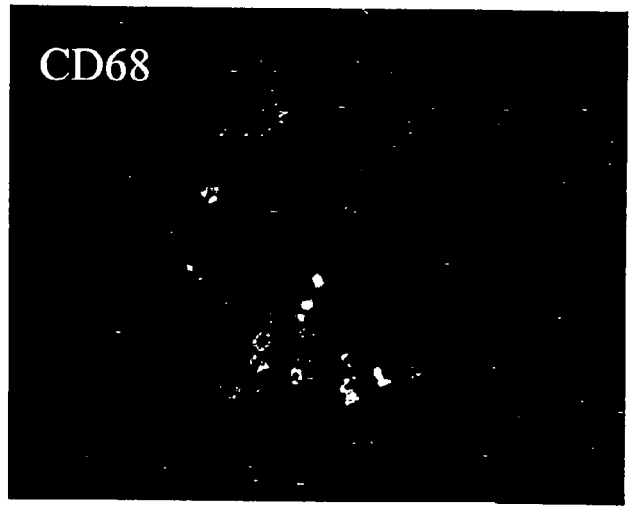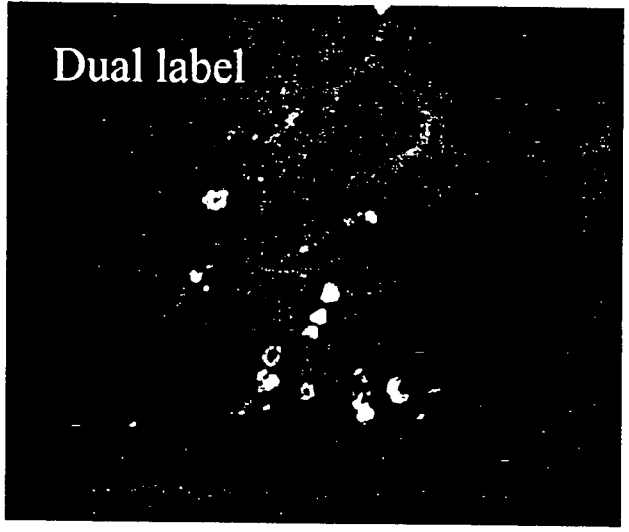
Fig. 68

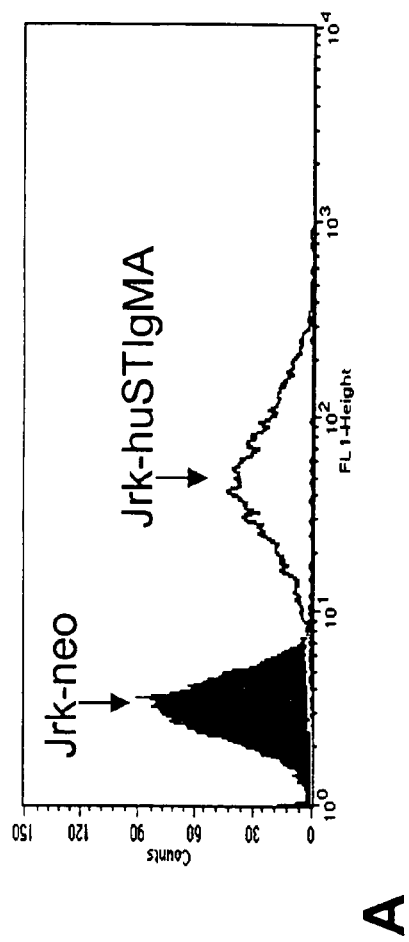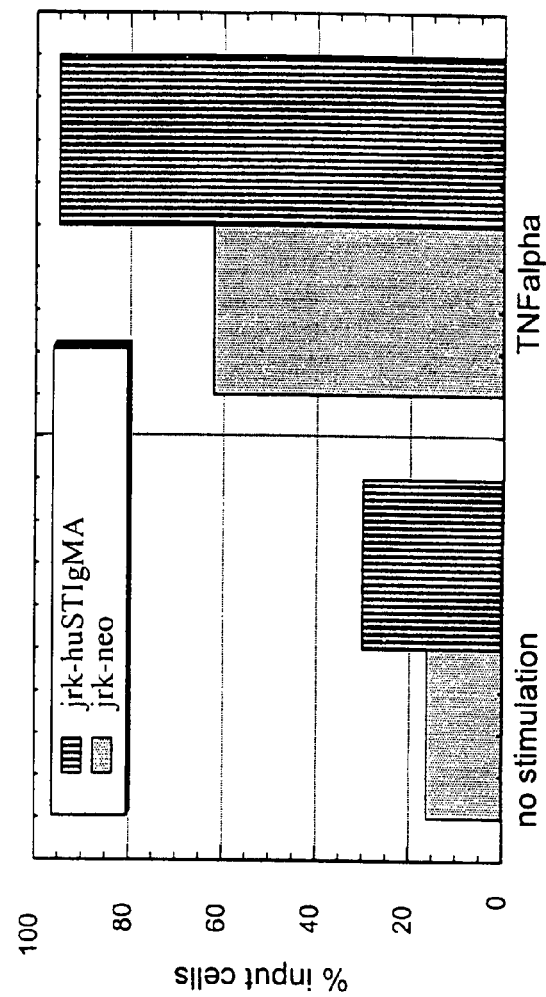
Fig 70

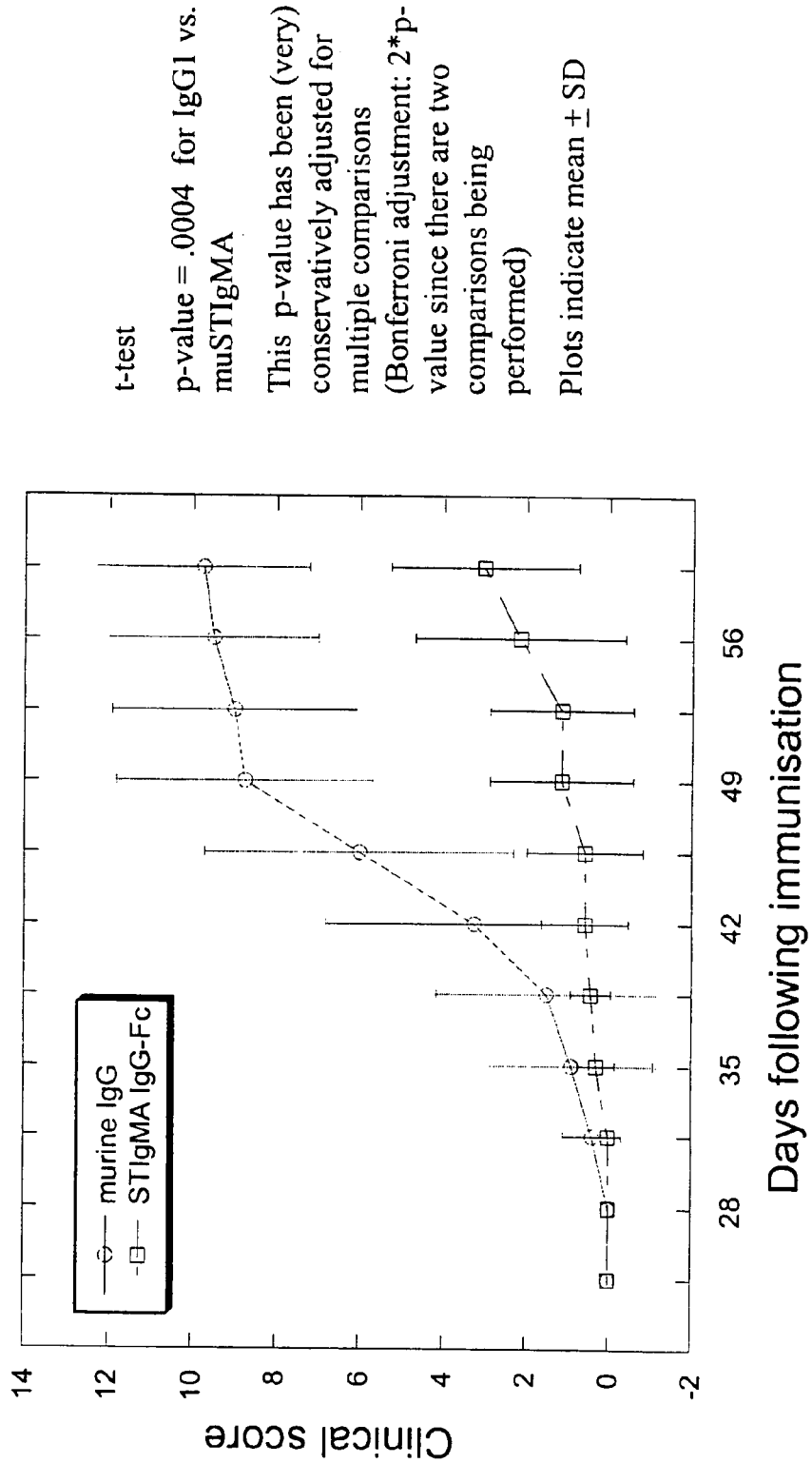
Figure 71: Effect of Systemic Injection of muSTIgMA-Fc on the Progression of CIA

SEQUENCE LISTING

<160> NUMBER OF SEQ ID NOS: 36

<210> SEQ ID NO 1
<211> LENGTH: 299
<212> TYPE: PRT

<213> ORGANISM: Homo sapiens

<400> SEQUENCE: 1

```
Met Gly Thr Lys Ala Gln Val Glu Arg Lys Leu Leu Cys Leu Phe Ile
 1               5                  10                  15
Leu Ala Ile Leu Leu Cys Ser Leu Ala Leu Gly Ser Val Thr Val His
                20                  25                  30
Ser Ser Glu Pro Glu Val Arg Ile Pro Glu Asn Asn Pro Val Lys Leu
            35                  40                  45
Ser Cys Ala Tyr Ser Gly Phe Ser Ser Pro Arg Val Glu Trp Lys Phe
        50                  55                  60
Asp Gln Gly Asp Thr Thr Arg Leu Val Cys Tyr Asn Asn Lys Ile Thr
65                  70                  75                  80
Ala Ser Tyr Glu Asp Arg Val Thr Phe Leu Pro Thr Gly Ile Thr Phe
                85                  90                  95
Lys Ser Val Thr Arg Glu Asp Thr Gly Thr Tyr Thr Cys Met Val Ser
            100                 105                 110
Glu Glu Gly Gly Asn Ser Tyr Gly Glu Val Lys Val Lys Leu Ile Val
        115                 120                 125
Leu Val Pro Pro Ser Lys Pro Thr Val Asn Ile Pro Ser Ser Ala Thr
130                 135                 140
Ile Gly Asn Arg Ala Val Leu Thr Cys Ser Glu Gln Asp Gly Ser Pro
145                 150                 155                 160
Pro Ser Glu Tyr Thr Trp Phe Lys Asp Gly Ile Val Met Pro Thr Asn
                165                 170                 175
Pro Lys Ser Thr Arg Ala Phe Ser Asn Ser Ser Tyr Val Leu Asn Pro
            180                 185                 190
Thr Thr Gly Glu Leu Val Phe Asp Pro Leu Ser Ala Ser Asp Thr Gly
        195                 200                 205
Glu Tyr Ser Cys Glu Ala Arg Asn Gly Tyr Gly Thr Pro Met Thr Ser
    210                 215                 220
Asn Ala Val Arg Met Glu Ala Val Glu Arg Asn Val Gly Val Ile Val
225                 230                 235                 240
Ala Ala Val Leu Val Thr Leu Ile Leu Leu Gly Ile Leu Val Phe Gly
                245                 250                 255
Ile Trp Phe Ala Tyr Ser Arg Gly His Phe Asp Arg Thr Lys Lys Gly
            260                 265                 270
Thr Ser Ser Lys Lys Val Ile Tyr Ser Gln Pro Ser Ala Arg Ser Glu
        275                 280                 285
Gly Glu Phe Lys Gln Thr Ser Ser Phe Leu Val
    290                 295
```

<210> SEQ ID NO 2
<211> LENGTH: 321
<212> TYPE: PRT
<213> ORGANISM: Homo sapiens

<400> SEQUENCE: 2

```
Met Gly Ile Leu Leu Gly Leu Leu Leu Leu Gly His Leu Thr Val Asp
 1               5                  10                  15
Thr Tyr Gly Arg Pro Ile Leu Glu Val Pro Glu Ser Val Thr Gly Pro
                20                  25                  30
Trp Lys Gly Asp Val Asn Leu Pro Cys Thr Tyr Asp Pro Leu Gln Gly
            35                  40                  45
Tyr Thr Gln Val Leu Val Lys Trp Leu Val Gln Arg Gly Ser Asp Pro
```

```
              50                  55                  60
Val Thr Ile Phe Leu Arg Asp Ser Ser Gly Asp His Ile Gln Gln Ala
 65                  70                  75                  80

Lys Tyr Gln Gly Arg Leu His Val Ser His Lys Val Pro Gly Asp Val
                 85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
130                 135                 140

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
        275                 280                 285

Leu Ile Ile Ser Leu Cys Cys Met Val Val Phe Thr Met Ala Tyr Ile
290                 295                 300

Met Leu Cys Arg Lys Thr Ser Gln Gln Glu His Val Tyr Glu Ala Ala
305                 310                 315                 320

Arg

<210> SEQ ID NO 3
<211> LENGTH: 390
<212> TYPE: DNA
<213> ORGANISM: Homo sapiens

<400> SEQUENCE: 3
cttcttgcca actggtatca ccttcaagtc cgtgacacgg aagacactg  ggacatacac      60 ttgtatggtc tctgaggaag gcggcaacag ctatggggag gtcaaggtca agctcatcgt     120
gcttgtgcct ccatccaagc ctacagttaa catcccctcc tctgccacca ttgggaaccg     180
ggcagtgctg acatgctcag aacaagatgg ttccccacct tctgaataca cctggttcaa     240
agatgggata gtgatgccta cgaatcccaa aagcaccgt gccttcagca actcttccta      300
tgtcctgaat ccacaacag gagagctggt ctttgatccc ctgtcagcct ctgatactgg      360
agaatacagc tgtgaggcac ggaatgggta                                      390

<210> SEQ ID NO 4
<211> LENGTH: 726
<212> TYPE: DNA
<213> ORGANISM: Homo sapiens
```

```
<220> FEATURE:
<223> OTHER INFORMATION: Homo sapiens

<400> SEQUENCE: 4
tctcagtccc ctcgctgtag tcgcggagct gtgttctgtt tcccaggagt ccttcggcgg      60
ctgttgtgct caggtgcgcc tgatcgcgat ggggacaaag gcgcaagctc gagaggaaac     120
tgttgtgcct cttcatattg gcgatcctgt tgtgctccct ggcattgggc agtgttacag     180
ttgcactctt ctgaacctga agtcagaatt cctgagaata atcctgtgaa gttgtcctgt     240
gcctactcgg gcttttcttc tccccgtgtg gagtggaagt tgaccaagg agacaccacc      300 agactcgttt gctataataa caagatcaca gcttcctatg aggaccgggt gaccttcttg     360
ccaactggta tcaccttcaa gtccgtgaca cgggaagaca ctgggacata cacttgtatg     420
gtctctgagg aaggcggcaa cagctatggg gaggtcaagg tcaagctcat cgtgcttgtg     480
cctccatcca agcctacagt taacatcccc tcctctgcca ccattgggaa ccgggcagtg     540
ctgacatgct cagaacaaga tggttcccca ccttctgaat acacctggtt caaagatggg     600
atagtgatgc ctacgaatcc caaaagcacc cgtgccttca gcaactcttc ctatgtcctg     660
aatcccacaa caggagagct ggtctttgat cccctgtcag cctctgatac tggagaatac     720
agctgt                                                                726

<210> SEQ ID NO 5
<211> LENGTH: 1503
<212> TYPE: DNA
<213> ORGANISM: Homo sapiens
<220> FEATURE:
<223> OTHER INFORMATION: Homo sapiens

<400> SEQUENCE: 5
gcaggcaaag taccagggcc gcctgcatgt gagccacaag gttccaggag atgtatccct      60
ccaattgagc accctggaga tggatgaccg gagccactac acgtgtgaag tcacctggca     120
gactcctgat ggcaaccaag tcgtgagaga taagattact gagctccgtg tccagaaact     180
ctctgtctcc aagcccacag tgacaactgg cagcggttat ggcttcacgg tgccccaggg     240
aatgaggatt agccttcaat gccagggttc ggggttctcc tcccatcagt tatatttggt     300
ataagcaaca gactaataac cagggaaccc atcaaagtag caaccctaag taccttactc     360
ttcaagcctg cggtgatagc cgactcaggc tcctatttct gcactgccaa gggccaggtt     420
ggctctgagc agcacagcga cattgtgaag tttgtggtca agactcctc aaagctactc     480 aagaccaaga ctgaggcacc tacaaccatg acataccct tgaaagcaac atctacagtg     540
aagcagtcct gggactggac cactgacatg gatggctacc ttggagagac cagtgctggg     600
ccaggaaaga gcctgcctgt ctttgccatc atcctcatca tctccttgtg ctgtatggtg     660 gttttttacca tggcctatat catgctctgt cggaagacat cccaacaaga gcatgtctac     720
gaagcagcca gggcacatgc cagagaggcc aacgactctg agaaaccat gagggtggcc     780 atcttcgcaa gtggctgctc cagtgatgag ccaacttccc agaatctggg gcaacaacta     840
ctctgatgag ccctgcatag acaggagta ccagatcatc gcccagatca atggcaacta     900
cgcccgcctg ctggacacag ttcctctgga ttatgagttt ctggccactg agggcaaaag     960
tgtctgttaa aaatgcccca ttaggccagg atctgctgac ataattgcct agtcagtcct    1020
tgccttctgc atggccttct tccctgctac ctctcttcct ggatagccca agtgtccgc     1080 ctaccaacac tggagccgct gggagtcact ggctttgccc tggaatttgc cagatgcatc    1140
```

-continued

```
tcaagtaagc cagctgctgg atttggctct gggcccttct agtatctctg ccggggggctt    1200 ctggtactcc tctctaaata ccagagggaa gatgcccata gcactaggac ttggtcatca    1260
tgcctacaga cactattcaa ctttggcatc ttgccaccag aagacccgag gggaggctca    1320
gctctgccag ctcagaggac cagctatatc caggatcatt tctctttctt cagggccaga    1380
cagcttttaa ttgaaattgt tatttcacag gccagggttc agttctgctc ctccactata    1440
agtctaatgt tctgactctc tcctggtgct caataaatat ctaatcataa cagcaaaaaa    1500
aaa                                                                   1503

<210> SEQ ID NO 6
<211> LENGTH: 319
<212> TYPE: PRT
<213> ORGANISM: Homo sapiens

<400> SEQUENCE: 6

Met Val Gly Lys Met Trp Pro Val Leu Trp Thr Leu Cys Ala Val Arg
 1               5                  10                  15

Val Thr Val Asp Ala Ile Ser Val Glu Thr Pro Gln Asp Val Leu Arg
            20                  25                  30

Ala Ser Gln Gly Lys Ser Val Thr Leu Pro Cys Thr Tyr His Thr Ser
        35                  40                  45

Thr Ser Ser Arg Glu Gly Leu Ile Gln Trp Asp Lys Leu Leu Leu Thr
    50                  55                  60

His Thr Glu Arg Val Val Ile Trp Pro Phe Ser Asn Lys Asn Tyr Ile
65                  70                  75                  80

His Gly Glu Leu Tyr Lys Asn Arg Val Ser Ile Ser Asn Asn Ala Glu
                85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
        115                 120                 125

Thr Lys Ser Arg Val Arg Leu Leu Val Leu Val Pro Pro Ser Lys Pro
    130                 135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190

Gly Gln Pro Val Ser Leu Lys Asn Ile Ser Thr Asp Thr Ser Gly Tyr
        195                 200                 205

Tyr Ile Cys Thr Ser Ser Asn Glu Glu Gly Thr Gln Phe Cys Asn Ile
    210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Ile Gly Ile Ile Ile
                245                 250                 255

Tyr Cys Cys Cys Cys Arg Gly Lys Asp Asp Asn Thr Glu Asp Lys Glu
            260                 265                 270

Asp Ala Arg Pro Asn Arg Glu Ala Tyr Glu Glu Pro Pro Glu Gln Leu
        275                 280                 285

Arg Glu Leu Ser Arg Glu Arg Glu Glu Asp Asp Tyr Arg Gln Glu
    290                 295                 300
```

-continued

Glu Gln Arg Ser Thr Gly Arg Glu Ser Pro Asp His Leu Asp Gln
305                 310                 315

<210> SEQ ID NO 7
<211> LENGTH: 2181
<212> TYPE: DNA
<213> ORGANISM: Homo sapiens

<400> SEQUENCE: 7

| | | | | | |
|---|---|---|---|---|---|
| cccacgcgtc | cgcccacgcg | tccgcccacg | ggtccgccca | cgcgtccggg | ccaccagaag | 60 |
| tttgagcctc | tttggtagca | ggaggctgga | agaaaggaca | gaagtagctc | tggctgtgat | 120 |
| ggggatctta | ctgggcctgc | tactcctggg | gcacctaaca | gtggacactt | atggccgtcc | 180 |
| catcctggaa | gtgccagaga | gtgtaacagg | accttggaaa | ggggatgtga | atcttccctg | 240 |
| cacctatgac | ccctgcaag | gctacaccca | agtcttggtg | aagtggctgg | tacaacgtgg | 300 |
| ctcagaccct | gtcaccatct | ttctacgtga | ctcttctgga | gaccatatcc | agcaggcaaa | 360 |
| gtaccagggc | cgcctgcatg | tgagccacaa | ggttccagga | gatgtatccc | tccaattgag | 420 |
| caccctggag | atgatgacc | ggagccacta | cacgtgtgaa | gtcacctggc | agactcctga | 480 |
| tggcaaccaa | gtcgtgagag | ataagattac | tgagctccgt | gtccagaaac | tctctgtctc | 540 |
| caagcccaca | gtgacaactg | gcagcggtta | tggcttcacg | gtgccccagg | gaatgaggat | 600 |
| tagccttcaa | tgccaggctc | ggggttctcc | tcccatcagt | tatatttggt | ataagcaaca | 660 |
| gactaataac | caggaaccca | tcaaagtagc | aaccctaagt | accttactct | tcaagcctgc | 720 |
| ggtgatagcc | gactcaggct | cctatttctg | cactgccaag | ggccaggttg | gctctgagca | 780 |
| gcacagcgac | attgtgaagt | ttgtggtcaa | agactcctca | aagctactca | agaccaagac | 840 |
| tgaggcacct | acaaccatga | catacccctt | gaaagcaaca | tctacagtga | agcagtcctg | 900 |
| ggactggacc | actgacatgg | atggctacct | tggagagacc | agtgctgggc | caggaaagag | 960 |
| cctgcctgtc | tttgccatca | tcctcatcat | tccttgtgc | tgtatggtgg | ttttaccat | 1020 |
| ggcctatatc | atgctctgtc | ggaagacatc | ccaacaagag | catgtctacg | aagcagccag | 1080 |
| gtaagaaagt | ctctcctctt | ccatttttga | ccccgtccct | gccctcaatt | ttgattactg | 1140 |
| gcaggaaatg | tggaggaagg | ggggtgtggc | acagacccaa | tcctaaggcc | ggaggccttc | 1200 |
| agggtcagga | catagctgcc | ttccctctct | caggcacctt | ctgaggttgt | tttggccctc | 1260 |
| tgaacacaaa | ggataattta | gatccatctg | ccttctgctt | ccagaatccc | tgggtggtag | 1320 |
| gatcctgata | attaattggc | aagaattgag | gcagaagggt | gggaaaccag | gaccacagcc | 1380 |
| ccaagtccct | tcttatgggt | ggtgggctct | tgggccatag | ggcacatgcc | agagaggcca | 1440 |
| acgactctgg | agaaaccatg | agggtggcca | tcttcgcaag | tggctgctcc | agtgatgagc | 1500 |
| caacttccca | gaatctgggc | aacaactact | ctgatgagcc | ctgcatagga | caggagtacc | 1560 |
| agatcatcgc | ccagatcaat | ggcaactacg | cccgcctgct | ggacacagtt | cctctggatt | 1620 |
| atgagtttct | ggccactgag | ggcaaaagtg | tctgttaaaa | atgccccatt | aggccaggat | 1680 |
| ctgctgacat | aattgcctag | tcagtccttg | ccttctgcat | ggccttcttc | cctgctacct | 1740 |
| ctcttcctgg | atagcccaaa | gtgtccgcct | accaacactg | gagccgctgg | gagtcactgg | 1800 |
| ctttgccctg | gaatttgcca | gatgcatctc | aagtaagcca | gctgctggat | ttggctctgg | 1860 |
| gcccttctag | tatctctgcc | ggggcttct | ggtactcctc | tctaaatacc | agagggaaga | 1920 |
| tgccctatagc | actaggactt | ggtcatcatg | cctacagaca | ctattcaact | ttggcatctt | 1980 |
| gccaccagaa | gacccgaggg | aggctcagct | ctgccagctc | agaggaccag | ctatatccag | 2040 |

-continued

```
gatcatttct ctttcttcag ggccagacag cttttaattg aaattgttat ttcacaggcc    2100
agggttcagt tctgctcctc cactataagt ctaatgttct gactctctcc tggtgctcaa    2160
taaatatcta atcataacag c                                              2181
```

<210> SEQ ID NO 8
<211> LENGTH: 1295
<212> TYPE: DNA
<213> ORGANISM: Homo sapiens

<400> SEQUENCE: 8

```
cccagaagtt caagggcccc cggcctcctg cgctcctgcc gccgggaccc tcgacctcct      60
cagagcagcc ggctgccgcc ccgggaagat ggcgaggagg agccgccacc gcctcctcct     120
gctgctgctg cgctacctgg tggtcgccct gggctatcat aaggcctatg gttttctgc     180 cccaaaagac caacaagtag tcacagcagt agagtaccaa gaggctattt tagcctgcaa     240
aaccccaaag aagactgttt cctccagatt agagtggaag aaactgggtc ggagtgtctc     300
ctttgtctac tatcaacaga ctcttcaagg tgattttaaa aatcgagctg agatgataga     360
tttcaatatc cggatcaaaa atgtgacaag aagtgatgcg gggaaatatc gttgtgaagt     420
tagtgcccca tctgagcaag gccaaaacct ggaagaggat acagtcactc tggaagtatt     480
agtggctcca gcagttccat catgtgaagt accctcttct gctctgagtg aactgtggt     540 agagctacga tgtcaagaca agaagggaa tccagctcct gaatacacat ggtttaagga     600
tggcatccgt ttgctagaaa atcccagact tggctcccaa agcaccaaca gctcatacac     660
aatgaataca aaaactggaa ctctgcaatt taatactgtt tccaaactgg acactggaga     720
atattcctgt gaagcccgca attctgttgg atatcgcagg tgtcctggga acgaatgca     780 agtagatgat ctcaacataa gtggcatcat agcagccgta gtagttgtgg ccttagtgat     840 ttccgttttgt ggccttggtg tatgctatgc tcagaggaaa ggctactttt caaaagaaac     900
ctccttccag aagagtaatt cttcatctaa agccacgaca atgagtgaaa atgtgcagtg     960
gctcacgcct gtaatcccag cactttggaa ggccgcggcg gcggatcac gaggtcagga    1020 gttctagacc agtctggcca atatggtgaa acccccatctc tactaaaata caaaaattag    1080
ctgggcatgg tggcatgtgc ctgcagttcc agctgcttgg gagacaggag aatcacttga    1140
acccgggagg cggaggttgc agtgagctga gatcacgcca ctgcagtcca gcctgggtaa    1200
cagagcaaga ttccatctca aaaaataaaa taaataaata aataaatact ggttttacc    1260 tgtagaattc ttacaataaa tatagcttga tattc                                 1295
```

<210> SEQ ID NO 9
<211> LENGTH: 312
<212> TYPE: PRT
<213> ORGANISM: Homo sapiens

<400> SEQUENCE: 9

```
Met Ala Arg Arg Ser Arg His Arg Leu Leu Leu Leu Leu Leu Arg Tyr
  1               5                  10                  15

Leu Val Val Ala Leu Gly Tyr His Lys Ala Tyr Gly Phe Ser Ala Pro
             20                  25                  30

Lys Asp Gln Gln Val Val Thr Ala Val Glu Tyr Gln Glu Ala Ile Leu
         35                  40                  45

Ala Cys Lys Thr Pro Lys Lys Thr Val Ser Ser Arg Leu Glu Trp Lys
     50                  55                  60

Lys Leu Gly Arg Ser Val Ser Phe Val Tyr Tyr Gln Gln Thr Leu Gln
```

```
              65                  70                  75                  80
Gly Asp Phe Lys Asn Arg Ala Glu Met Ile Asp Phe Asn Ile Arg Ile
                 85                  90                  95

Lys Asn Val Thr Arg Ser Asp Ala Gly Lys Tyr Arg Cys Glu Val Ser
                100                 105                 110

Ala Pro Ser Glu Gln Gly Gln Asn Leu Glu Glu Asp Thr Val Thr Leu
                115                 120                 125

Glu Val Leu Val Ala Pro Ala Val Pro Ser Cys Glu Val Pro Ser Ser
            130                 135                 140

Ala Leu Ser Gly Thr Val Val Glu Leu Arg Cys Gln Asp Lys Glu Gly
145                 150                 155                 160

Asn Pro Ala Pro Glu Tyr Thr Trp Phe Lys Asp Gly Ile Arg Leu Leu
                165                 170                 175

Glu Asn Pro Arg Leu Gly Ser Gln Ser Thr Asn Ser Ser Tyr Thr Met
                180                 185                 190

Asn Thr Lys Thr Gly Thr Leu Gln Phe Asn Thr Val Ser Lys Leu Asp
                195                 200                 205

Thr Gly Glu Tyr Ser Cys Glu Ala Arg Asn Ser Val Gly Tyr Arg Arg
            210                 215                 220

Cys Pro Gly Lys Arg Met Gln Val Asp Asp Leu Asn Ile Ser Gly Ile
225                 230                 235                 240

Ile Ala Ala Val Val Val Ala Leu Val Ile Ser Val Cys Gly Leu
                245                 250                 255

Gly Val Cys Tyr Ala Gln Arg Lys Gly Tyr Phe Ser Lys Glu Thr Ser
            260                 265                 270

Phe Gln Lys Ser Asn Ser Ser Ser Lys Ala Thr Thr Met Ser Glu Asn
                275                 280                 285

Val Gln Trp Leu Thr Pro Val Ile Pro Ala Leu Trp Lys Ala Ala Ala
            290                 295                 300

Gly Gly Ser Arg Gly Gln Glu Phe
305                 310

<210> SEQ ID NO 10
<211> LENGTH: 300
<212> TYPE: PRT
<213> ORGANISM: Mus musculus

<400> SEQUENCE: 10

Met Gly Thr Glu Gly Lys Ala Gly Arg Lys Leu Leu Phe Leu Phe Thr
  1               5                  10                  15

Ser Met Ile Leu Gly Ser Leu Val Gln Gly Lys Gly Ser Val Tyr Thr
                 20                  25                  30

Ala Gln Ser Asp Val Gln Val Pro Glu Asn Glu Ser Ile Lys Leu Thr
             35                  40                  45

Cys Thr Tyr Ser Gly Phe Ser Ser Pro Arg Val Glu Trp Lys Phe Val
         50                  55                  60

Gln Gly Ser Thr Thr Ala Leu Val Cys Tyr Asn Ser Gln Ile Thr Ala
65                  70                  75                  80

Pro Tyr Ala Asp Arg Val Thr Phe Ser Ser Ser Gly Ile Thr Phe Ser
                 85                  90                  95

Ser Val Thr Arg Lys Asp Asn Gly Glu Tyr Thr Cys Met Val Ser Glu
                100                 105                 110

Glu Gly Gly Gln Asn Tyr Gly Glu Val Ser Ile His Leu Thr Val Leu
            115                 120                 125
```

```
Val Pro Pro Ser Lys Pro Thr Ile Ser Val Pro Ser Ser Val Thr Ile
    130                 135                 140

Gly Asn Arg Ala Val Leu Thr Cys Ser Glu His Asp Gly Ser Pro Pro
145                 150                 155                 160

Ser Glu Tyr Ser Trp Phe Lys Asp Gly Ile Ser Met Leu Thr Ala Asp
                165                 170                 175

Ala Lys Lys Thr Arg Ala Phe Met Asn Ser Ser Phe Thr Ile Asp Pro
            180                 185                 190

Lys Ser Gly Asp Leu Ile Phe Asp Pro Val Thr Ala Phe Asp Ser Gly
        195                 200                 205

Glu Tyr Tyr Cys Gln Ala Gln Asn Gly Tyr Gly Thr Ala Met Arg Ser
    210                 215                 220

Glu Ala Ala His Met Asp Ala Val Glu Leu Asn Val Gly Gly Ile Val
225                 230                 235                 240

Ala Ala Val Leu Val Thr Leu Ile Leu Leu Gly Leu Leu Ile Phe Gly
                245                 250                 255

Val Trp Phe Ala Tyr Ser Arg Gly Tyr Phe Glu Thr Thr Lys Lys Gly
                260                 265                 270

Thr Ala Pro Gly Lys Lys Val Ile Tyr Ser Gln Pro Ser Thr Arg Ser
            275                 280                 285

Glu Gly Glu Phe Lys Gln Thr Ser Ser Phe Leu Val
    290                 295                 300

<210> SEQ ID NO 11
<211> LENGTH: 1842
<212> TYPE: DNA
<213> ORGANISM: Homo sapiens

<400> SEQUENCE: 11
gtctgttccc aggagtcctt cggcggctgt tgtgtcggga gcctgatcgc gatggggaca      60
aaggcgcaag tcgagaggaa actgttgtgc ctcttcatat ggcgatcct gttgtgctcc      120 ctggcattgg gcagtgttac agtgcactct tctgaacctg aagtcagaat tcctgagaat     180
aatcctgtga gttgtcctg tgcctactcg ggcttttctt ctccccgtgt ggagtggaag     240
tttgaccaag gagacaccac cagactcgtt tgctataata caagatcac agcttcctat     300 gaggaccggg tgaccttctt gccaactggt atcaccttca gtccgtgac acgggaagac     360 actgggacat acacttgtat ggtctctgag gaaggcggca cagctatgg ggaggtcaag     420 gtcaagctca tcgtgcttgt gcctccatcc aagcctacag ttaacatccc tcctctgcc     480 accattggga accgggcagt gctgacatgc tcagaacaag atggttcccc accttctgaa     540
tacacctggt tcaaagatgg gatagtgatg cctacgaatc ccaaaagcac ccgtgccttc     600
agcaactctt cctatgtcct gaatcccaca acaggagagc tggtctttga tcccctgtca     660
gcctctgata ctggagaata cagctgtgag gcacggaatg ggtatgggac accatgact     720 tcaaatgctg tgcgcatgga agctgtggag cggaatgtgg gggtcatcgt ggcagccgtc     780
cttgtaaccc tgattctcct gggaatcttg gttttggca tctggtttgc ctatagccga     840
ggccactttg acagaacaaa gaaagggact tcgagtaaga aggtgattta cagccagcct     900
agtgcccgaa gtgaaggaga attcaaacag acctcgtcat tcctggtgtg agcctggtcg     960
gctcaccgcc tatcatctgc atttgcctta ctcaggtgct actggactct ggcccctgat    1020
gtctgtagtt tcacaggatg ccttatttgt cttctacacc ccacagggcc cctacttct    1080 tcggatgtgt ttttaataat gtcagctatg tgccccatcc tccttcatgc cctccctccc    1140
```

-continued

```
tttcctacca ctgctgagtg gcctggaact tgtttaaagt gtttattccc catttctttg    1200
agggatcagg aaggaatcct gggtatgcca ttgacttccc ttctaagtag acagcaaaaa    1260
tggcgggggt cgcaggaatc tgcactcaac tgcccacctg ctggcaggg atctttgaat     1320 aggtatcttg agcttggttc tgggctcttt ccttgtgtac tgacgaccag ggccagctgt    1380
tctagagtgg gaattagagg ctagagcggc tgaaatggtt gtttggtgat gacactgggg    1440
tccttccatc tctggggccc actctcttct gtcttcccat gggaagtgcc actgggatcc    1500
ctctgccctg tcctcctgaa tacaagctga ctgacattga ctgtgtctgt ggaaaatggg    1560
agctcttgtt gtggagagca tagtaaattt tcagagaact tgaagcgaaa aggatttaaa    1620
accgctgctc taaagaaaag aaaactggag gctgggcgca gtggctcacg cctgtaatcc    1680
cagaggctga ggcaggcgga tcacctgagg tcgggagttc gggatcagcc tgaccaacat    1740
ggagaaaccc tgctggaaat acagagttag ccaggcatgg tggtgcatgc ctgtagtccc    1800
agctgctcag gagcctggca acaagagcaa aactccagct ca                      1842
```

```
<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucloetide probe

<400> SEQUENCE: 12
tcgcggagct gtgttctgtt tccc                                            24

<210> SEQ ID NO 13
<211> LENGTH: 50
<212> TYPE: DNA
<213> ORGANISM: Artificial Sequence
<220> FEATURE:
<223> OTHER INFORMATION: Synthetic oligonucloetide probe

<400> SEQUENCE: 13
tgatcgcgat ggggacaaag gcgcaagctc gagaggaaac tgttgtgcct                50

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucloetide probe

<400> SEQUENCE: 14
acacctggtt caaagatggg                                                 20

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucloetide probe

<400> SEQUENCE: 15
taggaagagt tgctgaaggc acgg                                            24

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucloetide probe
```

-continued

```
<400> SEQUENCE: 16
ttgccttact caggtgctac                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucloetide probe

<400> SEQUENCE: 17
actcagcagt ggtaggaaag                                                    20

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucloetide probe

<400> SEQUENCE: 18
tatccctcca attgagcacc ctgg                                               24

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucloetide probe

<400> SEQUENCE: 19
gtcggaagac atcccaacaa g                                                  21

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucloetide probe

<400> SEQUENCE: 20
cttcacaatg tcgctgtgct gctc                                               24

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucloetide probe

<400> SEQUENCE: 21
agccaaatcc agcagctggc ttac                                               24

<210> SEQ ID NO 22
<211> LENGTH: 50
<212> TYPE: DNA
<213> ORGANISM: Artificial Sequence
<220> FEATURE:
<223> OTHER INFORMATION: Synthetic oligonucloetide probe

<400> SEQUENCE: 22
tggatgaccg gagccactac acgtgtgaag tcacctggca gactcctgat                   50

<210> SEQ ID NO 23
```

<211> LENGTH: 260
<212> TYPE: PRT
<213> ORGANISM: Homo sapiens

<400> SEQUENCE: 23

Leu Ala Leu Gly Ser Val Thr Val His Ser Ser Glu Pro Glu Val Arg
1               5                   10                  15

Ile Pro Glu Asn Asn Pro Val Lys Leu Ser Cys Ala Tyr Ser Gly Phe
            20                  25                  30

Ser Ser Pro Arg Val Glu Trp Lys Phe Asp Gln Gly Asp Thr Thr Arg
        35                  40                  45

Leu Val Cys Tyr Asn Asn Lys Ile Thr Ala Ser Tyr Glu Asp Arg Val
    50                  55                  60

Thr Phe Leu Pro Thr Gly Ile Thr Phe Lys Ser Val Thr Arg Glu Asp
65                  70                  75                  80

Thr Gly Thr Tyr Thr Cys Met Val Ser Glu Glu Gly Gly Asn Ser Tyr
                85                  90                  95

Gly Glu Val Lys Val Lys Leu Ile Val Leu Val Pro Pro Ser Lys Pro
            100                 105                 110

Thr Val Asn Ile Pro Ser Ser Ala Thr Ile Gly Asn Arg Ala Val Leu
        115                 120                 125

Thr Cys Ser Glu Gln Asp Gly Ser Pro Pro Ser Glu Tyr Thr Trp Phe
    130                 135                 140

Lys Asp Gly Ile Val Met Pro Thr Asn Pro Lys Ser Thr Arg Ala Phe
145                 150                 155                 160

Ser Asn Ser Ser Tyr Val Leu Asn Pro Thr Thr Gly Glu Leu Val Phe
                165                 170                 175

Asp Pro Leu Ser Ala Ser Asp Thr Gly Glu Tyr Ser Cys Glu Ala Arg
            180                 185                 190

Asn Gly Tyr Gly Thr Pro Met Thr Ser Asn Ala Val Arg Met Glu Ala
        195                 200                 205

Val Glu Arg Asn Val Gly Val Ile Ala Ala Val Leu Val Thr Leu
    210                 215                 220

Ile Leu Leu Gly Ile Leu Val Phe Gly Ile Trp Phe Ala Tyr Ser Arg
225                 230                 235                 240

Gly His Phe Asp Arg Thr Lys Lys Gly Thr Ser Ser Lys Lys Val Ile
                245                 250                 255

Tyr Ser Gln Pro
            260

<210> SEQ ID NO 24
<211> LENGTH: 268
<212> TYPE: PRT
<213> ORGANISM: Homo sapiens

<400> SEQUENCE: 24

Val Thr Val Asp Ala Ile Ser Val Glu Thr Pro Gln Asp Val Leu Arg
1               5                   10                  15

Ala Ser Gln Gly Lys Ser Val Thr Leu Pro Cys Thr Tyr His Thr Ser
            20                  25                  30

Thr Ser Ser Arg Glu Gly Leu Ile Gln Trp Asp Lys Leu Leu Leu Thr
        35                  40                  45

His Thr Glu Arg Val Val Ile Trp Pro Phe Ser Asn Lys Asn Tyr Ile
    50                  55                  60

His Gly Glu Leu Tyr Lys Asn Arg Val Ser Ile Ser Asn Asn Ala Glu
65                  70                  75                  80

-continued

```
Gln Ser Asp Ala Ser Ile Thr Ile Asp Gln Leu Thr Met Ala Asp Asn
            85                  90                  95

Gly Thr Tyr Glu Cys Ser Val Ser Leu Met Ser Asp Leu Glu Gly Asn
            100                 105                 110

Thr Lys Ser Arg Val Arg Leu Leu Val Leu Val Pro Pro Ser Lys Pro
        115                 120                 125

Glu Cys Gly Ile Glu Gly Glu Thr Ile Ile Gly Asn Asn Ile Gln Leu
    130                 135                 140

Thr Cys Gln Ser Lys Glu Gly Ser Pro Thr Pro Gln Tyr Ser Trp Lys
145                 150                 155                 160

Arg Tyr Asn Ile Leu Asn Gln Glu Gln Pro Leu Ala Gln Pro Ala Ser
                165                 170                 175

Gly Gln Pro Val Ser Leu Lys Asn Ile Ser Thr Asp Thr Ser Gly Tyr
            180                 185                 190

Tyr Ile Cys Thr Ser Ser Asn Glu Glu Gly Thr Gln Phe Cys Asn Ile
        195                 200                 205

Thr Val Ala Val Arg Ser Pro Ser Met Asn Val Ala Leu Tyr Val Gly
    210                 215                 220

Ile Ala Val Gly Val Val Ala Ala Leu Ile Ile Ile Gly Ile Ile Ile
225                 230                 235                 240

Tyr Cys Cys Cys Cys Arg Gly Lys Asp Asp Thr Glu Asp Lys Glu
                245                 250                 255

Asp Ala Arg Pro Asn Arg Glu Ala Tyr Glu Glu Pro
            260                 265
```

<210> SEQ ID NO 25
<211> LENGTH: 263
<212> TYPE: PRT
<213> ORGANISM: Homo sapiens

<400> SEQUENCE: 25

```
Leu Cys Ser Leu Ala Leu Gly Ser Val Thr Val His Ser Ser Glu Pro
1               5                   10                  15

Glu Val Arg Ile Pro Glu Asn Asn Pro Val Lys Leu Ser Cys Ala Tyr
            20                  25                  30

Ser Gly Phe Ser Ser Pro Arg Val Glu Trp Lys Phe Asp Gln Gly Asp
        35                  40                  45

Thr Thr Arg Leu Val Cys Tyr Asn Asn Lys Ile Thr Ala Ser Tyr Glu
    50                  55                  60

Asp Arg Val Thr Phe Leu Pro Thr Gly Ile Thr Phe Lys Ser Val Thr
65                  70                  75                  80

Arg Glu Asp Thr Gly Thr Tyr Thr Cys Met Val Ser Glu Glu Gly Gly
            85                  90                  95

Asn Ser Tyr Gly Glu Val Lys Val Lys Leu Ile Val Leu Val Pro Pro
            100                 105                 110

Ser Lys Pro Thr Val Asn Ile Pro Ser Ser Ala Thr Ile Gly Asn Arg
        115                 120                 125

Ala Val Leu Thr Cys Ser Glu Gln Asp Gly Ser Pro Pro Ser Glu Tyr
    130                 135                 140

Thr Trp Phe Lys Asp Gly Ile Val Met Pro Thr Asn Pro Lys Ser Thr
145                 150                 155                 160

Arg Ala Phe Ser Asn Ser Ser Tyr Val Leu Asn Pro Thr Thr Gly Glu
                165                 170                 175

Leu Val Phe Asp Pro Leu Ser Ala Ser Asp Thr Gly Glu Tyr Ser Cys
```

```
                    180                 185                 190
Glu Ala Arg Asn Gly Tyr Gly Thr Pro Met Thr Ser Asn Ala Val Arg
            195                 200                 205
Met Glu Ala Val Glu Arg Asn Val Gly Val Ile Val Ala Ala Val Leu
        210                 215                 220
Val Thr Leu Ile Leu Leu Gly Ile Leu Val Phe Gly Ile Trp Phe Ala
225                 230                 235                 240
Tyr Ser Arg Gly His Phe Asp Arg Thr Lys Lys Gly Thr Ser Ser Lys
                245                 250                 255
Lys Val Ile Tyr Ser Gln Pro
                260

<210> SEQ ID NO 26
<211> LENGTH: 273
<212> TYPE: PRT
<213> ORGANISM: Homo sapiens

<400> SEQUENCE: 26

Leu Cys Ala Val Arg Val Thr Val Asp Ala Ile Ser Val Glu Thr Pro
1               5                   10                  15
Gln Asp Val Leu Arg Ala Ser Gln Gly Lys Ser Val Thr Leu Pro Cys
            20                  25                  30
Thr Tyr His Thr Ser Thr Ser Arg Glu Gly Leu Ile Gln Trp Asp
        35                  40                  45
Lys Leu Leu Leu Thr His Thr Glu Arg Val Val Ile Trp Pro Phe Ser
50                  55                  60
Asn Lys Asn Tyr Ile His Gly Glu Leu Tyr Lys Asn Arg Val Ser Ile
65                  70                  75                  80
Ser Asn Asn Ala Glu Gln Ser Asp Ala Ser Ile Thr Ile Asp Gln Leu
                85                  90                  95
Thr Met Ala Asp Asn Gly Thr Tyr Glu Cys Ser Val Ser Leu Met Ser
            100                 105                 110
Asp Leu Glu Gly Asn Thr Lys Ser Arg Val Arg Leu Leu Val Leu Val
        115                 120                 125
Pro Pro Ser Lys Pro Glu Cys Gly Ile Glu Gly Glu Thr Ile Ile Gly
130                 135                 140
Asn Asn Ile Gln Leu Thr Cys Gln Ser Lys Glu Gly Ser Pro Thr Pro
145                 150                 155                 160
Gln Tyr Ser Trp Lys Arg Tyr Asn Ile Leu Asn Gln Glu Gln Pro Leu
                165                 170                 175
Ala Gln Pro Ala Ser Gly Gln Pro Val Ser Leu Lys Asn Ile Ser Thr
            180                 185                 190
Asp Thr Ser Gly Tyr Tyr Ile Cys Thr Ser Ser Asn Glu Glu Gly Thr
        195                 200                 205
Gln Phe Cys Asn Ile Thr Val Ala Val Arg Ser Pro Ser Met Asn Val
210                 215                 220
Ala Leu Tyr Val Gly Ile Ala Val Gly Val Val Ala Ala Leu Ile Ile
225                 230                 235                 240
Ile Gly Ile Ile Ile Tyr Cys Cys Cys Cys Arg Gly Lys Asp Asp Asn
                245                 250                 255
Thr Glu Asp Lys Glu Asp Ala Arg Pro Asn Arg Glu Ala Tyr Glu Glu
            260                 265                 270
Pro
```

<210> SEQ ID NO 27
<211> LENGTH: 413
<212> TYPE: DNA
<213> ORGANISM: Homo sapiens

<400> SEQUENCE: 27

```
ctcgagccgc tcgagccgtg cggggaaata tcgttgtgaa gttagtgccc catctgagca      60
aggccaaaac ctggaagagg atacagtcac tctggaagta ttagtggctc cagcagttcc     120
atcatgtgaa gtaccctctt ctgctctgag tggaactgtg gtagagctac gatgtcaaga     180
caaagaaggg aatccagctc ctgaatacac atggtttaag gatggcatcc gtttgctaga     240
aaatcccaga cttggctccc aaagcaccaa cagctcatac acaatgaata caaaaactgg     300
aactctgcaa tttaatactg tttccaaact ggacactgga gaatattcct gtgaagcccg     360
caattctgtt ggatatcgca ggtgtcctgg ggaaacgaat gcaagtagat gat            413
```

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucloetide probe

<400> SEQUENCE: 28

```
atcgttgtga agttagtgcc cc                                               22
```

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucloetide probe

<400> SEQUENCE: 29

```
acctgcgata tccaacagaa ttg                                              23
```

<210> SEQ ID NO 30
<211> LENGTH: 48
<212> TYPE: DNA
<213> ORGANISM: Artificial Sequence
<220> FEATURE:
<223> OTHER INFORMATION: Synthetic oligonucloetide probe

<400> SEQUENCE: 30

```
ggaagaggat acagtcactc tggaagtatt agtggctcca gcagttcc                   48
```

<210> SEQ ID NO 31
<211> LENGTH: 310
<212> TYPE: PRT
<213> ORGANISM: Homo sapiens

<400> SEQUENCE: 31

```
Met Ala Leu Arg Arg Pro Pro Arg Leu Arg Leu Cys Ala Arg Leu Pro
 1               5                  10                  15

Asp Phe Phe Leu Leu Leu Leu Phe Arg Gly Cys Leu Ile Gly Ala Val
                20                  25                  30

Asn Leu Lys Ser Ser Asn Arg Thr Pro Val Val Gln Glu Phe Glu Ser
        35                  40                  45

Val Glu Leu Ser Cys Ile Ile Thr Asp Ser Gln Thr Ser Asp Pro Arg
    50                  55                  60

Ile Glu Trp Lys Lys Ile Gln Asp Glu Gln Thr Thr Tyr Val Phe Phe
65                  70                  75                  80
```

```
Asp Asn Lys Ile Gln Gly Asp Leu Ala Gly Arg Ala Glu Ile Leu Gly
                85                  90                  95
Lys Thr Ser Leu Lys Ile Trp Asn Val Thr Arg Arg Asp Ser Ala Leu
            100                 105                 110
Tyr Arg Cys Glu Val Val Ala Arg Asn Asp Arg Lys Glu Ile Asp Glu
        115                 120                 125
Ile Val Ile Glu Leu Thr Val Gln Val Lys Pro Val Thr Pro Val Cys
    130                 135                 140
Arg Val Pro Lys Ala Val Pro Val Gly Lys Met Ala Thr Leu His Cys
145                 150                 155                 160
Gln Glu Ser Glu Gly His Pro Arg Pro His Tyr Ser Trp Tyr Arg Asn
                165                 170                 175
Asp Val Pro Leu Pro Thr Asp Ser Arg Ala Asn Pro Arg Phe Arg Asn
            180                 185                 190
Ser Ser Phe His Leu Asn Ser Glu Thr Gly Thr Leu Val Phe Thr Ala
        195                 200                 205
Val His Lys Asp Asp Ser Gly Gln Tyr Tyr Cys Ile Ala Ser Asn Asp
    210                 215                 220
Ala Gly Ser Ala Arg Cys Glu Glu Gln Glu Met Glu Val Tyr Asp Leu
225                 230                 235                 240
Asn Ile Gly Gly Ile Ile Gly Gly Val Leu Val Val Leu Ala Val Leu
                245                 250                 255
Ala Leu Ile Thr Leu Gly Ile Cys Cys Ala Tyr Arg Arg Gly Tyr Phe
            260                 265                 270
Ile Asn Asn Lys Gln Asp Gly Glu Ser Tyr Lys Asn Pro Gly Lys Pro
        275                 280                 285
Asp Gly Val Asn Tyr Ile Arg Thr Asp Glu Glu Gly Asp Phe Arg His
    290                 295                 300
Lys Ser Ser Phe Val Ile
305                 310

<210> SEQ ID NO 32
<211> LENGTH: 399
<212> TYPE: PRT
<213> ORGANISM: Homo sapiens

<400> SEQUENCE: 32

Met Gly Ile Leu Leu Gly Leu Leu Leu Gly His Leu Thr Val Asp
 1               5                  10                  15
Thr Tyr Gly Arg Pro Ile Leu Glu Val Pro Glu Ser Val Thr Gly Pro
                20                  25                  30
Trp Lys Gly Asp Val Asn Leu Pro Cys Thr Tyr Asp Pro Leu Gln Gly
            35                  40                  45
Tyr Thr Gln Val Leu Val Lys Trp Leu Val Gln Arg Gly Ser Asp Pro
        50                  55                  60
Val Thr Ile Phe Leu Arg Asp Ser Ser Gly Asp His Ile Gln Gln Ala
65                  70                  75                  80
Lys Tyr Gln Gly Arg Leu His Val Ser His Lys Val Pro Gly Asp Val
                85                  90                  95
Ser Leu Gln Leu Ser Thr Leu Glu Met Asp Asp Arg Ser His Tyr Thr
            100                 105                 110
Cys Glu Val Thr Trp Gln Thr Pro Asp Gly Asn Gln Val Val Arg Asp
        115                 120                 125
Lys Ile Thr Glu Leu Arg Val Gln Lys Leu Ser Val Ser Lys Pro Thr
```

```
            130                 135                 140
Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Ile Ser Tyr Ile
                165                 170                 175

Trp Tyr Lys Gln Gln Thr Asn Asn Gln Glu Pro Ile Lys Val Ala Thr
                180                 185                 190

Leu Ser Thr Leu Leu Phe Lys Pro Ala Val Ile Ala Asp Ser Gly Ser
                195                 200                 205

Tyr Phe Cys Thr Ala Lys Gly Gln Val Gly Ser Glu Gln His Ser Asp
210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
                260                 265                 270

Glu Thr Ser Ala Gly Pro Gly Lys Ser Leu Pro Val Phe Ala Ile Ile
                275                 280                 285

Leu Ile Ile Ser Leu Cys Cys Met Val Val Phe Thr Met Ala Tyr Ile
                290                 295                 300

Met Leu Cys Arg Lys Thr Ser Gln Gln Glu His Val Tyr Glu Ala Ala
305                 310                 315                 320

Arg Ala His Ala Arg Glu Ala Asn Asp Ser Gly Glu Thr Met Arg Val
                325                 330                 335

Ala Ile Phe Ala Ser Gly Cys Ser Ser Asp Glu Pro Thr Ser Gln Asn
                340                 345                 350

Leu Gly Asn Asn Tyr Ser Asp Glu Pro Cys Ile Gly Gln Glu Tyr Gln
                355                 360                 365

Ile Ile Ala Gln Ile Asn Gly Asn Tyr Ala Arg Leu Leu Asp Thr Val
                370                 375                 380

Pro Leu Asp Tyr Glu Phe Leu Ala Thr Glu Gly Lys Ser Val Cys
385                 390                 395

<210> SEQ ID NO 33
<211> LENGTH: 305
<212> TYPE: PRT
<213> ORGANISM: Homo sapiens

<400> SEQUENCE: 33

Met Gly Ile Leu Leu Gly Leu Leu Leu Gly His Leu Thr Val Asp
  1               5                  10                  15

Thr Tyr Gly Arg Pro Ile Leu Glu Val Pro Glu Ser Val Thr Gly Pro
                20                  25                  30

Trp Lys Gly Asp Val Asn Leu Pro Cys Thr Tyr Asp Pro Leu Gln Gly
                35                  40                  45

Tyr Thr Gln Val Leu Val Lys Trp Leu Val Gln Arg Gly Ser Asp Pro
        50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
                100                 105                 110
```

```
Cys Glu Val Thr Trp Gln Thr Pro Asp Gly Asn Gln Val Val Arg Asp
            115                 120                 125

Lys Ile Thr Glu Leu Arg Val Gln Lys His Ser Ser Lys Leu Leu Lys
        130                 135                 140

Thr Lys Thr Glu Ala Pro Thr Thr Met Thr Tyr Pro Leu Lys Ala Thr
145                 150                 155                 160

Ser Thr Val Lys Gln Ser Trp Asp Trp Thr Thr Asp Met Asp Gly Tyr
                165                 170                 175

Leu Gly Glu Thr Ser Ala Gly Pro Gly Lys Ser Leu Pro Val Phe Ala
            180                 185                 190

Ile Ile Leu Ile Ile Ser Leu Cys Cys Met Val Val Phe Thr Met Ala
        195                 200                 205

Tyr Ile Met Leu Cys Arg Lys Thr Ser Gln Gln Glu His Val Tyr Glu
    210                 215                 220

Ala Ala Arg Ala His Ala Arg Glu Ala Asn Asp Ser Gly Glu Thr Met
225                 230                 235                 240

Arg Val Ala Ile Phe Ala Ser Gly Cys Ser Ser Asp Glu Pro Thr Ser
                245                 250                 255

Gln Asn Leu Gly Asn Asn Tyr Ser Asp Glu Pro Cys Ile Gly Gln Glu
            260                 265                 270

Tyr Gln Ile Ile Ala Gln Ile Asn Gly Asn Tyr Ala Arg Leu Leu Asp
        275                 280                 285

Thr Val Pro Leu Asp Tyr Glu Phe Leu Ala Thr Glu Gly Lys Ser Val
    290                 295                 300

Cys
305

<210> SEQ ID NO 34
<211> LENGTH: 280
<212> TYPE: PRT
<213> ORGANISM: Mus musculus

<400> SEQUENCE: 34

Met Glu Ile Ser Ser Gly Leu Leu Phe Leu Gly His Leu Ile Val Leu
1               5                   10                  15

Thr Tyr Gly His Pro Thr Leu Lys Thr Pro Glu Ser Val Thr Gly Thr
            20                  25                  30

Trp Lys Gly Asp Val Lys Ile Gln Cys Ile Tyr Asp Pro Leu Arg Gly
        35                  40                  45

Tyr Arg Gln Val Leu Val Lys Trp Leu Val Arg His Gly Ser Asp Ser
    50                  55                  60

Val Thr Ile Phe Leu Arg Asp Ser Thr Gly Asp His Ile Gln Gln Ala
65                  70                  75                  80

Lys Tyr Arg Gly Arg Leu Lys Val Ser His Lys Val Pro Gly Asp Val
                85                  90                  95

Ser Leu Gln Ile Asn Thr Leu Gln Met Asp Asp Arg Asn His Tyr Thr
            100                 105                 110

Cys Glu Val Thr Trp Gln Thr Pro Asp Gly Asn Gln Val Ile Arg Asp
        115                 120                 125

Lys Ile Ile Glu Leu Arg Val Arg Lys Tyr Asn Pro Pro Arg Ile Asn
    130                 135                 140

Thr Glu Ala Pro Thr Thr Leu His Ser Ser Leu Glu Ala Thr Thr Ile
145                 150                 155                 160

Met Ser Ser Thr Ser Asp Leu Thr Thr Asn Gly Thr Gly Lys Leu Glu
                165                 170                 175
```

```
Glu Thr Ile Ala Gly Ser Gly Arg Asn Leu Pro Ile Phe Ala Ile Ile
            180                 185                 190

Phe Ile Ile Ser Leu Cys Cys Ile Val Ala Val Thr Ile Pro Tyr Ile
        195                 200                 205

Leu Phe Arg Cys Arg Thr Phe Gln Gln Glu Tyr Val Tyr Gly Val Ser
    210                 215                 220

Arg Val Phe Ala Arg Lys Thr Ser Asn Ser Glu Glu Thr Thr Arg Val
225                 230                 235                 240

Thr Thr Ile Ala Thr Asp Glu Pro Asp Ser Gln Ala Leu Ile Ser Asp
                245                 250                 255

Tyr Ser Asp Asp Pro Cys Leu Ser Gln Glu Tyr Gln Ile Thr Ile Arg
                260                 265                 270

Ser Thr Met Ser Ile Pro Ala Cys
            275                 280

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucloetide primer

<400> SEQUENCE: 35
tctctgtctc caagcccaca g                                              21

<210> SEQ ID NO 36
<211> LENGTH: 19
<212> TYPE: DNA
<213> ORGANISM: Artificial Sequence
<220> FEATURE:
<223> OTHER INFORMATION: Synthetic oligonucloetide primer

<400> SEQUENCE: 36
ctttgaggag tctttgacc                                                 19
```

USE OF A33 ANTIGENS AND JAM-IT

The present application is a divisional of application Ser. No. 10/633,008, filed Jul. 31, 2003, now U.S. Pat. No. 7,192,589, which is a continuation in part of application Ser. No. 10/265,542 filed Oct. 3, 2002, now abandoned, which is a continuation in part of PCT international application no. PCT/US00/04414, filed Feb. 22, 2000, as a continuation in part of PCT international application no. PCT/US00/14042, filed May 22, 2000, as a continuation in part of PCT international application no. PCT/US00/32678, filed Dec. 1, 2000, as a continuation in part of U.S. application Ser. No. 09/254,465, filed Mar. 5, 1999, now, U.S. Pat. No. 6,410,708, as a continuation in part of PCT international application no. PCT/US99/05028, filed Mar. 8, 1999, as a continuation in part of U.S. application Ser. No. 09/380,138, filed Aug. 25, 1999 now abandoned as a continuation in part of U.S. application Ser. No. 09/380,139, filed Aug. 25, 1999, now abandoned, as a continuation in part of PCT international application no. PCT/US98/19330, filed Sep. 16, 1998, and as a continuation in part of U.S. application Ser. No. 09/953,499, filed Sep. 14, 2001, now U.S. Pat. No. 6,838,554, which in turn is a continuation application, claiming priority under 35 U.S.C. §120 as a continuation of PCT international application no. PCT/US98/24855, filed Nov. 20, 1998.

BACKGROUND OF THE INVENTION

1. Field of the Invention

The present invention relates generally to the identification, isolation and recombinant production of novel DNA and novel polypeptides the presence of which is associated with inflammatory diseases (inflammation associated antigens) and/or cancer, and to compositions and methods for the diagnosis and treatment of conditions characterized by such antigens.

2. Description of the Related Art

The inflammatory response is complex and is mediated by a variety of signaling molecules produced locally by mast cells, nerve endings, platelets, leukocytes and complement activation. Certain of these signaling molecules cause the endothelial cell lining to become more porous and/or even to express selections which act as cell surface molecules which recognize and attract leukocytes through specific carbohydrate recognition. Stronger leukocyte binding is mediated by integrins, which mediate leukocyte movement through the endothelium. Additional signaling molecules act as chemoattractants, causing the bound leukocytes to crawl towards the source of the attractant. Other signaling molecules produced in the course of an inflammatory response escape into the blood and stimulate the bone marrow to produce more leukocytes and release them into the blood stream.

Inflammation is typically initiated by an antigen, which can be virtually any molecule capable of initiating an immune response. Under normal physiological conditions these are foreign molecules, but molecules generated by the organism itself can serve as the catalyst as is known to occur in various disease states.

T-cell proliferation in a mixed lymphocyte culture or mixed lymphocyte reaction (MLR) is an established indication of the ability of a compound to stimulate the immune system. In an inflammatory response, the responding leukocytes can be neutrophilic, eosinophilic, monocytic or lymphocytic. Histological examination of the affected tissues provides evidence of an immune stimulating or inhibiting response. See *Current Protocols in Immunology*, ed. John E. Coligan, 1994, John Wiley and Sons, Inc.

Inflammatory bowel disease (IBD) is a term used to collectively describe gut disorders including both ulcerative colitis (UC) and Crohn's disease, both of which are classified as distinct disorders, but share common features and likely share pathology. The commonality of the diagnostic criteria can make it difficult to precisely determine which of the two disorders a patient has; however the type and location of the lesion in each are typically different. UC lesions are characteristically a superficial ulcer of the mucosa and appear in the colon, proximal to the rectum. CD lesions are characteristically extensive linear fissures, and can appear anywhere in the bowel, occasionally involving the stomach, esophagus and duodenum.

Conventional treatments for IBD usually involve the administration of anti-inflammatory or immunosuppressive agents, such as sulfasalazine, corticosteroids, 6-mercaptopurine/azathoprine, or cyclosporine all of which only bring partial relief to the afflicted patient. However when anti-inflammatory/immunosuppressive therapies fail, colectomies are the last line of defense. Surgery is required for about 30% of CD patients within the first year after diagnosis, with the likelihood for operative procedure increasing about 5% annually thereafter. Unfortunately, CD also has a high rate of reoccurrence as about 5% of patients require subsequent surgery after the initial year. UC patients further have a substantially increased risk of developing colorectal cancer. Presumably this is due to the recurrent cycles of injury to the epithelium, followed by regrowth, which continually increases the risk of neoplastic transformation.

A recently discovered member of the immunoglobulin superfamily known as Junctional Adhesion Molecule (JAM) has been identified to be selectively concentrated at intercellular junctions of endothelial and epithelial cells of different origins. Martin-Padura, I. et al., *J. Cell Biol.* 142(1): 117-27 (1998). JAM is a type I integral membrane protein with two extracellular, intrachain disulfide loops of the V-type. JAM bears substantial homology to A33 antigen (FIG. 1 or FIG. 18). A monoclonal antibody directed to JAM was found to inhibit spontaneous and chemokine-induced monocyte transmigration through an endothelial cell monolayer in vitro. Martin-Padura, supra. It has been recently discovered that JAM expression is increased in the colon of CRF2-4−/− mice with colitis. CRF 2-4−/− (IL-10R subunit knockout mice) develop a spontaneous colitis mediated by lymphocytes, monocytes and neutrophils. Several of the animals also developed colon adenocarcinoma. As a result, it is likely that the polypeptides disclosed herein are expressed in elevated levels in or otherwise associated with human diseases such as inflammatory bowel disease, other inflammatory diseases of the gut as well as colorectal carcinoma.

JAM and the polypeptides disclosed herein bear significant homology to A33 antigen, a known colorectal cancer-associated marker. The A33 antigen is expressed in more than 90% of primary or metastatic colon cancers as well as normal colon epithelium. In carcinomas originating from the colonic mucosa, the A33 antigen is expressed homogeneously in more than 95% of all cases. The A33 antigen, however, has not been detected in a wide range of other normal tissues, i.e., its expression appears to be organ specific. Therefore, the A33 antigen appears to play an important role in the induction of colorectal cancer.

Since colon cancer is a widespread disease, early diagnosis and treatment is an important medical goal. Diagnosis and treatment of colon cancer can be implemented using monoclonal antibodies (mAbs) specific therefore having fluorescent, nuclear magnetic or radioactive tags. Radioactive gene, toxins and/or drug tagged mAbs can be used for treatment in situ with minimal patient description. mAbs can also be used to diagnose during the diagnosis and treatment of colon cancers. For example, when the serum levels of the A33 antigen are elevated in a patient, a drop of the levels after surgery would indicate the tumor resection was successful. On the other hand, a subsequent rise in serum A33 antigen levels after surgery would indicate that metastases of the original tumor may have formed or that new primary tumors may have appeared.

Such monoclonal antibodies can be used in lieu of, or in conjunction with surgery and/or other chemotherapies. For example, preclinical analysis and localization studies in patients infected with colorectal carcinoma with a mAb to A33 are described in Welt et al., *J. Clin. Oncol.* 8: 1894-1906 (1990) and Welt et al., *J. Clin. Oncol.* 12: 1561-1571 (1994), while U.S. Pat. No. 4,579,827 and U.S. Ser. No. 424,991 (E.P. 199,141) are directed to the therapeutic administration of monoclonal antibodies, the latter of which relates to the application of anti-A33 mAb.

SUMMARY OF THE INVENTION

In one aspect, the present invention concerns a method of treating an inflammatory disorder in a mammal, comprising administering to the mammal a therapeutically effective amount of an antagonist of a native sequence STIgMA polypeptide.

In one embodiment, the STIgMA polypeptide is selected from the group consisting of polypeptides of SEQ ID NOS: 2, 32, 33, and 34.

In another embodiment, the antagonist is an antibody, such as a monoclonal antibody, which may have non-human complementarity determining region (CDR) residues and contains human framework region (FR) residues.

In a further embodiment, the antagonist is an immunoadhesin, which comprises a STIgMA extracellular domain sequence fused to an immunoglobulin constant region sequence.

In another embodiment, the inflammatory disorder is selected from the group consisting of: inflammatory bowel disease; systemic lupus erythematosus; rheumatoid arthritis; juvenile chronic arthritis; spondyloarthropathies; systemic sclerosis, for example, scleroderma; idiopathic inflammatory myopathies for example, dermatomyositis, polymyositis; Sjögren's syndrome; systemic vaculitis; sarcoidosis; autoimmune hemolytic anemia for example, immune pancytopenia, paroxysmal nocturnal hemoglobinuria; autoimmune thrombocytopenia, for example, idiopathic thrombocytopenic purpura, immune-mediated thrombocytopenia; thyroiditis, for example, Grave's disease, Hashimoto's thyroiditis, juvenile lymphocytic thyroiditis, atrophic thyroiditis; diabetes mellitus, immune-mediated renal disease, for example, glomerulonephritis, tubulointerstitial nephritis; demyelinating diseases of the central and peripheral nervous systems such as multiple sclerosis, idiopathic polyneuropathy; hepatobiliary diseases such as infectious hepatitis such as hepatitis A, B, C, D, E and other nonhepatotropic viruses; autoimmune chronic active hepatitis; primary biliary cirrhosis; granulomatous hepatitis; and sclerosing cholangitis; inflammatory and fibrotic lung diseases (e.g., cystic fibrosis); gluten-sensitive enteropathy; Whipple's disease; autoimmune or immune-mediated skin diseases including bullous skin diseases, erythema multiforme and contact dermatitis, psoriasis; allergic diseases of the lung such as eosinophilic pneumonia, idiopathic pulmonary fibrosis and hypersensitivity pneumonitis, transplantation associated diseases including graft rejection and graft-versus host disease.

In a different aspect, the invention concerns a method of diagnosing an inflammatory disorder in a mammal, said method comprising detecting the level of expression of a gene encoding a STIgMA polypeptide (a) in a test sample of cells obtained from said mammal, and (b) in a control sample of known normal cells of the same cell type, wherein a higher level of expression of said gene in the test sample as compared to the control sample is indicative of the presence of an immune related disorder in the mammal from which the test tissue cells were obtained.

In a further aspect, the invention concerns a method of diagnosing an inflammatory disorder in a mammal, said method comprising (a) contacting an anti-STIgMA antibody with a test sample of cells obtained from said mammal, and (b) detecting the formation of a complex between the antibody and STIgMA polypeptide in the test sample, wherein formation of said complex is indicative of the presence of an inflammatory disorder in said mammal.

The invention further concerns an isolated antibody which specifically binds a STIgMA polypeptide.

In a different aspect, the invention concerns an isolated nucleic acid molecule comprising a nucleotide sequence encoding a polypeptide having at least about 80%, or at least about 85% or at least about 90% or at least about 95% or at least about 99% sequence identity with the amino acid sequence of amino acids 21 to 276 of SEQ ID NO: 32, or amino acids 21 to 182 of SEQ ID NO: 33, or amino acids 21 to 180 of SEQ ID NO: 34.

The invention further concerns vectors and cells comprising the nucleic acids of the invention.

In another aspect, the invention concerns a polypeptide comprising an amino acid sequence selected from the group consisting of amino acids 21 to 276 of SEQ ID NO: 32, amino acids 21 to 182 of SEQ ID NO: 33, and amino acids 21 to 180 of SEQ ID NO: 34.

In yet another aspect, the invention concerns an immunoadhesin comprising amino acids from 1 or about 21 to about 276 of SEQ ID NO: 32, or amino acids from 1 or about 21 to about 182 of SEQ ID NO: 33, or amino acids 1 or about 21 to about 180 of SEQ ID NO: 34, fused to an immunoglobulin constant region sequence.

BRIEF DESCRIPTION OF THE DRAWINGS

FIG. 1 show a comparison between the polypeptides encoded by A33 antigen (SEQ ID NO: 6), DNA40628 (SEQ ID NO: 1), DNA45416 (SEQ ID NO: 2), DNA35638 (SEQ ID NO: 9) and JAM (SEQ ID NO: 10).

FIG. 2 shows the derived amino acid sequence (SEQ ID NO: 1) of a native sequence PRO301 polypeptide. This polypeptide is 299 amino acids long, having signal sequence at residue 1 to 27, an extracellular domain at residue 28 to about 235, Ig superfamily homology at residue 94 to 235, a potential transmembrane domain at residue 236 to about 258, and an intracellular domain at about residue 259 to 299.

FIG. 3 shows the amino acid sequence (SEQ ID NO: 2) derived from nucleotides 119-1081 of the nucleotide sequence shown in FIGS. 6A and 6B (DNA45416, SEQ ID NO: 7). Also shown in FIG. 3 as underlines are the locations of a glycosoaminoglycan site and a transmembrane domain.

FIG. 4A shows the consensus assembly DNA35936 (SEQ ID NO: 3), and FIG. 4B shows consen01 (SEQ ID NO: 4) which were both used in the isolation of DNA40628 (SEQ ID NO: 11). FIG. 4C shows consen02 (DNA42257) (SEQ ID NO: 5) which was used in the isolation of DNA45416 (SEQ ID NO: 7).

FIG. 5 shows the nucleotide sequence of a native sequence DNA40628 cDNA (SEQ ID NO: 11), which is a native sequence PRO301 cDNA also designated as "UNQ264" and/or "DNA40628-1216".

FIGS. 6A & B show a nucleotide sequence DNA45416 (SEQ ID NO: 7) which is a native sequence PRO362 cDNA also designated as "UNQ317" and/or "DNA45416-1251". Also presented are the initiator methionine and the protein translation for a full-length PRO362 polypeptide (SEQ ID NO: 2).

FIG. 7 shows the nucleotide sequence (SEQ ID NO: 8) of a native sequence PRO245 cDNA, wherein the nucleotide sequence is designated as "UNQ219" and/or "DNA35638".

FIG. 8 shows the oligonucleotide sequences OLI2162 (35936.f1) (SEQ ID NO: 12), OLI2163 (35936.p1) (SEQ ID NO: 13), OLI2164 (35936.f2) (SEQ ID NO: 14), OLI2165 (35936.r1) (SEQ ID NO: 15), OLI2166 (35936.f3) (SEQ ID NO: 16), OLI2167 (35936.r2) (SEQ ID NO: 17) which were used in the isolation of DNA40628.

FIGS. 9A & B show a double stranded representation of the DNA42257 (consen02) (SEQ ID NO: 5) along with the locations of five oligonucleotide primers, showed in underline, all used in the isolation of DNA45416 (SEQ ID NO: 7). The oligonucleotides depicted are: 42257.f1 (SEQ ID NO: 18), 42257.f2 (SEQ ID NO: 19), 42257.r1 (SEQ ID NO: 20), 42257.r2 (SEQ ID NO: 21) and 42257.p1 (SEQ ID NO: 22).

FIGS. 10A and B describe the Blast score, match and percent homology alignment between 2 overlapping fragments of DNA40628 and A33_HUMAN, a human A33 antigen precursor. FIG. 10A compares the coded residues 24 to 283 of DNA40628 (SEQ ID NO: 23) with the coded residues 17 to 284 of A33_HUMAN (SEQ ID NO: 24); FIG. 10B compares the coded residues 21 to 239 of DNA40628 (SEQ ID NO: 25) with the coded residues 12 to 284 of A33_HUMAN (SEQ ID NO: 26), respectively.

FIG. 11 shows the derived amino acid sequence of a native sequence PRO245 polypeptide (SEQ ID NO: 9) encoded by the nucleotide sequence of FIG. 7 (DNA35638, SEQ ID NO: 8). This polypeptide is a 312 amino acids in length, having signal sequence at residue 1 to 28 and a potential transmembrane domain at about residue 237 to about 259.

FIG. 12 indicates a 25.3% identity between the amino acid sequence encoded by DNA40628 (SEQ ID NO: 1) and A33 antigen (SEQ ID NO: 6).

FIG. 13 indicates a 20.8% identity between the amino acid sequence encoded by DNA45416 (SEQ ID NO: 2) and A33 antigen (SEQ ID NO: 6).

Figure 14:
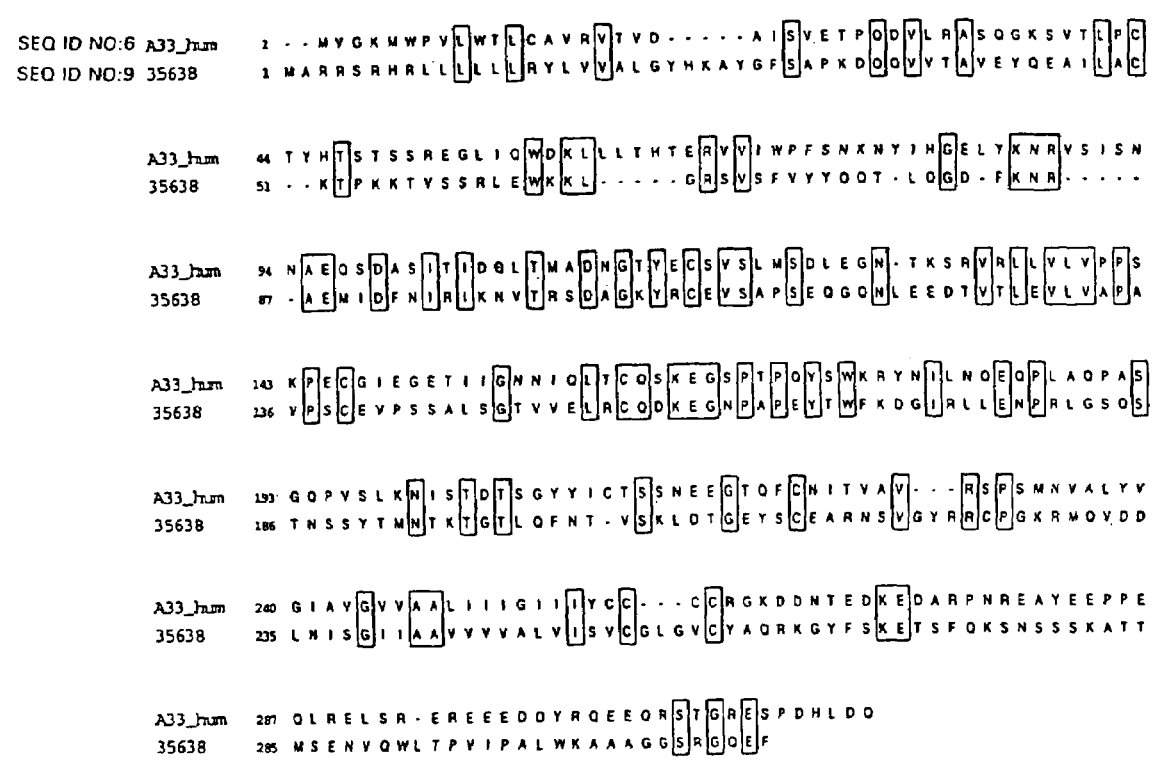

FIG. 14 indicates a 24.3% identity between the amino acid sequence encoded by DNA35638 (SEQ ID NO: 9) and A33 antigen (SEQ ID NO: 6).

FIG. 15 indicates a 67.6% identity between the amino acid sequence encoded by DNA40628 (SEQ ID NO: 1) and JAM (SEQ ID NO: 10).

FIG. 16 indicates a 23.3% identity between the amino acid sequence encoded by DNA45416 (SEQ ID NO: 2) and JAM (SEQ ID NO: 10).

FIG. 17 indicates a 34.2% identity between the amino acid sequence encoded by DNA35638 (SEQ ID NO: 29) and JAM (SEQ ID NO: 10).

FIG. 18 indicates a 26% identity between the amino acid sequence encoded by A33 antigen (SEQ ID NO: 6) and JAM (SEQ ID NO: 10).

FIG. 19 shows the results of the dot blot hybridization procedure described in Example 8.

FIG. 22 shows the amino acid sequence (SEQ ID NO: 31) of PRO1868 with ▼, representing a putative signal cleavage site, ●, representing conserved extracellular cysteines, the transmembrane domain underlined and the overlying dotted lines, representing potential N-glycosylation sites. This polypeptide is 310 amino acids in length, having signal sequence at residue 1 to 30 and a potential transmembrane domain at about residue 242 to about 266.

FIG. 34 shows in situ hybridization of PRO245 mRNA in human breast carcinoma tissue.

FIG. 35 shows immunohistochemical analysis of PRO362 in macrophages.

FIG. 36 shows immunohistochemical analysis of PRO362 in Kupffer cells.

FIG. 38 shows immunohistochemical analysis of PRO362 in Hofbauer cells.

Figure 56:
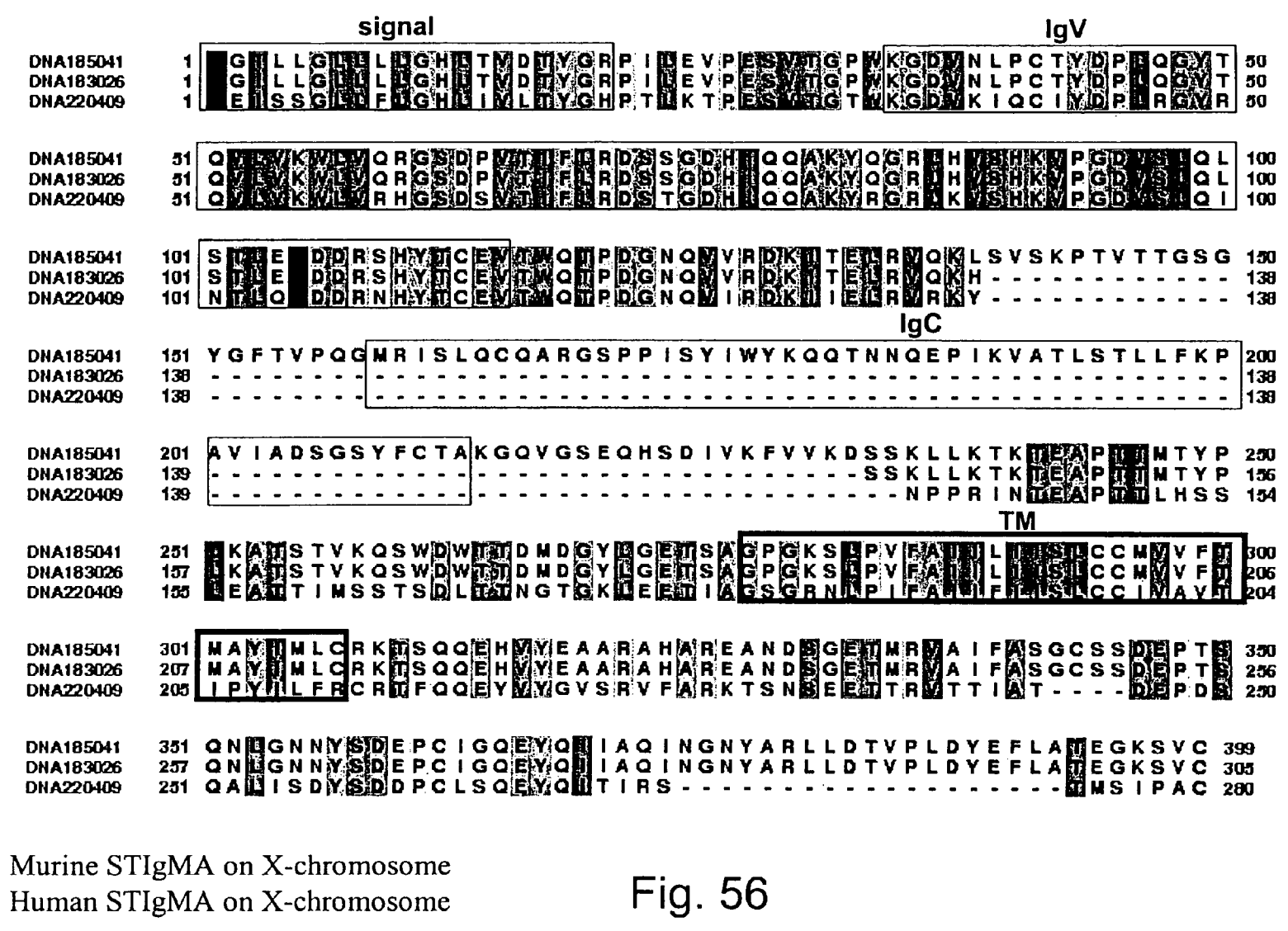

FIG. 56 shows the amino acid sequence of human STIgMA (hSTIgMA; SEQ ID NO: 32) and human STIgMA short (hSTIgMA short; SEQ ID NO: 33) and alignment with murine STIgMA (SEQ ID NO: 34). The hydrophobic leader sequence, transmembrane region, and potential N-linked glycosylation sites are shown. The Ig domain boundaries, deduced from the exon-intron boundaries of the human STIgMA gene, are indicated.

FIG. 62. Subcellular localization of STIgMA in monocyte-derived macrophages. Monocytes were cultured for 7 days in macrophage differentiation medium, fixed in acetone and stained with polyclonal anti STIgMA antibody 6F1 or CD63 and secondary goat-anti rabbit FITC. Cells were studied in a confocal microscope. STIgMA is found in the cytoplasm were it co-localizes with the lysosomal membrane protein CD63. STIgMA was also expressed at the trailing and leading edges of macrophages in a pattern similar to that of F-actin. Scale bar=10 μm.

FIG. 68. Co-staining of STIgMA and CD68 on heart interstitial macrophages. 5 µm sections were obtained from a human heart (autopsy) and stained with a monoclonal antibody to STIgMA (3C9) and a secondary anti-mouse FITC-labeled antibody. CD68 was detected by staining with a PE-labeled monoclonal antibody to CD68. Magnification: 20×.

FIG. 70. Cells expressing human STIgMA showed increased adherence to human endothelial cells. (A) STIgMA was stably expressed in a human Jurkat T-cell line. (B) Cells were preloaded with the fluorescent dye BCECF (Molecular Probes, Oregon) and added to a 96 well plate coated with a monolayer of human umbilical vein endothelial cells (HUVEC) treated with or without 10 ng/ml TNFα. After 3 washes, fluorescence was counted in a spectro-fluorometer which indicated the number of cells that remain adherent to the HUVEC cells. The graph was representative of 4 independent experiments.

FIG. 71. Inhibition of progression of collagen-induced arthritis (CIA) mouse model by muSTIgMA IgG-Fc fusion protein. A group of (CIA) mice (n=7) was given 100 µg of muSTIgMA IgG-Fc fusion protein (squares), whereas a CIA mouse control group (n=8) received 100 µg of murine IgG1 (circles), 3 times per week for 6 weeks. Mice were examined daily for signs of inflammation and scored on a scale of 0-16 (details in Example 25) and the results were plotted graphically (mean±SD, Student's T test p-value=0.0004 for control IgG1 vs. test muSTIgMA protein).

DETAILED DESCRIPTION OF THE PREFERRED EMBODIMENT

I. Definitions

Figure 20:
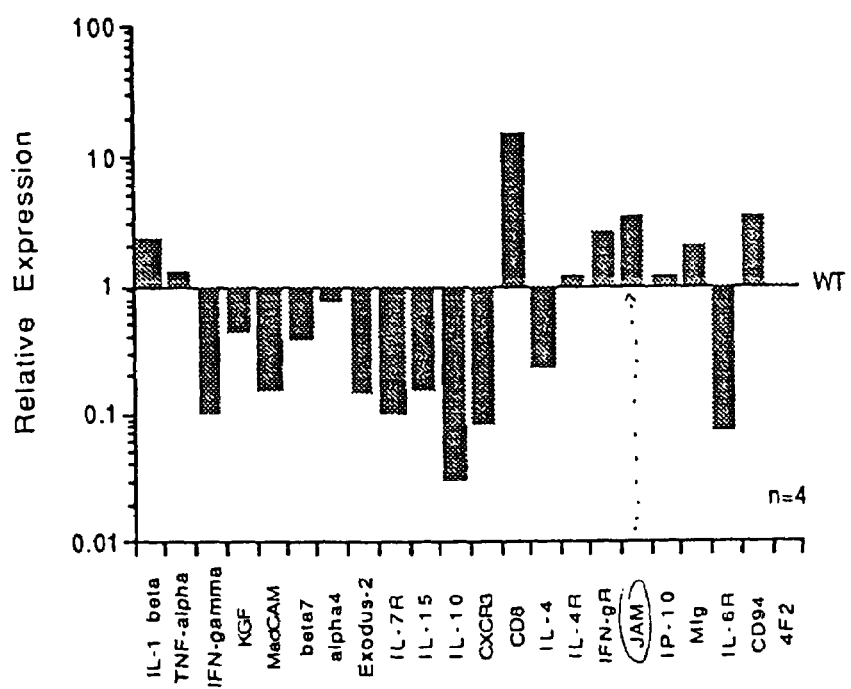
FIG. 20 shows the results of the TAQMAN™ mRNA expression assay described in Example 9.

The terms "PRO301", "PRO362, "PRO245", "PRO1868" or "PRO301 polypeptide," "PRO362 polypeptide," "PRO245 polypeptide," "PRO1868" and "cancer associated antigen" when used herein encompass native sequence PRO301, PRO362, PRO245, or PRO1868 respectively and variants thereof (which are further defined herein). In addition the terms "PRO301" and "JAM-1" are used interchangeably, as are the terms "PRO362," "JAM4," "STIGMA," and "STIgMA." Further, the terms "PRO245," "JAM-IT" and "JAM-2" are used interchangeably, as are the terms "PRO1868," "SHATR" and "JAM-3." The PRO301, PRO362, PRO245 or PRO1868 polypeptides may be isolated from a variety of sources, such as from human tissue types or from another source, or prepared by recombinant or synthetic methods. As noted, the listed designations are used to refer to the respective native sequence molecules and their variants.

Thus, for example, STIgMA includes a polypeptide comprising amino acids 1 to 321 of SEQ ID NO: 2; amino acids 1 to X of SEQ ID NO: 2 (wherein X is any of amino acids 271 to 280); amino acids 21 to 321 of SEQ ID NO: 2; amino acids 21 to X of SEQ ID NO: 2 (wherein X is any of amino acids 271 to 280); amino acids 1 to 399 of SEQ ID NO: 32; amino acids 21 to 399 of SEQ ID NO: 32; amino acids 1 to 305 of SEQ ID NO: 33; amino acids 21 to 305 of SEQ ID NO: 33; amino acids 1 to 280 of SEQ ID NO: 34; amino acids 21 to 280 of SEQ ID NO: 34; the extracellular domains and variants in which part or all of the transmembrane domain has been deleted or inactivated.

The term "inflammatory disease" and "inflammatory disorder" are used interchangeably and mean a disease or disorder in which a component of the immune system of a mammal causes, mediates or otherwise contributes to an inflammatory response contributing to morbidity in the mammal. Also included are diseases in which reduction of the inflammatory response has an ameliorative effect on progression of the disease. Included within this term are immune-mediated inflammatory diseases, including autoimmune diseases.

The term "T-cell mediated" disease means a disease in which T cells directly or indirectly mediate or otherwise contribute to morbidity in a mammal. The T cell mediated disease may be associated with cell mediated effects, lymphokine mediated effects, etc. and even effects associated with B cells if the B cells are stimulated, for example, by the lymphokines secreted by T cells.

Examples of immune-related and inflammatory diseases, some of which are T cell mediated, include, without limitation, inflammatory bowel disease, systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection and graft-versus host disease.

"Tumor", as used herein, refers to all neoplastic cell growth and proliferation whether malignant or benign, and all pre-cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The "pathology" of an immune related disease includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

The term "mammal" as used herein refers to any animal classified as a mammal, including, without limitation, humans, domestic and farm animals, and zoo, sports or pet animals such horses, pigs, cattle, dogs, cats and ferrets, etc. In a preferred embodiment of the invention, the mammal is a human.

Administration "in combination with" one or more further therapeutic agents includes simultaneous (concurrent) and consecutive administration in any order.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (Taxol®, Bristol-Myers Squibb Oncology, Princeton, N.J.) and doxetaxel (Taxotere®, Rhône-Poulenc Roher, Antony, France), toxotere, methotrexate, cisplatin, melphalan, vinblastine, bleomycin, etoposide, ifosfamide, mitomycin C, mitoxantrone, vincristine (Loucristine), vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormonal action on tumors such as tamoxifen and onapristone.

A "growth inhibitory agent" when used herein refers to a compound or composition which inhibits growth of a cell, especially cancer cells expressing or overexpressing any of the genes identified herein, either in vitro or in vivo. Thus, the growth inhibitory agent is one which significantly reduces the percentage of cells expressing or overexpressing such genes in S phase. Examples of growth inhibitory agents include agents that block cell cycle progression (at a place other than S phase), such as agents that induce G1 arrest and M-phase arrest. Classical M-phase blockers include the vinca alkaloids (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders, Philadelphia, 1995), especially page 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone, parathyroid hormone, thyroxine, insulin, proinsulin, relaxin, prorelaxin, glycoprotein hormones such as follicle stimulating hormone (FSH), thyroid stimulating hormone (TSH), and luteinizing hormone (LH), hepatic growth factor, fibroblast growth factor, prolactin, placental lactogen, tumor necrosis factor-α and β, mullerian-inhibiting substance, mouse gonadotropin-associated peptide, inhibin, activin, vascular endothelial growth factor, integrin, thrombopoietin (TPO), nerve growth factors such as NGF-β, platelet-growth factor, transforming growth factors (TGFs) such as TGF-α and TGF-β, insulin-like growth factor-I and -II, erythropoietin (EPO), osteoinductive factors, interferons such as interferon-α, -β, and -γ; colony stimulating factors (CSFs) such as macrophage-CSF (M-CSF), granulocyte-macrophage-CSF (GM-CSF), and granulocyte-CSF (G-CSF), interleukins (ILs) such as IL-1, IL-1α, IL-2, IL-3, IL-4, IL-5, IL-6, IL-7, IL-8, IL-9, IL-11, IL-12, a tumor necrosis factor such as TNF-α or TNF-β, and other polypeptide factors including LIF and kit ligand (KL). As used herein, the term cytokine includes proteins from natural sources or from recombinant cell culture and biologically active equivalents of the native sequence cytokines.

"Therapeutically effective amount" is the amount of active PRO301, PRO362, PRO245 or PRO1868 antagonist or agonist which is required to achieve a measurable inhibition or stimulation, as the case may be, of the inflammatory response.

A "native sequence PRO301, PRO362, PRO245 or PRO1868", comprises a polypeptide having the same amino acid sequence as a PRO301, PRO362, PRO245 or PRO1868 respectively, derived from nature. Such native sequence PRO301, PRO362, PRO245 or PRO1868 can be isolated from nature or can be produced by recombinant or synthetic means. The terms "native sequence PRO301", "native sequence PRO362," "native sequence PRO245" and "native sequence PRO1868" specifically encompass naturally-occurring truncated or secreted forms of PRO301, PRO362, PRO245 and PRO1868 respectively (e.g., an extracellular domain sequence), naturally-occurring variant forms (e.g., alternatively spliced forms) and naturally-occurring allelic variants of PRO301, PRO362, PRO245 or PRO1868, respectively.

In one embodiment, the native sequence PRO301 is a mature or full-length native sequence PRO301 comprising amino acids 1 to 299 of FIG. 2 (SEQ ID NO: 1), with or without the N-terminal signal sequence, with or without the initiating methionine at position 1, with or without the potential transmembrane domain at about position 236 to about 258, and with or without the intracellular domain at about position 259 to 299.

In another embodiment, the native sequence STIgMA polypeptide is a mature or full-length native sequence PRO362 comprising amino acids 1 to 321 of FIG. 3 (SEQ ID NO: 2), with or without an N-terminal signal sequence, with or without the initiating methionine at position 1, with or without of any or all of the potential transmembrane domain, at about positions 276-306, and with or without the intracellular domain at about positions 307 to 321. In a further embodiment, the native sequence STIgMA polypeptide is a mature or full-length polypeptide comprising amino acids 1 to 399 of SEQ ID NO: 32 (huSTIgMA), with or without an N-terminal signal sequence, with or without the initiating methionine at position 1, and with or without of any or all of the transmembrane domain at about positions 277 to 300. In a still further embodiment, the native sequence STIgMA polypeptide is a mature or full-length polypeptide comprising amino acids 1 to 305 of SEQ ID NO: 33 (huSTIgMA short), with or without an N-terminal signal sequence, with or without the initiating methionine at position 1, and with or without of any or all of the transmembrane domain at about positions 183 to 206. In a different embodiment, the native sequence STIgMA polypeptide is a mature or full length polypeptide comprising amino acids 1 to 280 of SEQ ID NO: 34 (muS-TIgMA), with or without an N-terminal signal sequence, with or without the initiating methionine at positions 1, and with or without of any or all of the transmembrane domain at about positions 181 to 204.

In yet another embodiment, the native sequence PRO245 polypeptide is a mature or full-length native sequence PRO245 polypeptide comprising amino acids 1 to 312 of FIG. 11 (SEQ ID NO: 9), with or without an N-terminal signal sequence, with or without the initiating methionine at position 1, with or without a potential transmembrane domain, and with or without an intracellular domain.

In yet another embodiment, the native sequence PRO1868 polypeptide is a mature or full-length native sequence PRO1868 polypeptide comprising amino acids 1 to 310 of FIG. 22 (SEQ ID NO: 31), with or without the N-terminal signal sequence at about positions 1 to 30, with or without the initiating methionine at position 1, with or without the potential transmembrane domain at about position 242 to about 266, and with or without the intracellular domain at about position 267 to 310.

The "PRO301, PRO362 (STIgMA), PRO245 or PRO1868 extracellular domain" or "PRO301, PRO362, PRO245 or PRO1868 ECD" refers to a form of the PRO301, PRO362 (STIgMA), PRO245 or PRO1868 polypeptide, respectively, which is essentially free of the transmembrane and cytoplasmic domains of the respective full length molecules. Ordinarily, PRO301 ECD, PRO362 (STIgMA) ECD, PRO245 ECD or PRO1868 ECD will have less than 1% of such transmembrane and/or cytoplasmic domains and preferably, will have less than 0.5% of such domains.

Optionally, PRO301 polypeptide ECD will comprise amino acid residues 1 or about 28 to X, wherein X is any amino acid from amino acid 231 to amino acid 241 of FIG. 2 (SEQ ID NO: 1).

Optionally, PRO362 (STIgMA) polypeptide ECD will comprise amino acid residues 1 or about 21 to X of FIG. 3 (SEQ ID NO: 2), or SEQ ID NO: 32, where X is any amino acid from about 271 to 281, or amino acid residues 1 or about 21 to X of SEQ ID NO: 33, where X is any amino acid from about 178 to 186, or amino acid residues 1 or about 21 to X of SEQ ID NO: 34, wherein X is any amino acid from about 176 to 184 of SEQ ID NO: 34.

Optionally, PRO245 polypeptide ECD will comprise amino acid residues 1 or about 29 to X, wherein X is any amino acid from amino acid 232 to amino acid 242.

Optionally, PRO1868 polypeptide ECD will comprise amino acid residues 1 or about 31 to X, wherein X is any amino acid from amino acid 237 to amino acid 247.

It will be understood that any transmembrane domain identified for the PRO301, PRO362 (STIgMA), PRO245 or PRO1868 polypeptides of the present invention is identified pursuant to criteria routinely employed in the art for identifying that type of hydrophobic domain. The exact boundaries of a transmembrane domain may vary but most likely by no more than about 5 amino acids at either end of the domain as initially identified.

"PRO301 variant" means an active PRO301 as defined below having at least about 80% amino acid sequence identity to (a) a DNA molecule encoding a PRO301 polypeptide, with or without its native signal sequence, with or without the initiating methionine, with or without the potential transmembrane domain, and with or without the intracellular domain or (b) the complement of the DNA molecule of (a). In a particular embodiment, the PRO301 variant has at least about 80% amino acid sequence homology with the PRO301 having the deduced amino acid sequence shown in FIG. 1 (SEQ ID NO: 1) for a full-length native sequence PRO301. Such PRO301 variants include, for instance, PRO301 polypeptides wherein one or more amino acid residues are added, or deleted, at the N- or C-terminus of the sequence of FIG. 2 (SEQ ID NO: 1). Preferably, the nucleic acid or amino acid sequence identity is at least about 85%, more preferably at least about 90%, and even more preferably at least about 95%. Preferably, the highest degree of sequence identity occurs within the extracellular domains (amino acids 28 to 235 of FIG. 2, SEQ ID NO: 1).

"PRO245 variant" means an active PRO245 as defined below having at least about 80% amino acid sequence identity to (a) a DNA molecule encoding a PRO245 polypeptide, with or without its native signal sequence, with or without the initiating methionine, with or without the potential transmembrane domain, and with or without the intracellular domain or (b) the complement of the DNA molecule of (a). In a particular embodiment, the PRO245 variant has at least about 80% amino acid sequence homology with the PRO245 having the deduced amino acid sequence shown in FIG. 1 (SEQ ID NO: 9) for a full-length native sequence PRO245. Such PRO245 variants include, for instance, PRO245 polypeptides wherein one or more amino acid residues are added, or deleted, at the N- or C-terminus of the sequence of SEQ ID NO: 9. Preferably, the nucleic acid or amino acid sequence identity is at least about 85%, more preferably at least about 90%, and even more preferably at least about 95%.

"PRO362 variant" means an active PRO362 polypeptide as defined below having at least about 80% amino acid sequence identity to (a) a DNA molecule encoding a PRO362 polypeptide, with or without its native signal sequence, with or without the initiating methionine, with or without the potential transmembrane domain, and with or without the intracellular domain or (b) the complement of the DNA molecule of (a). In a particular embodiment, the PRO362 variant has at least about 80% amino acid sequence homology with the PRO362 polypeptide having the deduced amino acid sequence shown in FIG. 3 (SEQ ID NO: 2) for a full-length native sequence PRO362 polypeptide. Such PRO362 polypeptide variants include, for instance, PRO362 polypeptides wherein one or more amino acid residues are added, or deleted, at the N- or C-terminus of the sequence of FIG. 3 (SEQ ID NO: 2). Ordinarily, a PRO362 polypeptide variant will have at least about 80% amino acid sequence identity, preferably at least about 85% amino acid sequence identity, more preferably at least about 90% amino acid sequence identity and even more preferably at least about 95% amino acid sequence identity with the amino acid sequence of FIG. 3 (SEQ ID NO: 2). Preferably, the highest degree of sequence identity occurs within the extracellular domains (amino acids 1 to X of FIG. 3, SEQ ID NO: 2, where X is any amino acid residue from 271 to 281).

A "STIgMA variant" specifically includes the PRO362 variants defined above, along with variants of SEQ ID NOS: 32, 33, and 34. In particular, STIgMA variants specifically include an active STIgMA polypeptide as defined below having at least about 80% amino acid sequence identity to (a) a DNA molecule encoding a polypeptide or SEQ ID NO: 32, 33, or 34, with or without its native signal sequence, with or without the initiating methionine, with or without all or part of the potential transmembrane domain, and with or without the intracellular domain or (b) the complement of the DNA molecule of (a). In a particular embodiment, the STIgMA variant has at least about 80% amino acid sequence homology with the STIgMA polypeptide having the deduced amino acid sequence of SEQ ID NO: 32, 33, or 34. Such STIgMA variants include, for instance, STIgMA polypeptides wherein one or more amino acid residues are added, or deleted, at the N- or C-terminus of the sequence of SEQ ID NOS: 32, 33, and 34. Ordinarily, a STIgMA polypeptide variant will have at least about 80% amino acid sequence identity, preferably at least about 85% amino acid sequence identity, more preferably at least about 90% amino acid sequence identity and even more preferably at least about 95% amino acid sequence identity with the amino acid sequence of SEQ ID NO: 32, 33, or 34. Preferably, the highest degree of sequence identity occurs within the extracellular domains.

"PRO1868 variant" means an active PRO1868 polypeptide as defined below having at least about 80% amino acid sequence identity to (a) a DNA molecule encoding a PRO1868 polypeptide, with or without its native signal sequence, with or without the initiating methionine, with or without the potential transmembrane domain, and with or without the intracellular domain or (b) the complement of the DNA molecule of (a). In a particular embodiment, the PRO1868 variant has at least about 80% amino acid sequence homology with the with the PRO1868 polypeptide having the deduced amino acid sequence of SEQ ID NO: 31 encoding a full-length native sequence PRO1868 polypeptide. Such PRO1868 polypeptide variants include, for instance, PRO1868 polypeptides wherein one or more amino acid residues are added, or deleted, at the N- or C-terminus of the sequence of SEQ ID NO: 31. Ordinarily, a PRO1868 polypeptide variant will have at least about 80% amino acid sequence identity, preferably at least about 85% amino acid sequence identity, more preferably at least about 90% amino acid sequence identity and even more preferably at least about 95% amino acid sequence identity with the amino acid sequence of SEQ ID NO: 31.

"Percent (%) amino acid sequence identity" with respect to the PRO301, PRO362 (STIgMA), PRO245 or PRO1868 sequences identified herein is defined as the percentage of amino acid residues in a candidate sequence that are identical with the amino acid residues in the PRO301, PRO362 (STIgMA), PRO245 or PRO1868 sequence, respectively, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the PRO301-, PRO362 (STIgMA), PRO245- or PRO1868- encoding sequences identified herein (e.g., DNA40628, DNA45416, DNA35638, DNA77624) is defined as the percentage of nucleotides in a candidate sequence that are identical with the nucleotides in the PRO301-, PRO362 (STIgMA)-, PRO245- or PRO1868-encoding sequence, respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express an encoded polypeptide where, for example, the nucleic acid molecule is in a chromosomal location different from that of natural cells.

An "isolated" PRO301, PRO362(STIgMA), PRO245 or PRO1868 polypeptide-encoding nucleic acid molecule is a nucleic acid molecule that is identified and separated from at least one contaminant nucleic acid molecule with which it is ordinarily associated in the natural source of the PRO301, PRO362 (STIgMA), PRO245 or PRO1868 polypeptide-encoding nucleic acid. An isolated PRO301, PRO362 (STIgMA), PRO245 or PRO1868 polypeptide-encoding nucleic acid molecule is other than in the form or setting in which it is found in nature. Isolated PRO301, PRO362, PRO245 or PRO1868 polypeptide-encoding nucleic acid molecules therefore are distinguished from the DNA40628, DNA45416, DNA35638 or DNA77624 nucleic acid molecules, respectively, as they exists in natural cells. However, an isolated PRO301, PRO362, PRO245 or PRO1868 polypeptide-encoding nucleic acid molecule includes PRO301, PRO362, PRO245 or PRO1868 polypeptide-encoding nucleic acid molecules contained in cells that ordinarily express PRO301, PRO362, PRO245 or PRO1868 polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, without limitation, single anti-PRO301, anti-PRO362 (anti-STIgMA), anti-PRO245 or anti-PRO1868 monoclonal antibodies (including agonist, antagonist, and neutralizing antibodies) and anti-PRO301, anti-PRO362, anti-PRO245 or anti-PRO1868 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of the invention fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" in the context of variants of the polypeptide of the invention refers to form(s) of proteins of the invention which retain the biologic and/or immunologic activities of a native or naturally-occurring polypeptide of the invention.

"Biological activity" in the context of an antibody, polypeptide or another molecule that can be identified by the screening assays disclosed herein (e.g. an organic or inorganic small molecule, peptide, etc.) refers, in part, to the ability of such molecules to alter infiltration of inflammatory cells into a tissue, to alter T-cell proliferation and to alter lymphokine release by cells. Another preferred activity an affect on vascular permeability.

The term "antagonist" is used in the broadest sense, and includes any molecule that partially or fully blocks, inhibits, or neutralizes a biological activity of a native polypeptide of the invention disclosed herein. In a similar manner, the term "agonist" is used in the broadest sense and includes any molecule that mimics or stimulates a biological activity of a native polypeptide of the invention disclosed herein. Suitable agonist or antagonist molecules specifically include agonist or antagonist antibodies or antibody fragments, fragments or amino acid sequence variants of native polypeptides of the invention, peptides, small molecules, including small organic molecules, etc.

A "small molecule" is defined herein to have a molecular weight below about 600 daltons.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., *NIH Publ. No.* 91-3242, Vol. I, pages 647-669 (1991)). The constant domains are not involved directly in binding an antibody to an antigen, but exhibit various effector functions, such as participation of the antibody in antibody-dependent cellular toxicity.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment. The designation "Fc" reflects the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 [1975], or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 [1991] and Marks et al., *J. Mol. Biol.*, 222: 581-597 (1991), for example. See also U.S. Pat. Nos. 5,750,373, 5,571,698, 5,403,484 and 5,223,409 which describe the preparation of antibodies using phagemid and phage vectors.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which several or all residues from a complementarity-determining region (CDR) of the recipient are replaced by residues from a CDR of a non-human species (donor antibody) such as mouse, rat or rabbit having the desired specificity, affinity, and capacity. In some instances, certain Fv framework region (FR) residues of the human immunoglobulin can also be replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 [1988]; and Presta, Curr. Op. Struct. Biol., 2: 593-596 (1992). The humanized antibody includes a "primatized" antibody where the antigen-binding region of the antibody is derived from an antibody produced by immunizing macaque monkeys with the antigen of interest. Antibodies containing residues from Old World monkeys are also possible within the invention. See, for example, U.S. Pat. Nos. 5,658,570; 5,693,780; 5,681,722; 5,750,105; and 5,756,096.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

An "isolated" polypeptide, including an isolated antibody, is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the polypeptide will be purified (1) to greater than 95% by weight of the compound as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated compound, e.g. antibody or other polypeptide, includes the compound in situ within recombinant cells since at least one component of the compound's natural environment will not be present. Ordinarily, however, isolated compound will be prepared by at least one purification step.

The word "label" when used herein refers to a detectable compound or composition which is conjugated directly or indirectly to a compound, e.g. antibody or polypeptide, so as to generate a "labeled" compound. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the compound of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

II. Compositions and Methods of the Invention

A. Preparation of the PRO301, PRO362, PRO245 or PRO1868 Polypeptides

1. Full-Length PRO301, PRO362, PRO245 or PRO1868 Polypeptides

The present invention provides newly identified and isolated nucleotide sequences encoding polypeptides referred to in the present application as PRO301, PRO362, PRO245 or PRO1868. In particular, Applicants have identified and isolated cDNA encoding a PRO301, PRO362, PRO245 or PRO1868 polypeptide, as disclosed in further detail in the Examples below. Using BLAST and FastA sequence alignment computer programs, Applicants found that full-length native sequence PRO301 (FIG. 2, SEQ ID NO: 1), PRO362 (FIG. 3, SEQ ID NO: 3), PRO245 (FIG. 11, SEQ ID NO: 9) and PRO1868 (SEQ ID NO: 31) have significant homology to both A33 antigen and JAM. (See FIGS. 1, 12-18). Accordingly, it is presently believed that PRO301, PRO362, PRO245 and PRO1868 disclosed in the present application are newly identified members of the A33 antigen protein family and may be associated with inflammatory disorders such as inflammatory bowel disease as well as human neoplastic diseases such as colorectal cancer.

2. PRO301, PRO362, PRO245 or PRO1868 Variants

In addition to the full-length native sequence PRO301, PRO362, PRO245 or PRO1868 described herein, it is contemplated that PRO301, PRO362, PRO245 or PRO1868 variants can be prepared. PRO301, PRO362, PRO245 or PRO1868 variants can be prepared by introducing appropriate nucleotide changes into the PRO301, PRO362, PRO245 or PRO1868 DNA, respectively, or by synthesis of the desired PRO301, PRO362, PRO245 or PRO1868 polypeptides. Those skilled in the art will appreciate that amino acid changes may alter post-translational processes of the PRO301, PRO362, PRO245 or PRO1868, such as changing the number or position of glycosylation sites or altering the membrane anchoring characteristics.

Variations in the native full-length sequence PRO301, PRO362, PRO245 or PRO1868 or in various domains of the PRO301, PRO362, PRO245 or PRO1868 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO301, PRO362, PRO245 or PRO1868 that results in a change in the amino acid sequence of the PRO301, PRO362, PRO245 or PRO1868 as compared with the native sequence PRO301, PRO362, PRO245 or PRO1868. Optionally the variation is by substitution of at least one amino acid with any other amino acid in one or more of the domains of the PRO301, PRO362, PRO245 or PRO1868. Guidance in determining which amino acid residue may be inserted, substituted or deleted without adversely affecting the desired activity may be found by comparing the sequence of the PRO301, PRO362, PRO245 or PRO1868 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO301, PRO362, PRO245 or PRO1868 variant DNA.

Scanning amino acid analysis can also be employed to identify one or more amino acids that may be varied along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

3. Modifications of PRO301, PRO362, PRO245 or PRO1868

Covalent modifications of PRO301, PRO362, PRO245 or PRO1868 are included within the scope of this invention. One type of covalent modification includes reacting targeted amino acid residues of the PRO301, PRO362, PRO245 or PRO1868 with an organic derivatizing agent that is capable of reacting with selected side chains or the N- or C-terminal residues of the PRO301, PRO362, PRO245 or PRO1868. Derivatization with bifunctional agents is useful, for instance, for crosslinking PRO301, PRO362, PRO245 or PRO1868 to a water-insoluble support matrix or surface for use in the method for purifying anti-PRO301, anti-PRO362, anti-PRO245 or anti-PRO1868 antibodies, respectively, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl) dithio]pro-pioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: *Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO301, PRO362, PRO245 or PRO1868 polypeptide included within the scope of this invention comprises altering the native glycosylation pattern of the polypeptide. "Altering the native glycosylation pattern" is intended for purposes herein to mean deleting one or more carbohydrate moieties found in native sequence PRO301, PRO362, PRO245 or PRO1868, and/or adding one or more glycosylation sites that are not present in the native sequence PRO301, PRO362, PRO245 or PRO1868, and/or alteration of the ratio and/or composition of the sugar residues attached to the glycosylation site(s).

Addition of glycosylation sites to the PRO301, PRO362, PRO245 or PRO1868 polypeptide may be accomplished by altering the amino acid sequence. The alteration may be made, for example, by the addition of, or substitution by, one or more serine or threonine residues to the native sequence PRO301, PRO362, PRO245 or PRO1868 (for O-linked glycosylation sites). The PRO301, PRO362, PRO245 or PRO1868 amino acid sequence may optionally be altered through changes at the DNA level, particularly by mutating the DNA encoding the PRO301, PRO362, PRO245 or PRO1868 polypeptide at preselected bases such that codons are generated that will translate into the desired amino acids.

Another means of increasing the number of carbohydrate moieties on the PRO301, PRO362, PRO245 or PRO1868 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO301, PRO362, PRO245 or PRO1868 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138: 350 (1987).

Another type of covalent modification of PRO301, PRO362, PRO245 or PRO1868 comprises linking the PRO301, PRO362, PRO245 or PRO1868 polypeptide to one of a variety of nonproteinaceous polymers, e.g., polyethylene glycol, polypropylene glycol, or polyoxyalkylenes, for example in the manner set forth in U.S. Pat. Nos. 4,640,835; 4,496,689; 4,301,144; 4,670,417; 4,791,192 or 4,179,337.

The PRO301, PRO362, PRO245 or PRO1868 of the present invention may also be modified in a way to form a chimeric molecule comprising PRO301, PRO362, PRO245 or PRO1868 fused to another, heterologous polypeptide or amino acid sequence. In one embodiment, such a chimeric molecule comprises a fusion of the PRO301, PRO362, PRO245 or PRO1868 with a tag polypeptide which provides an epitope to which an anti-tag antibody can selectively bind. The epitope tag is generally placed at the amino- or carboxyl-terminus of the PRO301, PRO362, PRO245 or PRO1868. The presence of such epitope-tagged forms of the PRO301, PRO362, PRO245 or PRO1868 can be detected using an antibody against the tag polypeptide. Also, provision of the epitope tag enables the PRO301, PRO362, PRO245 or PRO1868 to be readily purified by affinity purification using an anti-tag antibody or another type of affinity matrix that binds to the epitope tag. In an alternative embodiment, the chimeric molecule may comprise a fusion of the PRO301, PRO362, PRO245 or PRO1868 with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

4. Production and Isolation of PRO301, PRO362 PRO245 or PRO1868

The description below relates primarily to production of PRO301, PRO362, PRO245 or PRO1868 by culturing cells transformed or transfected with a vector containing PRO301, PRO362, PRO245 or PRO1868 nucleic acid. It is, of course, contemplated that alternative methods, which are well known in the art, may be employed to prepare PRO301, PRO362, PRO245 or PRO1868. For instance, the PRO301, PRO362, PRO245 or PRO1868 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO301, PRO362, PRO245 or PRO1868 may be chemically synthesized separately and combined using chemical or enzymatic methods to produce the full-length PRO301, PRO362, PRO245 or PRO1868.

a. Isolation of DNA Encoding PRO301, PRO362, PRO245 or PRO1868

DNA encoding PRO301, PRO362, PRO245 or PRO1868 may be obtained from a cDNA library prepared from tissue believed to possess the PRO301, PRO362, PRO245 or PRO1868 mRNA and to express it at a detectable level. Accordingly, human PRO301, PRO362, PRO245 or PRO1868 DNA can be conveniently obtained from a cDNA library prepared from human tissue, such as described in the Examples. The PRO301-, PRO362-, PRO245- or PRO1868-encoding gene may also be obtained from a genomic library or by oligonucleotide synthesis.

Libraries can be screened with probes (such as antibodies to PRO301, PRO362, PRO245 or PRO1868 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO301, PRO362, PRO245 or PRO1868 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

b. Selection and Transformation of Host Cells

Host cells are transfected or transformed with expression or cloning vectors described herein for PRO301, PRO362, PRO245 or PRO1868 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (M Press, 1991) and Sambrook et al., supra.

Methods of transfection are known to the ordinarily skilled artisan, for example, CaPO4 and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635).

In addition to prokaryotes, eukaryotic microbes such as filamentous fungi or yeast are suitable cloning or expression hosts for PRO301-, PRO362-, PRO245- or PRO1868-encoding vectors. *Saccharomyces cerevisiae* is a commonly used lower eukaryotic host microorganism.

Suitable host cells for the expression of glycosylated PRO301, PRO362, PRO245 or PRO1868 are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 cells transformed by SV40 (COS-7, ATCC CRL 1651); human embryonic kidney cells (293 or 293 cells subcloned for growth in suspension culture, Graham et al., *J. Gen Virol.*, 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor cells (MMT 060562, ATCC CCL51). The selection of the appropriate host cell is deemed to be within the skill in the art.

c. Selection and Use of a Replicable Vector

The nucleic acid (e.g., cDNA or genomic DNA) encoding PRO301, PRO362, PRO245 or PRO1868 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO301, PRO362, PRO245 or PRO1868 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO301, PRO362, PRO245 or PRO1868 DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including *Saccharomyces* and *Kluyveromyces*"—factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO301, PRO362, PRO245 or PRO1868 nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO301, PRO362, PRO245 or PRO1868 nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding PRO301, PRO362, PRO245 or PRO1868.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO301, PRO362, PRO245 or PRO1868 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO301, PRO362, PRO245 or PRO1868 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO301, PRO362, PRO245 or PRO1868 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO301, PRO362, PRO245 or PRO1868.

Still other methods, vectors, and host cells suitable for adaptation to the synthesis of PRO301, PRO362, PRO245 or PRO1868 in recombinant vertebrate cell culture are described in Gething et al., *Nature*, 293:620-625 (1981); Mantei et al., *Nature*, 281:40-46 (1979); EP 117,060; and EP 117,058.

d. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO301, PRO362, PRO245 or PRO1868 polypeptide or against a synthetic peptide based on the DNA sequences provided herein or against exogenous sequence fused to PRO301, PRO362, PRO245 or PRO1868 DNA and encoding a specific antibody epitope.

e. Purification of Polypeptide

Forms of PRO301, PRO362, PRO245 or PRO1868 may be recovered from culture medium or from host cell lysates. If membrane-bound, it can be released from the membrane using a suitable detergent solution (e.g. Triton-X 100) or by enzymatic cleavage. Cells employed in expression of PRO301, PRO362, PRO245 or PRO1868 can be disrupted by various physical or chemical means, such as freeze-thaw cycling, sonication, mechanical disruption, or cell lysing agents.

It may be desired to purify PRO301, PRO362, PRO245 or PRO1868 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO301, PRO362, PRO245 or PRO1868. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO301, PRO362, PRO245 or PRO1868 produced.

f. Detection of Cell Interactions

To determine whether the polypeptides of the invention are trafficking or cell adhesion molecules, a number of in vitro assays may be performed.

1) Flow Cytometry/FACS Analysis

To examine the interaction between PRO301, PRO362, PRO245 or PRO1868 with specific cell types, biotinylated human IgG fusion proteins, such as PRO301-human IgG fusion, PRO362-human IgG fusion, PRO245-human IgG fusion or PRO1868-human IgG fusion, may be generated. Cells that interact with the biotinylated fusion proteins may be isolated using streptavidin-conjugated magnetic beads. The cells that interact with the biotinylated fusion proteins may be further characterized and analyzed for surface CD-Ag expression by flow cytometry and/or FACS sorting. Cells examined for interaction with biotinylated PRO301-human IgG fusion, PRO362-human IgG fusion, PRO245-human IgG fusion or PRO1868-human IgG fusion, may include, for example, peripheral blood cells, such as NK cells, NK/T cells or cytolytic T cells and more specifically, purified B cells, neutrophils, monocytes or dendritic cells.

The inhibition of the interaction between PRO301, PRO362, PRO245 or PRO1868 with specific cell types may further be characterized by inhibition analysis, specifically the ability of antibodies, such as anti-PRO301, anti-PRO245, anti-PRO362 or anti-PRO1868 to inhibit such cell interaction.

2) Coimmunoprecipitation

Upon the identification of PRO301, PRO362, PRO245 or PRO1868-interacting cells, further analysis may be performed to identify the particular receptor responsible for the PRO301, PRO362, PRO245 or PRO1868 interaction. For example, coimmunoprecipitation analysis may be performed to identify the receptor on PRO245-interacting cells. Antibodies against PRO245 may be incubated with the PRO245-interacting cells. The immunoprecipitates may then be analyzed by SDS-PAGE and immunoblotting with antibodies against potential receptors. To determine whether the receptor for PRO245 is a protein that belongs to the JAM family of proteins, antibodies used for the immunoblotting may include anti-PRO301, anti-PRO362 or anti-PRO1868. Such analysis may result in the identification of a pair of interacting proteins that belong to the A33/JAM family of adhesion molecules.

5. Tissue Distribution

The location of tissues expressing the polypeptides of the invention can be identified by determining, for example, mRNA expression or protein expression in various human tissues. The location of such genes provides information about which tissues are most likely to be affected by the stimulating and inhibiting activities of the polypeptides of the invention. The location of a gene in a specific tissue also provides sample tissue for the activity blocking assays discussed below.

Gene expression in various tissues may be measured by conventional Southern blotting, Northern blotting to quantitate the transcription of mRNA (Thomas, *Proc. Natl. Acad. Sci. USA*, 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a polypeptide of the invention or against a synthetic peptide based on the DNA sequences encoding the polypeptide of the invention or against an exogenous sequence fused to a DNA encoding a polypeptide of the invention and encoding a specific antibody epitope. General techniques for generating antibodies, and special protocols for Northern blotting and in situ hybridization are provided below.

6. Antibody Binding Studies

The activity of the polypeptides of the invention can be further verified by antibody binding studies, in which the ability of anti-PRO301, anti-PRO362, anti-PRO245 or anti-PRO1868 antibodies to inhibit the effect of the PRO301, PRO362, PRO245 or PRO1868 polypeptides on tissue cells is tested. Exemplary antibodies include polyclonal, monoclonal, humanized, bispecific, and heteroconjugate antibodies, the preparation of which will be described herein below.

Antibody binding studies may be carried out in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

7. Cell-Based Assays

Cell-based assays and animal models for immune related diseases can be used to further understand the relationship between the genes and polypeptides identified herein and the development and pathogenesis of immune related disease.

In a different approach, cells of a cell type known to be involved in a particular immune related disease are transfected with the cDNAs described herein, and the ability of these cDNAs to alter immune function is analyzed. Suitable cells can be transfected with the desired gene, and monitored for immune function activity. Such transfected cell lines can then be used to test the ability of poly- or monoclonal antibodies or antibody compositions to alter immune function, for example to modulate T-cell proliferation or inflammatory cell infiltration. Cells transfected with the coding sequences of the genes identified herein can further be used to identify drug candidates for the treatment of immune related diseases.

In addition, primary cultures derived from transgenic animals (as described below) can be used in the cell-based assays herein, although stable cell lines are preferred. Techniques to derive continuous cell lines from transgenic animals are well known in the art (see, e.g. Small et al., *Mol. Cell. Biol.* 5, 642-648 [1985]).

One suitable cell based assay is the mixed lymphocyte reaction (MLR). *Current Protocols in Immunology*, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate the proliferation of activated T cells is assayed. A suspension of responder T cells is cultured with allogenic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. *Current Protocols in Immunology*, supra, 3.15, 6.3.

A proliferative T cell response in an MLR assay may be due to a mitogenic response or may be due to a stimulatory response by the T cells. Additional verification of the T cell stimulatory activity of the polypeptides of the invention can be obtained by a costimulation assay. T cell activation requires an antigen specific signal mediated through the major histocompatability complex (MHC) and a costimulatory signal mediated through a second ligand binding interaction, for example, the B7(CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive costimulation effect of T cell activation; conversely, CTLA-4 binding to B7 has a negative T cell deactivating effect. Chambers, C. A. and Allison, J. P., *Curr. Opin. Immunol.* (1997) 9:396. Schwartz, R. H., *Cell* (1992) 71:1065; Linsley, P. S, and Ledbetter, J. A., *Annu. Rev. Immunol.* (1993) 11:191; June, C. H. et al, *Immunol. Today* (1994) 15:321; Jenkins, M. K., *Immunity* (1994) 1:443-446.

Polypeptides of the invention, as well as other compounds of the invention, which are stimulators (costimulators) of T cell proliferation, as determined by MLR assays, for example, are useful in treating immune related diseases characterized by poor, suboptimal or inadequate immune function. These diseases are treated by stimulating the proliferation and activation of T cells (and T cell mediated immunity) and enhancing the immune response in a mammal through administration of a stimulatory compound, such as the stimulating polypeptides of the invention. The stimulating polypeptide may be a PRO301, PRO362, PRO245 or PRO1868 polypeptide or an agonist antibody therefor. Immunoadjuvant therapy for treatment of tumors, described in more detail below, is an example of this use of the stimulating compounds of the invention. Antibodies which bind to inhibitory polypeptides function to enhance the immune response by removing the inhibitory effect of the inhibiting polypeptides. This effect is seen in experiments using anti-CTLA-4 antibodies which enhance T cell proliferation, presumably by removal of the inhibitory signal caused by CTLA-4 binding. Walunas, T. L. et al, *Immunity* (1994) 1:405. This use is also validated in experiments with 4-1BB glycoprotein, a member of the tumor necrosis factor receptor family which binds to a ligand (4-1BBL) expressed on primed T cells and signals T cell activation and growth. Alderson, M. E. et al., *J. Immunol.* (1994) 24:2219. Inhibition of 4-1BB binding by treatment with an anti-4-1BB antibody increases the severity of graft-versus-host disease and may be used to eradicate tumors. Hellstrom, I. and Hellstrom, K. E., *Crit. Rev. Immunol.* (1998) 18:1.

On the other hand, polypeptides of the invention, such as antagonist antibodies, as well as other compounds of the invention, which are inhibitors of T cell proliferation/activation and/or lymphokine secretion, can be directly used to suppress the immune response. These compounds are useful to reduce the degree of the immune response and to treat immune related diseases characterized by a hyperactive, superoptimal, or autoimmune response. Alternatively, antibodies which bind to the stimulating polypeptides of the invention and block the stimulating effect of these molecules can be used to suppress the T cell mediated immune response by inhibiting T cell proliferation/activation and/or lymphokine secretion. Blocking the stimulating effect of the polypeptides suppresses the immune response of the mammal.

8. Animal Models

The results of the cell based in vitro assays can be further verified using in vivo animal models and assays for T-cell function. A variety of well known animal models can be used to further understand the role of the genes identified herein in the development and pathogenesis of immune related disease, and to test the efficacy of candidate therapeutic agents, including antibodies, and other antagonists of the native polypeptides, including small molecule antagonists. The in vivo nature of such models makes them particularly predictive of responses in human patients. Animal models of immune related diseases include both non-recombinant and recombinant (transgenic) animals. Non-recombinant animal models include, for example, rodent, e.g., murine models. Such models can be generated by introducing cells into syngenic mice using standard techniques, e.g. subcutaneous injection, tail vein injection, spleen implantation, intraperitoneal implantation, implantation under the renal capsule, etc.

Contact hypersensitivity is a simple in vivo assay of cell mediated immune function. In this procedure, epidermal cells are exposed to exogenous haptens which give rise to a delayed type hypersensitivity reaction which is measured and quantitated. Contact sensitivity involves an initial sensitizing phase followed by an elicitation phase. The elicitation phase occurs when the epidermal cells encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S, and Schwarz, T, *Immun. Today* 19(1):37-44 (1998).

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in *Current Protocols in Immunology*, supra, unit 4.3.

An animal model for skin allograft rejection is a means of testing the ability of T cells to mediate in vivo tissue destruction which is indicative of and a measure of their role in anti-viral and tumor immunity. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, NY, 1989, 889-992. A suitable procedure is described in detail in *Current Protocols in Immunology*, supra, unit 4.4. Other transplant rejection models which can be used to test the compounds of the invention are the allogeneic heart transplant models described by Tanabe, M. et al, *Transplantation* (1994) 58:23 and Tinubu, S. A. et al, *J. Immunol.* (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. The compounds of the invention can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al, *Molec. Med. Today* (1997) 554-561.

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in Current Protocols in Immunology, above, units 15.5. See also the model using a monoclonal antibody to CD18 and VLA-4 integrins described in Issekutz, A. C. et al., *Immunology* (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al, *Am. J. Respir. Cell Mol. Biol.* (1998) 18:777 and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al, *Nat. Med.* (1997) 3:183, in which the mice demonstrate histopathologic skin lesions resembling psoriasis. Another suitable model is the human skin/scid mouse chimera prepared as described by Nickoloff, B. J. et al, *Am. J. Path.* (1995) 146:580.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cell. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 623-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of effects on T cell proliferation. In these experiments, blocking antibodies which bind to the polypeptide of the invention, prepared as described above, are administered to the animal and the effect on immune function is determined.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

9. Immuno Adjuvant Therapy

In one embodiment, compounds of the invention having an immunostimulatory effect can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al, (1996) *Proc. Natl. Acad. Sci. USA,* 93:7149. It has been shown that costimulation of T cells induces tumor regression and an antitumor response both in vitro and in vivo. Melero, I. et al, *Nature Medicine* (1997) 3:682; Kwon, E. D. et al, *Proc. Natl. Acad. Sci. USA* (1997) 94:8099; Lynch, D. H. et al, *Nature Medicine* (1997) 3:625; Finn, O. J. and Lotze, M. T., *J. Immunol.* (1998) 21:114. The stimulatory compounds of the invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the compounds of the invention allows reduced amounts of the growth regulating, cytotoxic, or chemotherapeutic agents thereby potentially lowering the toxicity to the patient.

Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state a cell proliferates under conditions in which normal cells would not grow. Cancer manifests itself in a wide variety of forms, characterized by different degrees of invasiveness and aggressiveness.

Alteration of gene expression is intimately related to the uncontrolled cell growth and de-differentiation which are a common feature of all cancers. The genomes of certain well studied tumors have been found to show decreased expression of recessive genes, usually referred to as tumor suppression genes, which would normally function to prevent malignant cell growth, and/or overexpression of certain dominant genes, such as oncogenes, that act to promote malignant growth. Each of these genetic changes appears to be responsible for importing some of the traits that, in aggregate, represent the full neoplastic phenotype (Hunter, *Cell* 64, 1129 [1991]; Bishop, *Cell* 64, 235-248 [1991]).

A well known mechanism of gene (e.g. oncogene) overexpression in cancer cells is gene amplification. This is a process where in the chromosome of the ancestral cell multiple copies of a particular gene are produced. The process involves unscheduled replication of the region of chromosome comprising the gene, followed by recombination of the replicated segments back into the chromosome (Alitalo et al., *Adv. Cancer Res.* 47, 235-281 [1986]). It is believed that the overexpression of the gene parallels gene amplification, i.e. is proportionate to the number of copies made.

Proto-oncogenes that encode growth factors and growth factor receptors have been identified to play important roles in the pathogenesis of various human malignancies, including breast cancer. For example, it has been found that the human ErbB2 gene (erbB2, also known as her2, or c-erbB-2), which encodes a 185-kd transmembrane glycoprotein receptor ($p185^{HER2}$; HER2) related to the epidermal growth factor receptor (EGFR), is overexpressed in about 25% to 30% of human breast cancer (Slamon et al., *Science* 235:177-182 [1987]; Slamon et al., *Science* 244:707-712 [1989]).

It has been reported that gene amplification of a protooncogene is an event typically involved in the more malignant forms of cancer, and could act as a predictor of clinical outcome (Schwab et al., *Genes Chromosomes Cancer* 1, 181-193 [1990]; Alitalo et al., supra). Thus, erbB2 overexpression is commonly regarded as a predictor of a poor prognosis, especially in patients with primary disease that involves axillary lymph nodes (Slamon et al., [1987] and [1989], supra; Ravdin and Chamness, *Gene* 159:19-27 [1995]; and Hynes and Stem, *Biochim Biophys Acta* 1198:165-184 [1994]), and has been linked to sensitivity and/or resistance to hormone therapy and chemotherapeutic regimens, including CMF (cyclophosphamide, methotrexate, and fluoruracil) and anthracyclines (Baselga et al., *Oncology* 11 (3 Suppl 1):43-48 [1997]). However, despite the association of erbB2 overexpression with poor prognosis, the odds of HER2-positive patients responding clinically to treatment with taxanes were greater than three times those of HER2-negative patients (Ibid). A recombinant humanized anti-ErbB2 (anti-HER2) monoclonal antibody (a humanized version of the murine anti-ErbB2 antibody 4D5, referred to as rhuMAb HER2 or Herceptin7) has been clinically active in patients with ErbB2-overexpressing metastatic breast cancers that had received extensive prior anticancer therapy. (Baselga et al., *J. Clin. Oncol.* 14:737-744 [1996]).

10. Screening Assays for Drug Candidates

Screening assays for drug candidates are designed to identify compounds that bind or complex with the polypeptides encoded by the genes identified herein or a biologically active fragment thereof, or interfere with the expression and/or activity of the polypeptides encoded by genes identified herein or with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g. on a microtiter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed, e.g. by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular protein encoded by a gene identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature* (London) 340, 245-246 (1989); Chien et al., *Proc. Natl. Acad. Sci. USA* 88, 9578-9582 (1991)] as disclosed by Chevray and Nathans [*Proc. Natl. Acad. Sci. USA* 89, 5789-5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a gene identified herein and other intra- or extracellular components can be tested, a reaction mixture is usually prepared containing the product of the gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described above. The formation of a complex in the control reaction(s) but not in the reaction mixture containing the test compound indicates that the test compound interferes with the interaction of the test compound and its reaction partner.

11. Compositions and Methods for the Treatment of Immune Related Diseases

The compositions useful in the treatment of immune related diseases include, without limitation, antibodies, small organic and inorganic molecules, peptides, phosphopeptides, antisense and ribozyme molecules, triple helix molecules, etc. that inhibit or stimulate immune function, for example, T cell proliferation/activation, lymphokine release, or immune cell infiltration, depends on the disease to be treated.

For example, antisense RNA and RNA molecule act to directly block the translation of mRNA by hybridizing to targeted mRNA and preventing protein translation. When antisense DNA is used, oligodeoxyribonucleotides derived from the translation initiation site, e.g. between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g. Rossi, *Current Biology* 4, 469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g. PCT publication No. WO 97/33551, supra.

These molecules can be identified by any or any combination of the screening assays discussed above and/or by any other screening techniques well known for those skilled in the art.

12. Antibodies

Among the most promising drug candidates according to the present invention are antibodies and antibody fragments which may inhibit (antagonists) or stimulate (agonists) T cell proliferation, leucocyte infiltration, etc. Exemplary antibodies include polyclonal, monoclonal, humanized, bispecific and heteroconjugate antibodies.

a. Polyclonal Antibodies

Methods of preparing polyclonal antibodies are known to skilled artisan. Polyclonal antibodies can be raised in a mammal, for example, by one or more injections of an immunizing agent, and, if desired, an adjuvant. Typically, the immunizing agent and/or adjuvant will be injected in the mammal by multiple subcutaneous or intraperitoneal injections. The immunizing agent may include the PRO301, PRO362, PRO245 or PRO1868 polypeptide of the invention or a fragment or fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

b. Monoclonal Antibodies

Antibodies which recognize and bind to the polypeptides of the invention or which act as antagonists thereto may, alternatively be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO301, PRO362, PRO245 or PRO1868 polypeptide of the invention, an antigenic fragment or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against the polypeptide of the invention or having similar activity as the polypeptide of the invention. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxyapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies are preferably monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

c. Human and Humanized Antibodies

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and coworkers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991); U.S. Pat. No. 5,750,373]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature_Biotechnology 14, 845-51 (1996); Neuberger, Nature Biotechnology 14, 826 (1996); Lonberg and Huszar, Intern. Rev. Immunol. 13 65-93 (1995).

d. Bispecific Antibodies

Bispecific antibodies are monoclonal, preferably human or humanized, antibodies that have binding specificities for at least two different antigens. In the present case, one of the binding specificities may be for the polypeptide of the invention, the other one is for any other antigen, and preferably for a cell-surface protein or receptor or receptor subunit.

Methods for making bispecific antibodies are known in the art. Traditionally, the recombinant production of bispecific antibodies is based on the coexpression of two immunoglobulin heavy-chain/light-chain pairs, where the two heavy chains have different specificities (Milstein and Cuello, Nature, 305:537-539 [1983]). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are cotransfected into a suitable host organism. For further details of generating bispecific antibodies see, for example, Suresh et al., Methods in Enzymology, 121:210 (1986).

e. Heteroconjugate Antibodies

Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

f. Effect or Function Engineering

It may be desirable to modify the antibody of the invention with respect to effector function, so as to enhance the effectiveness of the antibody in treating an immune related disease, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B., J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design, 3:219-230 (1989).

g. Immunoconjugates

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated antibodies. Examples include $^{212}Bi$, $^{131}I$, $^{131}In$, $^{90}Y$ and $^{186}Re$.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tissue pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

h. Immunoliposomes

The proteins, antibodies, etc. disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent (such as doxorubicin) may be optionally contained within the liposome. See Gabizon et al., *J. National Cancer Inst.* 81 (19) 1484 (1989).

13. Pharmaceutical Compositions

The active molecules of the invention, including polypeptides and antibodies, as well as other molecules identified by the screening assays disclosed above, can be administered for the treatment of inflammatory diseases, in the form of pharmaceutical compositions.

Therapeutic formulations of the active molecule, preferably a PRO301, PRO362, PRO245 or PRO1868 polypeptide or antibody of the invention, are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Compounds identified by the screening assays of the present invention can be formulated in an analogous manner, using standard techniques well known in the art.

Lipofections or liposomes can also be used to deliver the polypeptide, antibody, or an antibody fragment, into cells. Where antibody fragments are used, the smallest fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90, 7889-7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active molecules may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37 C, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

14. Methods of Treatment

It is contemplated that the polypeptides, antibodies and other active compounds of the present invention may be used to treat various inflammatory diseases and conditions, such as T cell mediated diseases, including those characterized by infiltration of leucocyte cells into a tissue, stimulation of T-cell proliferation, inhibition of T-cell proliferation, increased or decreased vascular permeability or the inhibition thereof.

PRO301, PRO362, PRO245 and PRO1868 encode new members of a family of proteins characterized by homology to A33 antigen. The proinflammatory nature of these polypeptides is indicated in the in vitro assays described below. Accordingly, antagonists of these polypeptides would be useful to treat inflammatory diseases.

PRO301, PRO362, PRO245 and PRO1868 (SEQ ID NO: 1, SEQ ID NO: 2, SEQ ID NO: 9 and SEQ ID NO: 31, respectively), share homology with junctional adhesion molecule (JAM), Martin-Padura et al., *J. Cell Biol.* 1998 142(1): 117-27. The most substantial identity is shared by the PRO301 protein encoded by DNA40628 (SEQ ID NO: 1) at 67%. JAM is involved in the recruitment of monocytes in response to MCP-1, MCP-3 and LPS in vivo. Antibodies to JAM block monocyte transmigration in vivo. JAM is localized to the murine epithelia and endothelia as a junctional adhesion molecule for monocyte transmigration. Other leukocytes may also use JAM, but no information supports this notion. JAM is elevated in the colon of mice with colitis and likely plays a role in the recruitment of monocytes or leukocytes into the colonic lesion.

Exemplary conditions or disorders to be treated with antagonists of PRO301, PRO362, PRO245 or PRO1868 polypeptides, antibodies and other compounds of the invention, include, but are not limited to, inflammatory bowel disease (i.e., ulcerative colitis, Crohn's disease), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as cystic fibrosis, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid is infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stages have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class 1 molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis includes diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including eosinophilic pneumonia, idiopathic pulmonary fibrosis and hypersensitivity pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

Patients suffering from other diseases may benefit from enhancement of the immune and/or inflammatory response. Such diseases include, but are not limited to viral infection (including but not limited to AIDS, hepatitis A, B, C, D, E) bacterial infection, fungal infections, and protozoan and parasitic infections (molecules or derivatives/agonists which stimulate the MLR can be utilized therapeutically to enhance the immune response to infectious agents), diseases of immunodeficiency, including inherited, acquired, infectious induced (as in HIV infection), or iatrogenic (i.e. as from chemotherapy) immunodeficiency, and neoplasia.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that affect the T lymphocyte response in the MLR have utility in vivo in altering the immune response against neoplasia.

The inhibition of molecules with proinflammatory properties may also have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatitis.

PRO301, PRO362 and PRO245 polypeptides are active as stimulators of the proliferation of stimulated T-lymphocytes (Example 5). Thus, antagonists of PRO301, PRO362 and PRO245 would be useful in treating immune related disorders, particularly inflammatory disorders, such as by inhibiting the stimulatory effect of PRO301, PRO362 and PRO245 polypeptides. On the other hand, the PRO301, PRO362 and PRO245 polypeptides and agonists thereof would be useful in treating disorders that benefit from stimulation of an inflammatory response.

PRO1868 polypeptides of the invention induced redifferentiation of chondrocytes (Example 19). Thus, PRO1868 and agonists of PRO1868 may be used in the treatment of various bone and/or cartilage related disorders.

The PRO301, PRO362, PRO245 and PRO1868 polypeptides, antibodies and other compounds of the present invention are administered to a mammal, preferably a human, in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation (intranasal, intrapulmonary) routes. Intravenous or inhaled administration of polypeptides and antibodies is preferred.

In immunoadjuvant therapy, other therapeutic regimens, such administration of an anti-cancer agent, may be combined with the administration of the proteins, antibodies or compounds of the instant invention. For example, the patient to be treated with the immunoadjuvants of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the immunoadjuvant or may be given simultaneously therewith. Additionally, an anti-oestrogen compound such as tamoxifen or an anti-progesterone such as onapristone (see, EP 616812) may be given in dosages known for such molecules.

It may be desirable to also administer antibodies against other immune disease associated or tumor associated antigens, such as, without limitation, antibodies which bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient. Sometimes, it may be beneficial to also administer one or more cytokines to the patient. In one embodiment, the polypeptides or other compounds of the invention are coadministered with a growth inhibitory agent. For example, the growth inhibitory agent may be administered first, followed by a polypeptide or other compound of the invention. However, simultaneous administration or administration first is also contemplated. Suitable dosages for the growth inhibitory agent are those presently used and may be lowered due to the combined action (synergy) of the growth inhibitory agent and the polypeptide or other compound of the invention.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments. Preferably, it is desirable to determine the dose-response curve and the pharmaceutical composition of the invention first in vitro, and then in useful animal models prior to testing in humans.

For example, depending on the type and severity of the disease, about 1 µg/kg to 15 mg/kg (e.g. 0.1-20 mg/kg) of polypeptide or antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

15. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition, which is effective for diagnosing or treating the condition, and may have a sterile access port (for example the container may be an intravenous solution bag or a vial having a stopper pierceable by a hypodermic injection needle). The active agent in the composition is usually a polypeptide or an antibody of the invention. The label on, or associated with, the container indicates that the composition is used for diagnosing or treating the condition of choice, particularly an immune related condition. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

16. Diagnosis and Prognosis of Disease

Cell surface proteins, such as proteins, which are overexpressed in certain immune related diseases, are excellent targets for drug candidates or disease treatment. The same proteins along with secreted proteins encoded by the genes amplified in immune related disease states find additional use in the diagnosis and prognosis of these diseases. For example, antibodies directed against the protein products of genes amplified in multiple sclerosis, rheumatoid arthritis, or another immune related disease, can be used as diagnostics or prognostics. Such antibodies and a carrier (e.g., a buffer) may be included in a diagnostic kit in suitable packaging along with instructions for using the antibody to detect the protein product.

PRO1868 polypeptides were significantly overexpressed in various human tumor tissues (Example 20), for example lung and breast tumors. Thus, PRO1868 antibodies may be used to diagnose tumors in patients.

The expression of PRO362 polypeptides was found to be significantly increased in tissues associated with neoplasia, as well as inflammatory disease. The expression of PRO245 polypeptides was also significantly increased in tissues with chronic inflammatory diseases and neoplasms. Thus, PRO362 and PRO235 antibodies to diagnose inflamed tissues and neoplasms.

For example, antibodies, including antibody fragments, can be used to qualitatively or quantitatively detect the expression of proteins encoded by the overexpressed or highly expressed genes. The antibody preferably is equipped with a detectable, e.g. fluorescent label, and binding can be monitored by light microscopy, flow cytometry, fluorimetry, or other techniques known in the art. These techniques are particularly suitable, if the overexpressed gene encodes a cell surface protein. Such binding assays are well known in the art and may be performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va. 20110-2209.

Example 1

Isolation of cDNA Clones Encoding Human PRO301

The extracellular domain (ECD) sequences (including the secretion signal sequence, if any) from about 950 known secreted proteins from the Swiss-Prot public database were used to search EST databases. The EST databases included public EST databases (e.g., GenBank), a proprietary EST database (LIFESEQ®, Incyte Pharmaceuticals, Palo Alto, Calif.). The search was performed using the computer program BLAST or BLAST2 [Altschul et al., *Methods in Enzymology*, 266:460-480 (1996)] as a comparison of the ECD protein sequences to a 6-frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence encoding DNA35936 was assembled using phrap. In some cases, the consensus DNA sequence was extended using repeated cycles of blast and phrap to extend the consensus sequence as far as possible using the three sources of EST sequences listed above.

Based on this consensus sequence, oligonucleotides were synthesized: 1) to identify by PCR a cDNA library that contained the sequence of interest, and 2) for use as probes to isolate a clone of the full-length coding sequence. Forward and reverse PCR primers (notated as *.f and *.r, respectively) may range from 20 to 30 nucleotides (typically about 24), and are designed to give a PCR product of 100-1000 bp in length. The probe sequences (notated as *.p) are typically 40-55 bp (typically about 50) in length. In some cases, additional oligonucleotides are synthesized when the consensus sequence is greater than 1-1.5 kbp. In order to screen several libraries for a source of a full-length clone, DNA from the libraries was screened by PCR amplification, as per Ausubel et al., *Current Protocols in Molecular Biology*, with the PCR primer pair. A positive library was then used to isolate clones encoding the gene of interest by the in vivo cloning procedure suing the probe oligonucleotide and one of the PCR primers.

In order to screen several libraries for a source of a full-length clone, DNA from the libraries was screened by PCR amplification with the PCR primer pair identified above. A positive library was then used to isolate clones encoding the PRO301 gene using the probe oligonucleotide and one of the PCR primers.

RNA for construction of the cDNA libraries was isolated from human fetal kidney. The cDNA libraries used to isolated the cDNA clones were constructed by standard methods using commercially available reagents (e.g., Invitrogen, San Diego, Calif.; Clontech, etc.) The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

A cDNA clone was sequenced in its entirety. The full-length nucleotide sequence of native sequence DNA40628 is shown in FIG. 5 (SEQ ID NO: 11). Clone DNA40628 contains a single open reading frame with an apparent translational initiation site at nucleotide positions 52-54 (FIG. 5; SEQ ID NO: 11). The predicted polypeptide precursor is 299 amino acids long with a predicted molecular weight of 32583 daltons and pI of 8.29. Clone DNA40628 has been deposited with ATCC and is assigned ATCC deposit No. 209432.

Based on a BLAST and FastA sequence alignment analysis of the full-length sequence, PRO301 encoded by DNA40628 shows amino acid sequence identity to A33 antigen precursor (30%) and coxsackie and adenovirus receptor protein (29%).

The oligonucleotide sequences used in the above procedure were the following:

```
OLI2162 (35936.f1)
                                       (SEQ ID NO: 12)
TCGCGGAGCTGTGTTCTGTTTCCC

OLI2163 (35936.p1)
                                       (SEQ ID NO: 13)
TGATCGCGATGGGGACAAAGGCGCAAGCTCGAGAGGAAACTGTTGTGC
CT

OLI2164 (35936.f2)
                                       (SEQ ID NO: 14)
ACACCTGGTTCAAAGATGGG

OLI2165 (35936.r1)
                                       (SEQ ID NO: 15)
TAGGAAGAGTTGCTGAAGGCACGG

OLI2166 (35936.f3)
                                       (SEQ ID NO: 16)
TTGCCTTACTCAGGTGCTAC

OLI2167 (35936.r2)
                                       (SEQ ID NO: 17)
ACTCAGCAGTGGTAGGAAAG
```

Example 2

Isolation of cDNA Clones Encoding Human PRO362

The extracellular domain (ECD) sequences (including the secretion signal, if any) of about 950 known secreted proteins from the Swiss-Prot public protein database were used to search expressed sequences tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST-2 (e.g., Altshul et al., *Methods in Enzymology* 266: 460-480 (1996)) as a comparison of the ECD protein sequences to a 6 frame translation of the EST sequence. Those comparisons resulting in a BLAST score 70 (or in some cases 90) or greater that did not encode known proteins were clustered and assembled into consensus DNA sequences with the program "phrap" (Phil Green, University of Washington, Seattle, Wash.

A consensus DNA sequence was assembled relative to other EST sequences using phrap. This consensus sequence is herein designated DNA42257 (SEQ ID NO: 5) (see FIG. 4C). Based on the DNA42257 (SEQ ID NO: 5) consensus sequence shown in FIG. 4C, oligonucleotides were synthesized: 1) to identify by PCR a cDNA library that contained the sequence of interest, and 2) for use as probes to isolate a clone of the full-length coding sequence for PRO362. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

```
PCR primers (forward and reverse) were synthesized:
forward PCR primer 1 (42257.f1)
                                       (SEQ ID NO: 18)
5'-TATCCCTCCAATTGAGCACCCTGG-3' forward PCR primer 2 (42257.f2)
                                       (SEQ ID NO: 19)
5'-GTCGGAAGACATCCCAACAAG-3' reverse PCR primer 1 (42257.r1)
                                       (SEQ ID NO: 20)
5'-CTTCACAATGTCGCTGTGCTGCTC-3' reverse PCR primer 2 (42257.r2
                                       (SEQ ID NO: 21)
5'-AGCCAAATCCAGCAGCTGGCTTAC-3'
```

Additionally, a synthetic oligonucleotide hybridization probe was constructed from the consensus DNA42257 sequence which had the following nucleotide sequence:

```
Hybridization probe (42257.p1)
                                       (SEQ ID NO: 22)
5'-TGGATGACCGGAGCCACTACACGTGTGAAGTCACCTGGCAGACTCCT
GAT-3'.
```

In order to screen several libraries for a source of a full-length clone, DNA from the libraries was screened by PCR amplification with the PCR primer pairs identified above. A positive library was then used to isolate clones encoding the PRO362 gene using the probe oligonucleotide and one of the PCR primers.

RNA for construction of the cDNA libraries was isolated from human fetal brain tissue (LIB153). The cDNA libraries used to isolate the cDNA clones were constructed by standard methods using commercially available reagents such as those from Invitrogen, San Diego, Calif. The cDNA was primed with oligo dT containing a NotI site linked with blunt to SalI hemikinased adaptors, cleaved with NotI, sized appropriately be gel electrophoresis, and cloned in a defined orientation into a suitable cloning vector (such as pRKB or pRKD; pRK5B is a precursor of pRK5D that does not contain the SfiI site; see Holmes et al., *Science* 253: 1278-1280 (1991)) in the unique XhoI and NotI sites.

DNA sequencing of the clones isolated as described gave the full-length DNA sequence for an isolated PRO362 (herein designated as UNQ317 (DNA45416-1251) (SEQ ID NO: 7).

The entire nucleotide sequence of UNQ317 (DNA45416-1251) is shown in FIG. 6 (SEQ ID NO: 7). Clone UNQ367 (DNA45416-1251) (SEQ ID NO: 7) contains a single open reading frame with an apparent translational initiation site at nucleotide positions 1082-1084 (FIG. 6, SEQ ID NO: 7). The predicted polypeptide precursor is 321 amino acids long (FIG. 3, SEQ ID NO: 2). The full-length PRO362 protein shown if FIG. 3 has an estimated molecular weight of about 35,544 daltons and a pI of about 8.51. Analysis of the full-length PRO362 polypeptide as shown in FIG. 3 (SEQ ID NO: 2) evidences the presence of a glycosaminoglycan attachment site at about amino acid 149 to about amino acid 152 and a transmembrane domain from about amino acid 276 to about amino acid 306. Clone UNQ317 (DNA45416-1251) has been deposited with ATCC deposit No.: 209620.

Example 3

Isolation of cDNA Clones Encoding Human PRO245

The extracellular domain (ECD) sequences (including the secretion signal, if any) of about 950 known secreted proteins from the Swiss-Prot public protein database were used to search expressed sequences tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST-2 (e.g., Altshul et al., *Methods in Enzymology* 266: 460-480 (1996)) as a comparison of the ECD protein sequences to a 6 frame translation of the EST sequence. Those comparisons resulting in a BLAST score 70 (or in some cases 90) or greater that did not encode known proteins were clustered and assembled into consensus DNA sequences with the program "phrap" (Phil Green, University of Washington, Seattle, Wash.

A consensus DNA sequence was assembled relative to other EST sequences, wherein the consensus sequence is herein designated DNA30954 (SEQ ID NO: 27). Based on the DNA30954 consensus sequence, oligonucleotides were synthesized to identify by PCR a cDNA library that contained the sequence of interest and for use as probes to isolate a clone of the full-length coding sequence for PRO245.

A pair of PCR primers (forward and reverse) were synthesized:

```
                             (SEQ ID NO: 28)
forward PCR primer   5'-ATCGTTGTGAAGTTAGTGCCCC-3'

(SEQ ID NO: 29)
reverse PCR primer   5'-ACCTGCGATATCCAACAGAATTG-3'
```

Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair.

Additionally, a synthetic oligonucleotide hybridization probes was constructed from the consensus DNA30954 sequences which had the following nucleotide sequence:

```
hybridization probe:
                             (SEQ ID NO: 30)
5'-GGAAGAGGATACAGTCACTCTGGAAGTATTAGTGGCTCCAGCAGTT
CC-3'.
```

In order to screen several libraries for a source of a full-length clone, DNA form the libraries was screened by PCR amplification with the PCR primer pair identified above. A positive library was then used to isolated clones encoding the PRO245 gene using the probe oligonucleotide and one of the PCR primers.

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see Holmes et al., *Science* 253: 1278-1280 (1991)) in the unique XhoI and NotI sites.

DNA sequencing of the clones isolated as described above gave the full-length DNA sequence for a native sequence PRO245 [herein designated as UNQ219 (DNA35638) (SEQ ID NO: 8)] and the derived protein sequence (SEQ ID NO: 9).

The entire nucleotide sequence of UNQ219 (DNA35638) is shown in FIG. 7 (SEQ ID NO: 8). Clone UNQ219 (DNA35638) (SEQ ID NO: 8) contains a single open reading frame with an apparent translational initiation site at nucleotide positions 89-91 (Kozak et al., supra) and ending at the stop codon at nucleotide positions 1025-1027 (FIG. 7, SEQ ID NO: 8). The predicted polypeptide precursor is 312 amino acids long (FIG. 11) (SEQ ID NO: 9). Clone UNQ219 (DNA35638) has been deposited with the ATCC on Sep. 17, 1997 and is assigned ATCC deposit No. 209265.

Example 4

Inhibition of VEGF Stimulated Proliferation of Endothelial Cell Growth

Bovine adrenal cortical capillary endothelial (ACE) cells (from primary culture, maximum 12-14 passages) were plated on 96-well microtiter plates (Amersham Life Science) at a density of 500 cells/well per 100 μL in low glucose DMEM, 10% calf serum, 2 mM glutamine, 1× pen/strep and fungizone, supplemented with 3 ng/mL VEGF. Controls were plated the same way but some did not include VEGF. A test sample of the PRO301 and PRO245 polypeptide was added in a 100 μl volume for a 200 mcL final volume. Cells were incubated for 6-7 days at 37° C. The media was aspirated and the cells washed 1× with PBS. An acid phosphatase reaction mixture (100 μL, 0.1M sodium acetate, pH 5.5, 0.1% Triton-100, 10 mM p-nitrophenyl phosphate) was added. After incubation for 2 hours at 37° C., the reaction was stopped by addition of 10 mcL 1N NaOH. OD was measured on microtiter plate reader at 405 nm. Controls were no cells, cells alone, cells+FGF (5 ng/mL), cells+VEGF (3 ng/mL), cells+VEGF (3 ng/ml)+TGF-β (1 ng/ml), and cells+VEGF (3 ng/mL)+LIF (5 ng/mL). (TGF-β at a 1 ng/ml concentration is known to block 70-90% of VEGF stimulated cell proliferation.)

The results were assessed by calculating the percentage inhibition of VEGF (3 ng/ml) stimulated cells proliferation, determined by measuring acid phosphatase activity at $OD_{405}$ nm, (1) relative to cells without stimulation, and (2) relative to the reference TGF-β inhibition of VEGF stimulated activity. The results, shown in Table 1, are indicative of the utility of the PRO301 and PRO245 polypeptide in the inhibition of cell growth, especially cancer therapy and specifically in inhibiting tumor angiogenesis.

TABLE 1

| Compound Tested | Concentration | % Proliferation relative to control |
| --- | --- | --- |
| DNA40628 protein (SEQ ID NO: 1) | 7.0 nM | 1.02 |
| DNA40628 protein (SEQ ID NO: 1) | 70.0 nM | 0.88 |
| DNA40628 protein (SEQ ID NO: 1) | 700.0 nM | 0.44 |
| DNA40628 protein (SEQ ID NO: 1) | 0.01% | 0.92 |
| DNA40628 protein (SEQ ID NO: 1) | 0.1% | 0.85 |
| DNA40628 protein (SEQ ID NO: 1) | 1.0% | 0.68 |
| DNA35638 protein (SEQ ID NO: 9) | 0.01% | 0.76 |
| DNA35638 protein (SEQ ID NO: 9) | 0.1% | 0.35 |
| DNA35638 protein (SEQ ID NO: 9) | 1.0% | 0.11 |
| DNA35638 protein (SEQ ID NO: 9) | 0.48 nM | 1.03 |
| DNA35638 protein (SEQ ID NO: 9) | 4.8 nM | 0.95 |
| DNA35638 protein (SEQ ID NO: 9) | 48.0 nM | 0.49 |

Example 5

Stimulatory Activity in Mixed Lymphocyte Reaction (MLR) Assay

The following describes assays for determining whether PRO301, PRO362, PRO245 and PRO1868 polypeptides are able to stimulate proliferation of stimulated T-lymphocytes. Compounds which stimulate proliferation of lymphocytes are useful therapeutically where enhancement of an inflammatory response is beneficial, for example enhancement of the immune response against neoplasia. Antagonists to such compounds that stimulate proliferation of lymphocytes are useful therapeutically where a reduction in the inflammatory response is beneficial. A therapeutic agent may take the form of an agonist or an antagonist of the polypeptide of the invention, for example, murine-human chimeric, humanized or human antibodies against the polypeptide.

The basic protocol for this assay is described in *Current Protocol in Immunology*, Unit 3.12, J. E. Coligan, A. M. Kruisbeek, D H Marglies, E M Shevach and W Strober, Eds, National Institute of Health, Published by John Wiley & Sons, Inc.

More specifically, in one assay variant, peripheral blood mononuclear cells (PBMC) are isolated from mammalian individuals, for example a human volunteer, by leukopheresis (one donor will supply stimulatory PBMCs, the other donor will supply responder PBMCs). If desired, the cells are frozen in fetal bovine serum and DMSO after isolation. Frozen cells may be thawed overnight in assay media (37° C., 5% $CO_2$) and then washed and resuspended to $3\times10^6$ cells/ml of assay media (RPMI; 10% fetal bovine serum, 1% penicillin/streptomycin, 1% glutamine, 1% HEPES, 1% non-essential amino acids, 1% pyruvate).

The stimulator PBMCs are prepared by irradiating the cells (about 3000 Rads). The assay is prepared by plating in triplicate wells a mixture of: 100 μl of test sample diluted to 1% or 0.1%; 501 of irradiated stimulator cells and 50 of responder PBMC cells. 100 μL of cell culture media or 100 ml of CD4-IgG is used as the control. The wells are then incubated at 37° C., 5% $CO_2$ for 4 days. On day 5, each well is pulsed with tritiated thymidine (1.0 mC/well; Amersham). The cells are washed 3 times and then the uptake of the label is evaluated.

PRO301, PRO362 and PRO245 polypeptides were tested in another variant of the assay. In this variant assay, PBMC's were isolated from the spleens of BALB/c mice and C57B6 mice. The cells were teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs were isolated by overlaying these cells over Lympholyte M (Organon Teknika), centrifuging at 2000 rpm for 20 minutes, collecting and washing the mononuclear cell layer in assay media and resuspending the cells to $1\times10^7$ cells/ml of assay media. The assay was then conducted as described above.

The results, shown below in Table 2, indicate that the PRO301, PRO362 and PRO245 polypeptides of the invention are active as stimulators of the proliferation of stimulated T-lymphocytes. Positive increases over control are considered positive with increases of greater than or equal to 180% being preferred. However, any value greater than control indicates a stimulatory effect for the test protein.

TABLE 2

| Compound | Concentration | Percent Increase over Control |
| --- | --- | --- |
| DNA40628 protein (SEQ ID NO: 1) | 0.1% | 181.7 |
| DNA40628 protein (SEQ ID NO: 1) | 1.0% | 187.3 |
| DNA40628 protein (SEQ ID NO: 1) | 0.1% | 193.4 |
| DNA40628 protein (SEQ ID NO: 1) | 1.0% | 204.1 |
| DNA45416 protein (SEQ ID NO: 2) | 0.1% | 87.4 |
| DNA45416 protein (SEQ ID NO: 2) | 1.0% | 180.2 |
| DNA35638 protein (SEQ ID NO: 9) | 0.1% | 189.7 |
| DNA35638 protein (SEQ ID NO: 9) | 0.1% | 193.7 |
| DNA35638 protein (SEQ ID NO: 9) | 1.0% | 212.5 |
| DNA35638 protein (SEQ ID NO: 9) | 1.0% | 300.5 |

Example 6

Inflammatory Cell Infiltrates into Guinea Pig Skin

The following example shows that the polypeptides of the invention are proinflammatory in that they stimulate inflammatory cell infiltrates (i.e., neutrophilic, eosinophilic, monocytic or lymphocytic) into guinea pig skin. The assay described herein monitors the capacity of each protein to induce an inflammatory cell infiltrate into the skin of a guinea pig. Compounds which stimulate inflammatory infiltration are useful therapeutically where enhancement of an inflammatory response is beneficial. Compounds which inhibit proliferation of lymphocytes are useful therapeutically where suppression of an inflammatory response is beneficial. A therapeutic agent may take the form of antagonists of the polypeptides of the invention, for example, murine-human chimeric, humanized or human antibodies against the polypeptide.

Hairless guinea pigs (Charles River Labs) weighing 350 grams or more were anesthetized with ketamine (75-80 mg/kg body weight) and xylazine (5 mg/kg body weight)

intramuscularly. The protein samples of PRO301, PRO362 and PRO245 and control proteins were injected intradermally into the backs of each animal at a volume of 100 µl per injection site. There were approximately 16-24 injection sites per animal. One mL of Evans blue dye (1% in physiological buffered saline) was injected intracardially. The animals were euthanized after 6 hours and each skin injection site was biopsied and fixed in formalin. The skins were prepared for histopathological evaluation. Each site was evaluated for inflammatory cell infiltration into the skin. Sites with visible inflammatory cells were scored as positive. Samples inducing an inflammatory cell infiltrate were scored as proinflammatory substances.

TABLE 3

| Compound | Proinflammatory activity |
| --- | --- |
| DNA40628 protein (SEQ ID NO: 1) | + |
| DNA45416 protein (SEQ ID NO: 2) | + |
| DNA35638 protein (SEQ ID NO: 9) | + |
| Negative control | − |

Based on these results PRO1868 (SEQ ID NO: 31) also likely has proinflammatory activity.

Example 7

Interaction with Human Neutrophils

The following example shows the ability of the polypeptides of the invention to bind to human neutrophils, a molecule associated with inflammation and the inflammatory response.

Neutrophils isolated from the blood of human donors (PMN) as described in Scan. J. Clin. Lab Invest. Suppl. 97: 51-76 (1968), were incubated with an Ig-fusion of protein encoded by DNA40628 (prepared as discussed in the following examples) or a negative control humanized antibody.

Figure 21:
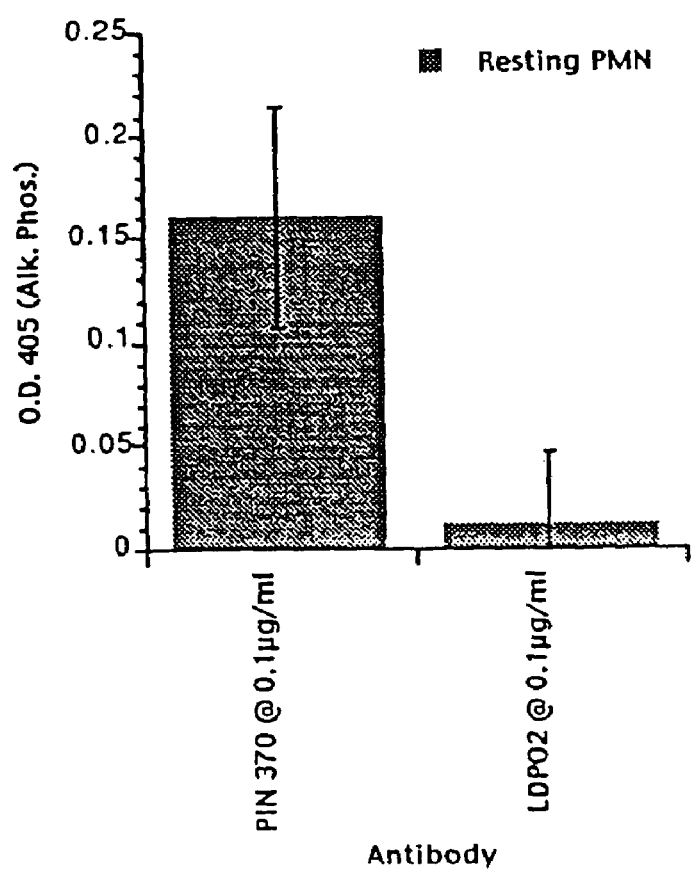
FIG. 21 shows the binding of protein encoded by DNA40628 to human neutrophils as described in Example 7.

The PMNs were resuspended in a microfuge tube in PBS at a density of $2 \times 10^6$ cell equivalents per condition. The cells were washed twice with ice cold PBS and pelleted at 400×g between washes. The PMN cells were blocked with 0.5% BSA in PBS (blocking reagent) at 4° C. for 1 hour. After the incubation, the cells were further washed two additional times with blocking reagent. The PMNs were pelleted after the final wash and resuspended in 1 ml of blocking buffer at 0.1 µg/ml in both DNA40628 protein and control antibody. The incubation was carried out for 2 hours at 4° C. The PMN cells were gently resuspended every 15 minutes on ice, then washed and pelleted 5 times in blocking buffer, with each wash lasting 5 minutes at 4° C. and pelleting occurring at 400×g. A 1:1000 dilution of goat and anti-human IgG Fc specific-alkaline phosphatase-conjugated in the blocking buffer was then applied to the PMN cells. The PMN cells were incubated for 1 hour at 4° C., with gently mixing every 15 minutes on ice. The PMN cells were then washed 5 times with blocking buffer, resuspended in the appropriate substrate for alkaline phosphatase and distributed in 4 equi-100 µl aliquots onto a microtiter plate. Color development was read at O.D. 405. The results are shown in FIG. 21.

Example 8

Dot Blot Tissue Hybridization

A human RNA master blot (Clontech) was hybridized overnight at 65° C. in EXPRESSHYB® buffer (Clontech) per the manufacturer's instructions with 100 nM of psoralen-biotin labeled DNA40628 cDNA probe (SEQ ID NO: 7). Streptavidin-alkaline phosphatase was used to detect the biotinylated probe. The blot was developed with CDP-star substrate (Ambion) and exposed for various times on Biomax film (Kodak). A cDNA hybridization analysis of human tissues show that DNA40628 mRNA is expressed in a wide range of tissues, but not in the cerebellum and spinal cord (FIG. 19). DNA40628 mRNA is highly expressed in the colon, prostate, stomach, ovary, salivary gland, kidney, lung, trachea and placenta.

Example 9

Gene Product Overexpression

This example shows that genes encoding the various proteins indicated in FIG. 20 are overexpressed in colitic colon of CRF2-4-/- "knock out" mice. Therapeutic agents may take the form of antagonists of the indicated gene products, for example, murine-human chimeric, humanized or human antibodies thereagainst.

CRF 2-4-/- mice (Spencer et al., J. Exp. Med. 187, 571-578 (1998)), are IL-10 receptor knockout animals that have a subunit of the gene encoding the IL-10 receptor removed. The mice are unresponsive to the downregulatory functions of IL-10 for macrophage activation, and cannot downregulate response to lipopolysaccharide triggering of macrophage TNF-α secretion. They develop a chronic colitis which can lead to colonic adenocarcinoma. The spontaneous colitis is mediated by lymphocytes, monocytes and neutrophils. IL-10 suppresses the inflammatory response by modulating expression of certain inflammatory cytokines.

The probes for the proteins indicated in FIG. 20 were created from mRNA templates for the indicated gene products and used in the 5'-nuclease assay (e.g., TAQMAN™) and real-time quantitative PCR (e.g., ABI PRIZM 7700 SEQUENCE DETECTION SYSTEM™ (Perkin-Elmer, Applied Biosystems Division, Foster City, Calif.). The results are reported in delta CT units. One unit corresponds to 1 PCR cycle or approximately a 2-fold amplification relative to normal, two units correspond to 4-fold, 3 units to 8-fold, etc. Quantitation was obtained using primers and a TAQMAN™ fluorescent tagged-mRNA derived from the tested inflammatory-related gene products indicated in FIG. 20. Regions of the indicated gene products which are most likely to contain unique nucleic acid sequences and which are least likely to have spliced out introns are preferred for the primer derivation, e.g. 3'-untranslated region.

The 5'-nuclease assay reaction is a fluorescent PCR-based technique which makes use of the 5'-exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reported fluorescent dye and a quencher fluorescent dye. Any laser-induced emission from the reporter dye is quenched by the quenching dye when the two dyes are located close together as they are on the probe. During the amplification reaction, the probe is cleaved by the Taq DNA polymerase enzyme in a template-dependent manner. The resultant probe fragments disassociate in solution, and the signal from the release reporter dye is free from the quenching effect of the second fluorophore. One molecule of reporter dye is liberated for each new molecule synthesized, and detection of the unquenched reporter dye provided the basis for quantitative interpretation of the data.

The 5'-nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The 5'-nuclease assay data are initially expressed as Ct, or the threshold cycle. This is defined as the cycle at which the reporter signal accumulates above the background level of fluorescence. The Ct values are used as quantitative measurement of the relative number of starting copies of a particular target sequence in a nucleic acid sample.

The results of the mRNA amplification are shown in FIG. 20. Expression in wild-type animals were compared with CRF2-4-/- KO animals with beta-actin as the reference standard. Four animals were measured in each group. All four KO animals were diagnosed with colitis and in addition, three of these had colon adenocarcinoma.

FIG. 20 shows that JAM mRNA is increased 3.3-fold in the colon of CRF2-4-/- mice with colitis.

As a result, it is likely that PRO301, PRO362, PRO245 and PRO1868 would also have elevated expression in inflammatory human disease, such as inflammatory bowel disease and other inflammatory diseases of the gut.

Example 10

Induction of Endothelial Cell Apoptosis

The ability of the polypeptides of the invention to induce apoptosis in endothelial cells was tested in human venous umbilical vein endothelial cells (HUVEC, Cell Systems). The first day, the cells were plated on 96-well microtiter plates (Amersham Life Sciences, cytostar-T scintillating microplate, RPNQ160, sterile, tissue-culture treated, individually wrapped), in 10% serum (CSG-medium, Cell Systems), at a density of $2 \times 10^4$ cells per well in a total volume of 100 µl. The second day, PRO301 and PRO245 polypeptide encoded by DNA40628 and DNA35638, respectively, was added in triplicate at dilutions of 1%, 0.33% and 0.11%. On the third day, the ability of the PRO301 and PRO245 polypeptides to induce apoptosis was determined using a commercially available kit, Apoptosis Detection Kit (R&D Systems, Minnesota) in which annexin V, a member of the calcium and phospholipid binding proteins, is used to detect apoptosis, following the protocol recommended by the manufacturer. Fluroescein-labeled annexin V and propidium iodide were added to the cells. Analysis was performed with cytometers equipped with a single laser emitting excitation light at 488 nm. In this test, live cells will not stain with either fluorochrome, necrotic cells will stain with both fluorochromes, and cells undergoing apoptosis will stain only with the annexin V-FITC reagent. The annexin V-FITC generated signal was detected in the FITC signal detector. The results are indicated in the Table 4 below.

TABLE 4

| Compound tested | Concentration | % over background fluorescence |
|---|---|---|
| DNA40628 protein (SEQ ID NO: 1) | 0.11% | 115.8 |
| DNA40628 protein (SEQ ID NO: 1) | 0.33% | 199.3 |
| DNA40628 protein (SEQ ID NO: 1) | 1.0% | 335.6 |
| DNA35638 protein (SEQ ID NO: 9) | 0.11% | 77.6 |
| DNA35638 protein (SEQ ID NO: 9) | 0.33% | 143.7 |
| DNA35638 protein (SEQ ID NO: 9) | 1.0% | 146.0 |
| DNA35638 protein (SEQ ID NO: 9) | 6.82 nM | 67.2 |
| DNA35638 protein (SEQ ID NO: 9) | 20.46 nM | 102.6 |
| DNA35638 protein (SEQ ID NO: 9) | 62.0 nM | 118.8 |

The ability of the protein compounds of the invention to induce endothelial cell apoptosis, particularly in combination with the disruption of cell junction formation as indicated in Example 4 is indicative that the compounds play roles in cell adhesion and transmigration. Similar to murine JAM, the compounds are likely cell junction molecules in epithelia and endothelia, which explains their broad tissue distribution. The induction of endothelial cell apoptosis indicates a role in cell growth and apoptosis.

Example 11

In Vitro Antitumor Assay

The antiproliferative activity of the PRO301 and PRO362 polypeptides of the invention was determined in the investigational, disease-oriented in vitro anti-cancer drug discovery assay of the National Cancer Institute (NCI), using sulforhodamine B (SRB) dye binding assay essentially as described by Skehan et al., *J. Natl. Cancer Inst.* 82: 1107-1112 (1990). The 60 tumor cell lines employed in this study ("the NCI panel") as well as conditions for their maintenance and culture in vitro have been described by Monks et al., *J. Natl. Cancer Inst.* 83: 757-766 (1991). The purpose of this screen is to initially evaluate the cytotoxic and/or cytostatic activity of the test compounds against different types of tumors (Monks et al., supra, Boyd, *Cancer: Princ. Pract. Oncol. Update* 3(10): 1-12 (1989)).

Cells from the approximately 60 human tumor cell lines were harvested with trypsin/EDTA (Gibco), washed once, resuspended in IMEM and their viability was determined. The cell suspensions were added by pipet (100 µL volume) into separate 96-well microtiter plates. The cell density for the 6-day incubation was less than for the 2-day incubation to prevent overgrowth. Inoculates were allowed a preincubation period of 24 hours at 37° C. for stabilization. Dilutions at twice the intended test concentration were added at time zero in 100 ml aliquots to the microtiter plates wells (1:2 dilution). Test compounds were evaluated at given half-log dilutions (1000 to 100,000 fold). Incubations took place for two days and six days in a 5% $CO_2$ atmosphere and 100% humidity.

After incubation, the medium was removed and the cells were fixed in 0.1 ml of 10% trichloroacetic acid at 40° C. The plates were rinsed five times with deionized water, dried, stained for 30 minutes with 0.1 ml of 0.4% sulforhodamine B dye (Sigma) dissolved in 1% acetic acid, rinsed four times with 1% acetic acid to remove unbound dye, dried, and the stain was extracted for five minutes with 0.1 ml of 10 mM Tris base [tris(hydroxymethyl)aminomethane], pH 10.5. The absorbance (OD) of sulforhodamine B at 492 nm was measured using a computer-interfaced, 96-well microtiter plate reader.

A test sample was considered positive if it showed at least 50% growth inhibitory effect at one or more concentrations. The positive results are shown in the following table, where the abbreviations are as follows:

NSCL=non-small lung carcinoma

CNS=central nervous system

Leuk=leukemia

Example 12

Use of PRO301, PRO362, PRO245 or PRO1868 as a Hybridization Probe

The following method describes use of a nucleotide sequence encoding a PRO301, PRO362, PRO245 or PRO1868 as a hybridization probe.

DNA comprising the coding sequence of native sequence PRO301, PRO362, PRO245 or PRO1868 (as shown in FIGS. 5-7 and 61, SEQ ID NO: 11, 7, 8 and 31), respectively, is employed as a probe to screen for homologous DNAs (such as those encoding naturally-occurring variants of PRO301,

TABLE 5

| Test compound | Concentration | Length of assay | Tumor cell line Type | Tumor cell line Designation |
|---|---|---|---|---|
| DNA40628 protein (SEQ ID NO: 1) | 0.075 nM | 6 | Colon Melanoma | HCC-2998 M14 |
| DNA40638 protein (SEQ ID NO: 1) | 700 nM | 6 | Melanoma | M14 |
| DNA40628 protein (SEQ ID NO: 1) | 152 nM | 6 | Colon Melanoma | SR LOX IMVI |
| DNA40628 protein (SEQ ID NO: 1) | 15.2 nM | 6 | Melanoma | LOX IMVI |
| DNA40628 protein (SEQ ID NO: 1) | 0.85 nM | 6 | NSCL Ovarian Prostate | HOP62 OVCAR-3 PC3 |
| DNA45416 protein (SEQ ID NO: 2) | 15 nM | 2 | Ovarian | SK-OV-3 |
| DNA45416 protein (SEQ ID NO: 2) | 15 nM | 6 | NSCL Prostate | NCI-H322M PC-3 |
| DNA45416 protein (SEQ ID NO: 2) | 4.7 nM | 6 | Melanoma | LOX IMVI |
| DNA45416 protein (SEQ ID NO: 2) | 47 nM | 6 | NSCL Colon | NCI-H322M Colo 205 |
| DNA45416 protein (SEQ ID NO: 2) | 152 nM | 2 | CNS Breast | SR-295 T047D |
| DNA45416 protein (SEQ ID NO: 2) | 152 nM | 6 | Leuk NSCL Colon CNS Melanoma | SR, HL-60 (TB), MOLT-4, K-562 NCI-H23, EKVX HCC-2998 U251 UACC-62, UACC-257, LOX IMVI |
| DNA35638 protein (SEQ ID NO: 9) | 0.35 nM | 2 | NSCL Ovarian | HOP92 OVCAR-4 |
| DNA35638 protein (SEQ ID NO: 9) | 0.35 nM | 2 | Leuk | SR |
| DNA35638 protein (SEQ ID NO: 9) | 0.35 nM | 6 | Colon | HCC-2998 |
| DNA35638 protein (SEQ ID NO: 9) | 3.5 nM | 6 | Leuk Colon | SR SW-620 |
| DNA35638 protein (SEQ ID NO: 9) | 6.2 nM | 6 | Colon | HCT-116 |
| DNA35638 protein (SEQ ID NO: 9) | 6.2 nM | 6 | Leuk | RPMI-8226 |

PRO362, PRO245 or PRO1868, respectively) in human tissue cDNA libraries or human tissue genomic libraries.

Hybridization and washing of filters containing either cDNA or genomic library DNAs is performed under the following high stringency conditions. Hybridization of radiolabeled PRO301-, PRO362-, PRO245 or PRO1868-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding a full-length native sequence PRO301, PRO362, PRO245 or PRO1868 are then identified using standard techniques known in the art.

Example 13

Expression of PRO301, PRO362, PRO245 or PRO1868 in E. coli

This example illustrates preparation of an unglycosylated form of PRO301, PRO362, PRO245 or PRO1868 by recombinant expression in E. coli.

The DNA sequence encoding PRO301, PRO362, PRO245 or PRO1868 is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO301, PRO362, PRO245 or PRO1868 coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones are grown overnight in liquid culture medium such as LB broth supplemented with antibiotics. The overnight culture is subsequently be used to inoculate a larger scale culture. The cells are then grown to a desired optical density, during which the expression promoter is turned on.

After culturing the cells for several more hours, the cells are harvested by centrifugation. The cell pellet obtained by the centrifugation can be solubilized using various agents known in the art, and the solubilized PRO301, PRO362, PRO245 or PRO1868 protein is purified, for example by using a metal chelating column under conditions that allow tight binding of the protein.

PRO301 was expressed in E. coli in a poly-His tagged form, using the following procedure. The DNA encoding PRO301 was initially amplified using selected PCR primers. The primers contained restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences were then ligated into an expression vector, which was used to transform an E. coli host based on strain 52 (W3110 fuhA (tonA) lon galE rpoHts(htpRts) clpP(lacIq). Transformants were first grown in LB containing 50 mg/ml carbenicillin at 30° C. with shaking until an O.D. 600 of 3-5 was reached. Cultures were then diluted 50-100 fold into CRAP media (prepared by mixing 3.57 g $(NH_4)_2SO_4$, 0.71 g sodium citrateA2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples were removed to verify expression by SDS-PAGE analysis, and the bulk culture is centrifuged to pellet the cells. Cell pellets were frozen until purification and refolding.

E. coli paste from 0.5 to 1 L fermentations (6-10 g pellets) was resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution was stirred overnight at 4° C. This step results in a denatured protein with all cysteine residues blocked by sulfitolization. The solution was centrifuged at 40,000 rpm in a Beckman Ultracentrifuge for 30 min. The supernatant was diluted with 3-5 volumes of metal chelate column buffer (6 M guanidine, 20 mM Tris, pH 7.4) and filtered through 0.22 micron filters to clarify. Depending the clarified extract was loaded onto a 5 ml Qiagen Ni-NTA metal chelate column equilibrated in the metal chelate column buffer. The column was washed with additional buffer containing 50 mM imidazole (Calbiochem, Utrol grade), pH 7.4. The protein was eluted with buffer containing 250 mM imidazole. Fractions containing the desired protein were pooled and stored at 4° C. Protein concentration was estimated by its absorbance at 280 nm using the calculated extinction coefficient based on its amino acid sequence.

The protein was refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes were chosen so that the final protein concentration was between 50 to 100 micrograms/ml. The refolding solution was stirred gently at 4° C. for 12-36 hours. The refolding reaction was quenched by the addition of TFA to a final concentration of 0.4% (pH of approximately 3). Before further purification of the protein, the solution was filtered through a 0.22 micron filter and acetonitrile was added to 2-10% final concentration. The refolded protein was chromatographed on a Poros R1/H reversed phase column using a mobile buffer of 0.1% TFA with elution with a gradient of acetonitrile from 10 to 80%. Aliquots of fractions with A280 absorbance were analyzed on SDS polyacrylamide gels and fractions containing homogeneous refolded protein were pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO301 protein, respectively, were pooled and the acetonitrile removed using a gentle stream of nitrogen directed at the solution. Proteins were formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 14

Expression of PRO301, PRO362, PRO245 or PRO1868 in Mammalian Cells

This example illustrates preparation of a glycosylated form of a PRO301, PRO362, PRO245 Or PRO1868 by recombinant expression in mammalian cells.

The vector, pRK5 (see EP 307,247, published Mar. 15, 1989), is employed as the expression vector. Optionally, the PRO301, PRO362, PRO245 or PRO186 DNA is ligated into pRK5 with selected restriction enzymes to allow insertion of the PRO301, PRO362, PRO245 or PRO1868 DNA using ligation methods such as described in Sambrook et al., supra. The resulting vector is called pRK5-PRO301, pRK5-PRO362, pRK5-PRO245 or pRK5-PRO1868, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO301, pRK5-PRO362, pRK5-PRO245 DNA or pRK5-PRO1868 is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO301, PRO362, PRO245 or PRO1868 polypeptide. The cultures containing transfected cells may undergo further incubation (in serum free medium) and the medium is tested in selected bioassays.

In an alternative technique, PRO301, PRO362, PRO245 or PRO1868 DNA may be introduced into 293 cells transiently using the dextran sulfate method described by Somparyrac et al., *Proc. Natl. Acad. Sci*, 12:7575 (1981). 293 cells are grown to maximal density in a spinner flask and 700 μg pRK5-PRO301, pRK5-PRO362, pRK5-PRO245 or pRK5-PRO1868 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO301, PRO362, PRO245 or PRO1868 can then be concentrated and purified by any selected method, such as dialysis and/or column chromatography.

In another embodiment, PRO301, PRO362, PRO245 or PRO1868 can be expressed in CHO cells. The pRK5-PRO301, pRK5-PRO362, pRK5-PRO245 or pRK5-PRO1868 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO301, PRO362, PRO245 or PRO1868 polypeptide, the culture medium may be replaced with serum free medium. Preferably, the cultures are incubated for about 6 days, and then the conditioned medium is harvested. The medium containing the expressed PRO301, PRO362, PRO245 or PRO1868 can then be concentrated and purified by any selected method.

Epitope-tagged PRO301, PRO362, PRO245 or PRO1868 may also be expressed in host CHO cells. The PRO301, PRO362, PRO245 or PRO1868 may be subcloned out of the pRK5 vector. The subclone insert can undergo PCR to fuse in frame with a selected epitope tag such as a poly-his tag into a Baculovirus expression vector. The poly-his tagged PRO301, PRO362, PRO245 or PRO1868 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO301, PRO362, PRO245 or PRO1868 can then be concentrated and purified by any selected method, such as by $Ni^{2+}$-chelate affinity chromatography.

PRO301, PRO362, PRO245 and PRO1868 were expressed in CHO cells by both a transient and stable expression procedure.

Stable expression in CHO cells was performed using the following procedure. The proteins were expressed as an IgG construct (immunoadhesin), in which the coding sequences for the soluble forms (e.g. extracellular domains) of the respective proteins were fused to an IgG1 constant region sequence containing the hinge, CH2 and CH2 domains and/or as a poly-His tagged form.

Following PCR amplification, the respective DNAs were subcloned in a CHO expression vector using standard techniques as described in Ausubel et al., *Current Protocols of Molecular Biology*, Unit 3.16, John Wiley and Sons (1997). CHO expression vectors are generally constructed to have compatible restriction sites 5= and 3= of the DNA of interest to allow the convenient shuttling of cDNAs. The vector used here for expression in CHO cells is as described in Lucas et al., *Nucl. Acids Res.* 24: 9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA were introduced into approximately 10 million CHO cells using the commercially available transfection reagent Superfect[7] (Qiagen), Dosper[7] or Fugene[7] (Boehringer Mannheim). The cells were grown as described in Lucas et al., supra. Approximately $3 \times 10^{-7}$ cells were frozen in an ampule for further growth and production as described below.

The ampules containing the plasmid DNA were thawed by placement into a water bath and mixed by vortexing. The contents were pipetted into a centrifuge tube containing 10 mLs of media and centrifuged at 1000 rpm for 5 minutes. The supernatant was aspirated and the cells were resuspended in 10 mL of selective media (0.2: m filtered PS20 with 5% 0.2: m diafiltered fetal bovine serum). The cells were then aliquoted into a 100 mL spinner containing 90 mL of selective media. After 1-2 days, the cells were transferred into a 250 mL spinner filled with 150 mL selective growth medium and incubated at 37EC. After another 2-3 days, a 250 mL, 500 mL and 2000 mL spinners were seeded with $3\times10^5$ cells/mL. The cell media was exchanged with fresh media by centrifugation and resuspension in production medium. Although any suitable CHO media may be employed, a production medium described in U.S. Pat. No. 5,122,469, issued Jun. 16, 1992 was actually used. 3 L production spinner is seeded at $1.2\times10^6$ cells/mL. On day 0, the cell number and pH were determined. On day 1, the spinner was sampled and sparging with filtered air was commenced. On day 2, the spinner was sampled, the temperature shifted to 33EC, and 30 mL of 500 g/L glucose and 0.6 mL of 10% antifoam (e.g., 35% polydimethylsiloxane emulsion, Dow Corning 365 Medical Grade Emulsion). Throughout the production, pH was adjusted as necessary to keep at around 7.2. After 10 days, or when viability dropped below 70%, the cell culture was harvested by centrifugation and filtering through a 0.22: m filter. The filtrate was either stored at 4EC or immediately loaded onto columns for purification.

For the poly-His tagged constructs, the proteins were purified using a Ni-NTA column (Qiagen). Before purification, imidazole was added to the conditioned media to a concentration of 5 mM. The conditioned media was pumped onto a 6 ml Ni-NTA column equilibrated in 20 mM Hepes, pH 7.4, buffer containing 0.3 M NaCl and 5 mM imidazole at a flow rate of 4-5 ml/min. at 4EC. After loading, the column was washed with additional equilibration buffer and the protein eluted with equilibration buffer containing 0.25 M imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80EC.

Immunoadhesin (Fc containing) constructs of the proteins were purified from the conditioned media as follows. The conditioned medium was pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275: L of 1 M Tris buffer, pH 9. The highly purified protein was subsequently desalted into storage buffer as described above for the poly-His tagged proteins. The homogeneity was assessed by SDS polyacrylamide gels and by N-terminal amino acid sequencing by Edman degradation.

PRO301, PRO362 PRO245 and PRO1868 were also produced by transient expression in COS cells.

Example 15

Expression of PRO301, PRO362, PRO245 or PRO1868 in Yeast

The following method describes recombinant expression of PRO301, PRO362, PRO245 or PRO1868 in yeast.

First, yeast expression vectors are constructed for intracellular production or secretion of PRO301, PRO362, PRO245 or PRO1868 from the ADH2/GAPDH promoter. DNA encoding PRO301, PRO362, PRO245 or PRO1868, a selected signal peptide and the promoter is inserted into suitable restriction enzyme sites in the selected plasmid to direct intracellular expression of PRO301, PRO362, PRO245 or PRO1868. For secretion, DNA encoding PRO301, PRO362, PRO245 or PRO1868 can be cloned into the selected plasmid, together with DNA encoding the ADH2/GAPDH promoter, the yeast alpha-factor secretory signal/leader sequence, and linker sequences (if needed) for expression of PRO301, PRO362, PRO245 or PRO1868.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO301, PRO362, PRO245 or PRO1868 can subsequently be isolated and purified by removing the yeast cells from the fermentation medium by centrifugation and then concentrating the medium using selected cartridge filters. The concentrate containing PRO301, PRO362, PRO245 or PRO1868 may further be purified using selected column chromatography resins.

Example 16

Expression of PRO301, PRO362, PRO245 or PRO1868 in Baculovirus-Infected Insect Cells The following method describes recombinant expression of PRO301, PRO362 or PRO245 in Baculovirus-infected insect cells.

The PRO301, PRO362, PRO245 or PRO1868 is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the PRO301, PRO362, PRO245 or PRO1868 or the desired portion of the PRO301, PRO362, PRO245 or PRO1868 (such as the sequence encoding the extracellular domain) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged PRO301, PRO362, PRO245 or PRO1868 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 Fm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged PRO301, PRO362, PRO245 or PRO1868 are pooled and dialyzed against loading buffer.

Alternatively, purification of the IgG tagged (or Fc tagged) PRO301, PRO362, PRO245 or PRO1868 can be performed using known chromatography techniques, including for instance, Protein A or protein G column chromatography.

PRO301, PRO362 and PRO245 were expressed in baculovirus infected Sf9 insect cells. While the expression was actually performed in a 0.5-2 L scale, it can be readily scaled up for larger (e.g. 8 L) preparations. The proteins were expressed as an IgG construct (immunoadhesin), in which the protein extracellular region was fused to an IgG1 constant region sequence containing the hinge, CH2 and CH3 domains and/or in poly-His tagged forms.

Following PCR amplification, the respective coding sequences were subcloned into a baculovirus expression vector (pb.PH.IgG for IgG fusions and pb.PH.His.c for poly-His tagged proteins), and the vector and BACULOGOLD™ baculovirus DNA (Pharmingen) were co-transfected into 105 Spodoptera frugiperda ("Sf9") cells (ATCC CRL 1711), using Lipofectin (Gibco BRL). pb.PH.IgG and pb.PH.His are modifications of the commercially available baculovirus expression vector pVL1393 (Pharmingen), with modified polylinker regions to include the His or Fc tag sequences. The cells were grown in Hink's TNM-FH medium supplemented with 10% FBS (Hyclone). Cells were incubated for 5 days at 28° C. The supernatant was harvested and subsequently used for the first viral amplification by infecting Sf9 cells in Hink's TNM-FH medium supplemented with 10% FBS at an approximate multiplicity of infection (MOI) of 10. Cells were incubated for 3 days at 28° C. The supernatant was harvested and the expression of the constructs in the baculovirus expression vector was determined by batch binding of 1 ml of supernatant to 25 mL of Ni-NTA beads (QIAGEN) for histidine tagged proteins or Protein-A Sepharose CL-4B beads (Pharmacia) for IgG tagged proteins followed by SDS-PAGE analysis comparing to a known concentration of protein standard by Coomassie blue staining.

The first viral amplification supernatant was used to infect a spinner culture (500 ml) of Sf9 cells grown in ESF-921 medium (Expression Systems LLC) at an approximate MOI of 0.1. Cells were incubated for 3 days at 28° C. The supernatant was harvested and filtered. Batch binding and SDS-PAGE analysis was repeated, as necessary, until expression of the spinner culture was confirmed.

The conditioned medium from the transfected cells (0.5 to 3 L) was harvested by centrifugation to remove the cells and filtered through 0.22 micron filters. For the poly-His tagged constructs, the protein construct were purified using a Ni-NTA column (Qiagen). Before purification, imidazole was added to the conditioned media to a concentration of 5 mM. The conditioned media were pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column was washed with additional equilibration buffer and the protein eluted with equilibration buffer containing 0.25 M imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of proteins were purified from the conditioned media as follows. The conditioned media were pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 mL of 1 M Tris buffer, pH 9. The highly purified protein was subsequently desalted into storage buffer as described above for the poly-His tagged proteins. The homogeneity of the proteins was verified by SDS polyacrylamide gel (PEG) electrophoresis and N-terminal amino acid sequencing by Edman degradation.

PRO301, PRO362 and PRO245 were also expressed in baculovirus infected High-5 cells using an analogous procedure. High-5 cells were grown to a confluency of 50% at 27° C., no $CO_2$, no penicillin and no streptomycin. For each 150 mm plate, 30 μg of pIE based vector containing PRO301, PRO362 or PRO245 was mixed with 1 ml Ex-Cell medium (Media: Ex-cell 401, 1/100 L-Glu JRH Biosciences, #14401-78P, note: medium is light sensitive), and in a separate tube, 100 μl of CELLFECTIN™ (GibcoBRL #10362-010) was mixed with 1 ml of Ec-Cell medium. The pIE1-1 and pIE1-2 vectors are designed for constitutive expression of recombinant proteins from the baculovirus ie1 promoter in stably-transformed insect cells (Cartier, J. L., et al., J. Virol. 68, 7728-7737)(1994). The plasmids differ only in the orientation of the multiple cloning sites and contain all promoter sequences known to be important for ie1-mediated gene expression in uninfected insect cells as well as the hr5 enhancer element. pIE1-1 and pIE1-2 include the ie1 translation initiation site and can be used to produce fusion proteins.

The two solutions were combined and allowed to incubate at room temperature for 15 minutes. 8 ml of Ex-Cell media was added to the 2 ml of DNA/CELLFECTIN™ mix and is layered on High-5 cells previously washed with Ex-Cell media. The plate was incubated in darkness for 1 hour at room temperature. The DNA/CELLFECTIN™ mix was aspirated, and the cells washed once with Ex-Cell to remove excess CELLFECTIN™. Fresh Ex-cell medium (30 ml) was added and the cells incubated for 3 days at 28° C. The supernatant was harvested and the expression of PRO301, PRO362 or PRO245 was determined by batch binding in a manner similar to that described for Sf9 cells.

Example 17

Preparation of Antibodies that Bind PRO301, PRO362, PRO245 and PRO1868

This example illustrates preparation of monoclonal antibodies which can specifically bind PRO301, PRO362, PRO245 or PRO1868.

Techniques for producing the monoclonal antibodies are known in the art and are described, for instance, in Goding, supra. Immunogens that may be employed include purified PRO301, PRO362, PRO245 and PRO1868, fusion proteins containing PRO301, PRO362, PRO245 and PRO1868, and cells expressing recombinant PRO301, PRO362, PRO245 and PRO1868 on the cell surface. Selection of the immunogen can be made by the skilled artisan without undue experimentation.

Mice, such as BALB/c, are immunized with the PRO301, PRO362, PRO245 and PRO1868 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect PRO301, PRO362, PRO245 and PRO1868 antibodies.

After a suitable antibody titer has been detected, the animals "positive" for antibodies can be injected with a final intravenous injection of PRO301, PRO362, PRO245 and PRO1868. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells are screened in an ELISA for reactivity against PRO301, PRO362, PRO245 or PRO1868. Determination of "positive" hybridoma cells secreting the desired monoclonal antibodies against PRO301, PRO362, PRO245 or PRO1868 is within the skill in the art.

The positive hybridoma cells can be injected intraperitoneally into syngenic BALB/c mice to produce ascites containing the anti-PRO301, anti-PRO362, anti-PRO245 or anti-PRO1868 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Human PRO245 and PRO1868 cDNA were isolated from a human colonic cDNA library by colony hybridization. Human IgG1 Fc fusion protein (immunoadhesins) of PRO245 (PRO245.Fc, also called JAM-IT.Fc or JAM2.Fc) and PRO1868 (PRO1868.Fc or JAM3.Fc) were prepared as described in Ashkenazi et al. *Curr. Opin. Immun.* 9:195 (1997) and purified over a protein A column (Amersham Pharmacia Biotech, N.J., USA). Identity was verified by N-terminal sequence analysis.

BALB/c females were immunized and boosted with 10 μg of PRO245.Fc or 8×His-tagged PRO1868 via footpad injection. Single clones were screened against PRO245.Fc or 8×His-tagged PRO1868. Select clones were tested for cross reactivity against A33/JAM family members and human IgG Fc. Clones were titrated out to single cell densities and rescreened. Clone 12D10.2F9 was discovered to be selectively reactive to JAM2 (PRO245) and not JAM or JAM3. Clone MaJIR1 was found to be selectively reactive to JAM3 and not to JAM or JAM2. Both clones were isolated and used for ascites generation. Abs were purified over a protein G column.

Figure 58:
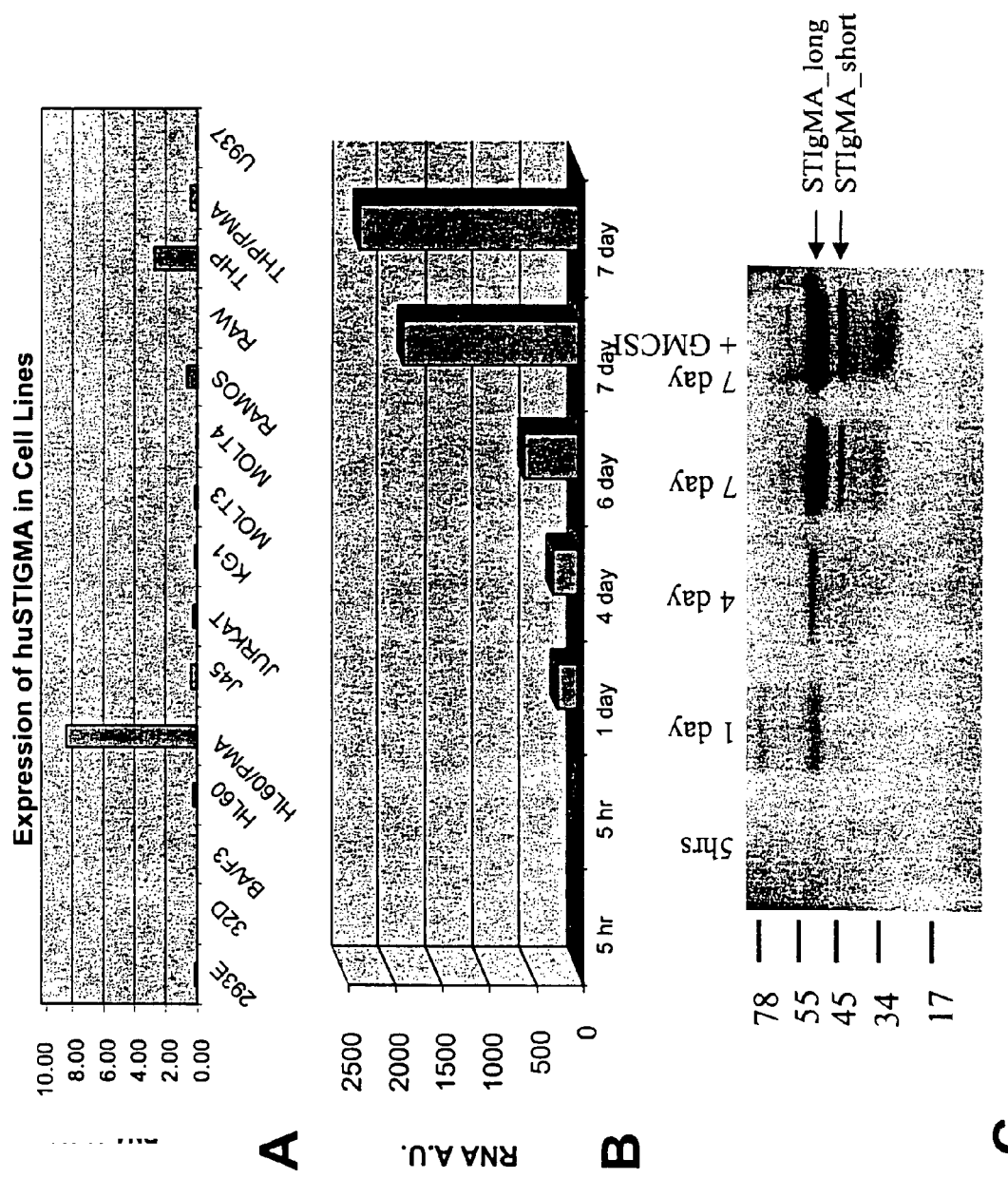
FIG. 58. (A) TAQMAN™ PCR analysis showing increased expression of human STIgMA in myelomonocytic cell lines HL60 and THP-1 and in differentiated macrophages. Low levels of expression were found in Jurkat T cells, MOLT3, MOLT4 and RAMOS B-cell lines. (B) Increased expression of STIgMA mRNA during in vitro monocyte differentiation. Monocytes isolated from human peripheral blood were differentiated by adhering to plastic over 7 day period. Total RNA was extracted at different time points during differentiation. (C) Increased expression of STIgMA protein during monocyte to macrophage differentiation. Monocytes were treated as indicated in (B), whole cell lysates were run on a gel and transferred to nitrocellulose membrane that was incubated with a polyclonal antibody (4F7) to human STIgMA. The polyclonal antibody recognized a 48 and 38 kDa band possibly representing the long and the short form of STIgMA.

Anti-PRO245 antibody 12D10.2F9 was specific for interaction with PRO245 expressing CHO cells and did not interact with human PRO301-expressing CHO cells (FIG. 58). Briefly, PRO245 cDNA was amplified by PCR from a human colon cDNA library (Clontech Laboratories, Palo Alto, Calif., USA) using primers specific for the 5' and 3' ends of the coding sequence. The fragment was purified and ligated into pSD5 expression vector, transfected into Chinese hamster ovary (CHO) cells and selected as described in Lucas et al. *Nuc. Acids Res.* 24:1774 (1996). Stable cell clones were screened for antibody reactivity. As can be seen in FIG. 58, The anti-PRO245 antibody (12D10.2F9) did not bind to huJAM expressing CHO transfectant CuL8r. CuL8r does interact with the anti-huJAM antibody 10A5.

Example 18

Isolation of cDNA Clones Encoding Human PRO1868 by Expression Cloning

Identification of PRO1868 was done by transiently transfecting pooled cDNA libraries encoding secreted and transmembrane proteins into COS cells grown on glass chamber slides. Twenty-four hours after transfection, PRO245 or PRO245-Fc fusions were added (0.5 μg/ml) and incubated for 30 minutes. PRO245/PRO245-Fc fusion binding was determined (Klein et al., *Nature*, 387:717 and 392:210 (1998)). Clones that were positive for the ability to bind to PRO245/PRO245-Fc fusions were selected for further characterization.

Example 19

Induction of Chondrocyte Re-Differentiation

The ability of the polypeptides of the invention to induce redifferentiation were tested in chondrocytes. Proteins with the ability to induce redifferentiation of chondrocytes are useful for the treatment of various bone and/or cartilage disorders such as, for example, sports injuries and arthritis.

Porcine chondrocytes were isolated by overnight collagenase digestion of articulary cartilage of metacarpophalangeal joints of 4-6 month old female pigs. The isolated cells were then seeded at 25,000 cells/cm$^2$ in Ham F-12 containing 10% FBS and 4 μg/ml gentamycin. The culture media was changed every third day and the cells were then seeded in 96 well plates at 5,000 cells/well in 100 μl of the same media without serum and 100 μl of the test PRO1868 polypeptide, 5 nM staurosporin (positive control) or medium alone (negative control) was added to give a final volume of 200 μl/well. After 5 days of incubation at 37° C., a picture of each well was taken and the differentiation state of the chondrocytes was determined. A positive result in the assay resulted when the redifferentiation of the chondrocytes was determined to be more similar to the positive control than the negative control.

PRO1868 polypeptides tested positive for the ability to induce redifferentiation of chondrocytes.

Example 20

Overexpression of PRO1868 Polypeptides in Cancerous Tumors

In the present example, the expression level of PRO1868 polypeptides in cancerous tissues was examined. Polypeptides that are overexpressed in cancerous tumors may be useful as not only diagnostic markers for the presence of one or more cancerous tumors, but also may serve as therapeutic targets for the treatment of those tumors.

For detection of overexpression of PRO1868 polypeptides, nucleic acid microarrays were used to identify differentially expressed genes in diseased tissues as compared to their normal counterparts. Using nucleic acid microarrays, test and control mRNA samples from test and control tissue samples are reverse transcribed and labeled to generate cDNA probes.

The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition. The methodology of hybridization of nucleic acids and microarray technology is well known in the art.

In the present example, cancerous tumors derived from various human tissues were studied for PRO1868 polypeptide-encoding gene expression relative to non-cancerous human tissue in an attempt to identify those PRO1868 polypeptides which are overexpressed in cancerous tumors. The specific preparation of nucleic acids for hybridization and probes, slides, and hybridization conditions are all detailed in U.S. Provisional Patent Application Ser. No. 60/193,767, filed on Mar. 31, 2000 and which is herein incorporated by reference. Two sets of experimental data were generated. In one set, cancerous human colon tumor tissue and matched non-cancerous human colon tumor tissue from the same patient ("matched colon control") were obtained and analyzed for PRO1868 polypeptide expression using the above described microarray technology. In the second set of data, cancerous human tumor tissue from a variety of different human tumors, including lung and breast tumors, was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

Nucleic acid probes derived from the herein described PRO1868 polypeptide-encoding nucleic acid sequences were used in the creation of the microarray and RNA from the tumor tissues listed above were used for the hybridization thereto. A value based upon the normalized ratio:experimental ratio was designated as a "cutoff ratio". Only values that were above this cutoff ratio were determined to be significant. PRO1868 polypeptides of the present invention are significantly overexpressed in various human tumor tissues, for example lung and breast tumors, as compared to a non-cancerous human tissue control.

These data indicate that the PRO polypeptides of the invention are useful as both diagnostic markers and therapeutic targets for the treatment of tumors.

Example 21

Induction of Cell Proliferation

A. Endothelial Cell Proliferation

The ability of polypeptides of the invention to induce proliferation in endothelial cells was tested in human umbilical vein endothelial cells (HUVEC, Cell Systems). Polypeptides with the ability to induce endothelial cell proliferation function as useful growth factors.

On day 0, pooled human umbilical vein endothelial cells (from cell lines, maximum of 12-14 passages) were plated in 96-well plates at 1000 cells/well per 100 microliter and incubated overnight in complete media [epithelial cell growth media (EGM, Clonetics), plus supplements: human epithelial growth factor (hEGF), bovine brain extract (BBE), hydrocortisone, GA-1000, and fetal bovine serum (FBS, Clonetics)]. On day 1, complete media was replaced by basal media [EGM plus 1% FBS] and addition of PRO1868 polypeptides at 1%, 0.1% and 0.01%. On day 7, an assessment of cell proliferation was performed by ALAMAR BLUE™ assay followed by Crystal Violet. Results were expressed as a % of the cell growth observed with control buffer.

PRO1868 polypeptides tested positive in this assay for the ability to induce proliferation of pooled human umbilical vein endothelial cells in culture, and as a result, to function as useful growth factors.

B. Human Coronary Artery Smooth Muscle Cell Proliferation

The ability of polypeptides of the invention to induce cell proliferation was tested in human coronary artery smooth muscle cells in culture. Polypeptides of the invention with the ability to induce cell proliferation are useful as growth factors.

On day 0, human coronary artery smooth muscle cells (from cell lines, maximum of 12-14 passages) were plated in 96-well plates at 1000 cells/well per 100 microliter and incubated overnight in complete media [smooth muscle growth media (SmGM, Clonetics), plus supplements: insulin, human epithelial growth factor (hEGF), human fibroblast growth factor (hFGF), GA-1000, and fetal bovine serum (FBS, Clonetics)]. On day 1, complete media was replaced by basal media [SmGM plus 1% FBS] and addition of PRO1868 polypeptides at 1%, 0.1% and 0.01%. On day 7, an assessment of cell proliferation was performed by ALAMAR BLUE™ assay followed by Crystal Violet. Results were expressed as a % of the cell growth observed with control buffer.

PRO1868 polypeptides tested positive in the assay for the ability to induce proliferation of human coronary artery smooth muscle cells in culture and to function as a useful growth factor.

Example 22

PRO mRNA and Polypeptide Expression

A. In Situ Hybridization and Immunohistochemistry

Expression of PRO362, PRO245 and PRO1868 mRNA was evaluated by in situ hybridization, immunohistochemistry and RT-PCR in various types of tissues.

For in situ hybridization, tissues were fixed (4% formalin), paraffin-embedded, sectioned (3-5 µm thick), deparaffinized, deproteinated (20 µg/ml) with proteinase K (15 minutes at 37° C.), and processed for in situ hybridization. Probes to the polypeptides of the invention were produced by PCR. Primers included T7 or T3 RNA polymerase initiation sites to allow for in vitro transcription of sense or antisense probes from the amplified products. $^{33}$P-UTP labeled sense and antisense probes were hybridized overnight (55° C.), washed (0.1×SSC for 2 hours at 55° C.), dipped in NBT2 nuclear track emulsion (Eastman Kodak, Rochester, N.Y.), exposed (4-6 weeks at 4° C.), and developed and counterstained with hematoxylin and eosin. Representative paired bright and darkfield images are typically shown.

Immunohistochemical staining was performed on 5 mm thick frozen sections using a DAKO Autostainer. Endogenous peroxidase activity was blocked with Kirkegaard and Perry Blocking Solution (1:10, 4 minutes at 20 C.). 10% NGS in TBS/0.05% Tween-20 (DAKO) was used for dilution and blocking. MAb 4F722.2 anti-STIgMA (anti-PRO362) or mouse IgG was used at 0.13 mg/ml. Biotinylated goat anti-mouse IgG (Vector Labs), Burlingame, Calif.) was used at 1:200 and detected with Vector Labs Standard ABC Elite Kit (Vector Labs, Burlingame, Calif.). Slides were developed using Pierce metal-enhanced diaminobenzidine (Pierce Chemicals, Rockford, Ill.). Dual immunohistochemistry for PRO362 (STIgMA) and CD68 expression was performed on frozen sections to demonstrate localization of STIgMA expression to macrophages. mAb 4F7.22.2 anti-STIgMA and anti-CD68 mAb KP-1 from (DAKO) were utilized and detected by phycoerythrin and FITC markers, respectively.

1. Tissues Examined

Expression was examined in a wide variety of tissues and cell types from humans and other mammals.

a. Normal Tissue

Normal human adult tissues that were examined included tonsil, lymph node, spleen, kidney, urinary bladder, lung, heart, aorta, coronary artery, liver, gall bladder, prostate, stomach, small intestine, colon, pancrease, thyroid gland, skin, adrenal gland, placenta, uterus, ovary, testis, retina, and brain (cerebellum, brainstem, cerebral cortex). Normal human fetal tissues including E12-E16 week-old brain, spleen, bowel and thyroid were also tested. In addition, expression was investigated in murine liver.

b. Inflamed Tissue

Inflamed tissues examined by in situ hybridization included tissues with chronic inflammatory disease such as lungs with chronic asthma, chronic bronchopneumonia, chronic bronchitis/chronic obstructive pulmonary disease, kidneys with chronic lymphocytic interstitial nephritis, and livers with chronic inflammation and cirrhosis due to chronic hepatitis C infection, autoimmune hepatitis or alcoholic cirrhosis.

c. Primary Neoplasms

Primary human neoplasms that were examined by in situ hybridization for PRO362, PRO245 and PRO1868 expression included breast carcinoma, pulmonary squamous cell carcinoma, pulmonary adenocarcinoma, prostatic adenocarcinoma, and colonic adenocarcinoma.

2. Results a. PRO362 Expression

Figure 23:
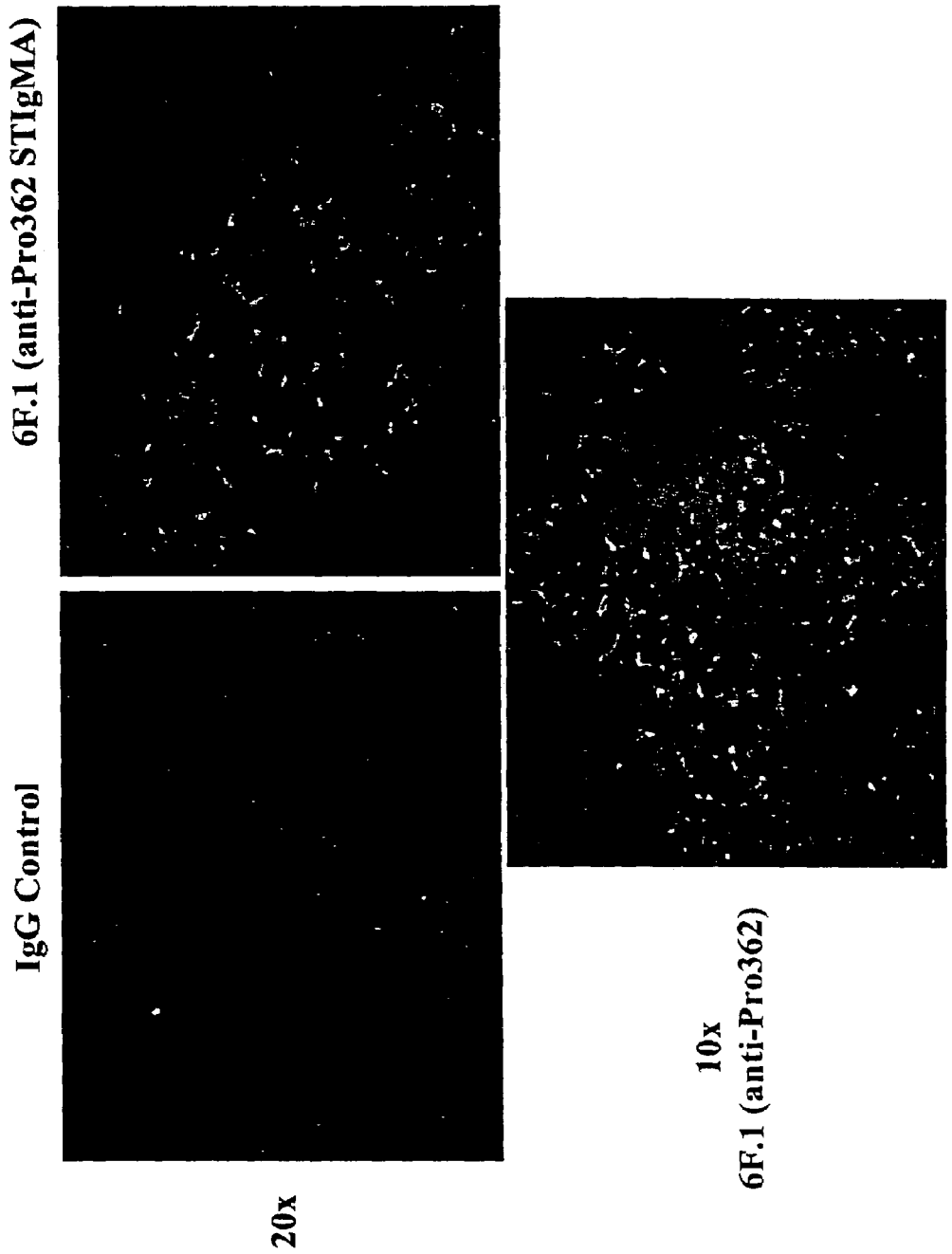
FIG. 23 shows in situ hybridization of PRO362 in mouse liver frozen sections.
Figure 24:
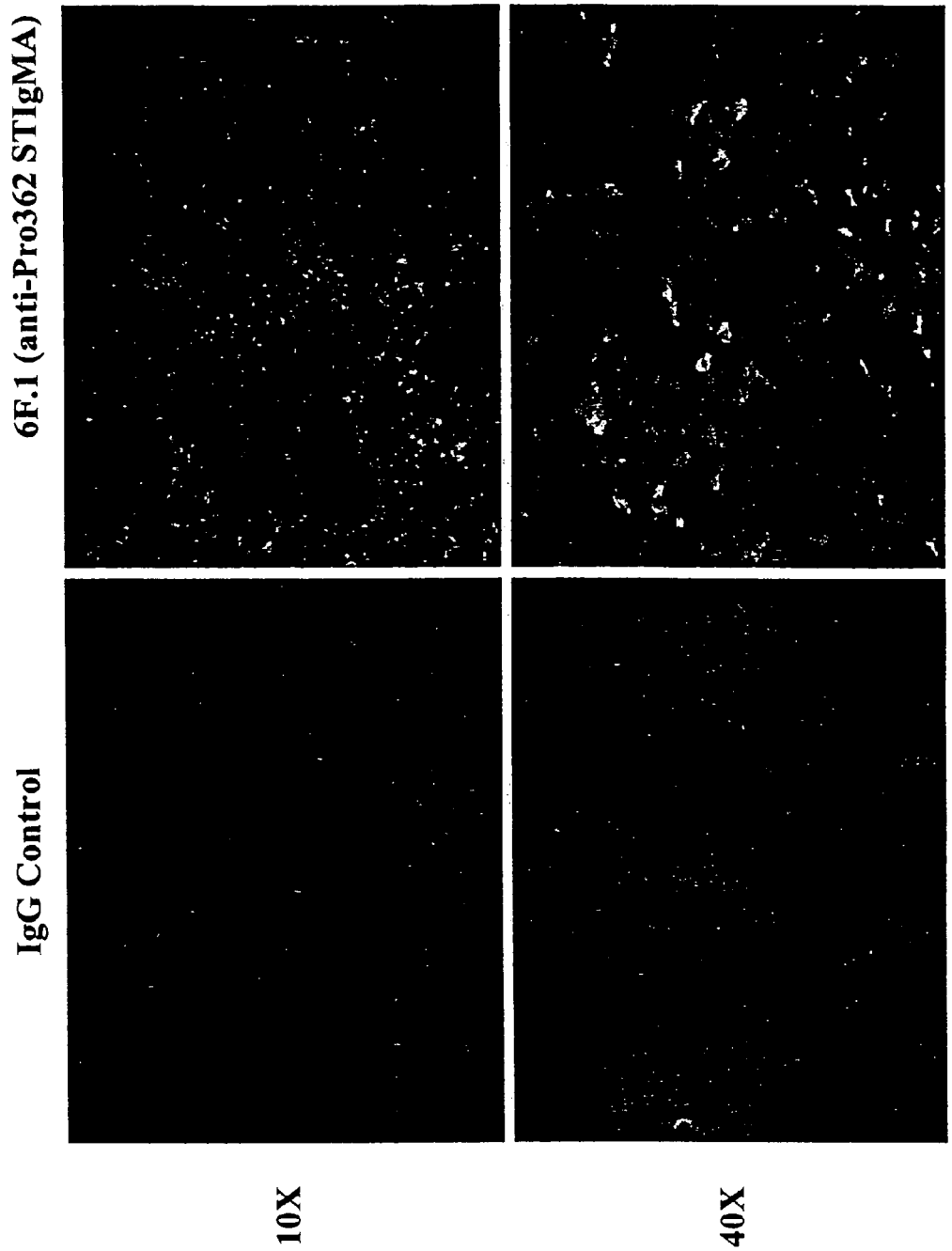
FIG. 24 shows in situ hybridization of PRO362 in human liver frozen sections.
Figure 25:
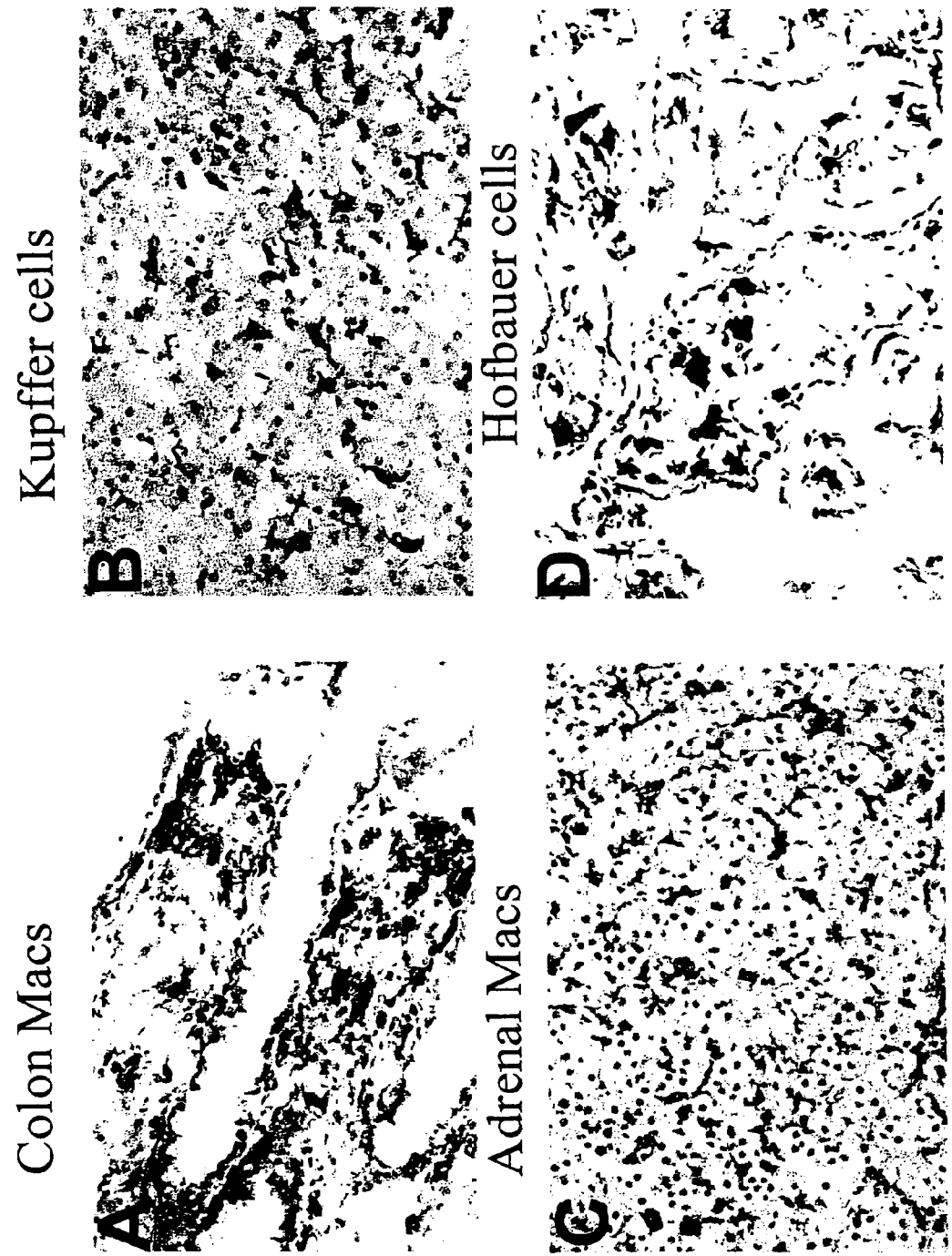
FIG. 25 shows in situ hybridization of PRO362 in colon macrophages (FIG. 25A), Kupffer cells (FIG. 25B), adrenal macrophages (FIG. 25C), Hofbauer cells (FIG. 25D).
Figure 26:
FIG. 26 shows in situ hybridization of PRO362 mRNA in Synovial cells.
Figure 27:
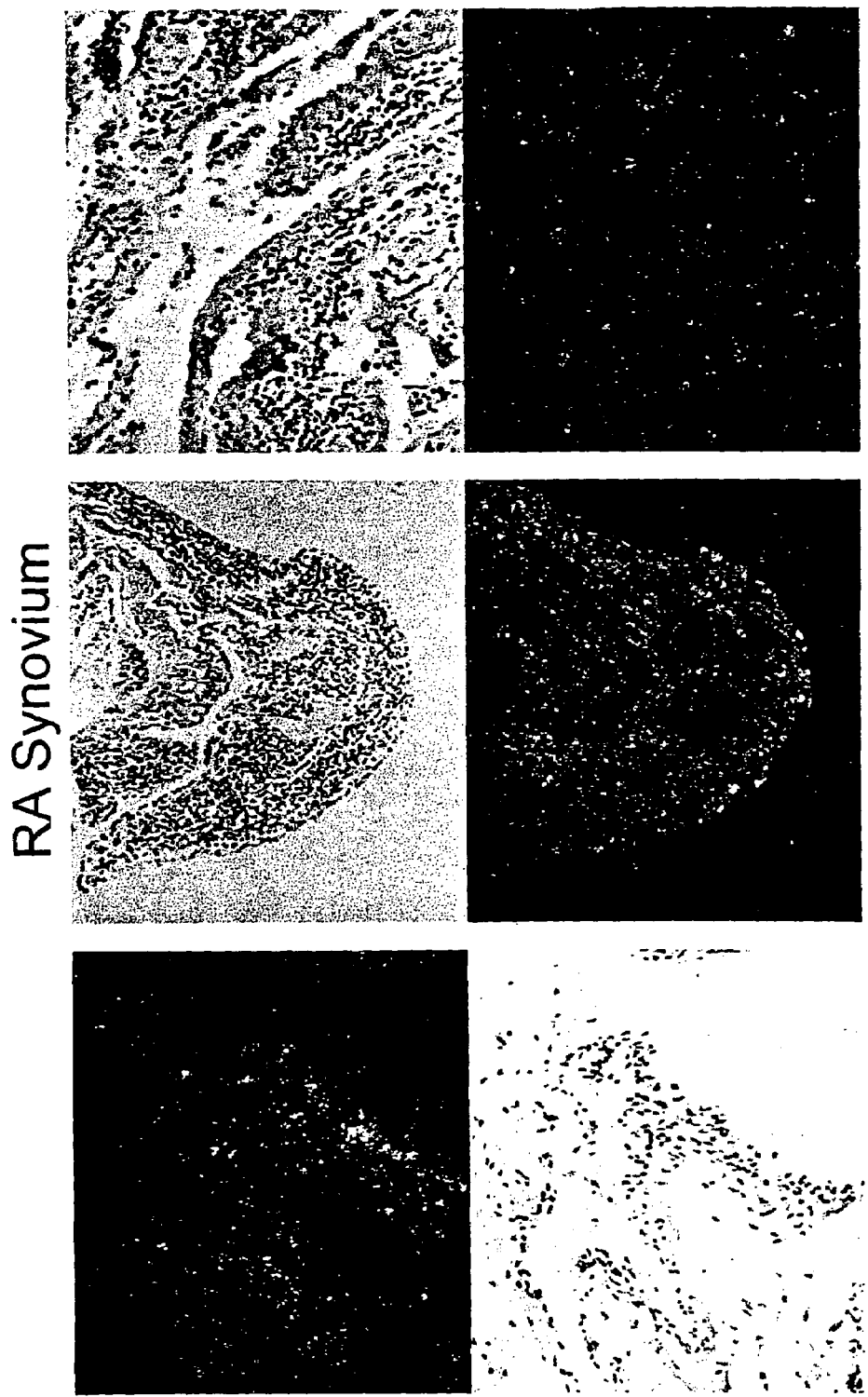
FIG. 27 shows in situ hybridization of PRO362 RNA in type A synovial cells.
Figure 28:
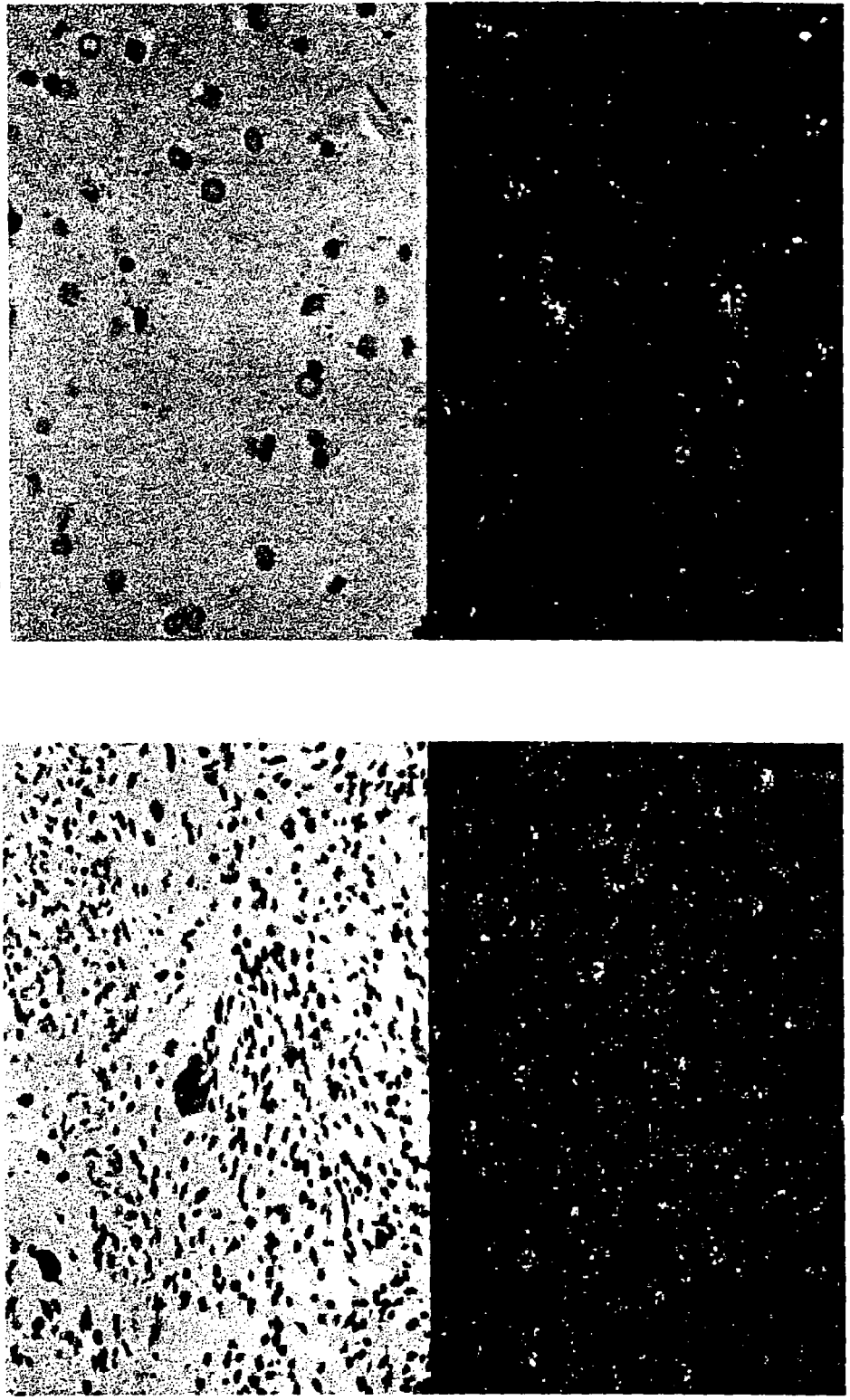
FIG. 28 shows in situ hybridization of PRO362 mRNA in brain microglia cells.
Figure 29:
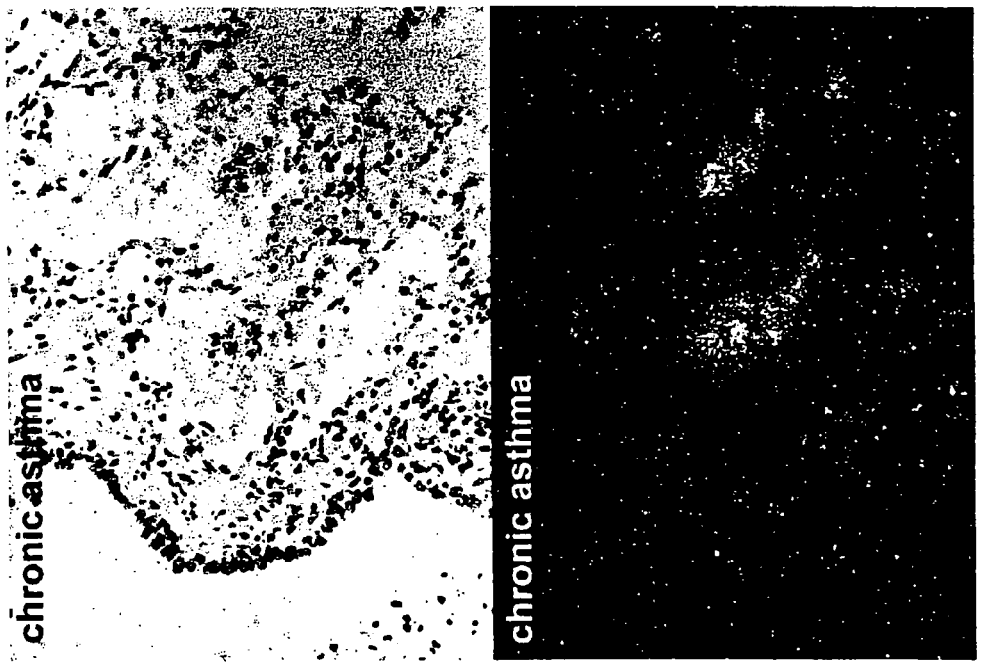
FIG. 29 shows in situ hybridization of PRO362 mRNA in cells from human asthmatic tissue.
Figure 30:
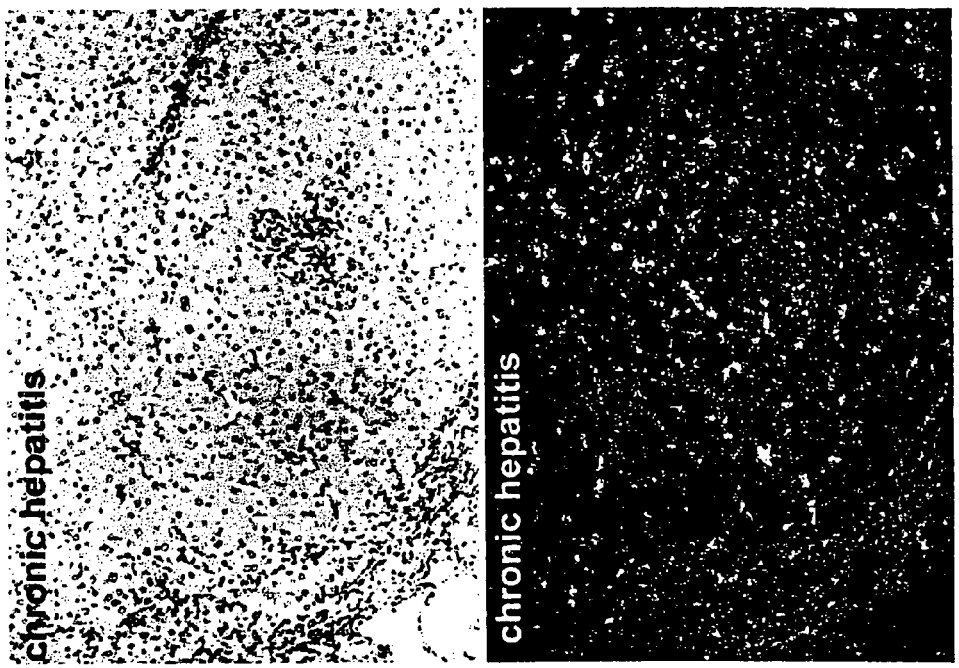
FIG. 30 shows in situ hybridization of PRO362 mRNA in cells from human chronic hepatitis tissue.

PRO362 was found to be expressed in mouse liver frozen sections (FIG. 23), human liver frozen sections (FIG. 24) and a number of tissue macrophage-like cells, including colon macrophages (FIG. 25A), Kupffer cells (FIG. 25B), adrenal macrophages (FIG. 25C), Hofbauer cells (FIG. 25D), synovial cells (FIG. 26), alveolar macrophages, resident macrophages in the intestinal lamina propria and interstitial macrophages in many tissues. PRO362 was also significantly expressed in brain microglia. The expression of PRO362 was significantly increased in these tissues when activated by the presence of neoplasia or inflammatory disease, including rheumatoid arthritis (FIG. 27), inflammatory bowel disease, chronic hepatitis (FIG. 28), pneumonia, chronic asthma (FIG. 29), glioma (FIG. 30) and bronchitis.

To further examine expression of PRO362, immunohistochemical staining was performed on various tissue types. Dual immunohistochemical staining for PRO362 and CD68 was performed on tissue macrophages, including adrenal gland macrophages, liver Kupffer cells, brain microglial cells, and placental Hofbauer cells was performed to determine whether PRO362 and CD68 are expressed in the same tissues.

Figure 37:
FIG. 37 shows immunohistochemical analysis of PRO362 in microglial cells.

PRO362 was found to be coexpressed with CD68 on adrenal gland macrophages (FIG. 35), liver Kupffer cells (FIG. 36), brain microglial cells (FIG. 37), and placental Hofbauer cells (FIG. 38).

b. PRO245 Expression

PRO245 was found to be significantly localized to epithelial tissue and inflamed tissues.

(i) Normal Tissue

Figure 31:
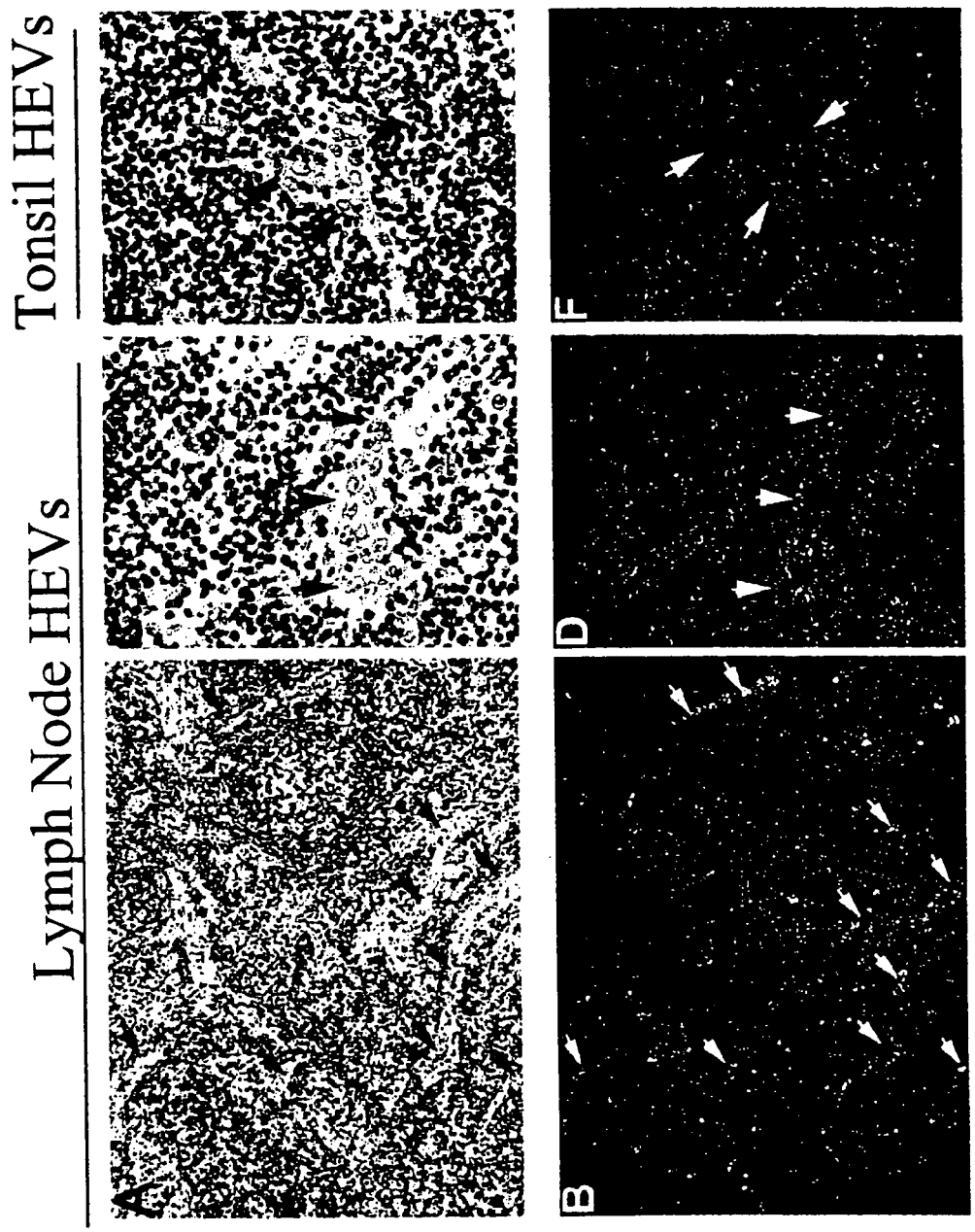
FIG. 31 shows in situ hybridization of PRO245 mRNA in lymph node and tonsil high endothelial venule (HEV) cells of normal human tissue.

Expression of PRO245 mRNA in normal adult human tissues was significant in the high endothelial venules (HEVs) in tonsils and lymph nodes (FIG. 31), the spermatogenic cells of the epithelium in the testicular seminiferous tubules (FIGS. 32I and J), and the intermediate trophoblasts of the placenta.

Expression of PRO245 mRNA in normal human fetal tissues was significant in endothelial cells, but more specifically, was found in the vascular endothelium of small and large vessels (excluding capillaries), in mesenteric vessels, mural vessels of the bowel wall, and small vessels of the developing mesenteric lymph nodes and thyroid.

Expression of PRO245 was not significant in the spleen, normal skin or foreskin, normal lung, thyroid, normal bowel, normal cardiac tissue or adrenal glands.

(ii) Inflamed Tissue

Figure 32:
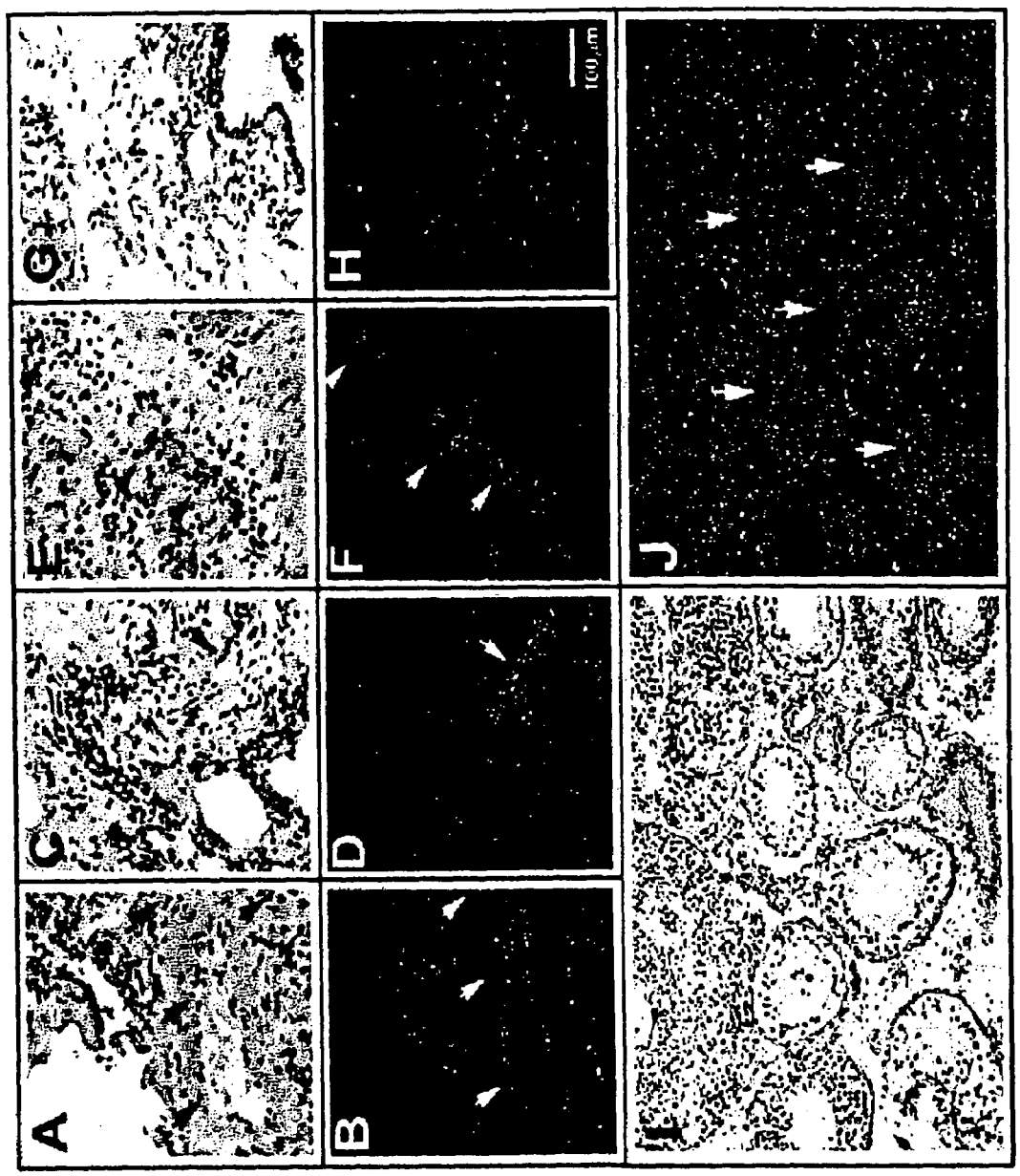
FIG. 32 shows in situ hybridization of PRO245 mRNA in arteriolar endothelium of inflamed and normal human lung tissue, as well as in normal seminiferous tubules of testis in spermatogenic cells.

The expression of PRO245 was more extensive in tissues with chronic inflammatory diseases. In biopsies of lung with chronic bronchopneumonia, PRO245 mRNA was expressed in the endothelium of small- (FIGS. 32A and B), medium- (FIGS. 32C and D), and large-caliber arterioles (FIGS. 32E and F) present within or immediately adjacent to foci of lymphocytic inflammation. PRO245 mRNA was not observed in normal lung tissue (FIGS. 32G and H). Further, PRO245 was found to be significantly expressed in the vascular endothelium in active or chronic inflammation in the following: arterioles, veins and capillaries from tissues associated with chronic interstitial pneumonia, superficial dermal vessels of psoriatic skin from tissues associated with psoriasis, arterioles from tissues associated with chronic sclerosing nephritis, vascular endothelium and capillaries in inflamed foci from tissues associated with appendicitis, endothelium of numerous vessels, HEVs, capillaries, small arterioles and veins from tissues associated with tonsil and perifollicular sinuses, and capillaries in periarterial interstitial tissue in aorta and aorta associated with atherosclerosis. PRO245 was not significantly expressed in aortic intima.

In biopsies of kidney with chronic lymphocytic interstitial nephritis and liver with chronic lymphocytic hepatitis, PRO245 expression was significant in the endothelium of arterioles in and adjacent to sites of lymphocytic inflammation. PRO245 expression was not significant in chronically inflammed or cirrhotic liver.

In biopsies of liver with chronic inflammation and cirrhosis, PRO245 was not significantly expressed.

PRO245 expression was not significantly expressed in inflamed large bowel or brain with meningitis.

(iii) Neoplastic Tissue

Figure 33:
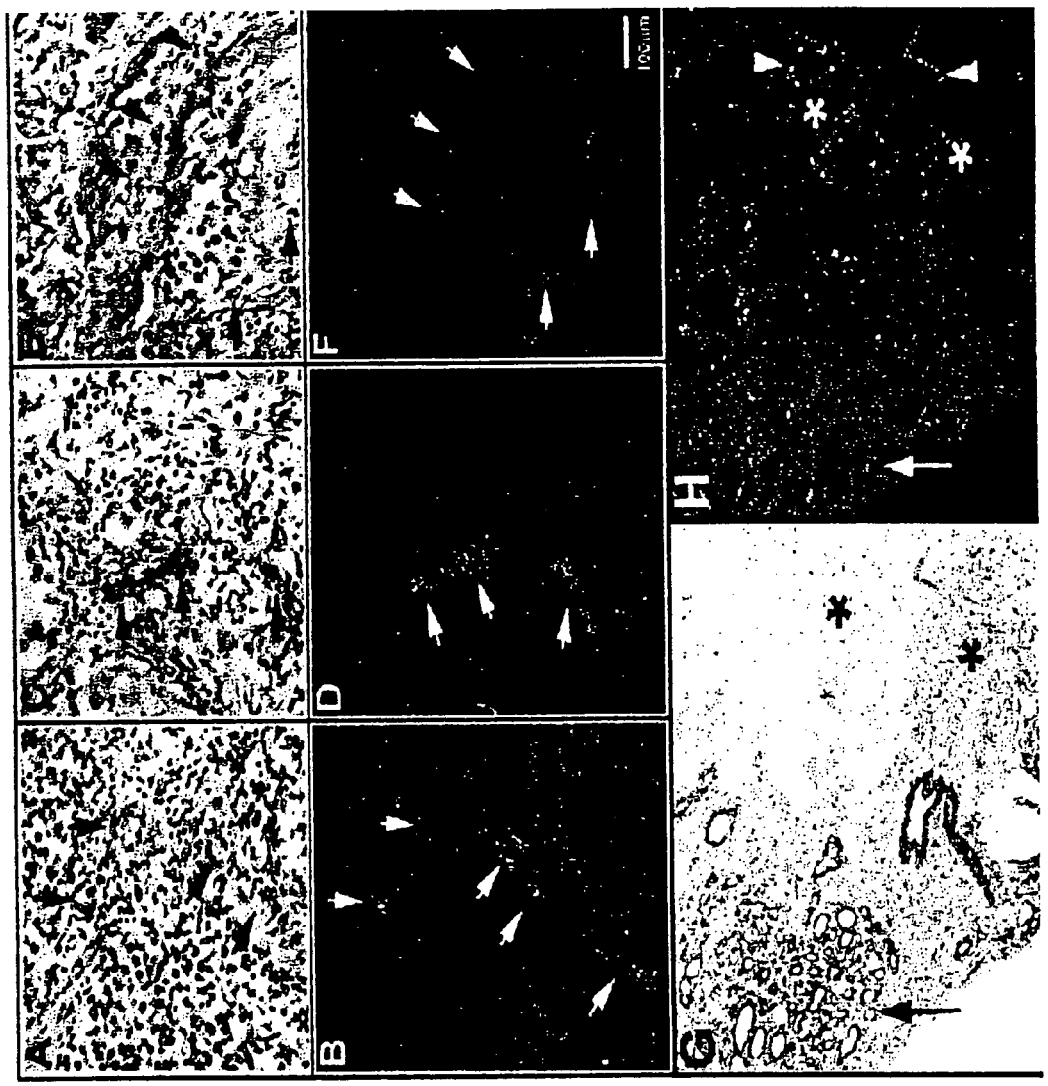
FIG. 33 shows in situ hybridization of PRO245 mRNA in human testicular, lung and mammary carcinoma tissue.

PRO245 expression was observed in the endothelium of small- and medium-caliber arterioles in a number of primary neoplasms, including colonic adenocarcinoma, testicular carcinoma (FIGS. 33A and B), pulmonary adenocarcinoma (FIGS. 33C and D), mammary adenocarcinoma (FIGS. 33E and F) and significantly in prostatic adenocarcinoma and colonic adenocarcinoma. PRO245 mRNA was found to be expressed in breast carcinoma (FIG. 34). However, PRO245 was not significantly expressed in adjacent normal breast tissue, as shown in FIGS. 33G and H, where breast carcinoma is denoted with an asterisk and normal breast tissue with an arrow. PRO245 expression is observed uniquely in vessels adjacent to the tumor (arrowheads), but not in normal tissue.

PRO245 expression was found in the vascular endothelium of epididymis and within areas of chronic lymphocytic inflammation in testicular carcinomas or seminomas, in the vascular endothelium of tumor foci within areas of chronic lymphocytic inflammation of lung adenocarcinoma, in the vascular endothelium in tumor foci within areas of chronic lymphocytic inflammation in lung squamous cell carcinoma, in the vascular endothelium adjacent to tumor foci and within areas of chronic lymphocytic inflammation of breast carcinomas, and in areas adjacent to vascular endothelium in arterioles, veins, and capillaries in chondrosarcomas.

c. PRO1868 Expression

PRO1868 was found to be expressed on NK cells, CD8+ T cells and dendritic cells.

B. Reverse Transcription-Polymerase Chain (RT-PCR)

Reverse Transcription-polymerase chain reaction (RT-PCR) is a sensitive technique for mRNA detection and quantitation that consists of synthesis of cDNA from RNA by reverse transcription. To detect expression of PRO1868, the presence of PRO1868 mRNA was detected by RT-PCR.

Figure 39:
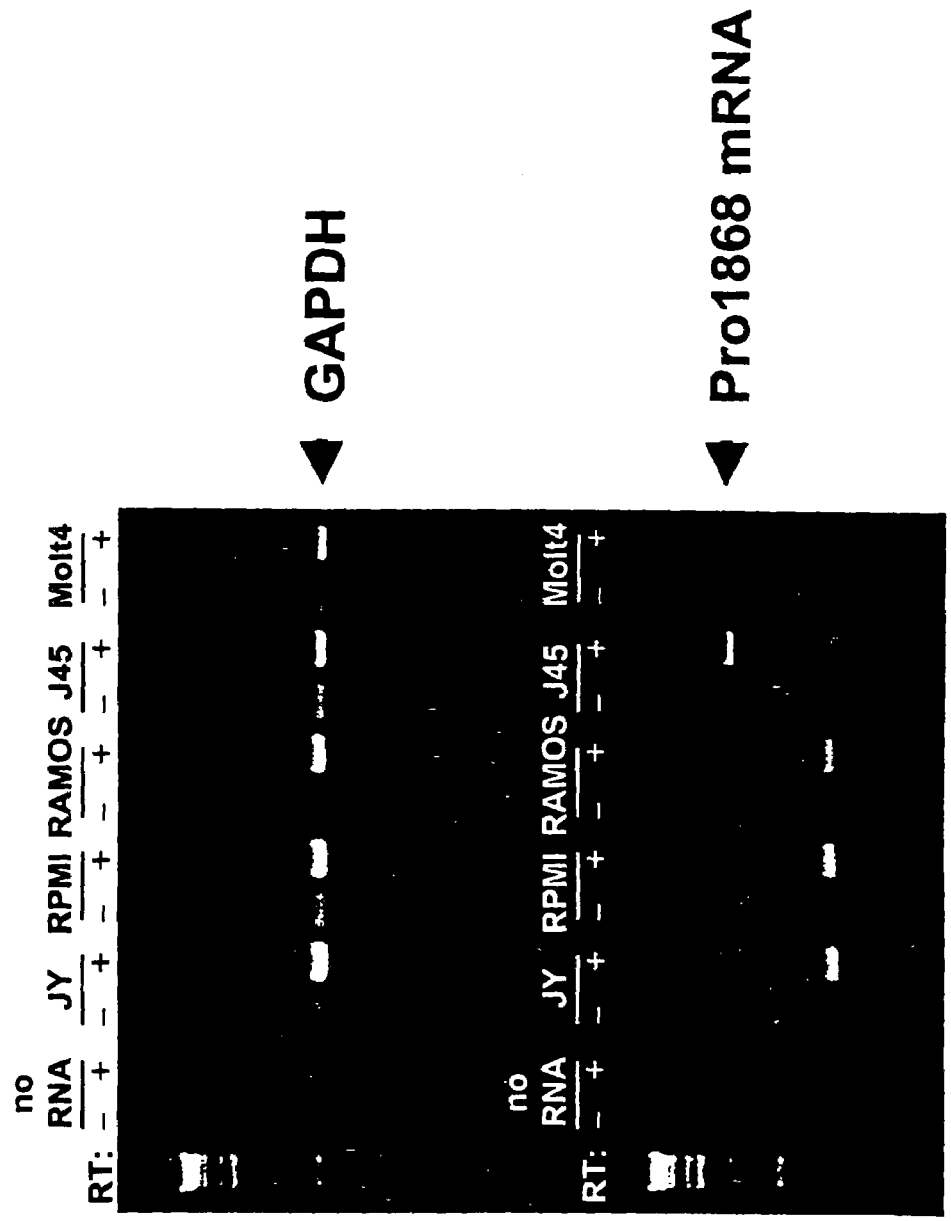
FIG. 39 shows SDS-PAGE analysis of PRO1868 mRNA detected by reverse-transcriptase PCR(RT-PCR) in T cell lines J45 and Molt4, and B cell lines JY, RPMI8866 and RAMOS.

PRO1868 mRNA was significantly detected by reverse-transcriptase PCR(RT-PCR) in the T cell lines, J45 and Molt5, but not in the B cell lines, JY, RPMI8866 and RAMOS (FIG. 39).

Example 22

Interaction of PRO245 with Specific Cell Types

As determined by flow cytometry, peripheral blood cells do not significantly express PRO245 (Table 6, top half). To determine whether PRO245 interacted with discrete subsets of peripheral blood cells a number of PRO245-cell assays were performed. These included magnetic or FACS sorting of PRO245-interacting cells. Peripheral blood was obtained for all experiments as described below.

A. Magnetic Sorting and Flow Cytometry

To determine whether PRO245 interacts with peripheral blood leukocytes, a biotinylated PRO245-human IgG fusion protein was generated, as described below. PRO245-interacting peripheral blood leukocytes were isolated using streptavidin-conjugated magnetic beads. Isolated cells were then examined for surface CD-Ag expression. Results obtained using biotinylated PRO-245-human IgG fusion were compared to results using biotinylated human IgG.

Biotinylated PRO245-human IgG fusion proteins or human IgG1 proteins were incubated for 1 hour at 4° C. with PBMC ($10 \mu g/10^7$) in SerF buffer (10% FBS (v/v; Life Technologies) plus 0.1% NaN3 (w/v; Sigma-Aldrich, St. Louis, Mo.) in HBSS without phenol red or sodium bicarbonate (HBSS+; Life Technologies) buffered with 10 mM HEPES (Life Technologies), pH 7.4). Cells were washed in SerF buffer and resuspended at $80 \mu l/10^7$ cells. Streptavidin magnetic beads (Miltenyi Biotec) were added at $20 \mu l/10^7$ cells and incubated for 15 minutes at 4 C, washed with SerF buffer, resuspended at 500 ml/108 cells, and passed over a positive selecting MACS column. Positively selected cells were eluted per the manufacturer's instructions, washed with SerF buffer, and analyzed by flow cytometry for surface CD Ags at $2 \times 10^5$ cells per condition. The data are presented as percentage positive, representing the percentage of positively stained cells in a total of $2 \times 10^5$ cells collected per staining condition for flow cytometry.

1. Protein Conjugation

PRO245-human IgG fusion, human IgG1, or PRO362-human IgG fusion were biotinylated with 200 µg of EZ-Link sulfo-NHS-LC-biotin (Pierce) per 1 mg of protein in PBS for 30 minutes at room temperature. Biotinylation was quenched with the addition of (final concentration) 200 mM Tris, pH 8, and incubated for 30 minutes at room temperature. Biotinylated proteins were then dialyzed extensively against PBS and concentrated to a concentration of 2 mg/ml with Centricon-10 microconcentrators (Millipore, Bedford, Mass.).

Alexa-488 (Molecular Probes, Eugene, Oreg.) protein conjugation kit was used per the manufacturer's instructions for the conjugation of Alexa-488 onto PRO245-human IgG fusion or human IgG1.

2. Flow Cytometry

Cells for use in flow cytometric analysis were blocked for 30 minutes at 4° C. with SerF buffer and stained with Abs to CD3, CD4, CD8, CD14, CD19 or CD56, conjugated to either FITC, PE, or CyChrome (BD PharMingen, San Diego, Calif.).

3. Results

The following four cell populations of peripheral blood leukocytes were found to significantly interact with PRO245: T cells (CD3+), CD8+ cells, B cells (CD19+) and NK cells (CD56+). The percentage of cells that were able to interact with PRO245 in a single experiment were as follows: 20.99% for CD3+ cells, 6.68% for CD8+ cells, 9.66% for CD19+ cells, and 36.89% for CD56+ cells. The percentage of cells that were able to interact with the human IgG control were as follows: 2.39% for CD3+ cells, 1.78% for CD8+ cells, 4.42% for CD19+ cells, and 6.69% for CD56+ cells.

B. FACS Sorting and Flow Cytometry

PRO245-human IgG fusion protein-binding peripheral blood cells were sorted by FACS sorting.

For FACS sorting, cells were incubated (30 minutes at 4° C.) with Alexa-488-conjugated human IgG1 or PRO245-human IgG fusion protein ($10 \mu g/10^6$ cells) in a modified SerF buffer (SerF buffer with 5 µg/ml anti-CD16 Ab 3G8 (BD PharMingen) and 20 µg/ml human IgG1 (Calbiochem, San Diego, Calif.)), washed and sorted on an Elite ESP (Beckman Coulter, Miami, Fla.). In these conditions, Alexa-488-conjugated PRO245 or human IgG was used as background. For competition assays, the competitor ($20 \mu g/10^6$ cells) was mixed with the cells for 20 minutes at room temperature in SerF buffer before Alexa-488-conjugated PRO245-human IgG fusion protein or human IgG were introduced. The cells were then washed and analyzed by flow cytometry as described above.

Figure 40:
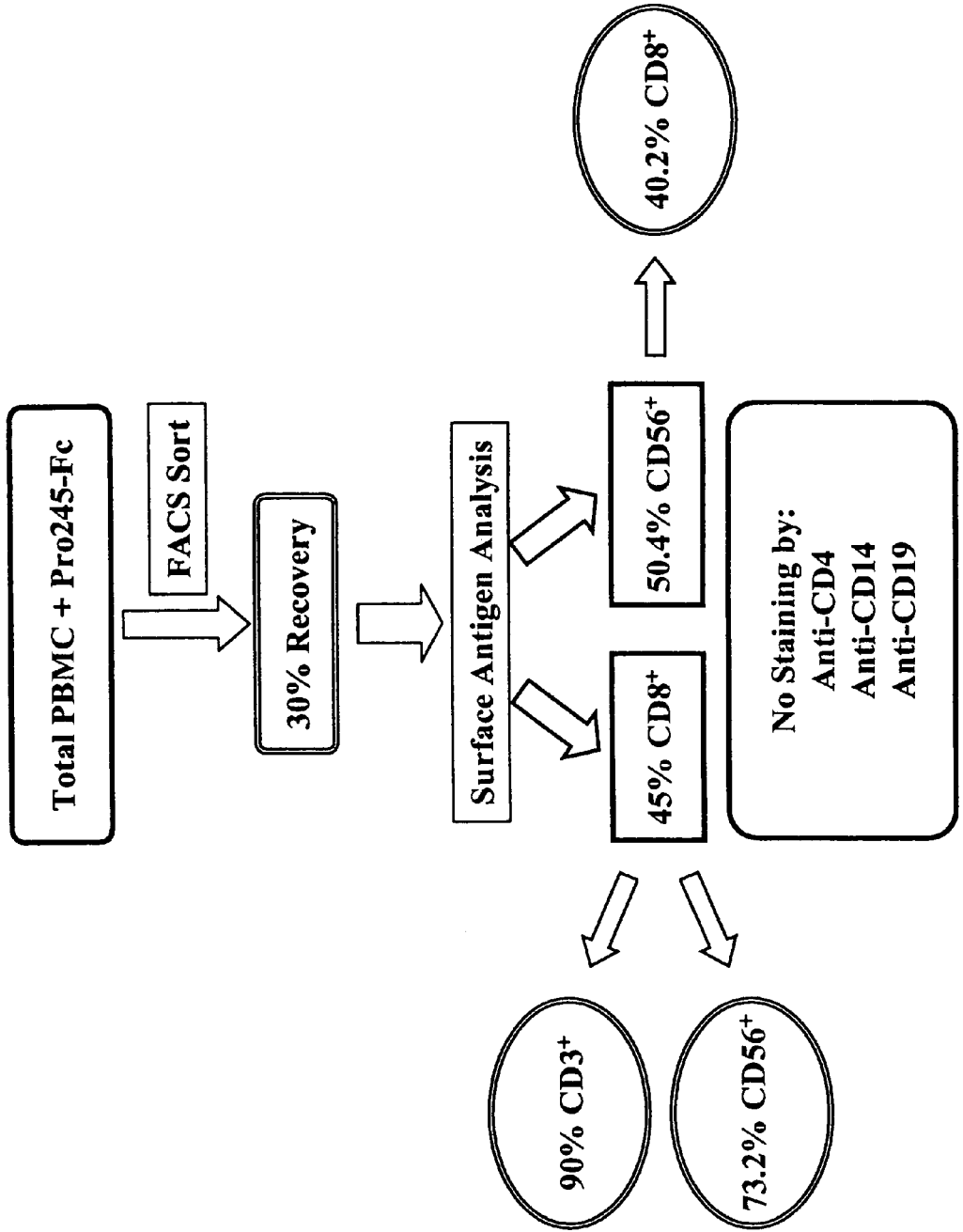
FIG. 40 shows a schematic summarizing PRO245 binding by cytolytic T cells, NK-T cells, and NK cells.

Of the cells that interact with PRO245-human IgG fusion protein (JAM-IT.Fc), 12.5% were CD3+ T cells, 32.4% were CD8+ T cells, and 50.4% were CD56+ NK cells. CD19+B cells were not detected in the FACS sorting assay. Of the CD56+ NK cells, 22.4% expressed CD3 and 40.2% expressed CD8. Of the CD8+ T cells, 23.5% expressed CD3 and 73.2% expressed CD56 (FIG. 40).

TABLE 6

Expression of PRO245 on peripheral blood cells and binding of peripheral blood cells to PRO245

| Primary Staining | Secondary Staining | | | | | | |
|---|---|---|---|---|---|---|---|
| | CD3 | CD4 | CD8 | CD14 | CD19 | CD56 | PMN |
| anti-PRO245 Positive | 0.2% | 0.1% | 0.1% | 0.7% | 0.1% | 0.3% | 0.9% |
| anti-PRO301 Positive | 76.7% | 73.9% | 80.4% | 99% | 90% | 85% | 98.7% |
| anti-mouse IgG Positive | 0.25 | 0.1% | 0.1% | 0.7% | 0.1% | 0.3% | 0.9% |
| Percent of total PRO245 binding cells | 12.6% | 1.1% | 32.4% | 0.3% | 0.4% | 50.4% | NA |
| Percent of PRO245 binding CD56 positive cells | 22.4% | 0.2% | 40.2% | 0.5% | 0.4% | | NA |
| Percent of PRO245 binding CD8 positive cells | 23.5% | 0.1% | | 0.6% | 0.3% | 73.2% | NA |

C. Binding to Purified Cells

Purified B cells, neutrophils, CD14+ monocytes, peripheral blood dendritic cells (PBDCs) from Clonetics (San Diego, Calif.), peripheral blood CD56+ NK cells obtained by negative selection, and J45, a CD3+ T cell line, were analyzed for their ability to interact with Alexa-488-conjugated PRO245-human IgG fusion protein by flow cytometry. The ability to interact with Alexa-488-conjugated human IgG1 protein was analyzed at the same time as a control.

Blood was obtained from healthy adult volunteers by venous puncture and separated using Ficoll-Plaque PLUS (Amersham Pharmacia Biotech) per the manufacturer's instructions. PBMC were obtained from the interface, washed in cold PBS, lysed (with 0.2% NaCl for 30 seconds and neutralized with 1.6% NaCl) as needed, counted, and kept on ice at $5 \times 10^7$ cells/ml until use. By flow cytometric analysis, no contaminating platelets were observed in the purified PBMC fractions. Neutrophils were obtained from the pellet after lysis of contaminating RBCs. Neutrophils were washed in cold PBS, counted, and kept at $5 \times 10^7$ cells/ml until use on ice. To isolated peripheral blood subsets, "untouched" MACS kits (Miltenyi Biotec, Auburn, Calif.) were used following the manufacturer's instructions.

Figure 41:
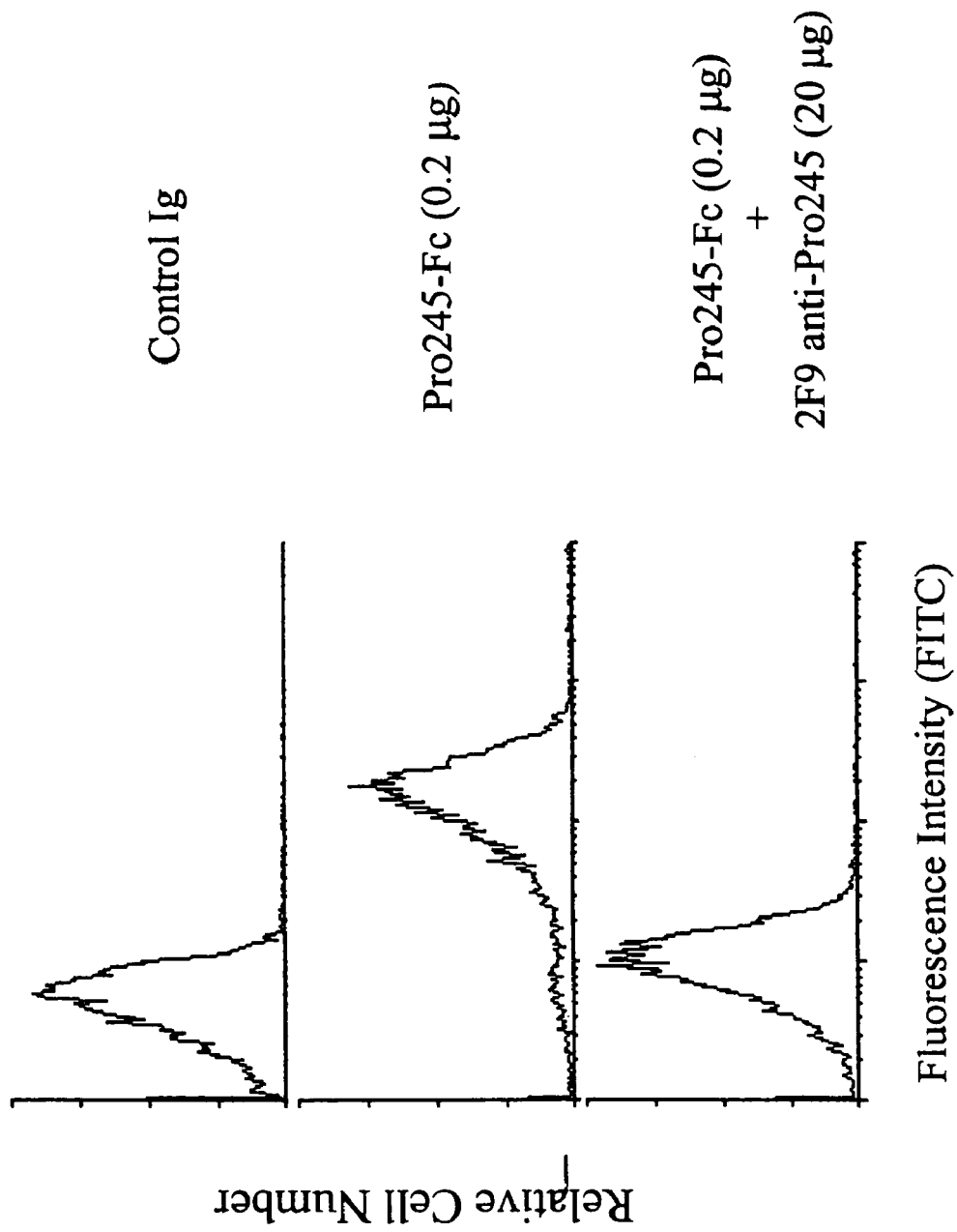
FIG. 41 shows flow cytometry results of binding between NK (CD56+) cells and PRO245-Fc fusion protein.
Figure 46:
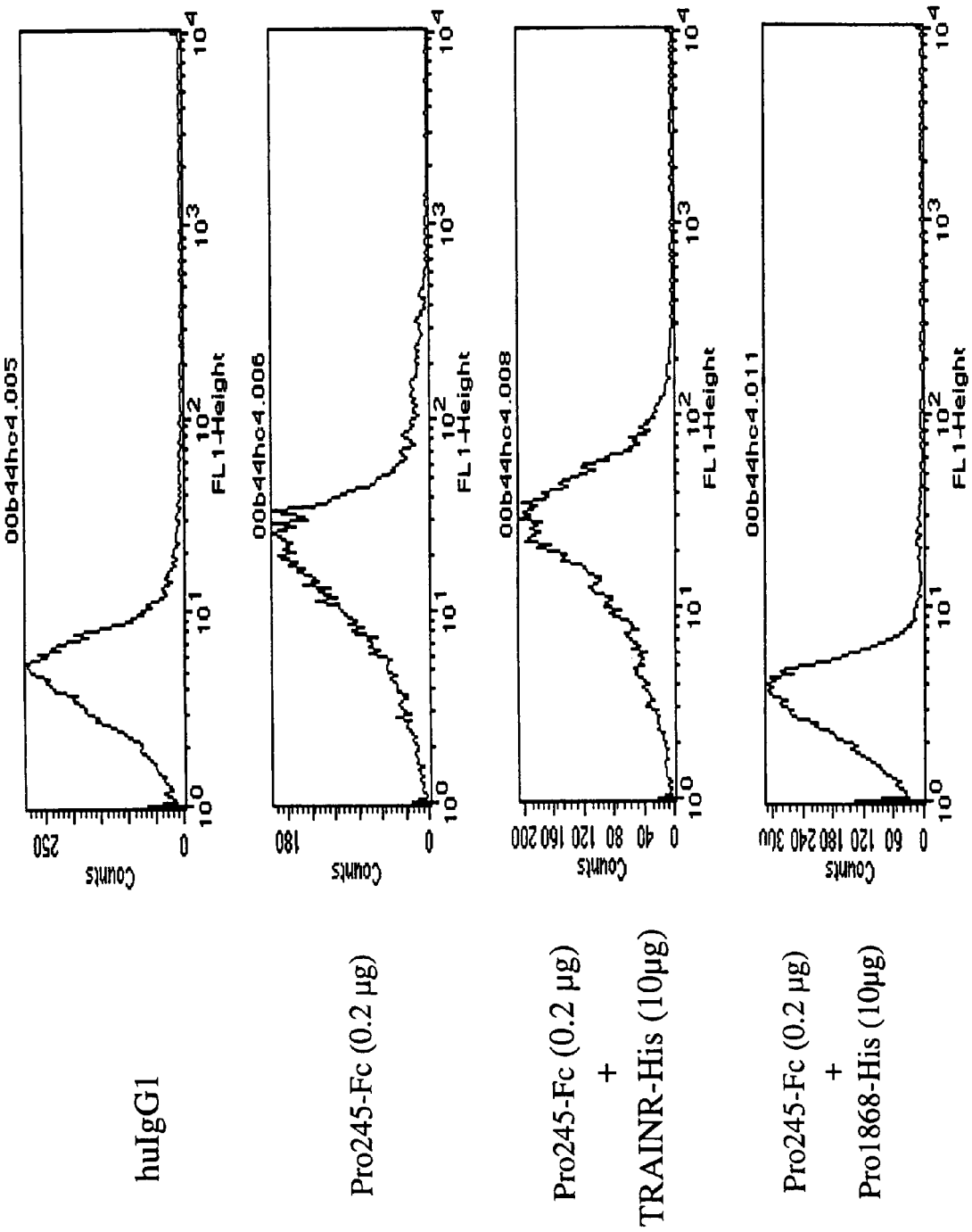
FIG. 46 shows flow cytometry results of the ability of His-tagged-PRO1868 to block PRO245-Fc fusion protein to NK (CD56+) cells.
Figure 53:
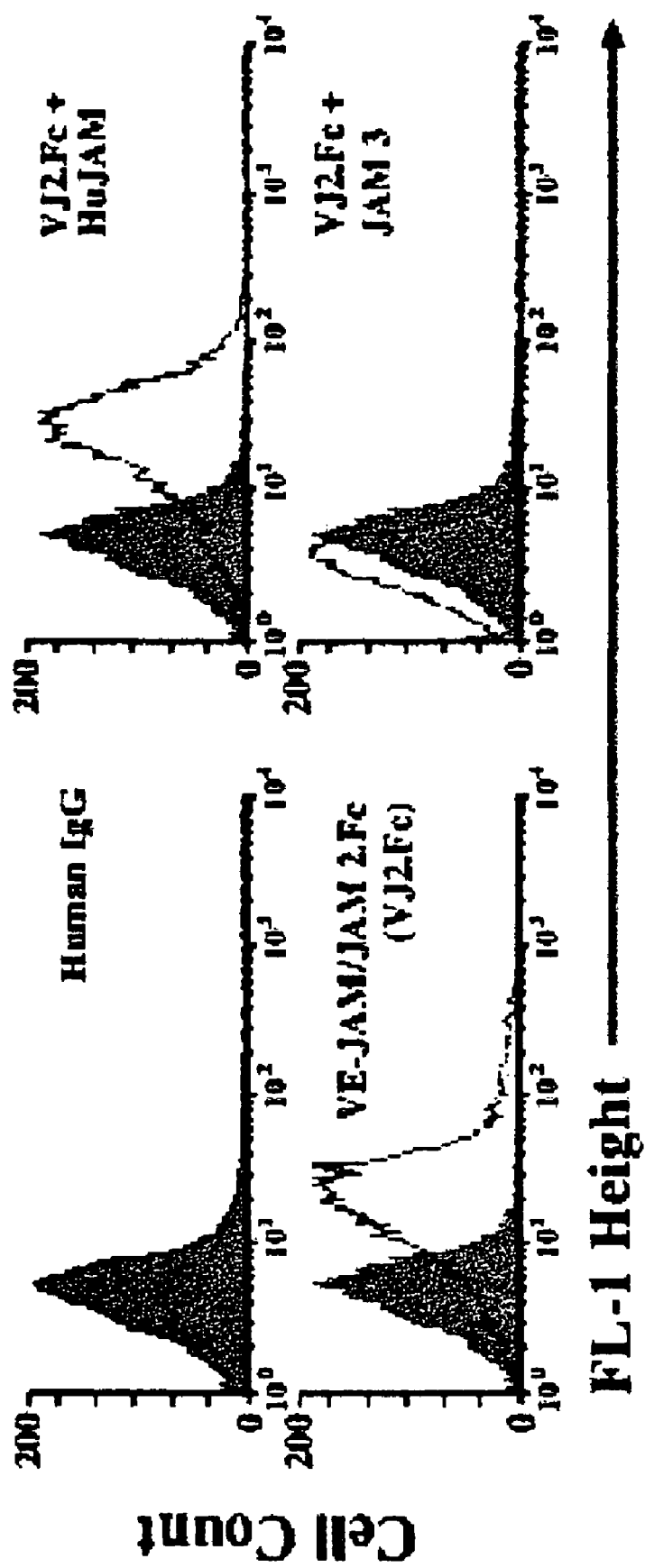
FIG. 53 shows flow cytometry results indicating the ability of 6× His-tagged PRO1868 protein to compete with binding between CD56+ NK cells and PRO245-Fc fusion protein.

Purified B cells, neutrophils and CD14+ monocytes did not interact with PRO245-human IgG fusion protein as detected by flow cytometry. However, a number of other cell types were found to interact with PRO245.Fc. FIG. 41 shows that PRO245.Fc interacts with CD56+ NK cells. This interaction was specific, as it was blocked by the addition of an anti-PRO245 antibody. PRO1868 (also called 77624, JAM3 and SHATr) was found to block the interaction of PRO245 and CD56+ NK cells (FIG. 46, bottom, and FIG. 53, lower right). Addition of unlabeled, His tagged PRO1868 (JAM3) blocked the shift in fluorescence observed with the addition of PRO245.Fc. On the other hand, as can be seen in FIG. 53, upper right, addition of PRO301 does not block the interaction of PRO245 and NK cells.

Figure 42:
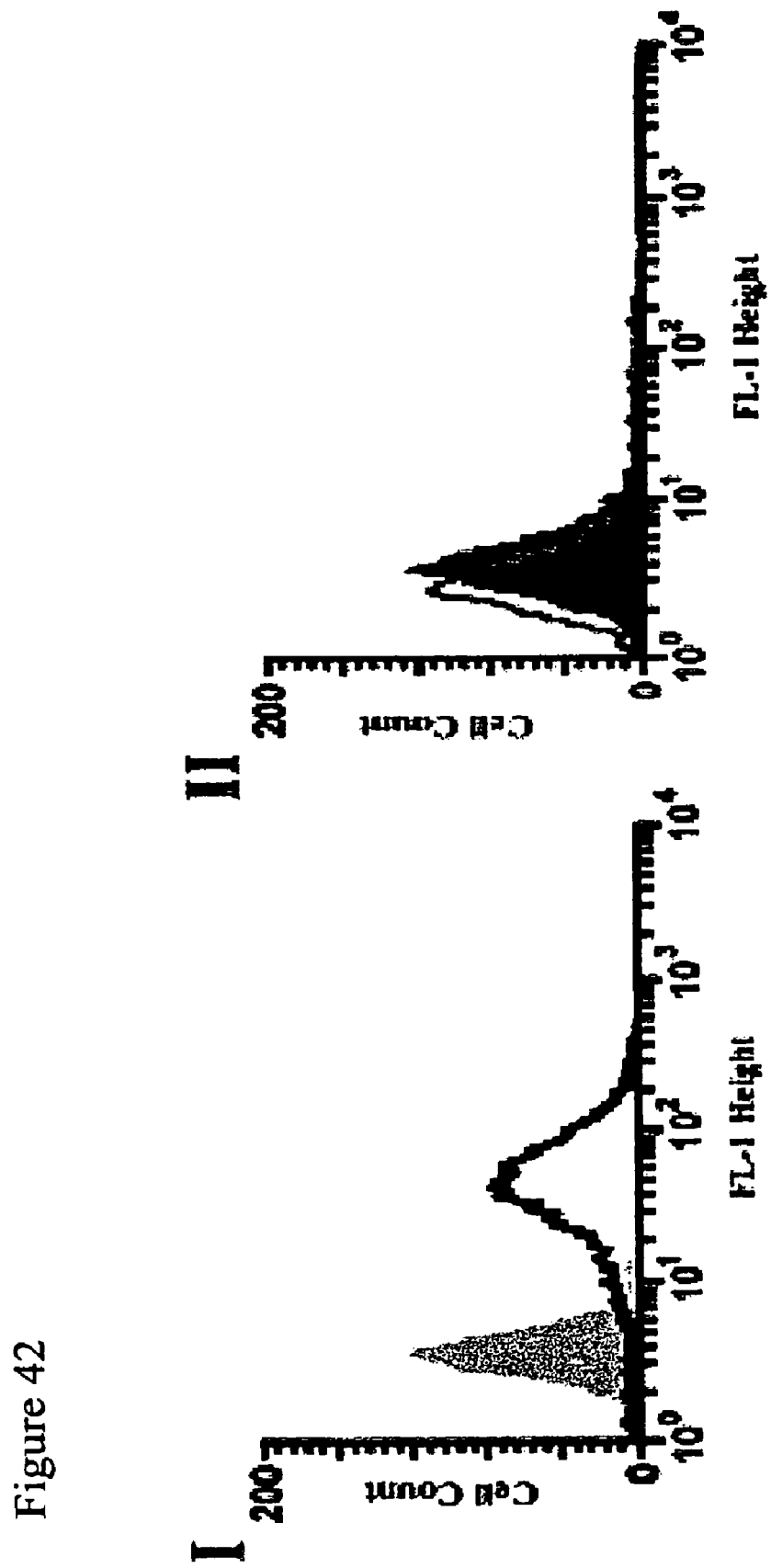
FIG. 42 shows flow cytometry results of binding between peripheral blood dendritic cells (PBDCs) and PRO245-Fc fusion protein.

Peripheral blood dendritic cells (PBDCs) also interact with, but do not express PRO24 (FIG. 42). PBDC were obtained from Clonetics. FIG. 41I shows that PRO245.Fc (solid line) interacts strongly with the PBDCs compared to human IgG1 (shaded histogram). However, PBDS were not observed to express PRO245 (FIG. 41II; mouse IgG-filled histogram; anti-PRO245 antibody 12D10.2F9-solid line).

Figure 43:
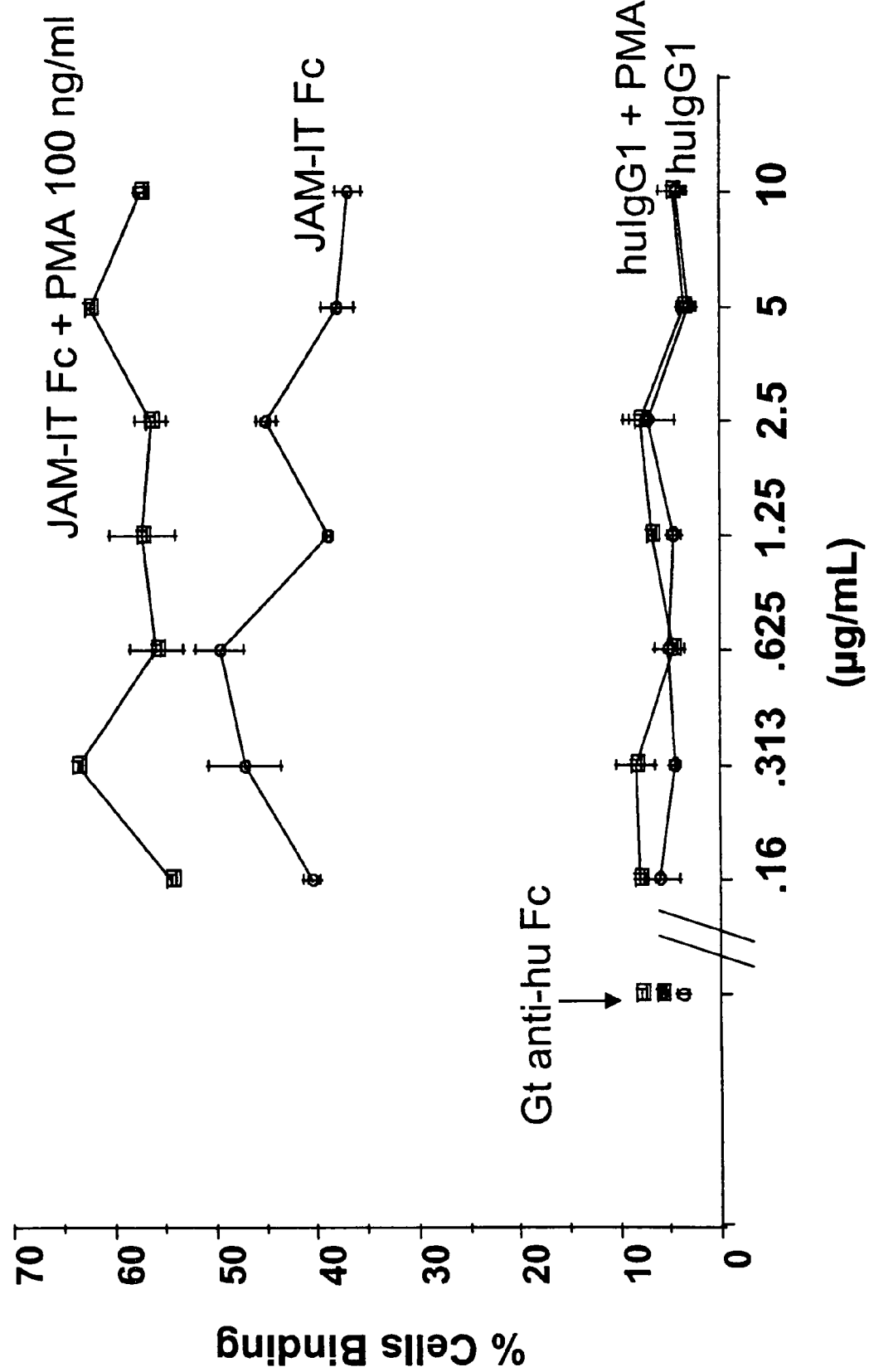
FIG. 43 shows a graph representing flow cytometry results of binding between J45 T cells and PRO245-Fc fusion protein.
Figure 44:
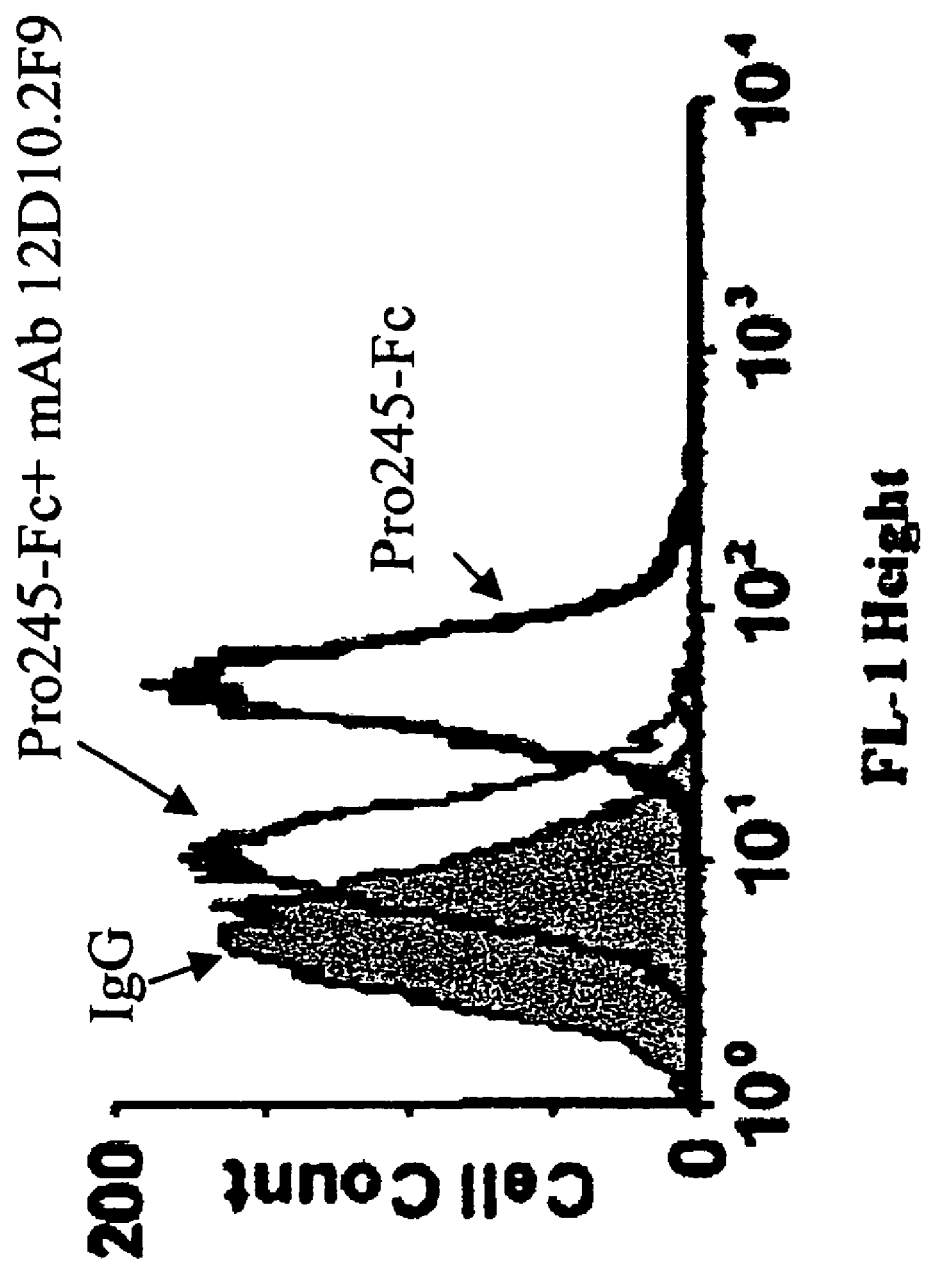
FIG. 44 shows flow cytometry results of binding between J45 T cells and PRO245-Fc fusion protein.
Figure 45:
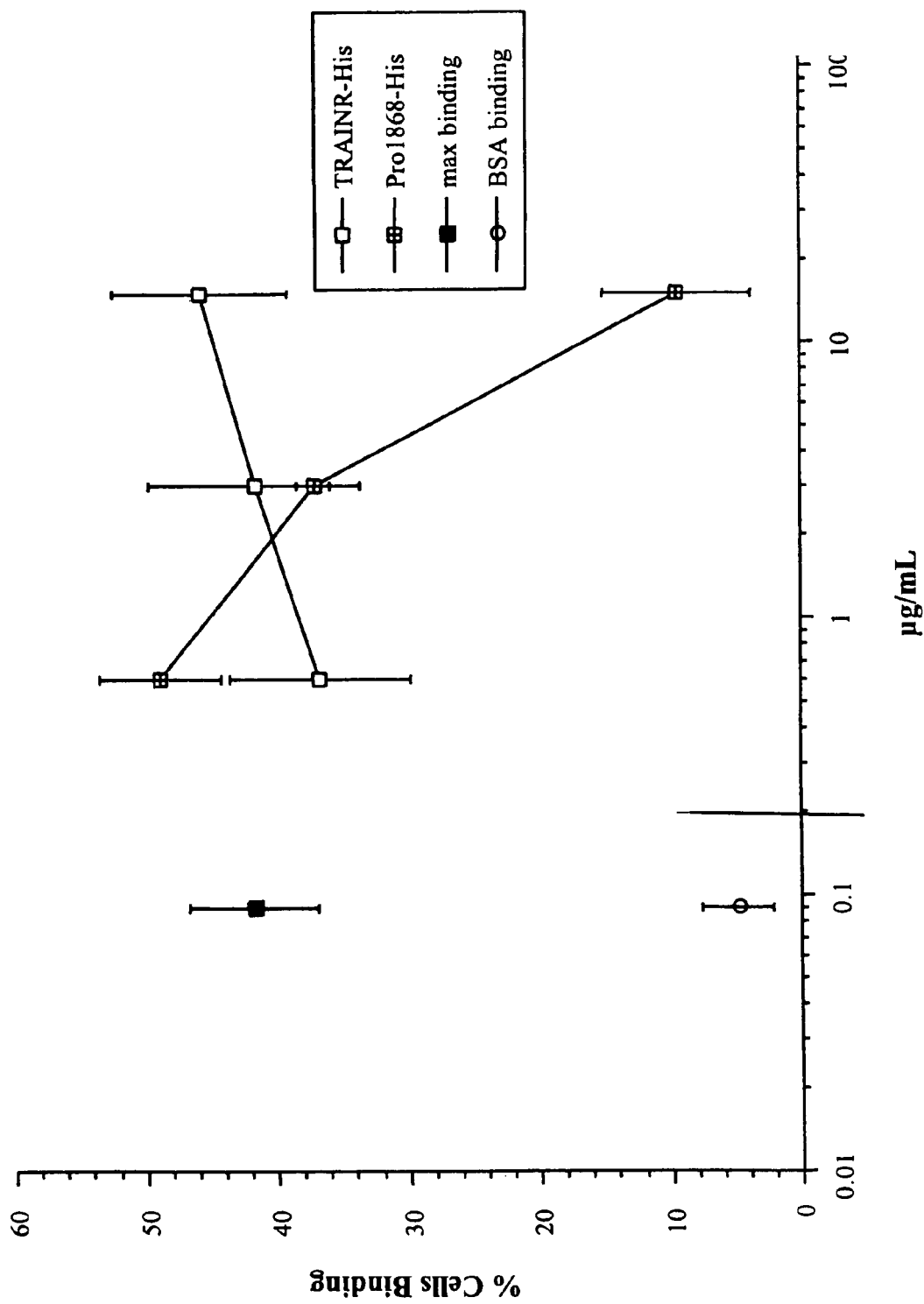
FIG. 45 shows a graph of flow cytometry results that demonstrates the ability of excess His-tagged-PRO1868 to block J45 cell adherence to PRO245-Fc fusion protein.
Figure 52:
FIG. 52 shows data representing inhibition of the adhesion of J45 cells to PRO245-Fc fusion protein by anti-PRO1868 antibodies. Data are representative of three independent experiments; error bars represent the SD in an n=6 condition.

In addition, J45 T cells, which have no detectable surface expression of PRO245, were found to interact with PRO245 (FIGS. 43 and 44). Interaction between Alexa-488 conjugated PRO245-Fc fusion protein and J45 cells was detected by a shift in the peak of fluorescence when compared to the conjugated human IgG1 (FIG. 44). The shift was blocked by addition of anti-PRO245 antibody (FIG. 44). The interaction between Alexa-488 conjugated PRO245-Fc fusion protein and J45 cells was also inhibited by unlabeled PRO1868 (His-PRO1868 protein) (FIG. 45). Further, an anti-PRO1868 antibody (MaJIR1) was found to inhibit PRO245 dependent J45 adhesion, while mouse IgG had no effect on adhesion (FIG. 52).

Accordingly, PRO245-interacting cell types were as follows: CD56+ cells, including CD56+ NK cells, CD56+CD3+ NK/T cells, CD56+CD3+ CD8+ cytolytic T cells, PBDCs and J45 T cells. Further, excess PRO1868 protein inhibited PRO245 binding to J45 and CD56+ NK cells, and anti-PRO1868 antibodies inhibited PRO245 binding to CD56+ NK cells.

D. Plate-Based Adhesion Assay

For plate-based analysis of cells that are able to interact with PRO245, microtitre wells (NUNC Maxisor 96-well plates; VWR, Scientific Products, Brisbane, Calif.) were coated with conditions at 50 µl/well (in HBSS+), 10 µl/ml for 2 hours at room temperature, unless otherwise noted. For adhesion assays, 50 µl of 10 µg/ml goat anti-human IgG1 Fc-specific Ab, for example PRO245-human IgG fusion protein, was first coated and blocked before the addition of conditions in binding/blocking buffer (BBB; HBSS+containing 10% (v/v) FBS) for 1 hour at room temperature before the addition of coating condition. Cells ($5 \times 10^6$ cells/ml in BBB) were treated (10 minutes at 37° C. with 5% $CO_2$) with 5 mg/ml 2',7'-bis-(2-carboxyethyl)-5 (and -6)-carboxyfluorescein, acetoxymethyl esther (BCECF AM) (Molecular Probes), washed, and allowed to adhere to coated wells ($2 \times 10^5$ cells/well in BBB) for 1 hour at 37° C./5% $CO_2$.

Plates were read on a SpectraMax fluorescence plate reader (Molecular Devices, Sunnyvale, Calif.) for total applied fluorescence, gently washed three times (by aspiration with a 28-gauge needle), and read for total adherent fluorescence. Percentage of adherence was calculated using the following equation: ((total fluorescence of adherent)/(total fluorescence of applied))×100. Blank wells consisted of BBB-coated wells exposed to BCECF AM-labeled J45 cells. Values obtained from the blank wells (percentage of adherence) were subtracted from all experimental conditions to derive a final value.

Figure 47:
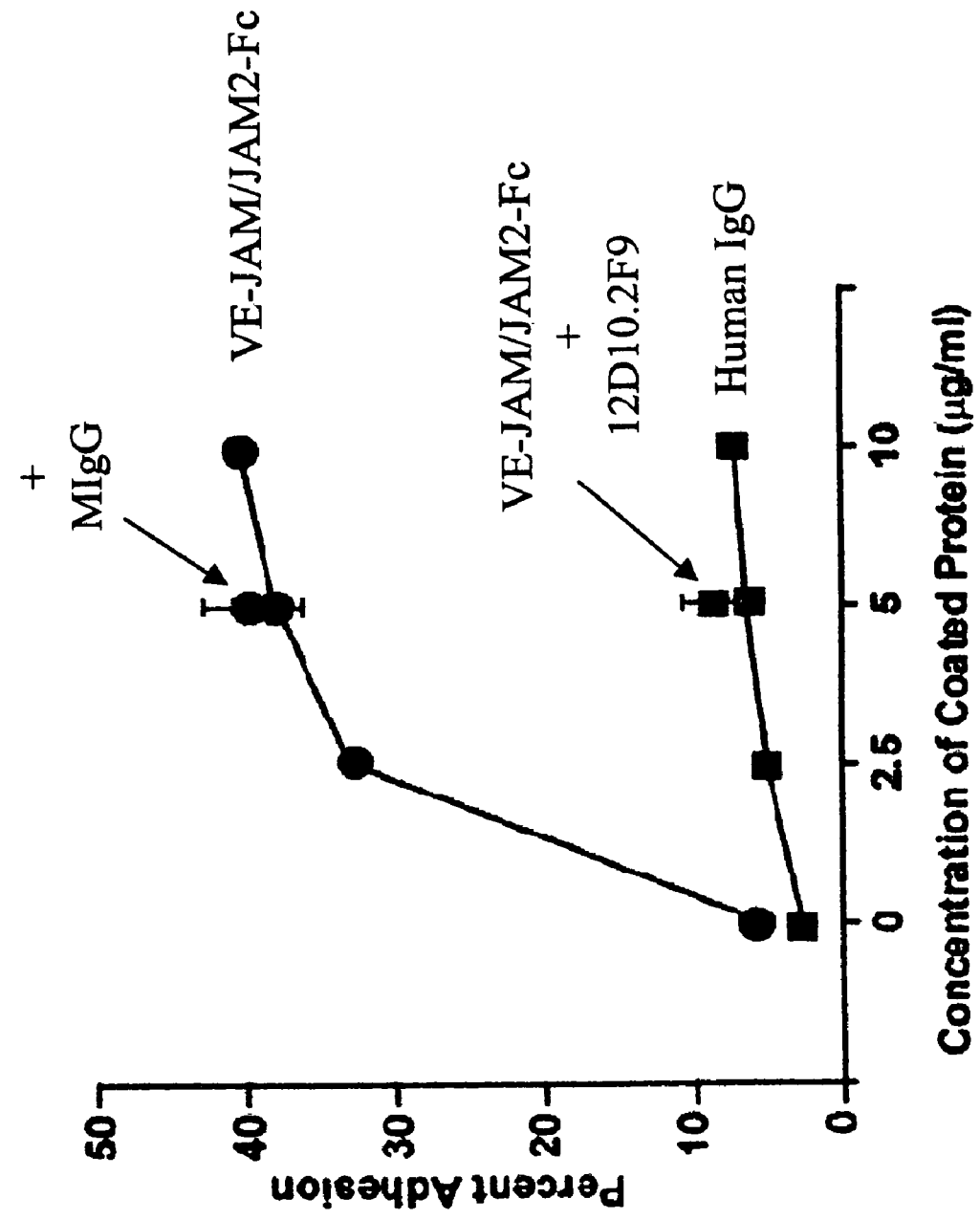
FIG. 47 shows a graph representing the percent adhesion of labeled J45 cells to wells coated with varying concentrations of PRO245.

Using the plate-based adhesion assay, J45 T cells were found to adhere to PRO245-human IgG fusion (VJ2.Fc) coated wells (FIG. 47). Anti-PRO245 antibodies, but not mouse IgG, inhibited adhesion of J45 cells to PRO245-human IgG1 fusion protein, indicating that the interaction is specific (FIG. 47).

Example 23

Identification of Receptors for PRO245

To identify the protein in PRO245-interacting cells that is responsible for the interaction, immunoprecipitation studies were performed.

A. CD56+ NK Cells and J45 Cells

To isolate the cell surface receptor on J45 or NK cells for PRO245, PRO245 interacting cells were biotinylated and then lysed. The supernatants from the lysed cells were subjected to immunoprecipitation with a Fc-cross-linked PRO245-human IgG fusion protein A matrix. The precipitates were analyzed by Western blotting.

1. Biotinylation

For biotinylated conditions, cells were first washed in HBSS+ before being biotinylated (200 µg/$10^6$ cells) with sulfo-NHS-LC-biotin for 30 minutes at 4° C. Cells were washed with TBS for 30 minutes at 4° C. to quench the biotinylation.

2. Lysis

Cells were lysed (108 cells/ml) with lysis buffer (HBSS+ containing 1% Triton X-100 and 1 Complete-Mini EDTA free protease inhibitor tablet (Roche Biochemicals, Indianapolis, Ind.) per 7 ml of lysis buffer) for 30 minutes at 4° C. Lysates were spun at 22,000×g for 1 hour at 4° C. and 0.2 µm filtered. Lysates were precleared for 2 hours at 4° C. with 5 µl/$10^6$ cells of recombinant protein A beads (Amersham Pharmacia Biotech).

3. Immunoprecipitation

Cleared lysates were 0.2 µm filtered and incubated for 2 hours at 4° C. with 5 µg/$10^6$ cells of either PRO245-human IgG fusion protein or human IgG1, conjugated to protein A matrix using the ImmunoPure Protein A IgG Plus Orientation kit (Pierce). Beads were pelleted and washed with lysis buffer and denatured by the addition of 15 µl/$10^6$ cells of nonreducing SDS sample buffer (Standard sample buffer with 2 mM iodoacetamide, but without DTT or 2-mercaptoethanol) and boiled for 3 minutes at 100° C.

4. Western Blotting

Samples at a concentration of 15 µl/lane were resolved on a 4-20% Bio-Rad Tris-HCl Ready Gel (Bio-Rad, Hercules, Calif.) and transferred onto 0.2-µm Protran nitrocellulose membrane (Schleicher & Schuell, Keene, N. H.) at 100 mA for 2 hours at 4° C. Blots were blocked for 1 hour in Blotto (TBS containing 5% nonfat milk and 0.05% TWEEN™ 20; Bio-Rad). For biotinylated samples, HRP-conjugated streptavidin (Pierce) was used at 0.5 µg/ml for 30 minutes at room temperature. For nonbiotinylated samples, anti-PRO1868 antibodies (MaJIR1) was used at 10 µg/ml in Blotto and incubated for 1 hour at 25° C. before the application of 1 µg/ml HRP-conjugated goat anti-mouse IgG (Caltag Laboratories, Burlingame, Calif.) in Blotto for 30 minutes at room temperature. Blots were washed thoroughly with TTBS (TBS containing 0.05% Tween 20 (and developed with the ECL Plus reagent (Amersham Pharmacia Biotech) before exposing onto Kodak BioMax ML film and development with Kodak M35A X-OMAT Film Processor (Eastman Kodak).

5. Results

Figure 48:
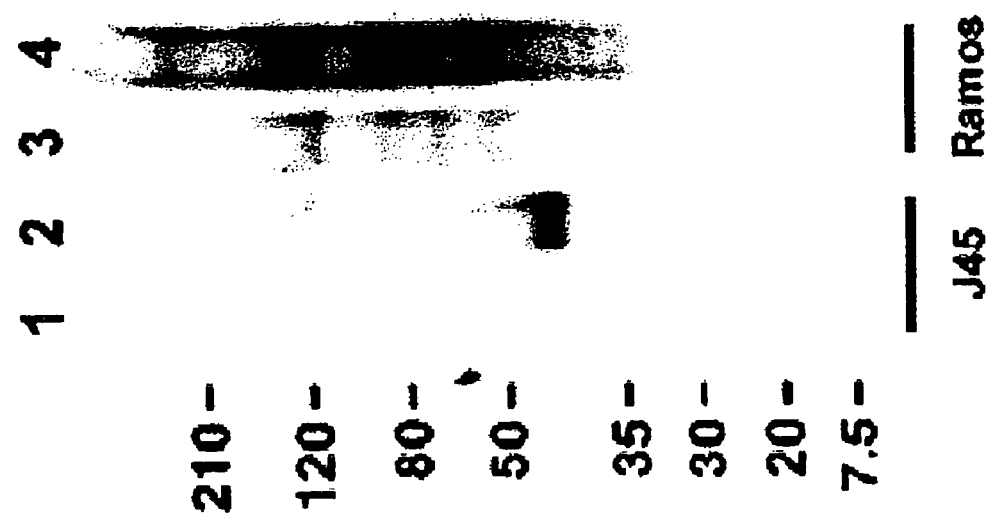
FIG. 48 shows immunoprecipitation of biotinylated J45 cells to Fc-cross-linked PRO245-Fc fusion protein A matrix.

Immunoprecipitation of biotinylated samples with an Fc-cross-linked PRO245-human IgG fusion protein A matrix and analysis by Western blotting allowed identification of a single streptavidin-reactive band of about 40 kDa that interacts with PRO245-human IgG fusion (FIG. 48). The 40 kDa band was not present in immunoprecipitations performed with an Fc-cross-linked human IgG protein A matrix, nor in PRO245-immunoprecipitations performed with an Fc-cross-linked human IgG protein A matrix in the non-PRO245-binding Ramos/HH B cell line.

Figure 49:
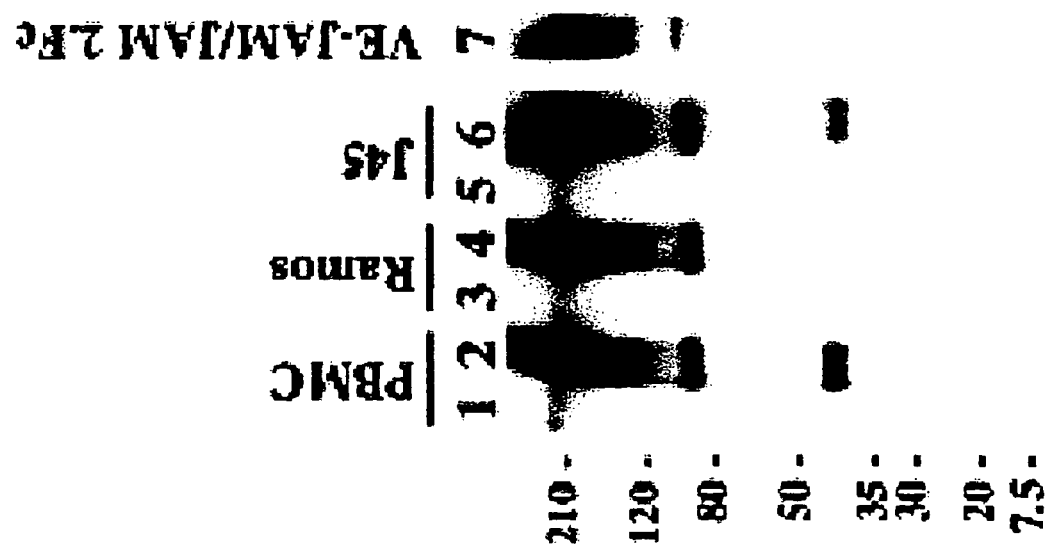
FIG. 49 shows immunoprecipitation of PRO1868 from J45 and PBMC cells using PRO245-Fc fusion protein cross-linked protein A matrices.

To determine whether the 40 kDA band represented PRO1868, immunoprecipitation was performed on non-biotinylated samples from Ramos/HH cells (non-PRO245 interacting), MOLT4 cells (PRO245 binding) and PBMCs (PRO245 binding) with PRO245-human IgG fusion protein A matrixes. The precipitates were analyzed by immunoblotting with anti-PRO1868 antibodies. The immunoblotting verified that the 40 kDa PRO245-interacting band represented PRO1868 (FIG. 49).

6. Confirmation of Binding Between PRO245 and PRO1868 by ELISA

Figure 50:
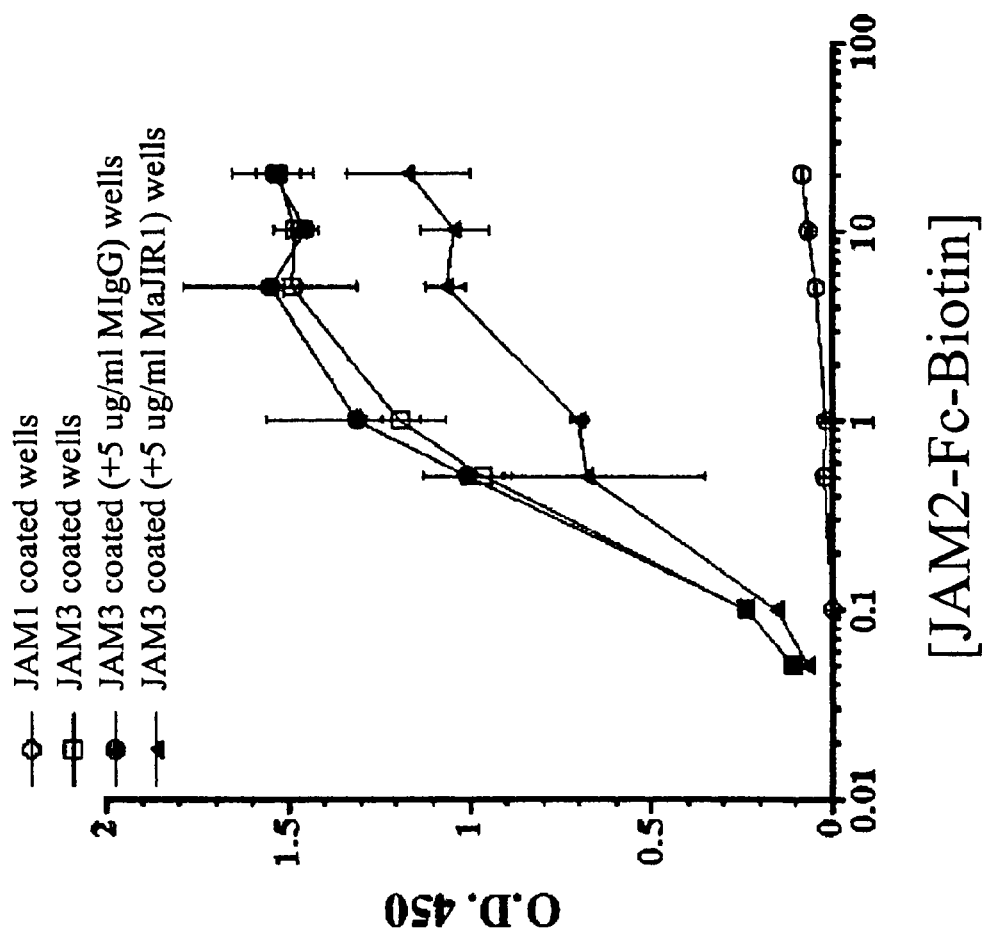
FIG. 50 shows a graph representing the binding of biotinylated PRO245 to wells coated with PRO1868.
Figure 51:
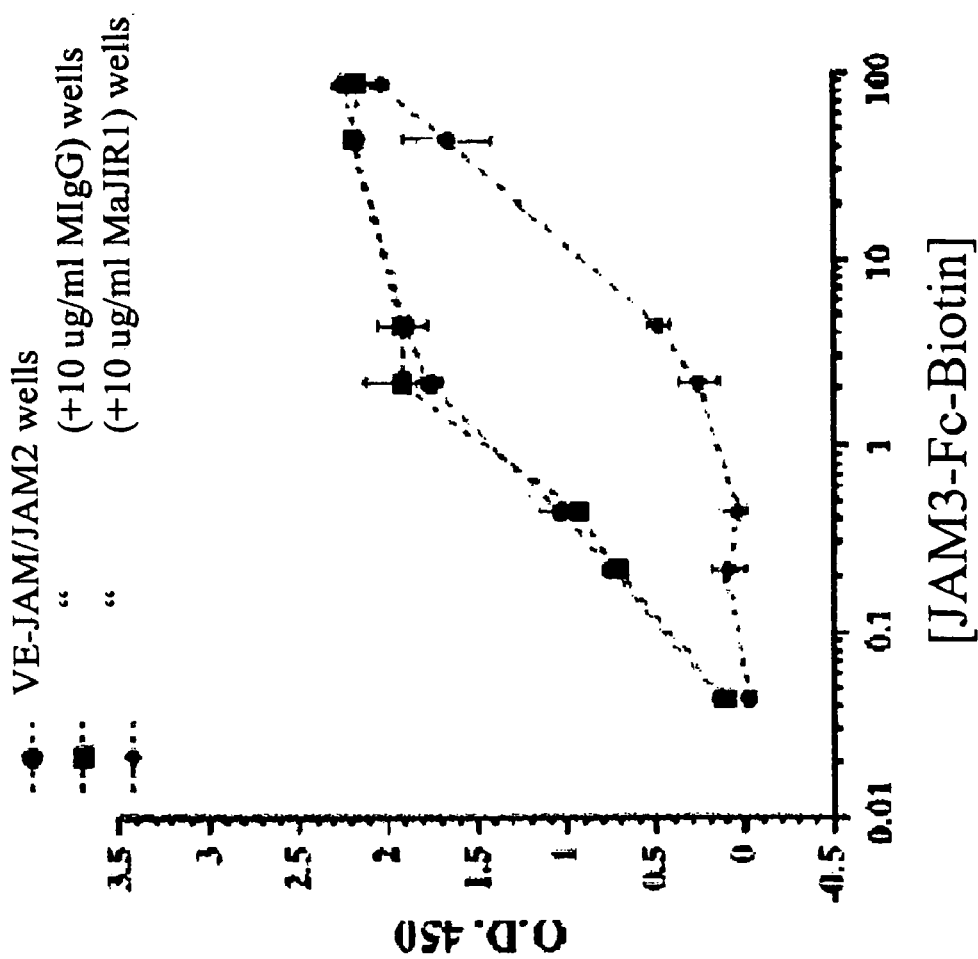
FIG. 51 shows a graph representing the binding of biotinylated PRO1868 to wells coated with PRO245-Fc.

Using anti-PRO1868 antibodies, purified PRO245 and PRO1868 fusion proteins, an interaction between PRO245 and PRO1868 was confirmed in a plate-based assay. Plate-bound PRO1868-Fc fusion protein (JAM3.Fc) or a control human PRO301-Fc fusion protein (huJAM.Fc) were exposed to biotinylated PRO245-Fc fusion protein in the presence of 0.25 µg/well mouse IgG or an anti-PRO1868 Ab (FIG. 50). Streptavidin HRP was used to detect binding between the PRO1868-Fc fusion protein-coated wells to PRO245-Fc biotin. Alternatively, PRO245-Fc fusion was captured onto a plate, and biotinylated PRO1868-Fc fusion was used at specific concentrations to examine the PRO245-PRO1868 interaction (FIG. 51). Further, inhibition of such a plate-based interaction between PRO245 and PRO1868 by anti-PRO1868 antibodies and anti-PRO245 antibodies was tested.

For ELISA, the plates were blocked after condition coating with BBB for 30 minutes at room temperature and incubated with binding conditions for 1 hour at room temperature. For conditions requiring EDTA, a modified BBB (HBSS without calcium and magnesium containing EDTA instead of the normal HBSS+) was used throughout the experiment. Plates were washed three times, incubated with 1 µg/ml streptavidin HRP (Pierce) for 30 minutes at room temperature, and assessed via color development using the tetramethylbenzidine substrate (Kirkegaard & Perry Laboratories, Gaithersburg, Md.) and read on the ThermoMax Microplate Reader (Molecular Devices).

An interaction between PRO245 and PRO1868 was identified through the plate-based assays (FIGS. 50 and 51). FIG. 50 shows that PRO1868.Fc (JAM3.Fc) coated wells demonstrated PRO245.Fc binding while PRO301.Fc coated wells did not. Mouse IgG (MIgG) had no effect on binding while the anti-PRO1868 antibody (MaJIR1) inhibited PRO245 binding. When PRO245.Fc was bound to the plate (FIG. 51), interaction of PRO245.Fc and PRO1868.Fc was again observed. In addition, the anti-PRO1868 antibody MaJIR1 was again able to inhibit the interaction, while the mouse IgG had no effect.

B. Panel of Potential Receptors

PRO245 polypeptide was incubated with a panel of potential receptor molecules for the purpose of identifying the receptor/ligand interaction. The identification of a ligand for a known receptor, a receptor for a known ligand or a novel receptor/ligand pair is useful for a variety of indications including, for example, targeting bioactive molecules (linked to the ligand or receptor) to a cell known to express the receptor or ligand, use of the receptor or ligand as a reagent to detect the presence of the ligand or receptor in a composition suspected of containing the same, wherein the composition may comprise cells suspected of expressing the ligand or receptor, modulating the growth of or another biological or immunological activity of a cell known to express or respond to the receptor or ligand, modulating the immune response of cells or toward cells that express the receptor or ligand, allowing the preparation of agonists, antagonists and/or antibodies directed against the receptor or ligand which will modulate the growth of or a biological or immunological activity of a cell expressing the receptor or ligand, and various other indications which will be readily apparent to the ordinarily skilled artisan.

A PRO245 polypeptide of the present invention suspected of being a ligand for a receptor is expressed as a fusion protein containing the Fc domain of human IgG (an immunoadhesin). Receptor-ligand binding is detected by allowing interaction of the PRO245 immunoadhesin polypeptide with cells (e.g. COS cells) expressing candidate receptors, including the PRO1868 polypeptide receptor, and visualization of bound immunoadhesin with fluorescent reagents directed toward the Fc fusion domain and examination by microscope. Cells expressing candidate receptors are produced by transient transfection, in parallel, of defined subsets of a library of cDNA expression vectors, for example, encoding PRO1868 polypeptides, that may function as receptor molecules. Cells are then incubated for 1 hour in the presence of the PRO245 polypeptide immunoadhesin being tested for possible receptor binding. The cells are then washed and fixed with paraformaldehyde. The cells are then incubated with fluorescent conjugated antibody directed against the Fc portion of the PRO245 polypeptide immunoadhesin (e.g. FITC conjugated goat anti-human-Fc antibody). The cells are then washed again and examined by microscope. A positive interaction is judged by the presence of fluorescent labeling of cells transfected with cDNA encoding a particular PRO1868 polypeptide receptor or pool of receptors and an absence of similar fluorescent labeling of similarly prepared cells that have been transfected with other cDNA or pools of cDNA. If a defined pool of cDNA expression vectors is judged to be positive for interaction with a PRO245 polypeptide immunoadhesin, the individual cDNA species that comprise the pool are tested individually (the pool is "broken down") to determine the specific cDNA that encodes a receptor able to interact with the PRO245 polypeptide immunoadhesin.

In another embodiment of this assay, an epitope-tagged potential ligand PRO245 polypeptide (e.g. 8 histidine "His" tag) is allowed to interact with a panel of potential receptor polypeptide molecules that have been expressed as fusions with the Fc domain of human IgG (immunoadhesins). Following a 1 hour co-incubation with the epitope tagged PRO245 polypeptide, the candidate receptors are each immunoprecipitated with protein A beads and the beads are washed. Potential ligand interaction is determined by western blot analysis of the immunoprecipitated complexes with antibody directed towards the epitope tag. An interaction is judged to occur if a band of the anticipated molecular weight of the epitope tagged protein is observed in the western blot analysis with a candidate receptor, but is not observed to occur with the other members of the panel of potential receptors.

Using these assays, the following receptor/ligand interactions have been herein identified: PRO245 (DNA35638-1141) binds to PRO1868 (DNA77624-2515).

C. JAM Family Proteins

Flow cytometry analysis was performed to further investigate the interactions of members of the JAM protein family. PRO245 was expressed in CHO cells as described in Example 14. The PRO245-expressing CHO cells were then incubated with His-tagged JAM proteins, including PRO245, PRO301, and PRO1868. Binding of His-tagged PRO362, PRO1868 or PRO301 proteins to PRO245-expressing CHO cells were analyzed by flow cytometry.

Figure 54:
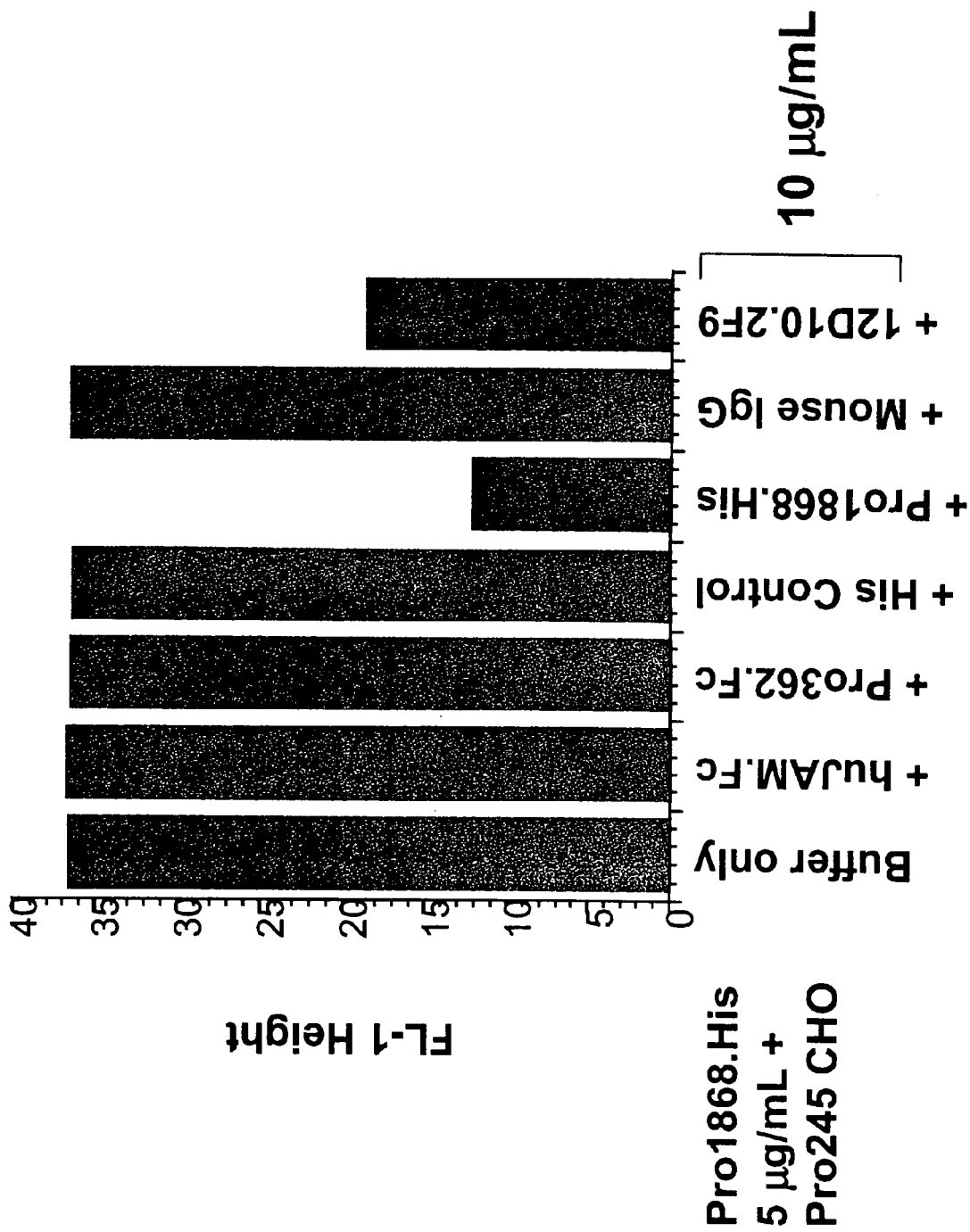
FIG. 54 shows binding of PRO1868 to PRO245 expressing CHO cells under various conditions.
Figure 55:
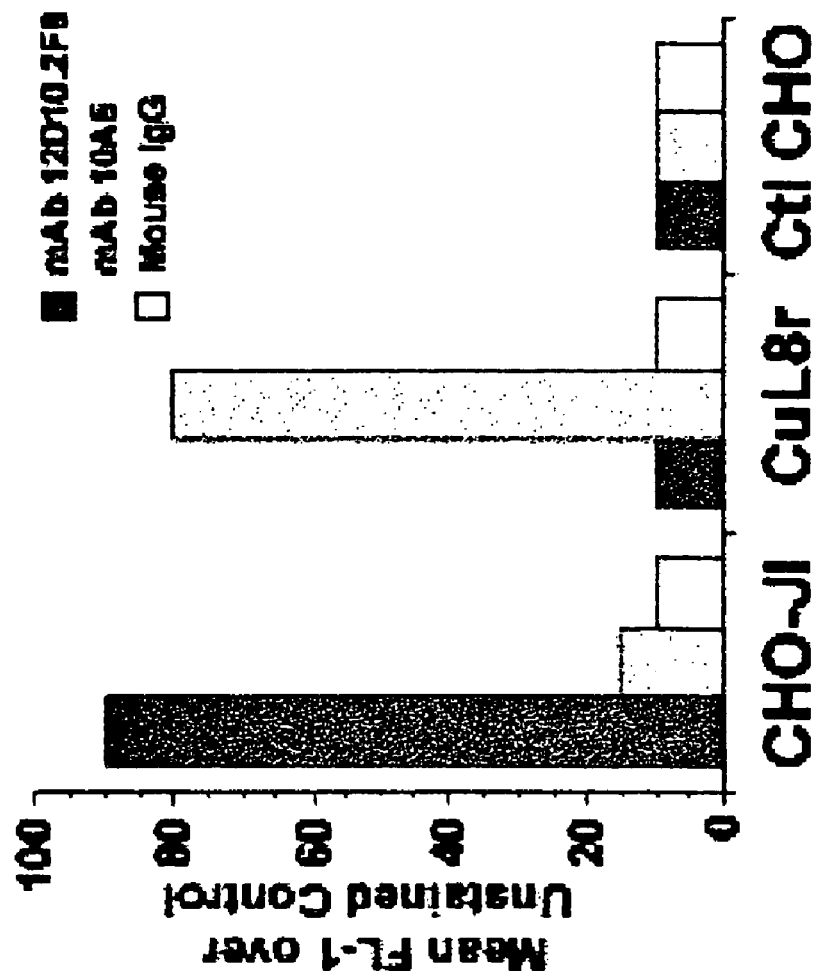
FIG. 55 shows specific binding of anti-PRO1868 antibodies to PRO245-expressing CHO cells (CuL8r).

For binding of PRO1868 to PRO245-expressing CHO cells, 5 µg/ml of PRO1868-HIS (SHATr.His) tagged protein was incubated with PRO245-expressing CHO cells. PRO1868 (SHATr.His) was able to interact with PRO245-expressing CHO cells (FIG. 54). Varying competitor proteins were examined for their ability to inhibit binding of PRO1868 to PRO245. PRO1868 protein (SHATr.His) and anti-PRO245 antibody (12D10.2F9) were able to compete with PRO1868-HIS tagged protein for binding of PRO245 on the surface of CHO cells (FIG. 54). In contrast, PRO301.Fc, PRO362.Fc, mouse IgG and His control were not able to inhibit binding (FIG. 54).

Based on the results described above, PRO245 interacts with PRO1868.

Example 24

Involvement of STIGMA (PRO362) in Chronic Inflammation

The novel macrophage associated receptor with homology to A33 antigen and JAM1 was cloned as described in Example 2 and below, and was identified as a single transmembrane Ig superfamily member macrophage associated (STIgMA or PRO362 or JAM4).

STIgMA is expressed as two spliced variants, one containing an N-terminal IgV like domain and a C-terminal IgC2 like domain and a spliced form lacking the C-terminal domain. Both receptors have a single transmembrane domain and a cytoplasmic domain containing tyrosine residues which are constitutively phosphorylated in macrophages in vitro.

The present study demonstrates that STIgMA is selectively expressed on a subset of tissue resident macrophages, and is associated with chronic inflammation.

Materials and Methods

Cells

Blood was obtained from healthy adult volunteers by venous puncture and separated using Ficoll-Paque PLUS (Amersham Pharmacia Biotech) per manufacturers instruction. PBMCs were obtained from the interface, washed in cold PBS, lysed with 0.2% NaCl for 30 s and neutralized with 1.6% NaCl. Cells were counted and kept on ice until use. To isolate peripheral blood subsets, untouched MACS kits (Miltenyi Biotech, Auburn, Calif.) were used following the manufacturers instructions. To culture differentiated macrophages, negatively selected monocytes were transferred to 6 well culture dishes in HGDMEM containing 20% fetal bovine serum and 10% human serum. Medium was replaced at day 5. For flow cytometric analysis, cells were dissociated from the culture dish using ice-cold cell dissociation solution (Sigma). Lysates for Western blot analysis were prepared by adding 0.5 ml lysis buffer directly to the wells. Lysates were mixed with sample buffer containing SDS and beta-mercaptoethanol, run on a Tris-Glycine gel and transferred to a nitrocellulose membrane.

Flow Cytometry

Cells for use in flow cytometric analysis were blocked for 30 min at 4 C with PBS containing 2% fetal bovine serum and 5 µg/ml human IgG (Calbiochem, San Diego, Calif.). Nex, cells were incubated with 3C9, an anti-STIgMA (anti-PRO362) monoclonal antibody. After washing in PBS, cells were stained with phycoerythrin (PE)-conjugated antibodies to CD11b, CD 14, CD163, CD15, CD68 were obtained from Pharmingen.

Cell-Cell Adhesion Studies

A pRK expression vector containing full length STIgMA was stably expressed in a human Jurkat T-cell line using neomycin selection and autoclone sorting as described elsewhere. Cells were preloaded with the fluorescent dye BCECF (Molecular Probes, Oregon) and added to a 96 well Maxisorb plate (CORNING™) coated with a monolayer of human umbilical vein endothelial cells (HUVEC) treated with or without 10 ng/ml TNFalpha. Cells were gently washed by loading the wells with incubation buffer (HBSS contained 10 mM CaCl, 10 mM magnesium and 1.5 mM NaCl) followed by inverting the plate on a piece of blotting paper. After 3 washes, fluorescence was counted in a fluorospectrometer. The fluorescent readout is representative of the number of cells that remain adherent to the HUVEC cells.

Northern Blot Analysis

Multiple tissue Northern blots (CLONTECH) were probed with a $^{32}$P labeled probe of random-primed full-length STIgMA cDNA using Ambion kit according to manufacturers recommendations. Blots were exposed to a phosphorimaging screen and analyzed with a Storm phosphorimager.

Real Time RtPCR Analysis

For quantitative PCR analysis (TAQMAN™), total mRNA from human tissues or primary cells (100 ng) was recommended (PerkinElmer Life Sciences) with primers based on the coding sequence of STIgMA.

Fc- and His-Fusion Protein Production

Human STIgMA was cloned into the baculovirus expression vector pHIF (Pharmingen). The HIS-tagged STIgMA fusion protein consisted of the extracellular domain of STIgMA fused to 8 histidines. His-tagged fusion protein was purified from the supernatant of baculovirus-infected insect cells grown in suspension using nickel affinity resin.

Monoclonal and Polyclonal Antibody Production

BALBc females were immunized and boosted with 10 µg STIgMA-His8 via footpad injections, as previously described. Single clones were screened against STIgMA (PRO362)-His by ELISA. Selected clones selected clones were tested against JAM family members and human IgG Fc. Clones were titrated out to single cell densities and rescreened. Clone 3C9 (IgG1) was found to be selectively reactive to STIgMA. Clones were used for ascites generation and purified over protein G (Amersham Pharmacia Biotech); protein concentration was determined using the Pierce BCA reagent (Pierce, Rockford, Ill.).

Polyclonal antibodies were generated by injecting 150 µg STIgMA-His in New Zealand Rabbits. Serum titers were determined by ELISA. Serum was collected at the peak of circulating IgG levels and purified over a protein A column.

In Situ Hybridization

PCR primers (upper 5'-TCTCTGTCTCCAAGCCCA-CAG (SEQ ID NO: 35), and lower, 5'-CTTTGAG-GAGTCTTTGACC (SEQ ID NO: 36)) were designed to amplify a 700 bp fragment of huJAM4. Primers included T7 or T3 RNA polymerase initiation sites to allow for in vitro transcription of sense or antisense probes, respectively, from the amplified products. Normal human tissues included tonsil, lymph node, spleen, kidney, lung and heart. Tissues with chronic inflammatory disease included lung with chronic asthma, chronic bronchitis, livers with chronic inflammation and cirrhosis due to chronic hepatitis C infection. Tissues were fixed in 4% formalin, paraffin embedded, sectioned (3-5 µm thick) deparaffinized, deproteinated with 20 µg/ml proteinase K (15 min at 37° C.) and processed for in situ hybridization as described elsewhere.

Immunohistochemistry

Immunohistochemical staining was performed on 5-µm thick frozen sections using a DAKO autostainer. Endogenous peroxidase activity was blocked with Kirkegaard and Perry blocking solution (1:10, 4 min 20° C.). Normal goat serum (NGS) at 10% in TBS/0.05% Tween-20 was used for dilution and blocking. Mab 3C9 was used at 1 ug/ml. Slides were developed using metal-enhanced diaminobenzidine (Pierce Chemicals). For immunofluorescence staining of sections, sections were blocked with PBS/10% NGS and incubated with mAb 3C9 for 1 hr at 20° C. A rabbit-anti mouse FITC-labeled secondary antibody conjugated to FITS was used as detections agent. For double staining procedure, sections were subsequently stained with a PE-conjugated monoclonal antibody to human CD68.

Results

Molecular Cloning of Human STIgMA

HuSTIgMA was cloned from a human fetal cDNA library using degenerate primers recognizing conserved Ig domains of human JAM1. Sequencing of several clones revealed an open reading frame of 400 amino acids. Blast searches confirmed similarity to Z39Ig, a type 1 transmembrane protein (Langnaese et al., Biochim Biophys Acta 1492 (2000) 522-525. The extracellular region of STIgMA consisted of 21 g-like domains, comprising an N-terminal V-set domain and a C-terminal C2-set domain. Using 3' and 5' primers, a splice variant of STIgMA, STIgMA short which lacks the membrane proximal IgC domain and is 50 amino acids shorter was cloned.

Cloning of Murine STIgMA and Sequence Comparison with Human STIgMA

The murine expressed sequence tags (EST) database was searched using the full open reading frame of huSTIgMA (PRO362) and the tblastn algorithm. DNA sequencing of 3 clones gave rise to identical complete open reading frames of 280 amino acids. Primers to the 3 prime regions were used to clone a full length transcript from a mouse spleen library. The murine clone resembled the spliced form of hu STIgMA in that, it lacked the C-terminal Ig-like domain. The extracellular IgV-domain was well conserved between the human and murine receptor with 93% identity. The murine cytoplasmic domain was poorly conserved being 20 amino acids shorter than its human counterpart and was 40% identical.

Figure 57:
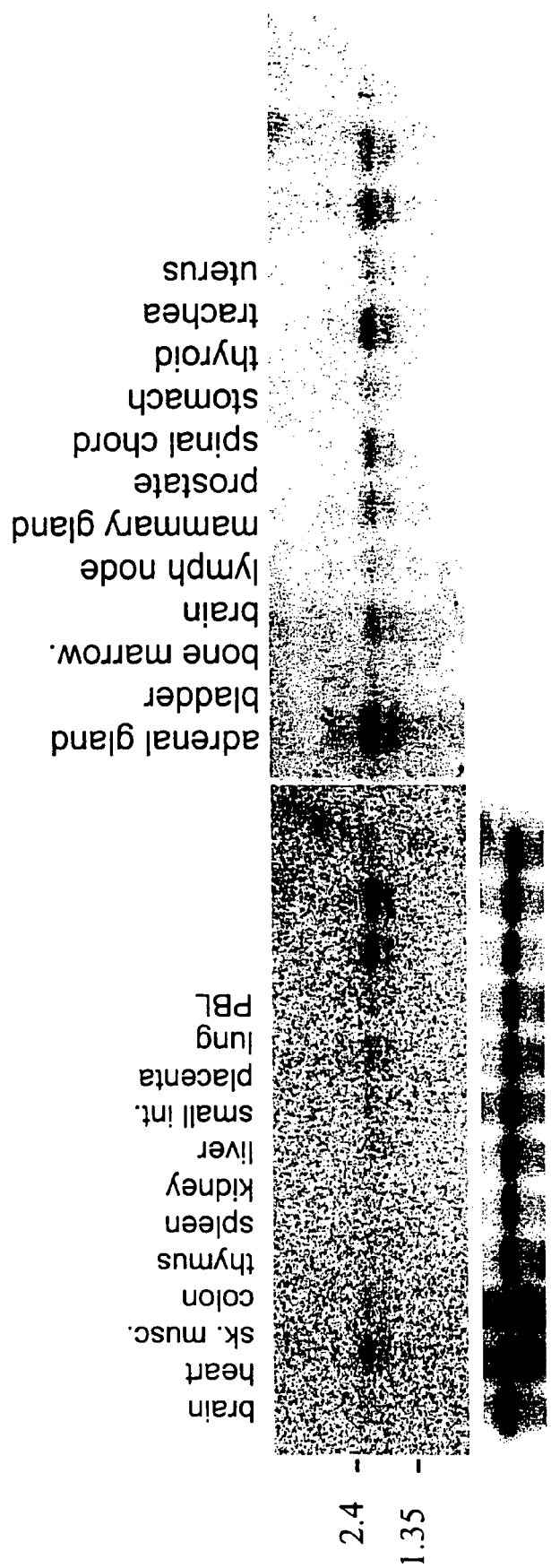
FIG. 57. Northern blot analysis showing expression of human STIgMA in placenta, lung, heart, liver and adrenal gland (A). Two transcripts of 1.5 and 1.8 kb were present in the human tissues expressing STIgMA.

STIgMA is Expressed on a Subset of Resident Macrophages in Diverse Tissues and its Expression is Increased in Inflammation Northern blot analysis of huSTIgMA showed two transcripts of 1.8 and 2.2 kb (FIG. 57) with highest expression in the adrenal gland, lung and placenta, and lower expression in heart, spinal chord, thyroid gland, mammary gland and lymph node. In all tissues, the 2.2 kb transcript was the most abundantly expressed transcript and presumably, encodes the long form of STIgMA.

TAQMAN™ Real-Time PCR Analysis

To identify specific cell lines expressing STIgMA, real-time quantitative PCR and primers/probes specific for the N-terminal Ig domain was used. Low but detectable mRNA expression was found in the myeloid cell line HL-60 treated with PMA and the monocytic cell line THP-1. Expression was absent in B- and T-cell lines (FIG. 58A).

STIgMA (PRO362) Expression on Differentiated Monocytes.

In order to establish details of when STIgMA was expressed in differentiating monocytes/macrophages, we determined STIgMA mRNA levels in non-adherent monocytes and in adherent monocytes, induced to differentiate in the presence of human autologous serum. STIgMA mRNA levels gradually increased over time and reached maximum levels at 7 days following plating (FIG. 58B). At this differentiation stage, mRNA levels were 100 fold higher as compared to those in undifferentiated monocytes.

Western blotting of monocyte/macrophage lysates showed an increase in STIgMA protein expression (FIG. 58C) in parallel with the increase in STIgMA mRNA expression, indicating that STIgMA was expressed when monocytes differentiated to form macrophages. A band of 48 kDa and a band of 40 kDa appeared on the blot, presumably representing the long and the short forms of human STIgMA.

Molecular Characterization of STIgMA (PRO362)

Figure 59:
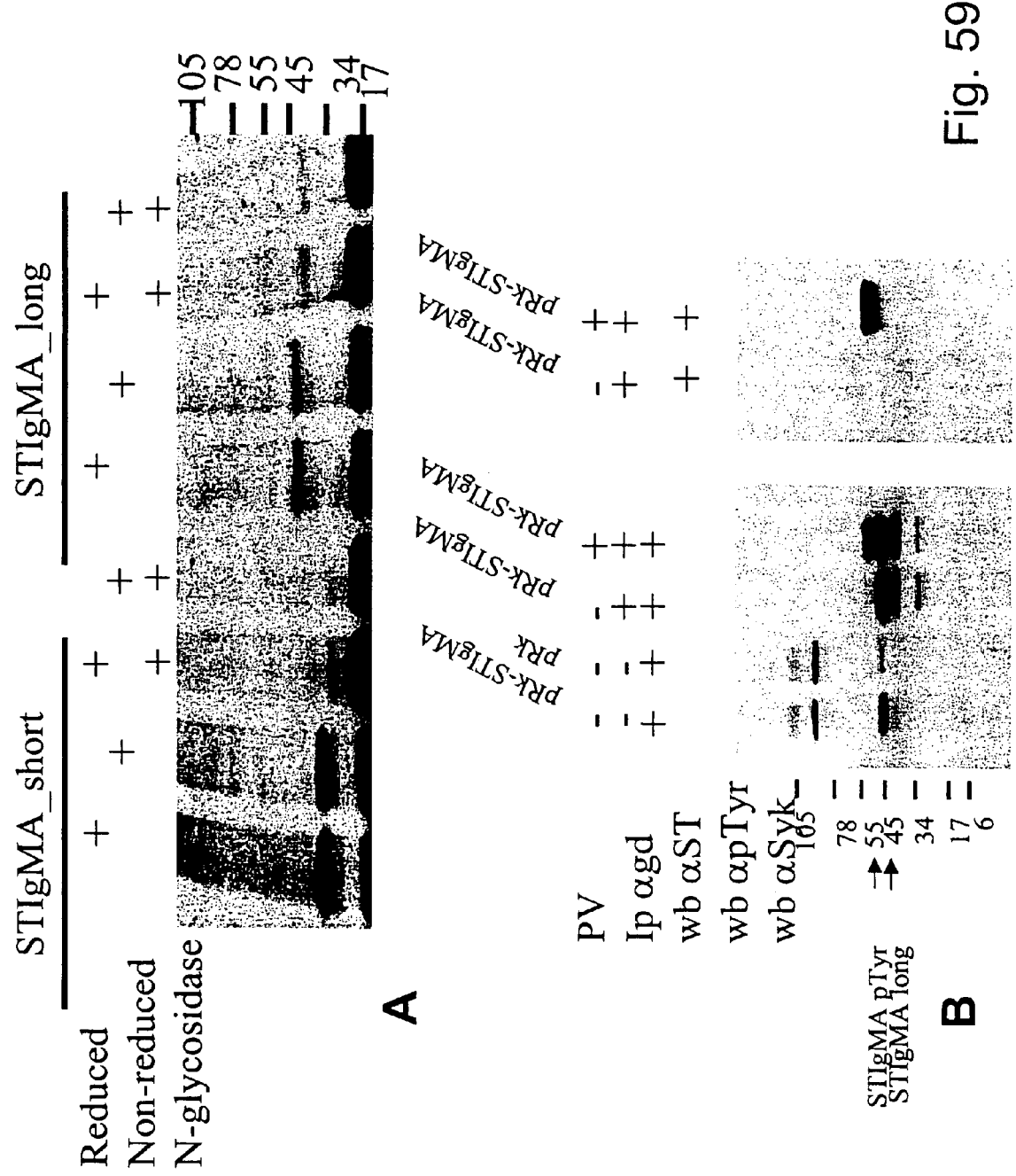
FIG. 59. Molecular characterization of huSTIgMA protein in cell lines. (A) HuSTIgMA-gd was transiently expressed in 293E cells, immunoprecipitated with anti gd and blots incubated with anti gd or a polyclonal antibody to the extracellular domain of STIgMA. (B) huSTIgMA expressed in 293 cells is a monomeric N-glycosylated protein. STIgMA is tyrosine phosphorylated upon treatment of HEK293 cells with sodium pervanadate but does not recruit Syk kinase. Phosphorylated STIgMA migrated at a slightly higher molecular mass compared to non-phosphorylated STIgMA.

STIgMA migrated similarly under reduced and non-reduced conditions indicating that it was expressed as a monomer (FIG. 59A). Only slight changes in migration patterns were observed when STIgMA was deglycosylated using PNGase F, indicating insignificant N-glycosylation. STIgMA was phosphorylated when STIgMA overexpressing cells were treated with pervanadate (FIG. 59B). Phosphorylated STIgMA migrated as a slightly higher Mw protein (55 kDa). In human HEK 293 cells, tyrosine-phosphorylated STIgMA cytoplasmic domain does not recruit Syk kinase (results not shown).

Figure 60:
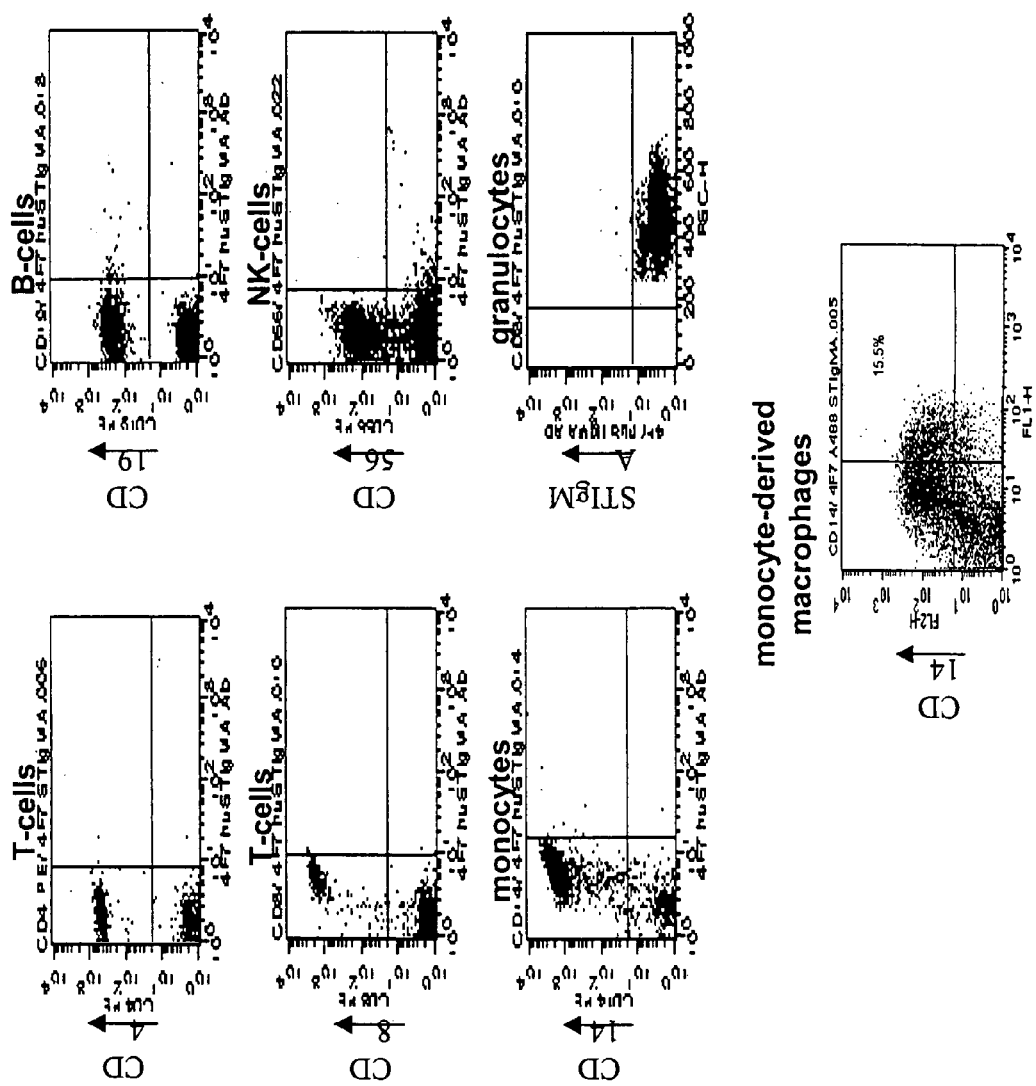
FIG. 60. Selective expression of STIgMA on human monocyte-derived macrophages. Peripheral blood mononuclear cells were stained with antibodies specific for B, T, NK cells, monocytes and with a ALEXA™ A488 conjugated monoclonal antibody (3C9) to STIgMA. Expression was absent in all peripheral blood leukocytes as well as in monocyte derived dendritic cells, but was expressed in in vitro differentiated macrophages.

Flow Cytometry Analysis of STIgMA Expression on Peripheral Blood Mononuclear Cells In order to determine the expression pattern of STIgMA in circulating leukocytes, flow cytometric analysis was performed on lymphocytes isolated from blood from a healthy donor using monoclonal anti-human STIgMA antibody 3C9 directly conjugated with ALEXA™ A488. Counterstaining was performed with PE conjugate antibodies to several immune-cell surface antigens. STIgMA was absent on the surface of all leukocytes, including B-T-Nk cells, monocytes and granulocytes (FIG. 60). STIgMA was however expressed on monocytes cultured for 7 days in macrophage differentiation medium.

Regulation of STIgMA Expression in Monocytes

Figure 61A:
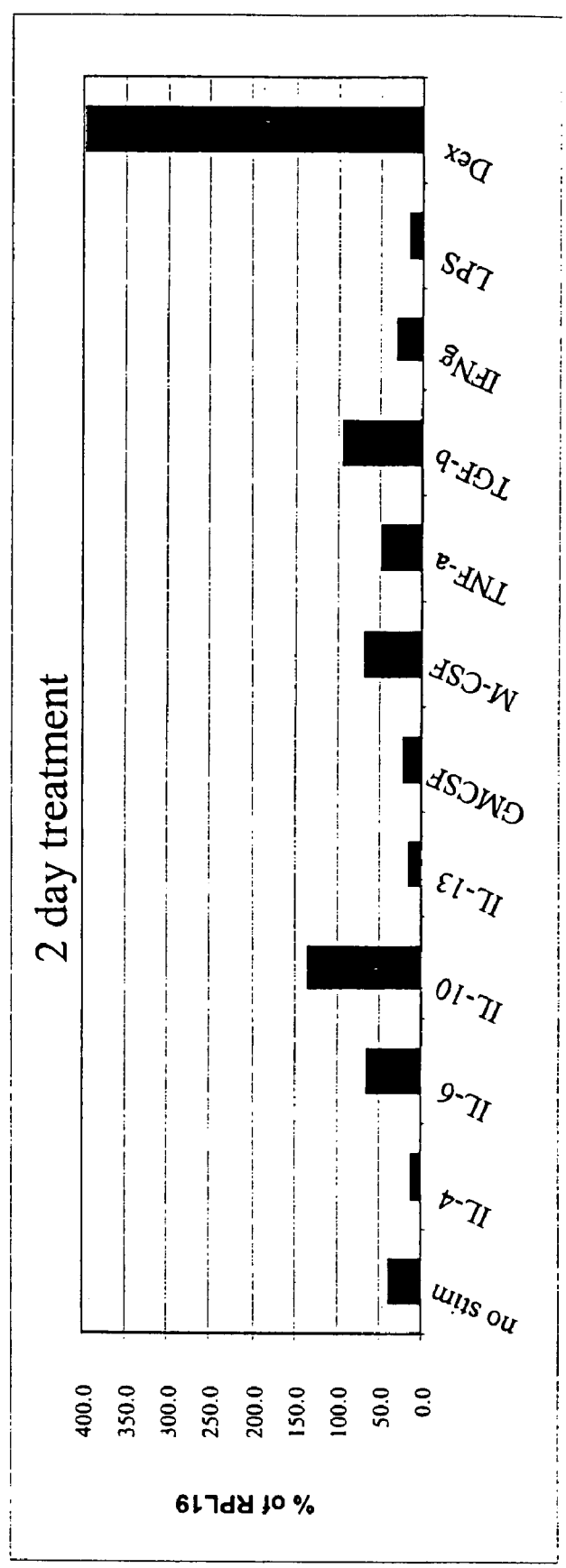
FIG. 61. STIgMA mRNA and protein expression was increased by IL-10 and dexamethasone. (A) Real-time PCR shows increased expression of STIgMA mRNA following treatment with IL-10, TGFbeta and was highly induced by dexamethasone but was down-regulated by treatment with LPS, IFNγ, and TNFα. (B) Ficoll-separated peripheral blood mononuclear cells were treated with various cytokines and dexamethasone for 5 days and double-stained with anti CD14 and anti STIgMA. Flow analysis showed a dramatic increase in STIgMA expression on the surface of monocytes treated with dexamethasone and after treatment with IL-10 and LPS.
Figure 61B:
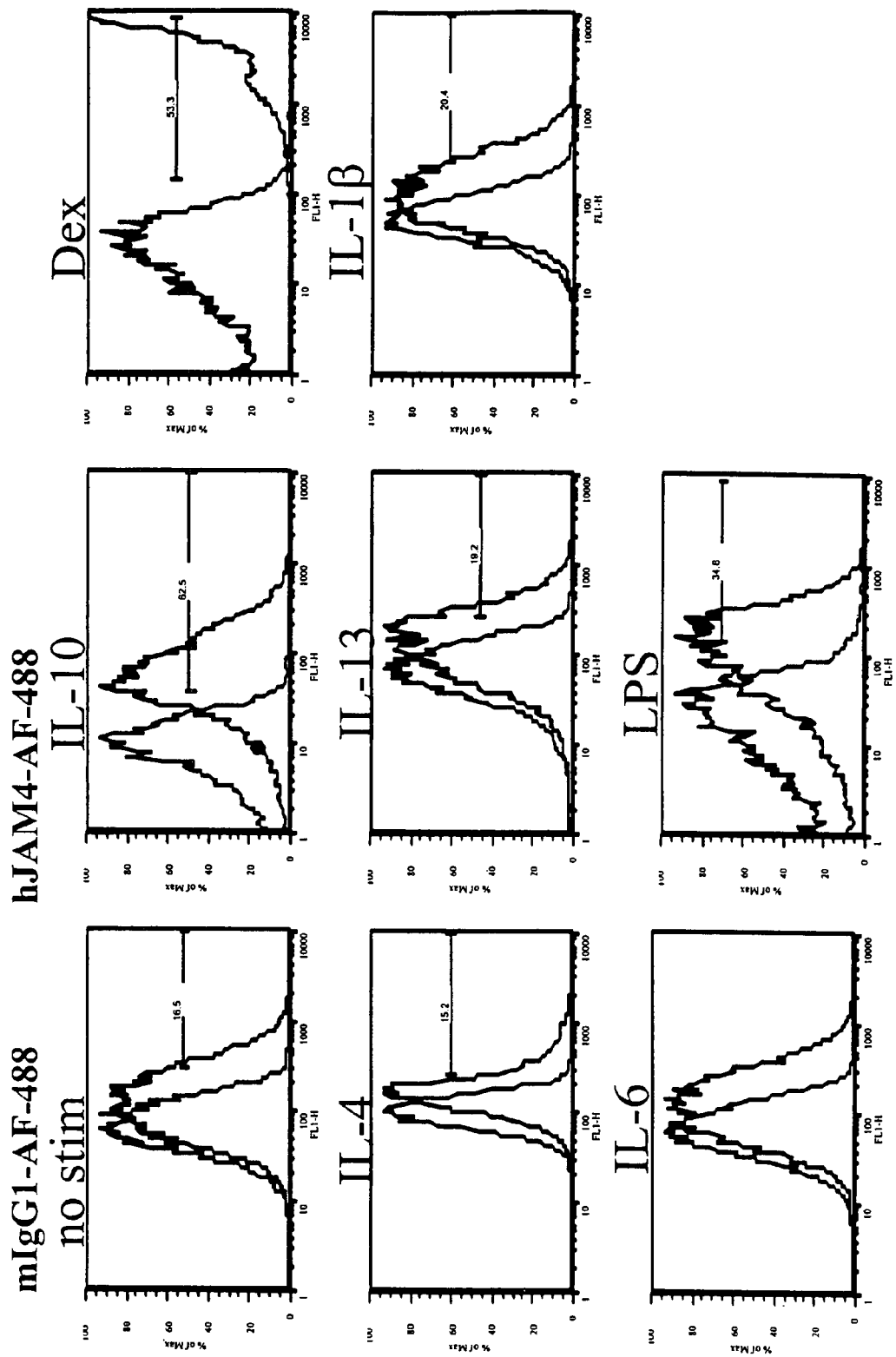

In order to study the regulation of expression of STIgMA, 7 day macrophages were cultured in the presence of various pro- and anti-inflammatory cytokines and STIgMA expression levels were determined by real-time PCR or flow analysis. Expression of STIgMA mRNA was increased after treatment of macrophages for 2 days with IL-10 and TGF-β and down regulated by IL-4, IL13 and LPS (FIG. 61A). Treatment with dexamethasone increased expression to 5 fold compared to control non-treated macrophages. In order to determine the regulation of cell-surface expressed STIgMA, flow cytometry was performed on peripheral blood monocytes treated with various cytokines and dexamethasone for 5 days. STIgMA was detected using monoclonal antibody clone 3C9 conjugated to ALEXA™ A488. Cells were co-stained with anti CD-14 antibodies. Increased surface expression of STIgMA was found following treatment of monocytes with IL-10 and LPS for 5 days (FIG. 61B). A dramatic increase in surface STIgMA expression was found after treatment with dexamethasone.

Subcellular Distribution of STIgMA

In order to study the subcellular distribution of STIgMA, MDMs were kept in culture for 15 days after which they were fixed and stained with a monoclonal antibody (clone 3C9) or polyclonal rabbit antibody 4F7 followed by FITC conjugated secondary antibody and a PE-labeled anti CD63 antibody. Confocal microscopy showed high expression of STIgMA in the perinuclear cytoplasm, overlapping with the expression of the lysosomal membrane protein CD63 (FIGS. 62A,B). STIgMA was also expressed in the leading and trailing edges of the macrophages where its staining pattern did not overlap with that of CD63.

Expression of STIgMA in Normal and Disease Tissues

Figure 63:
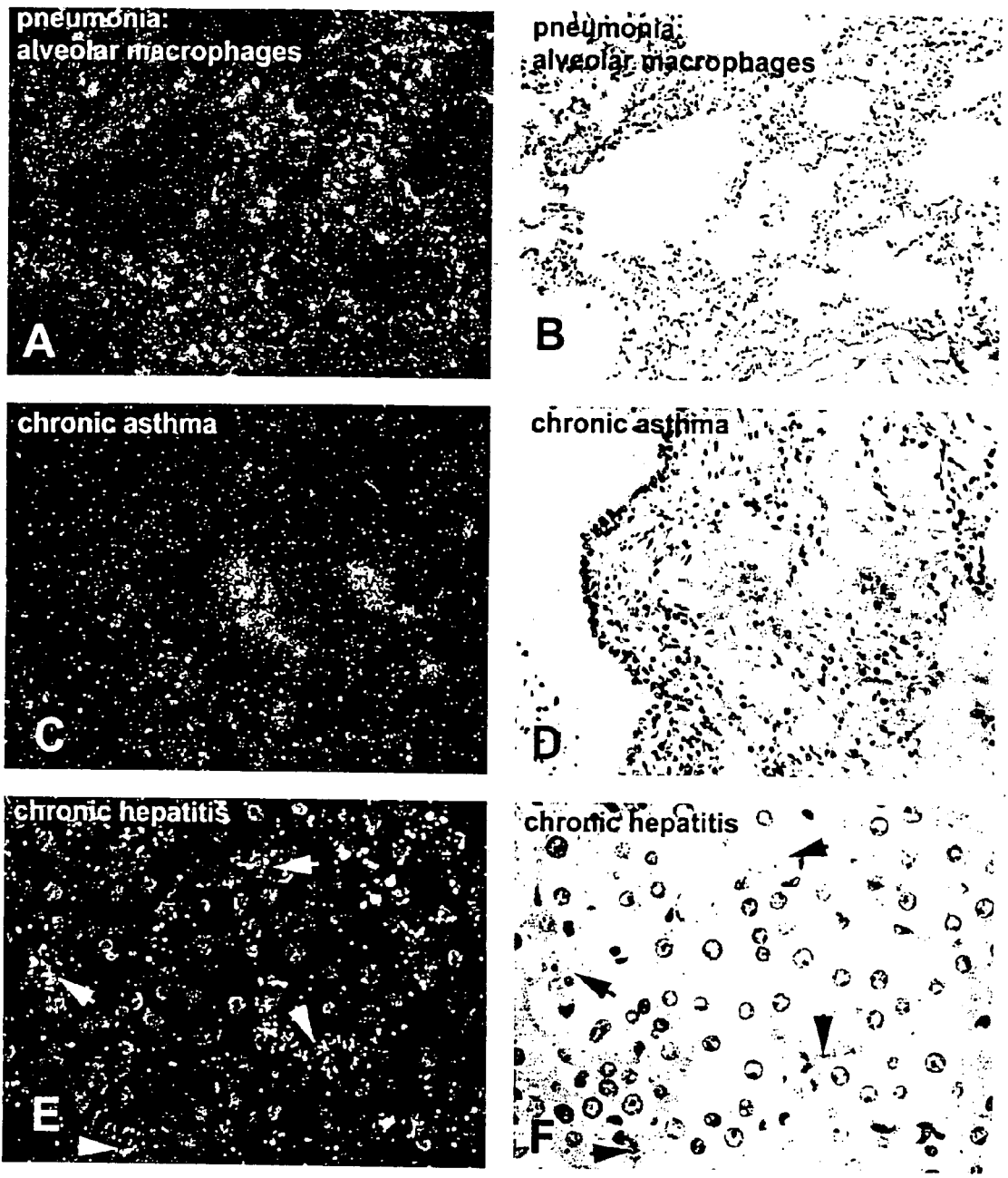
FIG. 63. Localization of STIgMA mRNA in chronic inflammatory diseases. In situ hybridization showed the presence of STIgMA mRNA in alveolar macrophages obtained from tissue of a patient with pneumonia (A, B) or a patient with chronic asthma (C, D). STIgMA mRNA was also expressed in liver Kupffer cells in tissue obtained from a liver biopsy of a patient with chronic hepatitis (E, F).

STIgMA expression in tissue resident macrophages and changes in its expression in tissues with chronic inflammatory diseases was studied. Using in situ hybridization, STIgMA mRNA expression was determined on panels of paraformaldehyde-fixed human tissues. High expression levels were found in alveolar macrophages obtained from a lung autopsy of a patient with pneumonia or chronic asthma (FIG. 63A-D). High mRNA expression was found in Kupffer cells in the liver of a patient with chronic hepatitis (FIGS. 63E, F).

Figure 64:
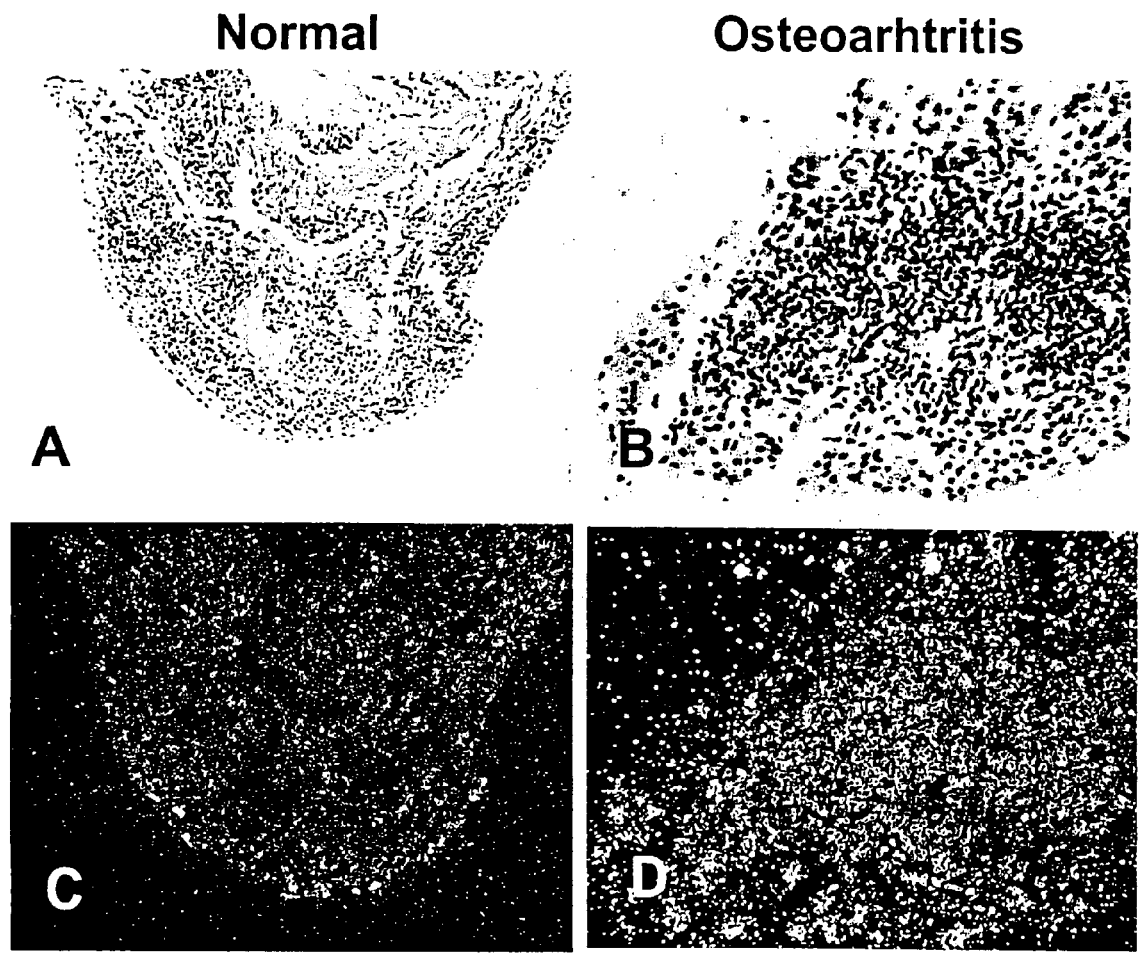
FIG. 64. STIgMA mRNA expression was increased in inflamed synovium. STIGMA mRNA was low or absent in synovial membranes of a joint obtained from a knee replacement of a patient with no joint inflammation (A, C) but was highly expressed in cells, potentially synoviocytes or synovial macrophages, in the pannus of a patient with osteoarthritis (B, D).
Figure 65:
FIG. 65. Detection of STIgMA protein with polyclonal antibody 6F1 in cells lining the synovium of a patient with degenerative joint disease (A, B, C). No immunohistochemical detection of STIgMA was found in a control synovium (D).

In a previous study (Walker, Biochimica et Biophysica Acta 1574 (2002) 387-390), and in electronic screening of libraries, high expression of STIgMA mRNA was found in the synovium of patients with rheumatoid arthritis. Therefore, the expression pattern of STIgMA in synovium obtained from patients with rheumatoid arthritis, osteoarthritis and degenerative bone disease was studied. High expression of STIgMA mRNA was found in synovial cells obtained from a patient with osteoarthritis (FIG. 64A-D). Synovial cells in the superficial layers had the highest expression of STIgMA (FIG. 64D). In addition, polyclonal antibody 6F1 was used to study STIgMA expression in frozen sections of human synovium obtained from a patient with rheumatoid arthritis. STIgMA was expressed in a subset of synovial cells (20-40%) and in tissue macrophages in the synovium (FIG. 65A-C). These cells were, most likely, type A macrophage-like synovial cells. Staining was absent in control synovium (FIG. 65D).

Figure 66:
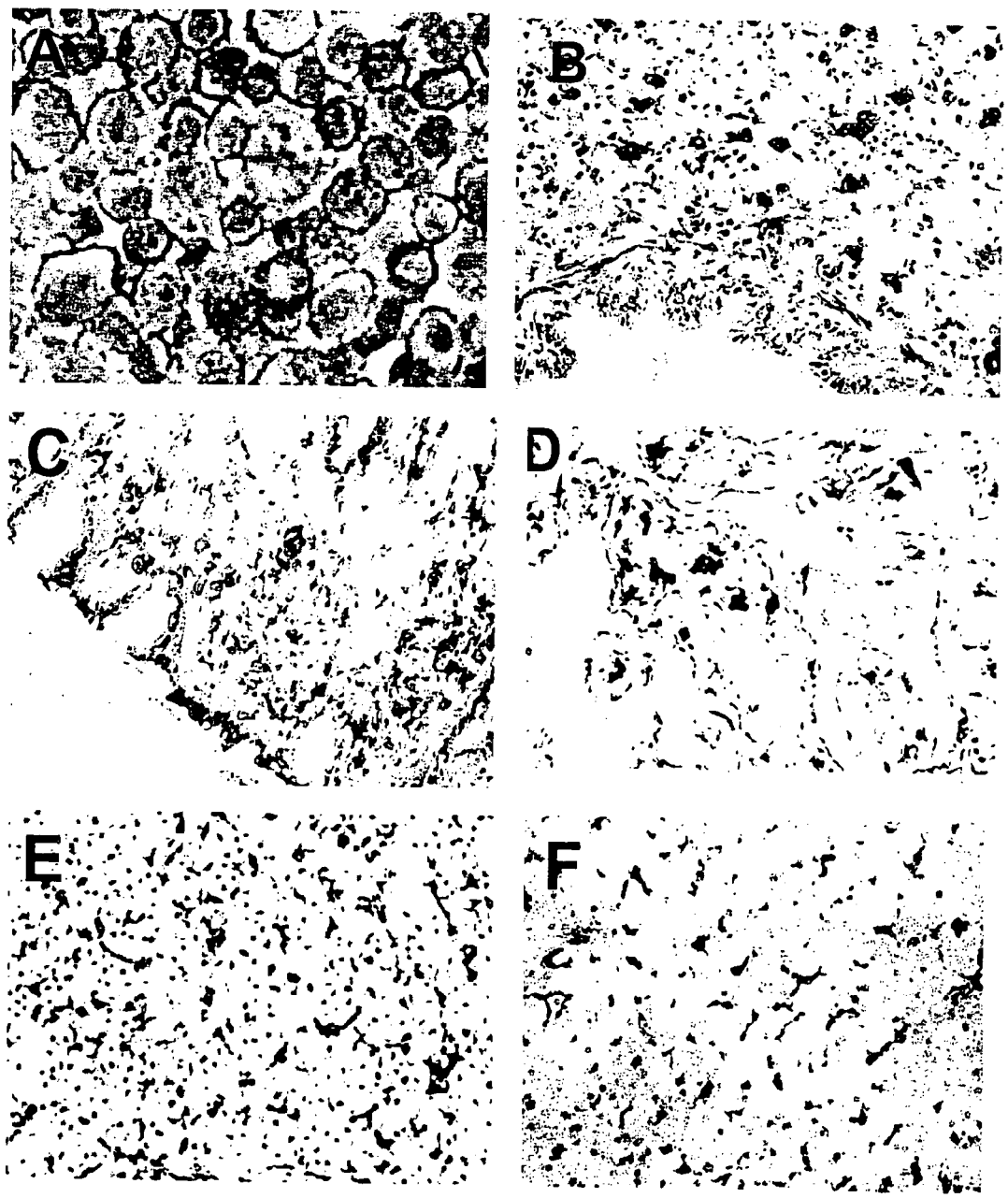
FIG. 66. STIgMA protein was expressed in a subtype of tissue resident macrophages and its expression was increased in chronic inflammatory diseases. (A) STIgMA was expressed on the membrane of CHO cells stably expressing STIgMA. High expression of STIgMA protein was found in alveolar macrophages (B) in tissues obtained from a patient with chronic asthma. (C) Expression of STIgMA in histiocytes of the human small intestine. The section was obtained from surgically removed tissue and could have contained a neoplasm. (D) Expression of STIgMA protein in Hofbauer cells in human pre-term placenta. High expression of STIgMA protein in macrophages was present in the adrenal gland (E) and in Kupffer cells of human liver (F). Staining was performed on 5 μm thick acetone-fixed sections using DAB as the chromogen. Images were photographed at a 20× and 40× magnification.

Expression of STIgMA protein was found on macrophages in a number of different tissues. Frozen sections prepared from CHO cells stably expressing STIgMA show membrane localization of STIgMA (FIG. 66A). STIgMA protein was found in alveolar macrophages (FIG. 66B), histiocytes in the lamina propria of the small intestine (FIG. 66C), Hofbauer cells in the placenta (FIG. 66D), macrophagesin the adrenal gland (FIG. 66E) and Kupffer cells in the liver (FIG. 66F).

Figure 67:
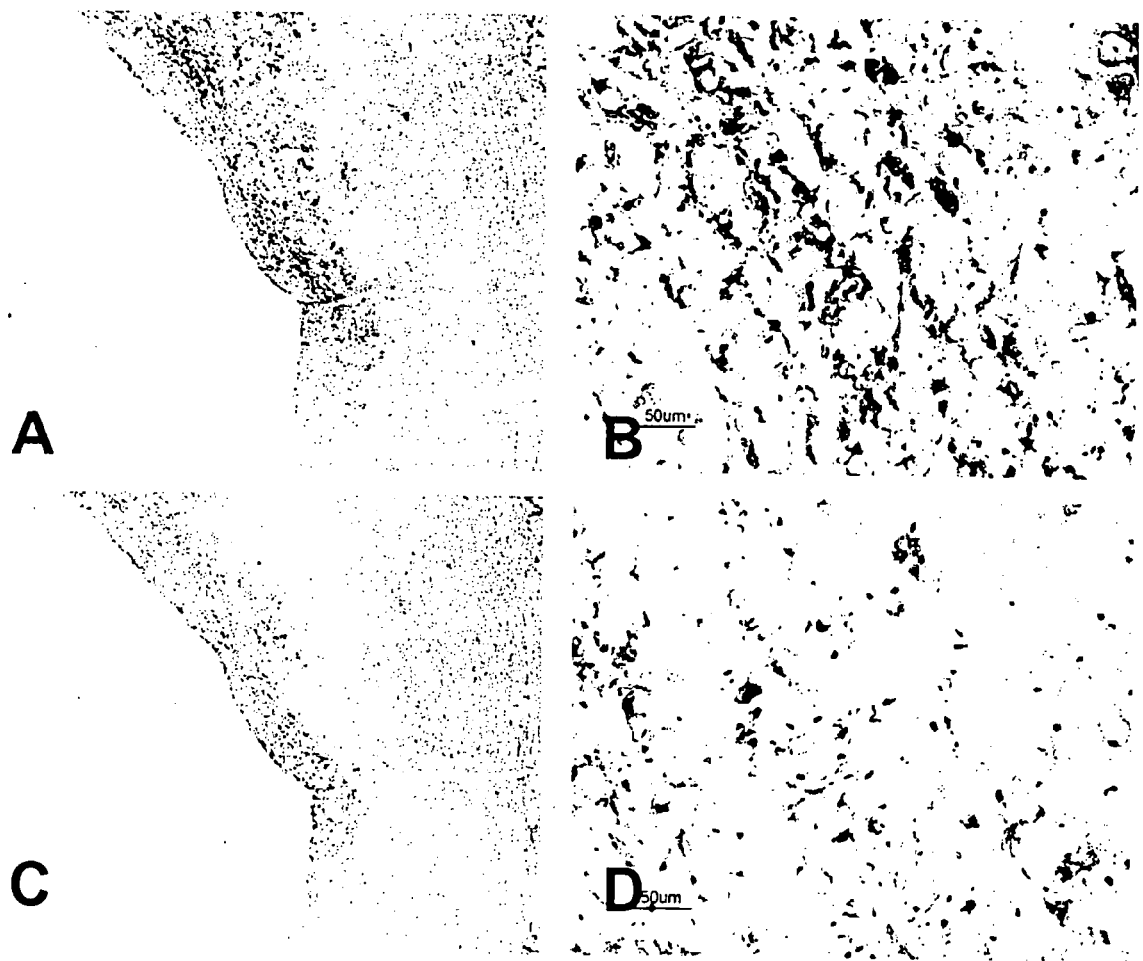
FIG. 67. Immunohistochemical staining of CD68 and STIgMA on a vascular plaque obtained from a patient with atherosclerosis. Consecutive sections were fixed and stained with a monoclonal antibody to human CD68 (A, B) and a polyclonal antibody 6F1 raised against human STIgMA (C, D). STIgMA appeared in a population of macrophages and phoam cells present in the atherosclerotic plaque, and overlapped with CD68 positive macrophages, as judged from staining on consecutive sections. Magnification: 10× (A, C) and 20× (B, D).

Atherosclerotic plaques contained a high number of macrophages or macrophage-foam cells that adhered tightly to the luminal wall of the aorta. Considering a role for STIgMA in macrophage-endothelium adhesion, the expression of STIgMA in atherosclerotic plaques was studied. Alternate sections of plaques were stained with anti CD63 (FIGS. 67A and B) or anti-STIgMA (FIGS. 67C and D). Overlapping staining patterns of anti-CD63 and STIgMA was found on foam cells aligning the vessel wall indicating a role for STIgMA in atherosclerosis.

In order to determine whether STIgMA was selectively expressed on macrophages, double staining immunofluorescence was performed on heart interstitial macrophages (FIG. 68). As shown in the overlay (FIG. 68C) most of the interstitial macrophages positive for STIgMA were also positive for CD68. Not all CD68 positive macrophages were positive for STIgMA, indicating that the latter was specific for a subtype of tissue resident macrophages.

Figure 69:
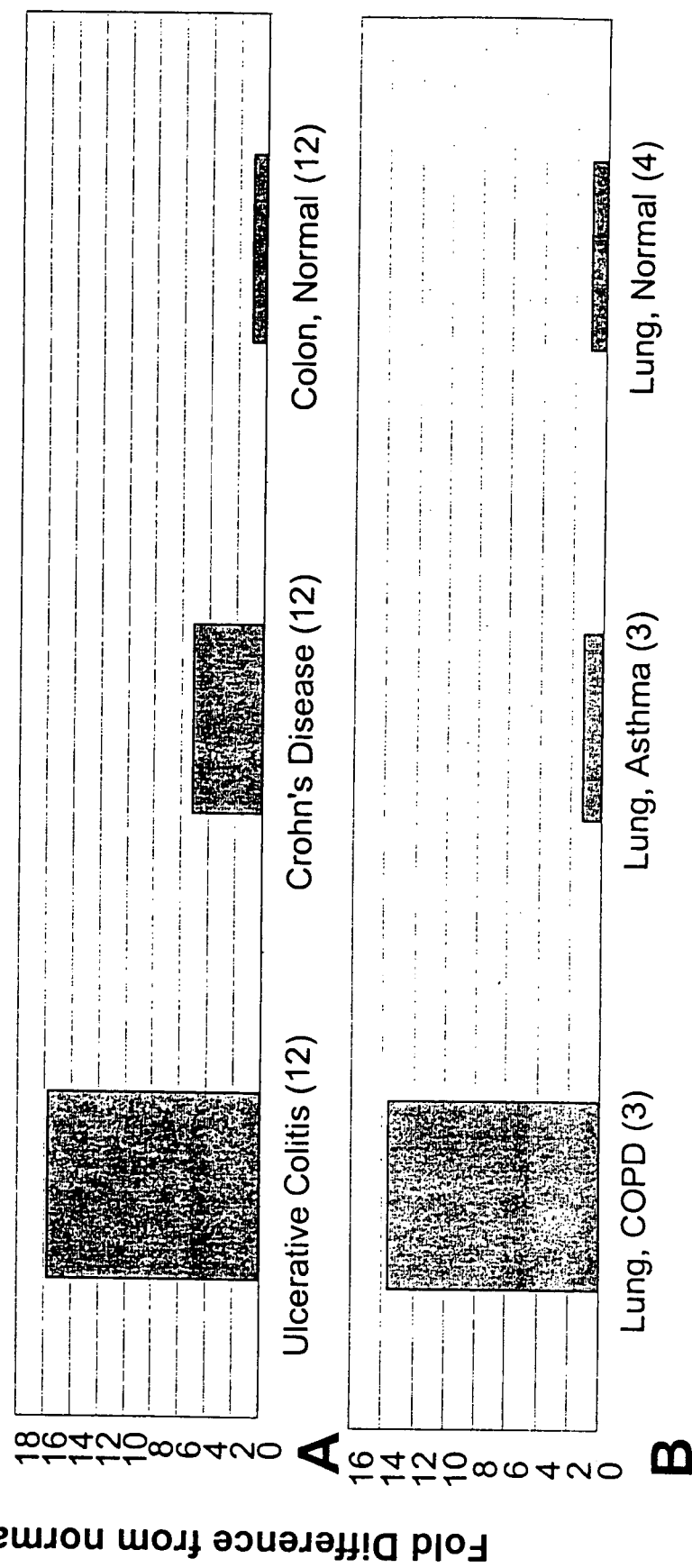
FIG. 69. STIgMA mRNA is significantly increased in colon tissue obtained from patients with ulcerative colitis, Crohn's disease, chronic occlusive pulmonary disease (COPD) and asthma. Real-time PCR was performed on total RNA extracted from the various tissues. mRNA for STIgMA was significantly increased in tissues obtained from patients with ulcerative colitis, Crohn's disease and COPD. Statistical analysis was performed using the Mann-Whitney U-test.

In order to quantitatively determine mRNA expression levels in inflammatory bowel disease (IBD) syndrome, mRNA was extracted from colon tissue obtained from patients with ulcerative colitis, Crohn's disease or from patients with no manifestation of IBD. Real time PCR was performed using primers specific for STIgMA, to measure relative expression levels. Expression levels were 16 fold higher in a patient with ulcerative colitis and, 5 fold higher in a patient with Crohn's disease, as compared to control tissue (FIG. 69A). Similarly, relative RNA equivalents were determined in lung tissue and was found to be highest in tissue from a patient with chronic occlusive pulmonary disease (COPD: 14 fold over normal) and was not significantly different from normal in a patient with asthma (FIG. 69B).

Molecules of the Ig superfamily are well known to mediate cell surface recognition and cell-cell adhesion. Since STIgMA expression was high in interstitial macrophages aligning blood vessels, STIgMA involvement in macrophage-endothelial cell adhesion was studied. A Jurkat cell line, stably transfected with full length STIgMA-long (FIG. 70A) was loaded with the fluorescent dye BCECF and added to the wells of a 96 well maxisorb plate on which a monolayer of HUVEC cells had been cultured. Adhesion was measured by the amount of fluorescence retained after 3 gentle washes. Jurkat cells expressing STIgMA were more adherent to both, control and TNFα stimulated endothelium, as compared to Jurkat cells stably transfected with a control plasmid (FIG. 70B).

Discussion

This study, for the first time, described the tissue distribution, regulation of expression and molecular characterization of a novel Ig superfamily member STIgMA/Z39Ig and confirmed its selective expression in tissue resident macrophages.

STIgMA expression was found on resident macrophages which had a fully differentiated phenotype. Its expression was increased in tissues with chronic inflammation like, rheumatoid arthritis and inflammatory bowel disease. The increase of STIgMA expression in these diseases, which was often characterized as Th2 type diseases, may be in line with the regulation of its expression by Th2 cytokines in vitro. Whether this increased expression is due to an increased presence of STIgMA positive macrophages or an increased expression on the inflammatory macrophages has yet to be determined.

STIgMA may mediate one of the effector functions of human macrophages, which include bacterial recognition, phagocytosis, antigen presentation and cytokine release. However, so far, no evidence was found for its role in any of these processes. STIgMA contained 3 tyrosine residues in its cytoplasmic domain which can be phosphorylated by tyrosine kinases. Therefore, STIgMA may act as a receptor. So far, no ligand has been found for STIgMA.

These results indicated a role for STIgMA in adhesion, and possibly motility, of macrophages to the endothelial cell wall of vessels.

STIgMA expression was increased in non-microbial inflammatory diseases like ulcerative colitis and chronic occlusive pulmonary disease (COPD) but was downregulated in isolated macrophages upon treatment with LPS or other bacterial cell wall components like lipoteichoic acid and bacterial lipoprotein. Long term treatment, over 2 days, with LPS caused an increase in the expression of STIgMA. This could be due to an autocrine effect of IL-10 secreted by LPS-stimulated macrophages. A striking up-regulation of STIgMA, both at the mRNA and protein levels, was observed upon treatment of monocytes or macrophages with dexamethasone. Few monocyte/macrophage surface receptors have been found to increase in expression upon dexamethasone treatment. One example is CD163, but its induction by dexamethasone is far less dramatic. The up-regulation of STIgMA by anti-inflammatory cytokines IL10 and TGFβ was of considerable interest and indicates that STIgMA may mediate the anti-inflammatory role of glucocorticosteroids.

As described here, STIgMA was expressed on a subset of CD68 positive macrophages which may represent activated macrophages. Using blocking and activating antibodies to STIgMA and STIgMA-Fc fusion protein, its role in macrophage effector function, adhesion and migration and its role in chronic inflammatory diseases has been investigated, and is described in Example 25.

Only few cell surface markers were specifically expressed on differentiated macrophages, such as CD68 and CD163. Although CD68 was apparently expressed on all human macrophage populations, the antigen could also be detected on other myeloid cells and also on certain non-myeloid cells. Therefore, STIgMA represented the first cell surface antigen selectively expressed on a subset of interstitial mature macrophages.

Example 25

STIGMA Fusion Proteins in Collagen-Induced Arthritis (CIA) in DBA-1J mice

This experiment aimed to compare STIgMA fusion proteins to control murine IgG1 in the development of disease and progression of CIA (collagen-induced arthritis, an experimental animal model system of rheumatoid arthritis).

As discussed in Example 24, STIgMA is highly and specifically expressed on a subset of macrophages and is elevated in tissues with chronic inflammation. Murine STIgMA is highly expressed in macrophages and synoviocytes in inflamed joints of mice with collagen-induced arthritis. In vitro studies have shown that STIgMA is involved in adhesion of macrophages to endothelium. STIgMA-Fc fusion protein influences the course of an autoimmune disease, in this case collagen-induced arthritis in mice, either by influencing the properties of tissue macrophages or by influencing immune response of other cells (e.g. T cells, B cell, epithelial cells, endothelial cells). This may result in alleviation of inflammation, swelling and long term bone erosion in joints.

Animal Model Species: Mouse

Strain(s): DBA-1J

Supplier(s): JACKSON

Age Range: 7 to 8 week old

Pain Category: 3—These procedures cause more than minimal or transient pain and/or distress but cannot be performed using anesthetics, analgesics or tranquilizers without adversely affecting the study.

The mouse was chosen as the species to study CIA because CIA is an inflammatory polyarthritis with clinical and pathological features similar to human RA (rheumatoid arthritis). This animal model has been used by many laboratories and the histopathology of CIA resembles those seen in RA with synovial proliferation that progresses to pannus formation, cartilage degeneration/destruction and marginal bone erosions with subsequent joint deformities. Also, mouse is phylogenetically the lowest mammal.

Also, there is no in vitro model available to mimic the complex, multifactorial pathogenesis of RA (Rheumatoid Arthritis).

Experimental Design

Treatment Groups:

1) mIgG1 isotype 6 mg/kg in 200 μl saline subcutaneous (SC) 3 times/wk for 7 weeks (n=8).

2) muSTIgMA (PRO362) 4 mg/kg in 100 μl saline SC 3 times/wk for 7 weeks (n=8).

Mice were immunized interdermally with bovine CII (100 ug, Sigma, St Louis) emulsified in CFS (Difco). Mice were rechallenged with CII in IFA (Difco) 21 days later. Starting on day 24, one group of mice (n=7) was given 100 ug muS-TIgMA (PRO362) Fc three times per week for 6 weeks, and the second group (n=8) received 100 ug of murine IgG1, as a control. Mice were examined daily for signs of joint inflammation and scored as follows: 0, normal; 1, erythema and mild swelling confined to the ankle joint; 2, erythema and mild swelling extending from the ankle to metatarsal and metacarpal joints, 3 erythema and moderate swelling extending from the ankle to metatarsal or metacarpal joints. 4, erythema and severe swelling extending from the ankle to the digits. The maximum arthritic score per paw was 4, and the maximal score per mouse was 16 (FIG. 71).

All mice were immunized with 100 μg bovine collagen type II in 100 μl complete Freunds Adjuvant (CFA) on day 0. Collagen type II in CFA was injected intradermally at the base of the tail on the right side. On day 21, a 2nd immunization with 100 μg bovine collagen type II in 100 μl of incomplete Freunds adjuvant was given i.d. at the left side of the tail. Animals were checked daily (M-F) by the investigative staff. Nestlets were used as an enrichment device, and to provide extra padding for the animals. If necessary, moistened food was provided at the bottom of the cages. Debilitated animals were sacrificed after consultation with the veterinary staff. Terminal faxitron X-Rays and microCT were taken at the end of study and joint lesion/erosion was evaluated. In addition, animals were weighed before treatment and at termination.

On day 35 and at the termination of the study, mice in Groups 1 to 8 were bled for serum pK and to determine anti-collagen type II antibody titer (100 μl orbital bleed).

On day 70 all mice were terminally bled intracardially under 3% isoflurane for a terminal hemogram, for a differential leukocyte count and for serum pK (G3) evaluation.

The mice were euthanized at day 70, post induction of arthritis. All four limbs were collected for radiographs, 5CT and histopathology.

Housing and Diet for Animals

Cotton pad and moistened feed was provided on the floor of the cage to promote access to food and comfort.

Drugs Used for Restraint

Isoflurane—inhalation to effect

Euthanasia Methods Exsanguination by Cardiac Puncture (Percutaneous) Under anesthesia Isoflurane—inhalation to effect Results Systemic injection of the STIgMA fusion protein, muS-TIgMA-Fc, into a collagen-induced arthritic mouse (animal model for rheumatoid arthritis) showed significant (see FIG. 71: p-value=0.0004) reduction in the progression of CIA in the test group of mice that received the STIgMA fusion protein (squares) versus the control group of mice that received IgG1 (circles).

DEPOSIT OF MATERIAL

The following materials have been deposited with the American Type Culture Collection, 10801 University Boulevard, Manassas, Va. 20110-2209, USA (ATCC):

| Designation | ATCC Dep. No. | Deposit Date |
|---|---|---|
| pRK5-based plasmid DNA40628-1216 | 209432 | Nov. 7, 1997 |
| DNA45416-1251 | 209620 | Feb. 5, 1998 |
| DNA35638-1141 | 209265 | Sep. 16, 1997 |
| DNA77624-2515 | 203553 | Dec. 22, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC '122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A polypeptide comprising amino acids 21 to 276 of SEQ ID NO: 32.

2. The polypeptide of claim 1 comprising amino acids 1 to 276 of SEQ ID NO: 32.

3. An immunoadhesin comprising amino acids 21 to 276 of SEQ ID NO: 32, fused to an immunoglobulin constant region sequence.

4. The immunoadhesin of claim 3 wherein said constant region sequence is an immunoglobulin heavy chain constant region sequence.

* * * * *